(12) United States Patent
Stillman et al.

(10) Patent No.: US 8,895,526 B2
(45) Date of Patent: Nov. 25, 2014

(54) IDENTIFICATION OF RNAI TARGETS AND USE OF RNAI FOR RATIONAL THERAPY OF CHEMOTHERAPY-RESISTANT LEUKEMIA AND OTHER CANCERS

(75) Inventors: Bruce Stillman, Cold Spring Harbor, NY (US); Scott W. Lowe, Cold Spring Harbor, NY (US); Anthony Mazurek, Cold Spring Harbor, NY (US); Johannes Ekkehart Zuber, Cold Spring Harbor, NY (US); Christopher Vakoc, Oyster Bay, NY (US); Katherine McJunkin, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 13/260,540

(22) PCT Filed: Mar. 29, 2010

(86) PCT No.: PCT/US2010/029083
§ 371 (c)(1),
(2), (4) Date: Jun. 4, 2012

(87) PCT Pub. No.: WO2010/111712
PCT Pub. Date: Sep. 30, 2010

(65) Prior Publication Data
US 2012/0272346 A1     Oct. 25, 2012

Related U.S. Application Data

(60) Provisional application No. 61/164,125, filed on Mar. 27, 2009.

(51) Int. Cl.
*C12N 15/11* (2006.01)
*A01K 67/027* (2006.01)

(52) U.S. Cl.
CPC ....... *A01K 67/0271* (2013.01); *A01K 2227/105* (2013.01); *C12N 15/111* (2013.01); *C12N 2310/14* (2013.01); *C12N 2310/531* (2013.01); *C12N 2799/027* (2013.01); *C12N 2840/203* (2013.01); *C12N 2830/003* (2013.01); *A01K 2207/12* (2013.01); *A01K 2267/0393* (2013.01); *A01K 2267/0331* (2013.01); *A01K 2207/05* (2013.01); *C12N 2330/51* (2013.01); *C12N 2320/11* (2013.01)
USPC ........................................................ 514/44 A

(58) Field of Classification Search
USPC ........................................................ 514/44 A
See application file for complete search history.

(56) References Cited

U.S. PATENT DOCUMENTS

| 2006/0029460 A1 | 2/2006 | Russo | |
|---|---|---|---|
| 2006/0294604 A1 * | 12/2006 | Fridman et al. ................. | 800/14 |
| 2009/0022685 A1 | 1/2009 | Lowe et al. | |
| 2010/0075915 A1 * | 3/2010 | Yu et al. .......................... | 514/49 |

FOREIGN PATENT DOCUMENTS

WO    WO2009/017670 A2 *   2/2009

OTHER PUBLICATIONS

Bracken et al. The EMBO Journal vol. 22, pp. 5323-5335, 2003.*
Fellman et al. Mol. Cell. 2011, 41:733-746.*
Kresmans et al. J Nucl Med 2008: 49:1546-1554.*
Shon et al., "The alternative spliced insoform AML1-ETO9A is detectable is all T(8:21)-Positive Acute Myeloid Leukemias: Correlation of the Expression Level with Clinical Outcome," Haematologica, vol. 92, pp. 335 (2007).
International Search Report mailed on Aug. 30, 2010, for International Application No. PCT/US10/029083 filed Mar. 29, 2010.
Written Opinion mailed on Aug. 30, 2010, for International Application No. PCT/US10/029083 filed Mar. 29, 2010.

* cited by examiner

*Primary Examiner* — Brian Whiteman
(74) *Attorney, Agent, or Firm* — Wilmer Cutler Pickering Hale and Dorr LLP

(57) ABSTRACT

Provided is a mosaic mouse model for use in determining the potency of an shRNA in vivo for reducing survival of cancer cells of chemotherapy-resistant leukemia. The syngeneic mouse recipient is transplanted with tet-on competent leukemia cells carrying a bicistronic nucleic acid construct comprising a promoter operably linked to a fusion gene associated with chemotherapy-resistant leukemia, and a sequence encoding a reverse tet-transactivator protein, such that both coding sequences are co-expressed from the promoter. Also provided are methods of treating soft tissue cancers.

7 Claims, 59 Drawing Sheets

Hairpins that impair HCT116 proliferation greater than 2-fold.

| Gene | Hairpin ID | Total # cells in culture / average total # cells in negative control cultures |
|---|---|---|
| RRM1 | V2HS_93885 | 0.068 |
| RPA1 | V2HS_32160 | 0.109 |
| RPA3 | V2HS_32105 | 0.164 |
| PES1 | V2HS_254080 | 0.177 |
| PES1 | V2HS_196673 | 0.278 |
| RPA3 | V2HS_32101 | 0.316 |
| PCNA | V2HS_152708 | 0.357 |
| CDCA5 | V2HS_70809 | 0.364 |
| PES1 | V2HS_253534 | 0.392 |
| DDX5 | V2HS_24065 | 0.405 |
| C8ORF1 | V2HS_15119 | 0.417 |
| INTS7 | V2HS_96517 | 0.422 |
| C8ORF1 | V2HS_15118 | 0.443 |
| MCM5 | V2HS_84917 | 0.446 |
| FLJ10154 | V2HS_135540 | 0.460 |
| SLD5 | V2HS_138608 | 0.465 |
| C9ORF76 | V2HS_176960 | 0.494 |

FIG. 2

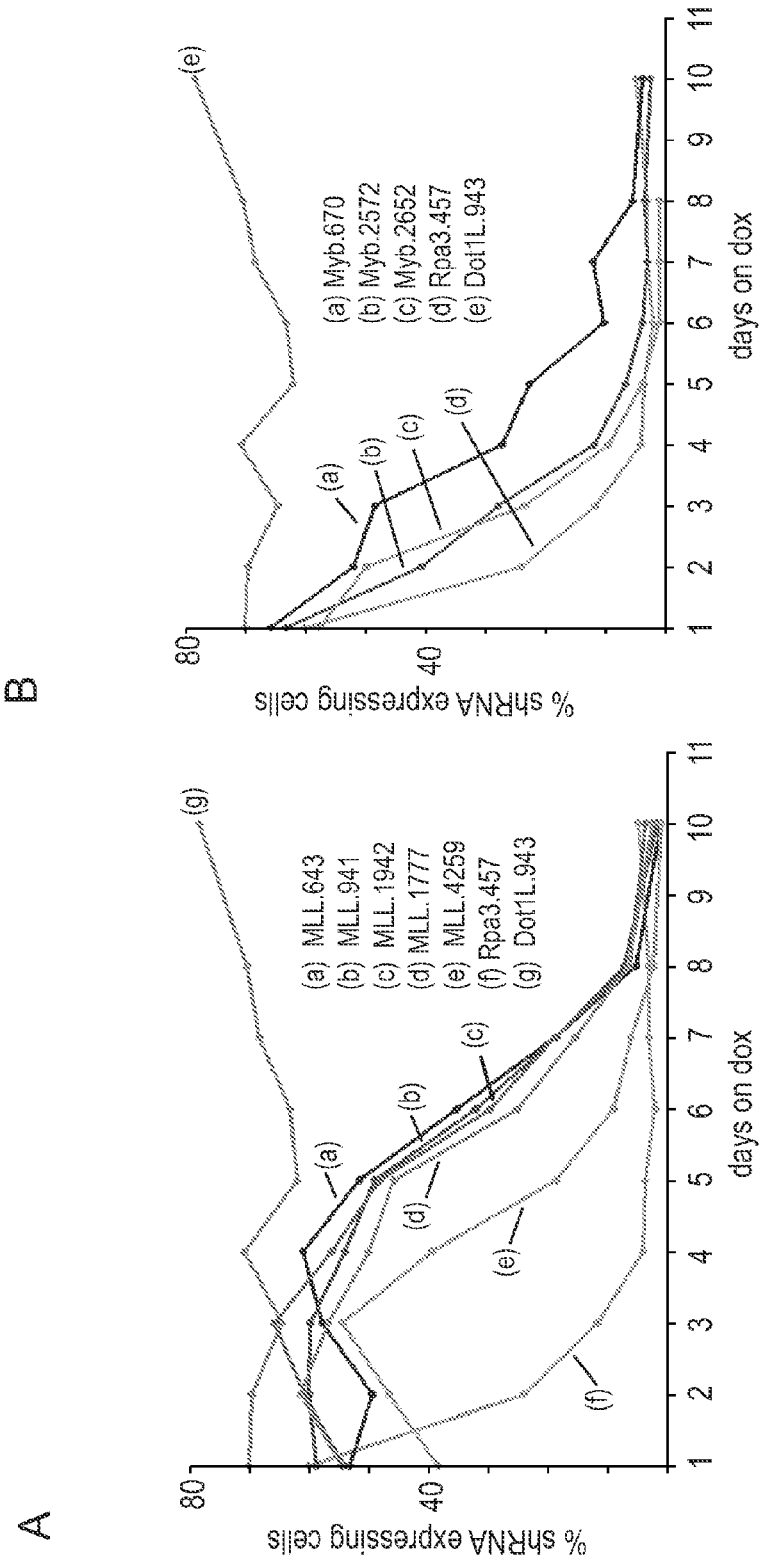
FIGS 10A-B

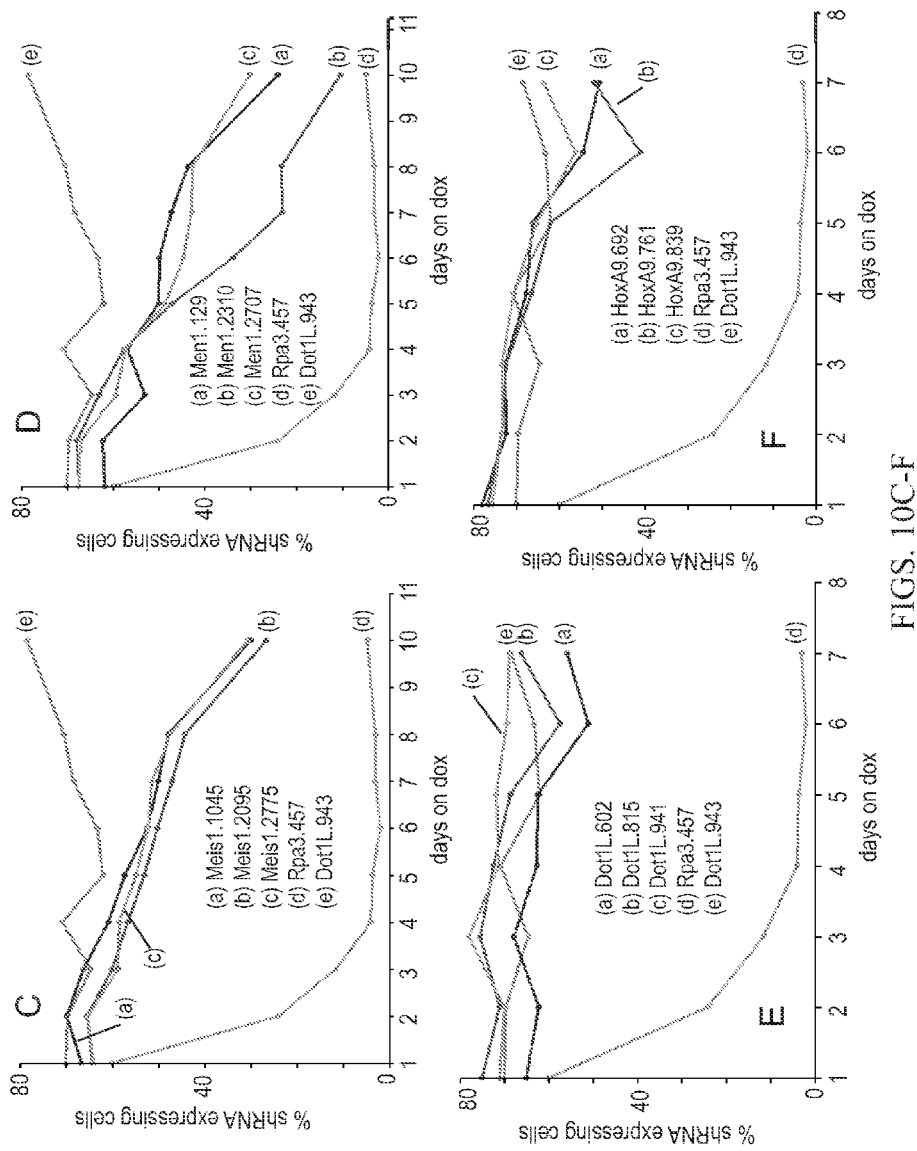
FIGS. 10C-F

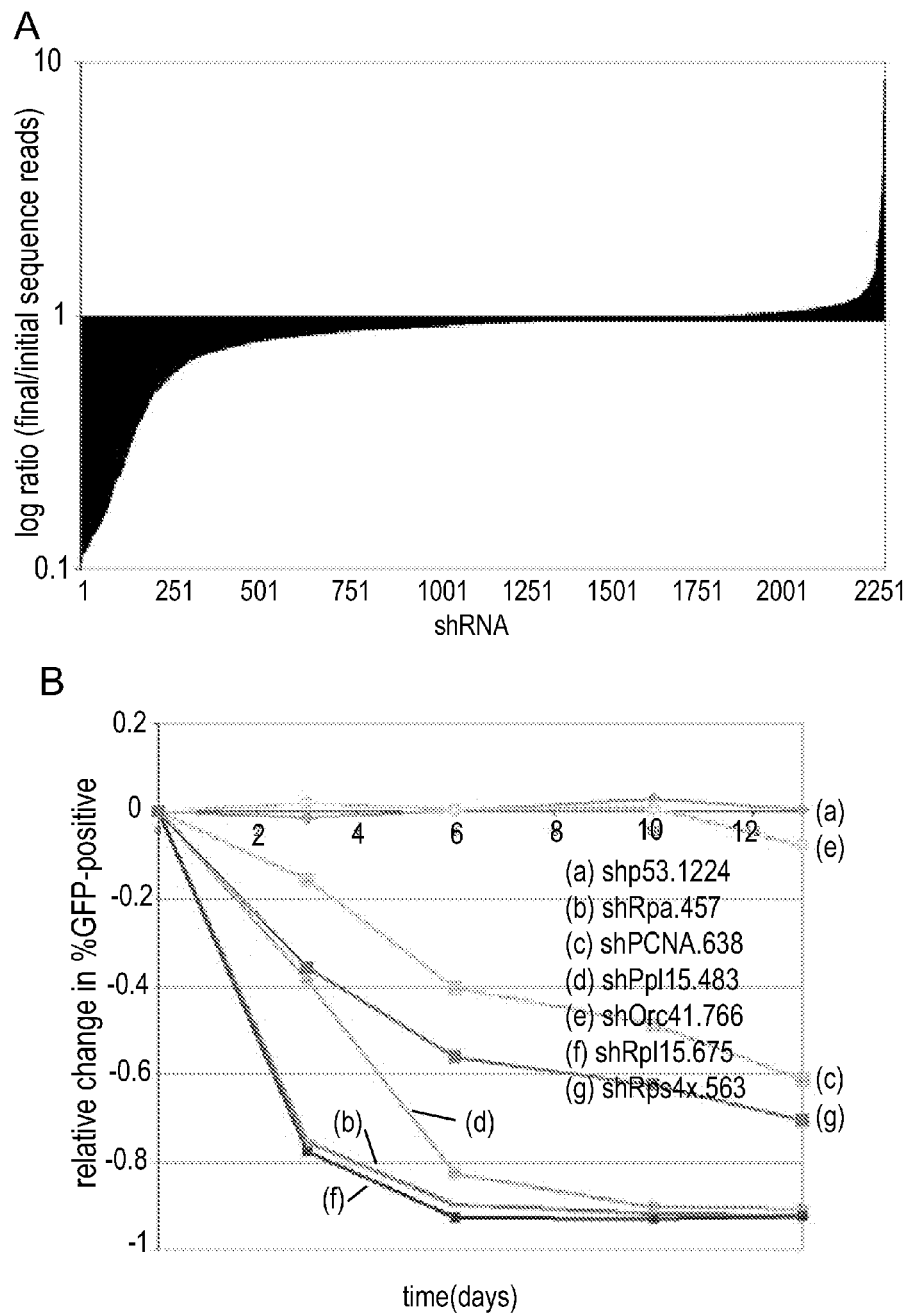
FIGS. 11A-B

A
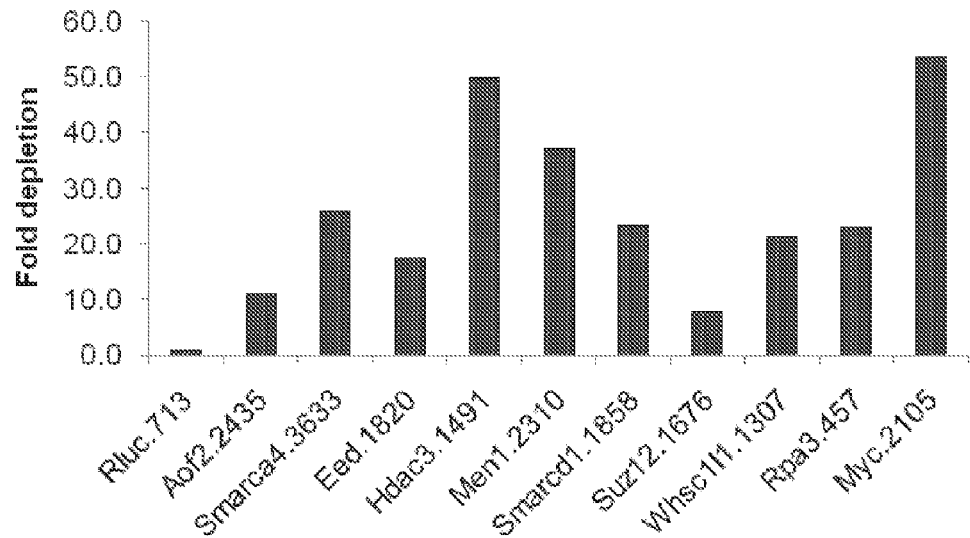
B
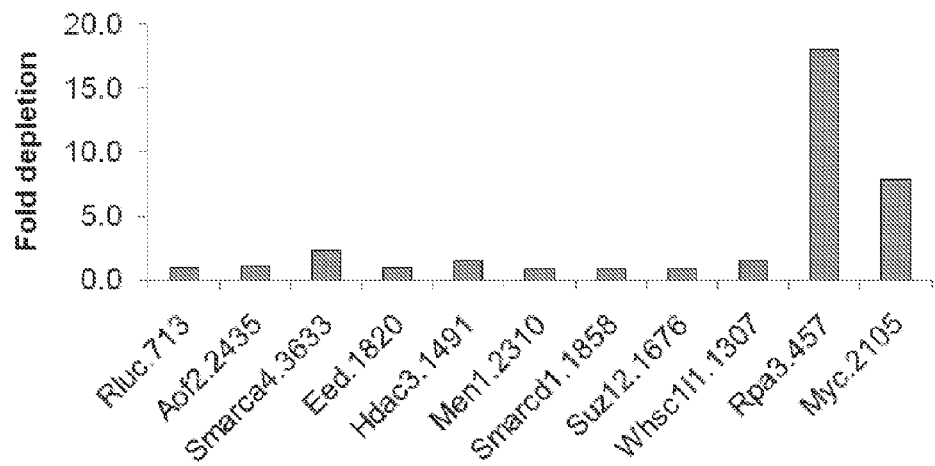
FIG. 23A-B

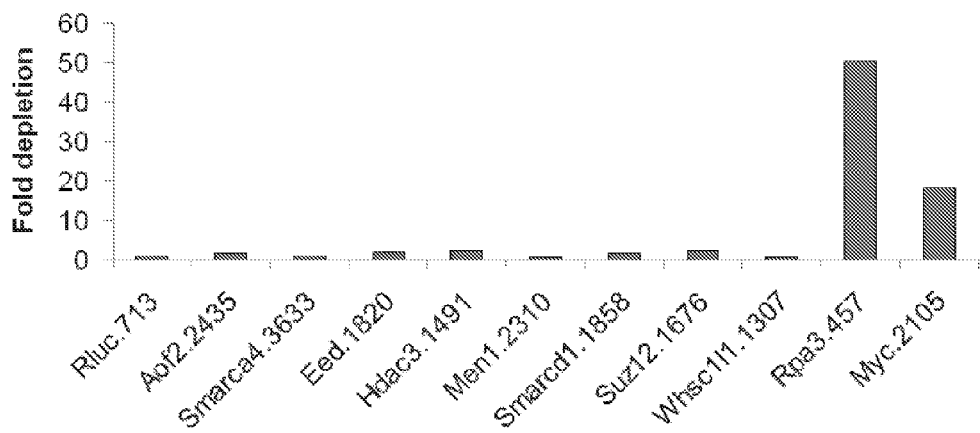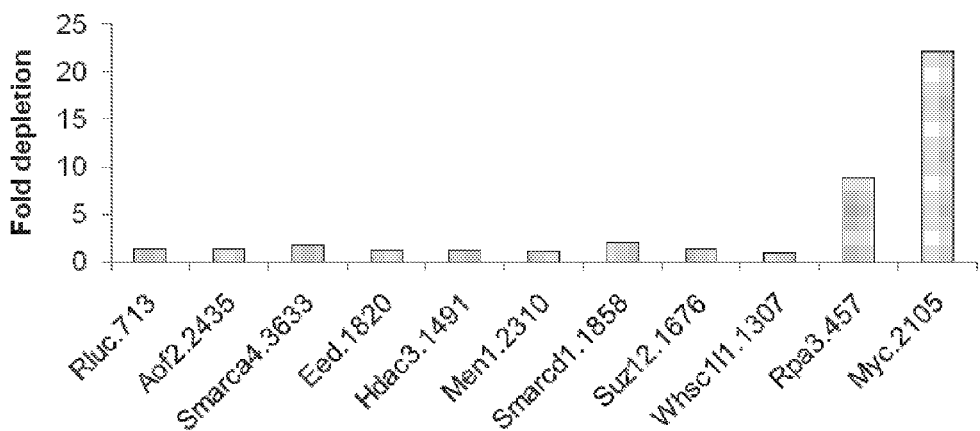
FIG. 23C-D

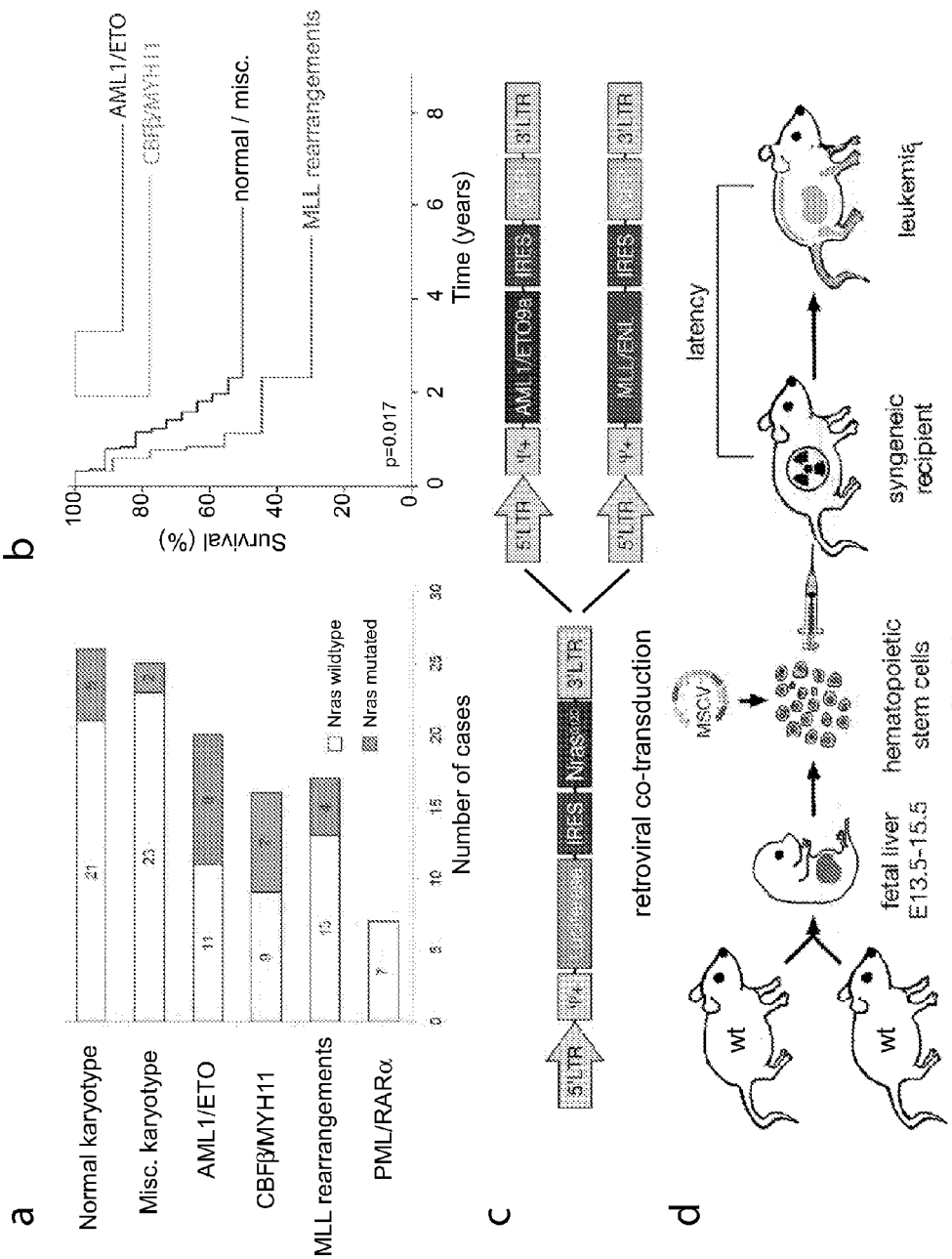
FIG. 30A-D

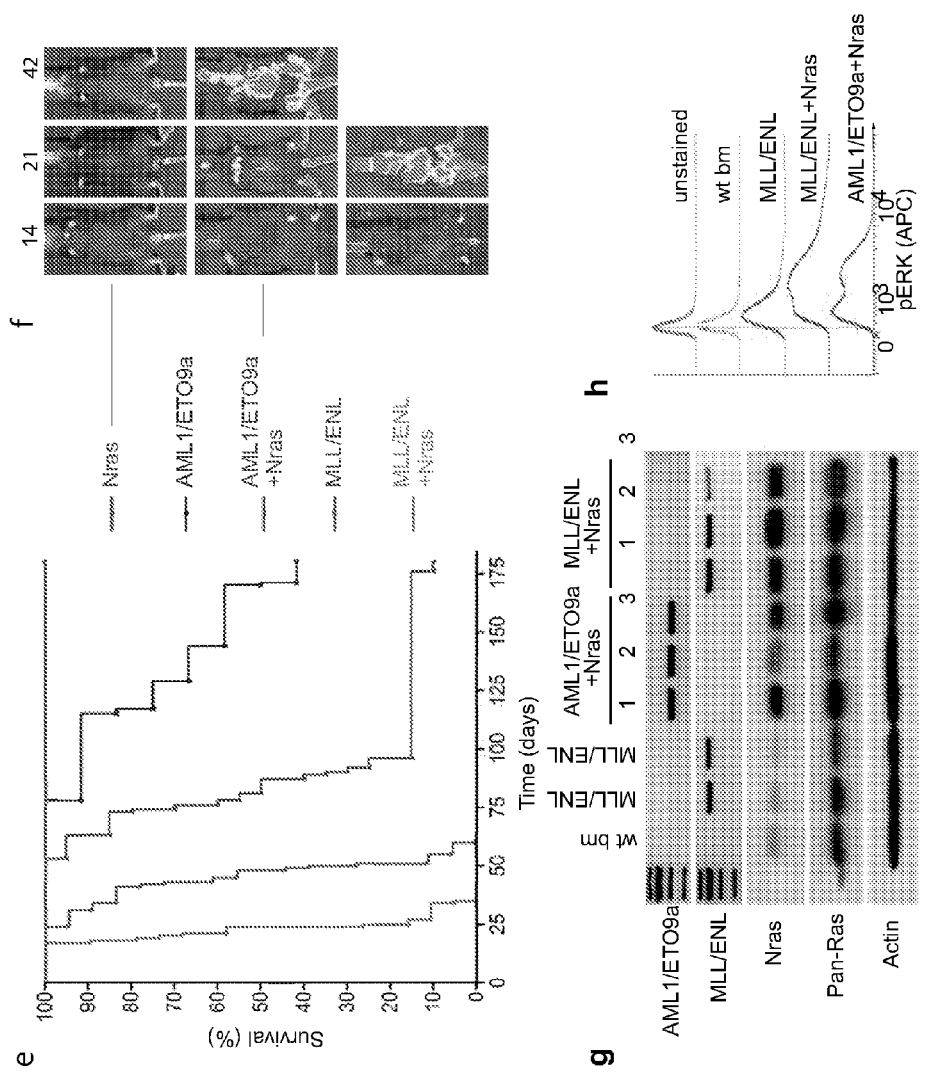
FIG. 30E-H

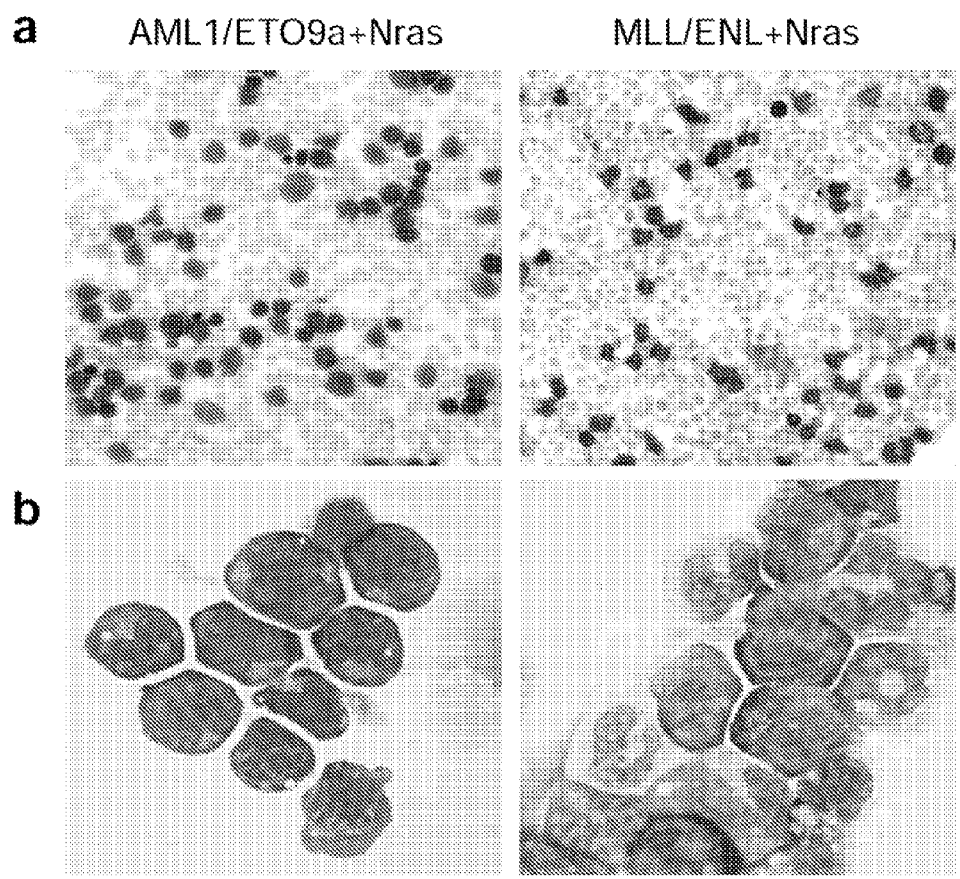
FIG. 31A-B

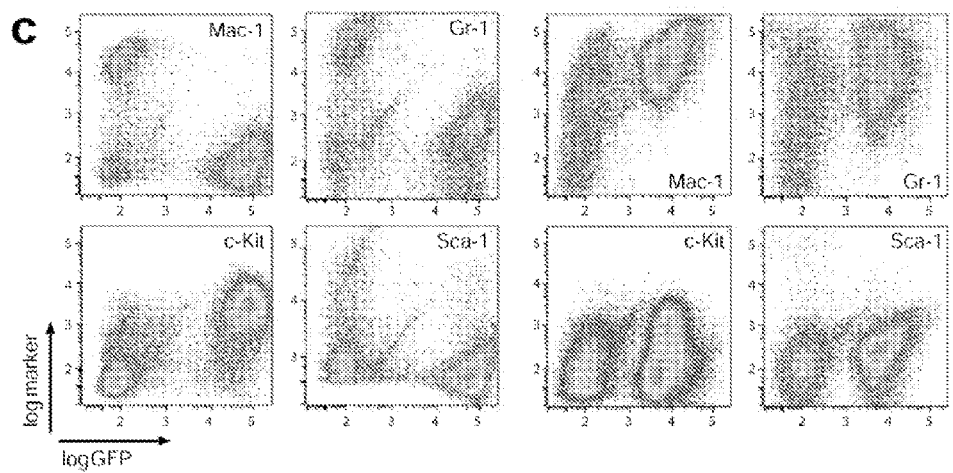
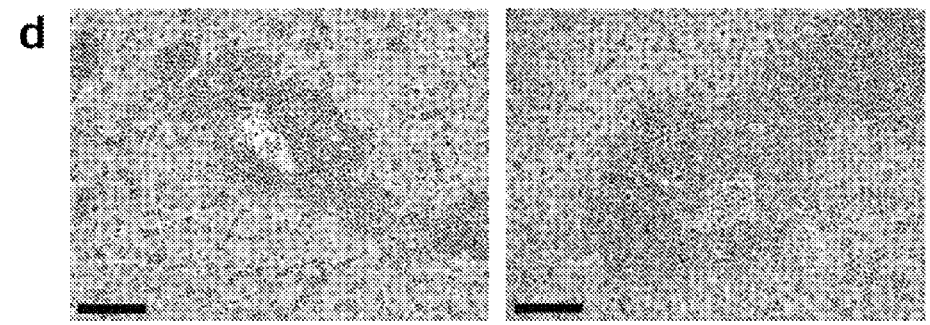
FIG. 31C-D

FIG. 34
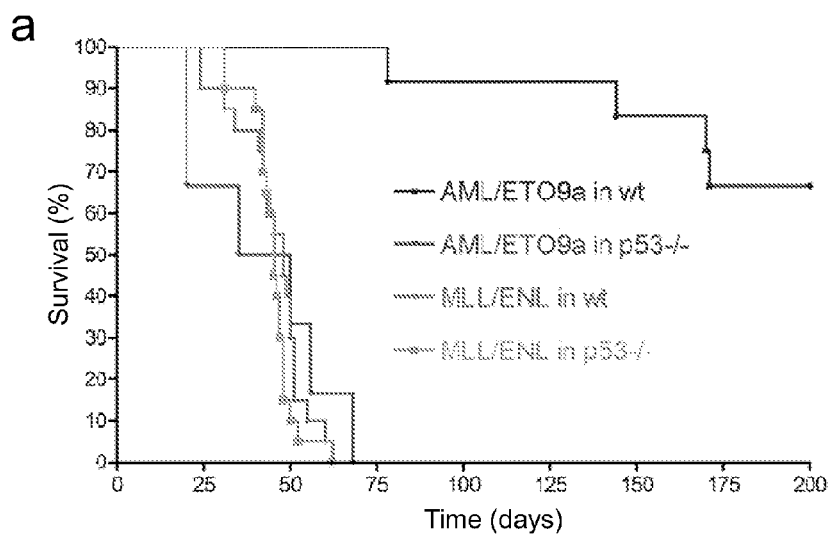
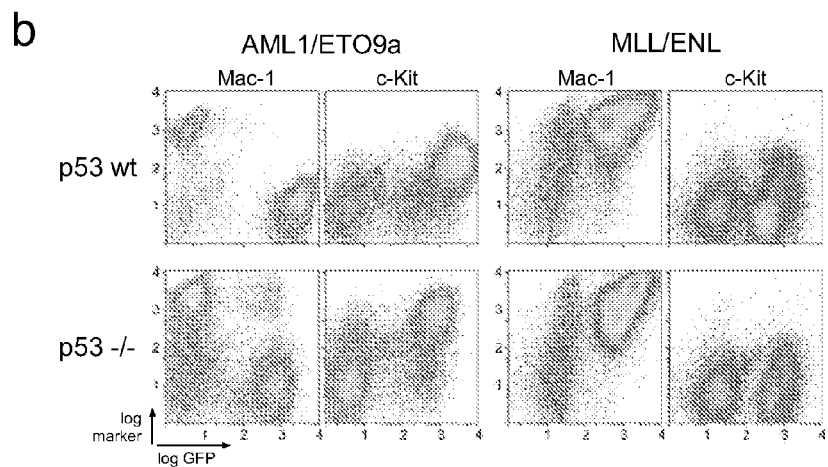
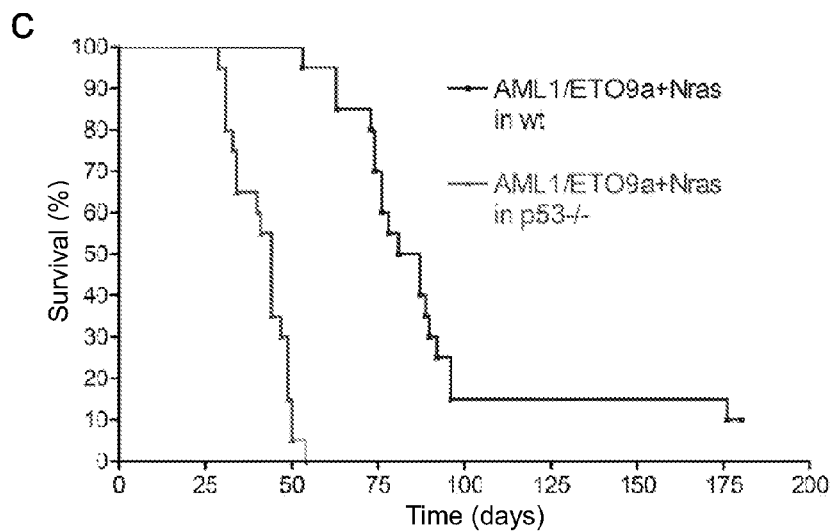

Depleting (all verified for knockdown)

General Killers
- Myc.1405
- Myc.1888
- Myc.1891
- Myc.2105
- Pcna.1186
- Pcna.566
- Rpa1.1620
- Rpa3.278
- Rpa3.457
- Rpa3.561

MLL specific killers
- Bcl2.1132
- Bcl2.1422
- Bcl2.2169
- Bcl2.757
- Bcl2.906
- Mcl1.1334
- Mcl1.1792
- Mcl1.2018
- Myb.2572
- Myb.2652
- Myb.670
- Telo2.921

Neutral

Neutral & functional shRNAs
- Braf.3750
- Braf.5053
- Kit.1241
- Kit.2021
- Kit.221
- Kit.4813
- Luciferase.1309
- Trp53.1224
- Map2k1.1200
- Map2k1.2337
- Ptgs2.1082
- Ptgs2.2058
- Ptgs2.284
- Ptgs2.3711
- Renilla.713

Low KD
- Bcl2.1067
- Bcl2.1125
- Bcl2.1135
- Bcl2.1243
- Bcl2.1535
- Bcl2.2891
- Bcl2.5768
- Braf.3826
- Mcl1.2575
- Pcna.1216
- Rpa1.1531
- Rpa1.2483
- Telo2.1213
- Telo2.1618

Neutral KD not tested
- Fosb.1165
- Fosb.281
- Fosb.3536
- Fosb.436
- Lin28.2180
- Lin28.2186
- Lin28.2270
- Lin28.2430
- Mn1.1403
- Mn1.2479
- Mn1.2545
- Mn1.5760
- Mn1.5864

FIG. 40

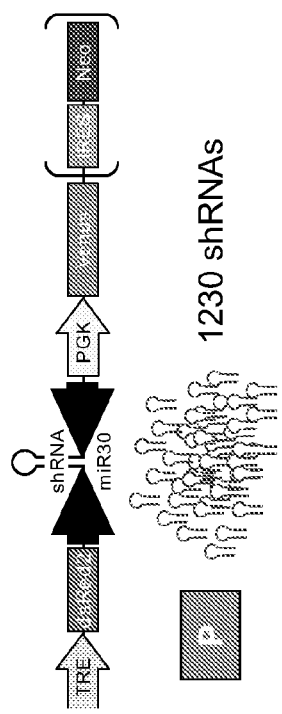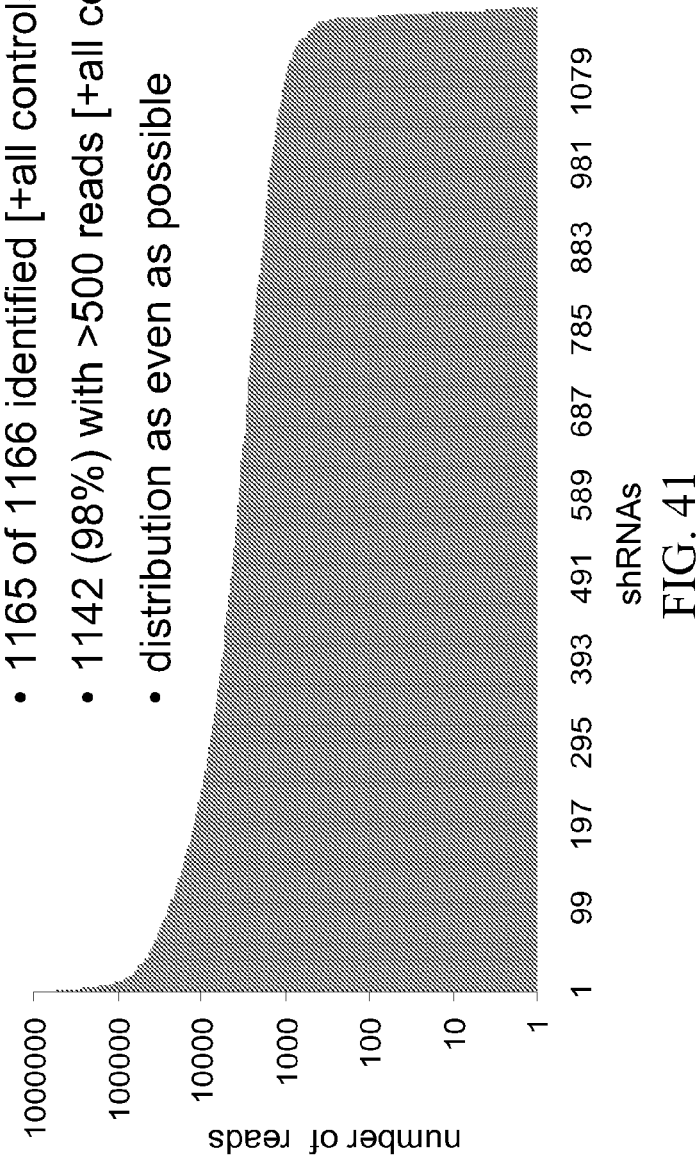
FIG. 41

US 8,895,526 B2

IDENTIFICATION OF RNAI TARGETS AND USE OF RNAI FOR RATIONAL THERAPY OF CHEMOTHERAPY-RESISTANT LEUKEMIA AND OTHER CANCERS

This application is a U.S. National Phase Application under 35 U.S.C. §371 of International Patent Application No. PCT/US2010/29083, filed on Mar. 29, 2010, which claims the benefit of the filing date of U.S. Provisional Patent Application No. 61/164,125, filed Mar. 27, 2009, the contents of each of which are hereby incorporated by reference in their entireties.

This patent disclosure contains material which is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights.

Throughout this application, patent applications, published patent applications, issued and granted patents, texts, and literature references are cited. For the purposes of the United States and other jurisdictions that allow incorporation by reference, the disclosures of these publications are incorporated by reference into this application.

SEQUENCE LISTING

The instant application contains a Sequence Listing which has been submitted in ASCII format via EFS-Web and is hereby incorporated by reference in its entirety. Said ASCII copy, created on May 20, 2013, is named 287000.157US2_SL.txt and is 73,601 bytes in size.

1. BACKGROUND OF THE INVENTION

This invention relates in part to the use of RNA interference (RNAi) technology in cancer cells to knock out genes encoding DNA replication proteins, resulting in cell cycle arrest, and cytotoxicity. RNAi technology enables specific suppression of the expression of virtually any gene and provides a new tool for drug target discovery, validation, and therapy. To obtain functional RNAi reagents for biological, biomedical, and clinical applications, it is important to identify potent interfering RNA molecules (RNAi molecules) for a gene of interest.

Cancer is the second leading cause of death in industrialized countries, resulting from a combination of mutations in certain oncogenes and tumor suppressor genes. Cancer can arise due to deregulation at many points of the cell cycle and during cell differentiation. Cell cycle checkpoints are a critical mechanism for assessing DNA damage. When damage is found, the checkpoint either arrests the cell cycle until the damage is repaired or targets the cell for destruction via apoptosis if repairs cannot be made.

Chromosomal translocations involving the MLL gene on chromosome 11q23 are found in about 10% of all human leukemias and define one of the most adverse genetic markers associated with chemotherapy resistance and poor prognosis. MLL is a H3K4 methyltransferase that acts as transcriptional master regulator in normal hematopoiesis. Fusion proteins resulting from 11q23 translocations are thought to misdirect transcriptional activation, reestablish self-renewal capacity and thereby promote leukemogenesis. Various MLL cofactors, as well as downstream target genes, have been shown to be involved in MLL-leukemogenesis and have been proposed as targets for therapeutic intervention.

2. SUMMARY OF THE INVENTION

The role of particular DNA replication genes in cancer cell proliferation is not well understood. In the present invention tet-regulated in vivo RNAi was applied to evaluate the role of candidate drug target genes in established MLL-fusion leukemia. To facilitate these studies a bioluminescent tet-on competent AML mouse model was established based on cooperation of MLL/AF9 and oncogenic Nras, which reflects a common genetic association in human AML. Coexpression of MLL/AF9 and $Nras^{G12D}$ resulted in aggressive myelomonocytic leukemias (mean survival 21 days), which are refractory to combined chemotherapy. To evaluate the potency of single-gene directed approaches in these resistant AMLs a series of tet-regulatable shRNAs targeting (i) essential genes involved in DNA replication [Rpa1, Rpa3, PCNA], (ii) MLL associated genes [MLL, HoxA9, Meis1, Men1, Dot1L, Myb], (iii) genes encoding epigenetic modifiers [AOF2, EED, HDAC, MEN1, SMARCA4, SMARCD1, SUZ12, WHSC 1l1] and (iii) other controls [Luciferase, Braf], were transduced and the effects of doxycycline-induced shRNA expression was studied in vitro and in vivo using a dual-color tet-shRNA vector that allows precise tracking of shRNA expressing cells.

In results of these experiments potent antileukemic effects of multiple shRNAs targeting Rpa1, Rpa3, PCNA and certain MLL associated genes (MLL itself, Meis1, Men1, Myb), and certain epigenetic modifier genes (Eed, Suz12, Aof2, Smarca4, Smarcd1, Men1, Hdac3, and Whs1l1), were seen. In parallel assays using tet-on competent Mefs the antileukemic effects of shRNAs targeting MLL-associated genes as well as certain epigenetic modifier genes are shown not to be due to general cytotoxicity. After selection shRNA carrying MLL/AF9+Nras AML cells were transplanted into secondary recipient mice. Following leukemia onset in bioluminescent imaging mice were treated with oral doxycycline, which induced rapid and durable remissions upon induction of Rpa3 and Myb shRNAs, while those expressing Braf control shRNAs progressed under therapy. Similar rapid and durable remissions were achieved using shRNAs targeting certain epigenetic modifier genes. These results have characterized a number of genes as essential for the survival of established MLL/AF9 induced AML, amongst them four MLL-associated genes (MLL, Men1, Meis1, Myb) that are dispensable in Mefs and seven epigenetic modifier genes (Eed, Suz12, Aof2, Smarca4, Smarcd1, Men1, Hdac3, and Whs1l1) that are dispensible when tested in four non-transformed hematopoietic cell lines. These studies demonstrate the power of tet-regulated RNAi to identify and evaluate genetic Achilles' heels in chemotherapy-resistant leukemia.

Using RNAi, we screened DNA replication genes in vitro for modifiers of human cancer cell proliferation. The in vitro RNAi screens yielded surprising results: inhibitory RNAs targeting some DNA replication genes were strongly antiproliferative, while knockdown of many other such genes did not confer strong anti-proliferative effects. In particular, si- and shRNAs targeting genes encoding replication protein A3 (RPA3), ribonucleotide reductase M1 (RRM1), cell division cycle 45 (CDC45) and pescadillo 1 (PES1) significantly impair human cancer cell proliferation.

In vivo mouse leukemia models expressing inducible shRNAs were designed in order to identify particular RNAi molecules exhibiting the most potent in vivo efficacy for therapeutically curing chemoresistant leukemia, in particular leukemia involving MLL gene rearrangements. In particular, inducible shRNAs targeting genes encoding replication protein A3 (RPA3) and MYB exhibited potent efficacy in curing chemotherapy resistant leukemia in vivo, while numerous other inducible shRNAs targeted against genes putatively involved in cancer cell proliferation had only marginal effects.

In one aspect, the invention provides a method for inhibiting proliferation of a cancer cell, the method comprising introducing into the cancer cell a small interfering RNA (siRNA) comprising a sequence that is complementary to a nucleotide sequence of a target gene encoding a DNA replication protein. In some embodiments, the method can further comprise administering a chemotherapy drug to the cancer cell to further inhibit proliferation of the cell. In some embodiments, cell proliferation can be inhibited through cell death (apoptosis). Cancer cell proliferation can be inhibited in cultured cells in vitro, for example in screening methods. Cancer cell proliferation can also be inhibited in vivo, in a therapeutic context. Chemotherapy drugs that can be used according to the method include, but are not limited to, an alkylating agent, a nitrosourea, an anti-metabolite, a topoisomerase inhibitor, a mitotic inhibitor, an anthracycline, a corticosteroid hormone, a sex hormone, a targeted anti-tumor compound, and combinations thereof.

In a certain embodiment of the invention, the DNA replication protein is selected from the group consisting of RPA3, RRM1, CDC45, and PES1. In some embodiments, the siRNA can comprise a sequence selected from the following:

```
RPA3:
                                      (SEQ ID NO: 1)
CAUCUUAUGUCCAGUUUAA (SEQ ID NO: 2)
CACCAUCUUGUGUACAUCU

RRM1:
                                      (SEQ ID NO: 3)
CAGAUCUUUGAAACUAUUU

CDC45:
                                      (SEQ ID NO: 4)
CAGUCAAUGUCGUCAAUGUAU

PES1:
                                      (SEQ ID NO: 5)
GCCUUGAGAAGAAGAAGUA (SEQ ID NO: 6)
GUUGGACUCCGAGAGUUGU (SEQ ID NO: 7)
CGGAACAAAGCCCGGAAGA
```

In another aspect, the invention provides a method for inhibiting proliferation of a cancer cell, the method comprising introducing into the cancer cell an expression vector comprising a sequence encoding a short hairpin RNA (shRNA) operably linked to a RNA polymerase promoter, wherein the shRNA comprises a loop and a duplex region that comprises a sequence complementary to a nucleotide sequence of a target gene encoding a DNA replication protein. In some embodiments, the sequence encoding the shRNA can be operably linked to an inducible promoter. In some embodiments the inducible promoter can be a tet-responsive TRE promoter. In some embodiments, the method can further comprise administering a chemotherapy drug to the cancer cell. Chemotherapy drugs that can be used according to the method include, but are not limited to, an alkylating agent, a nitrosourea, an anti-metabolite, a topoisomerase inhibitor, a mitotic inhibitor, an anthracycline, a corticosteroid hormone, a sex hormone, a targeted anti-tumor compound, and combinations thereof.

In a certain embodiment of the invention, the DNA replication protein is selected from the group consisting of RPA3, RRM1, CDC45 and PES1. In some embodiments, the sequence encoding the shRNA can be or comprise a sequence selected from the following:

```
RPA3:
                                      (SEQ ID NO: 8)
TGCTGTTGACAGTGAGCGCACATCTTATGTCCAGTTTAAATAGTGAAGCC

ACAGATGTATTTAAACTGGACATAAGATGTATGCCTACTGCCTCGGA (SEQ ID NO: 9)
TGCTGTTGACAGTGAGCGACCACCATCTTGTGTACATCTTTAGTGAAGCC

ACAGATGTAAAGATGTACACAAGATGGTGGCTGCCTACTGCCTCGGA

RRM1:
                                      (SEQ ID NO: 10)
TGCTGTTGACAGTGAGCGCGCAGATCTTTGAAACTATTTATAGTGAAGCC

ACAGATGTATAAATAGTTTCAAAGATCTGCTTGCCTACTGCCTCGGA

CDC45:
                                      (SEQ ID NO: 11)
TGCTGTTGACAGTGAGCGACCAGTCAATGTCGTCAATGTATAGTGAAGCC

ACAGATGTATACATTGACGACATTGACTGGCTGCCTACTGCCTCGGA

PES1:
                                      (SEQ ID NO: 12)
TGCTGTTGACAGTGAGCGCGGCCTTGAGAAGAAGAAGTATTAGTGAAGCC

ACAGATGTAATACTTCTTCTTCTCAAGGCCTTGCCTACTGCCTCGGA (SEQ ID NO: 13)
TGCTGTTGACAGTGAGCGACGTTGGACTCCGAGAGTTGTATAGTGAAGCC

ACAGATGTATACAACTCTCGGAGTCCAACGCTGCCTACTGCCTCGGA (SEQ ID NO: 14)
TGCTGTTGACAGTGAGCGACCGGAACAAAGCCCGGAAGAATAGTGAAGCC

ACAGATGTATTCTTCCGGGCTTTGTTCCGGGTGCCTACTGCCTCGGA
```

In some embodiments, the expression vector is a plasmid or a viral vector. In a certain embodiment, the viral vector is a retroviral vector, for example, a lentiviral vector. Where the vector is a retroviral vector, it can further comprise long terminal repeat (LTR) sequences located 5' and/or 3' to the sequence encoding the shRNA.

RNA polymerase promoters suitable for use in the invention include RNA polymerase II (pol II) and RNA polymerase III (pol III) promoters. In one embodiment, the pol II promoter is selected from a CMV promoter and a U1 promoter. In another embodiment, the pol III promoter is selected from a U6 promoter, an H1 promoter, and an SRP promoter. In some embodiments, the promoter is a U6 promoter. In some embodiments, the promoter can be an inducible promoter. In some embodiments the inducible promoter can be a tet-responsive TRE promoter.

Expression of the shRNA in the cell can be transient or stable. In certain embodiments, the expression vector is episomal, resulting in transient expression of the shRNA. In other embodiments, the expression vector is chromosomally integrated and produces a stably expressing cell line. In certain embodiments expression of the shRNA in the cell can be inducible. In certain embodiments expression of the shRNA in the cell can be suppressable.

The shRNA comprises a stem region and a loop region. The stem region comprises a double-stranded (duplex) region of base paired nucleotides. The duplex region can comprise from 19 to 29 base pairs. The base pairs can be contigous or non-contiguous. In a certain embodiment, the duplex region contains 29 contiguous or non-contiguous base pairs. The loop region is useful at 3 to 23 nucleotides in length.

In one aspect, the invention provides a method for identifying a compound that enhances the therapeutic efficacy of an RNAi molecule in vivo for eliminating inhibits cell proliferation. The method can comprise (1) introducing into a cancer cell an RNAi molecule that is complementary to a nucleotide sequence of a target gene, wherein the target gene encodes a DNA replication protein; (2) contacting the cancer cell with a candidate compound; and (3) determining whether the candidate compound inhibits cell proliferation, thereby identifying a compound that inhibits cell proliferation. In one embodiment, the method further comprises (4) administering an effective amount of the compound to a non-human animal having a tumor; and (5) monitoring tumor growth in the non-human animal. In some embodiments, the method can further comprise comparing tumor growth in the non-human animal treated with the compound to tumor growth in the non-human animal not treated with the compound. The RNAi molecule introduced into a cancer cell can be a small interfering RNA (siRNA) or a short hairpin RNA (shRNA). In one embodiment, the siRNA comprises a nucleic acid sequence that is complementary to a nucleotide sequence of a target gene, wherein the target gene encodes a DNA replication protein. In a further embodiment, the shRNA is operably linked to a RNA polymerase promoter, wherein the shRNA comprises a loop and a duplex region, wherein the duplex region comprises a sequence that is complementary to a nucleotide sequence of a target gene, and wherein the target gene encodes a DNA replication protein. The DNA replication protein can be selected from the group consisting of replication protein A3 (RPA3), ribonucleotide reductase M1 (RRM1), cell division cycle 45 (CDC45) and pescadillo 1 (PES1). In some embodiments, the non-human animal can be a mouse.

The invention provides a mosaic mouse model for chemotherapy-resistant leukemia. The model can be used to design rational cancer therapies based on the particular genotype of the cancer cells. For example, in some instances, particular gene fusions are responsible for conferring chemoresistance. Determination of such oncogenic genotypes can facilitate treatment design. In particular, the vectors of the invention provide an enhanced screening system based on robust RNAi expression. RNAi molecules directed against the oncogene strongly and specifically deplete the cancer cells.

The bicistronic vectors of the invention link expression of a tet-activator protein to an oncogene. Since the oncogene is critical for maintaining the tumor phenotype, the linkage of tet activation to oncogene expression results in a model wherein the clones that form tumors are the same clones that are sensitive to tet activation. Thus, tumor cells will respond specifically and sensitively to doxycycline, which allows specific assessment of shRNA potency and effect. This approach can be used to design/identify RNAi molecules for treating patients, based on identification of shRNA with most potent effects against cancer cells in vivo.

Therefore, in one aspect, the invention provides an inducible nucleic acid vector comprising: a nucleic acid encoding a short hairpin RNA operably linked to an inducible promoter, wherein the promoter is induced in the presence of tetracycline or doxycyclin, wherein expression of the short hairpin RNA produces siRNA which in turn inhibits expression of one or more DNA replication proteins; a first marker gene linked to the nucleic acid encoding the short hairpin RNA, wherein the marker gene is co-expressed with the short hairpin RNA on a single transcript, so as to allow monitoring of expression of the short hairpin RNA; and a second marker gene that is expressed from a promoter other than the inducible promoter, so as to provide for separate monitoring of integration of the inducible vector in a genome.

The invention provides a mouse model for use in determining the potency of an shRNA in vivo for reducing survival of cancer cells of chemotherapy-resistant leukemia, comprising a syngeneic mouse recipient transplanted with tet-on competent leukemia cells, wherein said tet-on competent leukemia cells carry a bicistronic nucleic acid construct comprising a promoter operably linked to a fusion gene associated with chemotherapy-resistant leukemia, and a sequence encoding a reverse tet-transactivator protein, such that both coding sequences are co-expressed from said promoter.

"Tet-on competent" cells are cells comprising a bicistronic construct that co-expresses (i) a fusion protein or other oncogene that maintains survival and/or growth of the leukemia cell; and (ii) a reverse tet-transactivator protein.

Tet-on competent leukemia cells can be obtained from a mouse transplanted with hematopoietic stem and progenitor cells stably transformed with the bicistronic nucleic acid construct, wherein expression of said construct in the transplanted cells gives rise to leukemia in the mouse. In some embodiments, the hematopoietic stem and progenitor cells are stably transformed with a nucleic acid construct comprising a marker gene; and a sequence encoding a mutant RAS protein before being transplanted into the mouse.

In some embodiments, the tet-on competent leukemia cells are stably transformed with a second nucleic acid construct comprising: (i) a tetracycline responsive first promoter operably linked to a sequence encoding a first marker gene and a sequence encoding an shRNA and/or shRNA precursor, wherein both coding sequences are co-expressed from said first promoter; and (ii) a constitutive, second promoter operably linked to a sequence encoding a second marker gene before being transplanted into the syngeneic mouse recipient. Preferably, the first and second markers provide for separate, independent monitoring of expression of the shRNA and/or shRNA precursor, and of integration of said second nucleic acid construct.

The sequence encoding the reverse tet-transactivator protein can be translated from an internal ribosomal entry site (IRES). The tetracycline inducible promoter can be induced in the presence of tetracycline, doxycycline, or a tetracycline analog.

A "gene associated with chemotherapy-resistant leukemia" is a fusion gene or other oncogene characteristic of a human leukemia genotype that confers on leukemia cells resistance to chemotherapeutic treatment. The fusion gene associated with chemotherapy-resistant leukemia is preferably an MLL fusion gene, or AML1/ETO fusion gene. In particular, the fusion gene can preferably be selected from the group consisting of MLL/ENL, MLL/AF9, AML1/ETO9a.

In a particular embodiment, the invention provides a mouse model for determining potency of an shRNA in vivo for inhibition of survival of cancer cells of chemoresistant leukemia, wherein the mouse co-expresses oncogenic Nras and an MLL fusion protein and a marker protein; and wherein the mouse contains an inducible vector, comprising: a nucleic acid encoding a short hairpin RNA operably linked to an inducible promoter, wherein the promoter is induced in the presence of tetracycline or doxycycline, wherein expression of the short hairpin RNA produces siRNA which in turn inhibits expression of one or more DNA replication proteins; a first marker gene linked to the nucleic acid encoding the short hairpin RNA, wherein the marker gene is co-expressed with the short hairpin RNA on a single transcript, so as to monitor expression of the short hairpin RNA; and a second marker gene that is expressed from a promoter other than the inducible promoter, so as to provide for separate monitoring of integration of the inducible vector in a genome.

In another aspect, the invention provides an in vivo method for determining the potency of an shRNA for reducing survival of cancer cells of chemotherapy-resistant leukemia, the method comprising:

a) providing tet-on competent leukemia cells by transplanting a syngeneic mouse with hematopoietic stem- and progenitor cells stably transformed with a bicistronic nucleic acid construct comprising a promoter operably linked to a fusion gene associated with chemotherapy-resistant leukemia, and a sequence encoding a reverse tet-transactivator protein, wherein both coding sequences are co-expressed from said promoter, and wherein expression of the construct in the transplanted cells gives rise to leukemia in the mouse, and isolating the leukemia cells from the mouse;

b) stably transforming the tet-on competent leukemia cells of step (a) with a second nucleic acid construct comprising a tetracycline responsive first promoter operably linked to a sequence encoding a first marker protein and a sequence encoding an shRNA and/or shRNA precursor, wherein both coding sequences are co-expressed from said first promoter; and a constitutive, second promoter operably linked to a sequence encoding a second marker protein;

c) transplanting the cells of step (a) into a secondary syngeneic mouse recipient;

d) administering tetracycline, doxycycline or a tet analog to the recipient mouse of step (b) to induce expression of the shRNA and/or shRNA precursor in the leukemia cells; and e) monitoring progression or regression of leukemia in said secondary recipient mouse.

The tet-on competent leukemia cells of step (a) can be stably transformed by retroviral infection.

Progression or regression of leukemia can be monitored through expression of a first marker protein and/or a second marker protein. In some instances, the bicistronic nucleic acid construct of step (a) further comprises a marker gene encoding a protein other than the first or second marker protein encoded by the second nucleic acid construct, and progression or regression of leukemia is monitored through expression of said marker gene.

In some embodiments, expression of the shRNA and/or shRNA precursor in the leukemia cells is monitored by expression of the first marker protein encoded by the second nucleic acid construct. Integration of the second nucleic acid construct in the leukemia cells can be monitored by expression of the second marker protein from said second construct.

Also provided is an in vivo method for screening a plurality of shRNAs to identify an shRNA which inhibits survival of cancer cells in vivo in a chemoresistant mouse model of acute myeloid leukemia, the method comprising (a) administering to the mouse one or more shRNAs and (b) determining whether the mouse of step (a) exhibits inhibition of survival of cancer cells as compared to a second mouse of the mouse model, wherein inhibition of survival of cancer cells indicates that the shRNA can be useful to treat the chemoresistant leukemia.

Also provided are in vitro and in vivo methods for screening pools of RNAi molecules for inhibitory effects on cancer cells. The combination of tet-on competent cancer models and tet-regulatable shRNA expression vectors allows for monitoring shRNA expression, for example using fluorescent and/or other reporter genes (e.g. TRMPV and derivates), which facilitates pooled shRNA negative selection screening. In such approaches tet-on competent cancer cells can be transduced with sequences that encode pools of shRNAs. In one embodiment, the cancer cells used can be cells of the tet-on cancer models described herein (such as the MLL/AF9+Nras AML model), either in vitro or in vivo. shRNA containing cells can then be selected, for example by using drug selection (e.g. G418) or fluorescence-activated cell sorting (FACS). Selected cell populations harboring a library of shRNAs then can be cultured in the absence or presence of doxycyline (off dox and on dox, respectively) or injected into syngeneic recipient mice that are either treated with doxycyline or left untreated. The representation of each shRNA within the pool can be determined, for example by deep sequencing of shRNA cassettes in a given cell population. Based on the comparison of shRNA representation (for example, as determined based on deep sequencing read numbers) before the assay (t0) or from cell populations left without doxycycline treatment (e.g. off dox), to after the assay or from cell populations where shRNAs were induced and the cells were sorted for shRNA expressing cells (e.g. on dox), shRNAs having inhibitory effects can be identified. For example, shRNAs having inhibitory effects are predicted to loose representation (show less reads) upon shRNA induction (e.g. on dox). For example, in one embodiment, the present invention provides an in vitro or in vivo method for screening pools of RNAi molecules for inhibitory effects on cancer cells, the method comprising: (a) administering to a population of tet-on cancer cells a pool of sequences that encode shRNAs, (b) selecting cells that express shRNAs, (c) either culturing the cells that express shRNAs in the presence or absence or presence of doxycycline, or injecting cells that express shRNAs into syngeneic recipient mice that are either treated with doxycyline or left untreated, (d) determining the representation of each shRNA within each pool before and after of doxycycline treatment, wherein shRNAs that have an inhibitory effect on cancer cells have lower representation after doxycycline treatment than before doxycycline treatment. Variations on this scheme are apparent from the disclosure, including the disclosure in Example 13.

The invention also provides a method for treating chemotherapeutic-resistant leukemia in a subject in need thereof, wherein the subject exhibits a known genotype associated with a chemotherapy-resistant leukemia, the method comprising:

a) determining which known genotype associated with a chemotherapy-resistant leukemia is present in a subject suffering from a chemotherapy-resistant leukemia;

b) administering to the subject an RNAi molecule directed against a gene whose expression is necessary for survival of the chemotherapy-resistant leukemia cell with said known genotype, wherein the gene is selected from the group consisting of: RPA3, RRM1, Rp115, c-Myb, Bcl2, Mcl1 or Men1, so as to inhibit survival of cancer cells in the subject, and thereby treat the chemotherapeutic-resistant leukemia in the subject.

The chemotherapy-resistant leukemia can be acute myeloid leukemia.

The known genotype can comprise a chromosomal rearrangement resulting in a MLL fusion protein, or AML1/ETO fusion protein. In a preferred embodiment, the MLL or AML fusion protein is selected from the group consisting of MLL/ENL, MLL/AF9, AML1/ETO9a.

In some embodiments, the RNAi molecule can be directed against RPA3, Rp115, c-Myb, Bcl2, Mcl1 or Men1. In other embodiments, the RNAi molecule can be directed against another gene expression is necessary for survival of the cancer cell. In one aspect, the RNAi molecule can comprise a nucleotide sequence selected from SEQ ID NOs: 1-14 and 39-190, or a portion of that sequence.

Also provided is a method for treating cancer in a subject in need thereof, the method comprising: administering to the subject an RNAi molecule directed against a gene whose expression is necessary for survival of the cancer cell, wherein the RNAi molecule is directed against a gene selected from the group of RPA3 and RRM1, so as to inhibit survival of cancer cells in the subject, and thereby treat the cancer in the subject. The RNAi molecule can comprise a nucleotide sequence selected from SEQ ID NOs: 1-14 or a portion of that nucleotide sequence. Preferably, the cancer is resistant to chemotherapeutic treatment. In preferred embodiments, the patient is diagnosed with a bladder cancer or liver cancer.

In another aspect, the invention provides a method for treating chemotherapeutic-resistant acute myeloid leukemia in a subject in need thereof, wherein the subject exhibits a protein fusion comprising MLL fused to a protein, the method comprising: determining which known genetic aberration characteristic of acute myeloid leukemia is present in a subject suffering from acute myeloid leukemia; and administering to the subject an RNAi molecule directed against a gene whose expression is necessary for survival of the chemotherapy-resistant leukemia cell with said known genotype. Preferably, such gene targets and/or RNAi molecules are validated through use of the in vivo methods of this invention for determining the potency of an shRNA for reducing survival of chemotherapy-resistant leukemia cell with a known genotype. Preferably, the RNAi molecule, or the sequence encoding the shRNA comprises a sequence that is selected from the group consisting of: SEQ ID NOs: 8-14 and 39-190, or a portion of that nucleotide sequence, so as to inhibit survival of cancer cells in the subject, and thereby treat the chemotherapeutic-resistant acute myeloid leukemia in the subject.

Also provided is a method for treating a soft tissue cancer in a subject in need thereof, wherein the subject exhibits a gene translocation or mutation associated with the soft tissue cancer, the method comprising: administering to the subject an RNAi molecule directed against a gene whose expression is necessary for survival of the soft tissue cancer cell. Preferably, such gene targets and/or RNAi molecules are validated through use of the in vivo methods of this invention for determining the potency of an shRNA for reducing survival of a cancer cell with a known genotype. Preferably, the RNAi molecule, or the sequence encoding the shRNA comprises a sequence that is selected from the group consisting of: SEQ ID NOs: 8-14 and 39-190 or a portion of that nucleotide sequence, so as to inhibit survival of cancer cells in the subject, and thereby treat the soft tissue cancer in the subject. The soft tissue cancer can be, for example, liver cancer or lymphoma, and in some embodiments the soft tissue cancer is a chemotherapy resistant cancer.

3. BRIEF DESCRIPTION OF THE DRAWINGS

FIG. 1 shows the identification of hairpins that inhibit growth of HCT116 cultures in a proliferation assay results. HCT116 cultures in 24-well plates were infected separately with amphotropic retrovirus encoding 254 different shRNAs targeting 83 cell cycle and/or E2F regulated genes. On day 1 following infection each culture was suspended in media containing 1.5 µg/mL puromycin to select for cells transduced with the hairpins, then seeded to 6-well plates. On day 5 following infection, cells in each culture were suspended in media and counted using a hemacytometer. Results for each culture were normalized to the average of the number of cells counted in cultures transduced with hairpins targeting either of two different genes not endogenous to HCT116 cells (EBNA1 and Ff-luciferase).

FIG. 2 shows hairpins that inhibited HCT116 proliferation greater than two-fold. The hairpin ID corresponds to Open Biosystems' catalog number for the respective shRNA. This can be used to access shRNA sequence information from the Open Biosystems website.

FIGS. 3A-3C show growth analysis of HCT116 cultures transduced with shRNAs targeting either RPA subunits (FIG. 3A), RRM1 (FIG. 3B), PES1 (FIG. 3C), or negative controls. HCT116 cultures in a 24-well plate were transduced separately with shRNAs targeting either RPA1, RPA3, RRM1, PES1, EBNA1, or Ff-luciferase. On day 1 following transduction, each culture was suspended in media containing 1.5 µg/mL puromycin then seeded to 6-well plates. On day 3 following transduction, each culture was suspended and counted using a hemacytometer. Each suspension was diluted and seeded to 5 wells of a E-well plate where each well was seeded with 100,000 cells in media containing 1.5 µg/mL puromycin. In 24-hour increments, one culture for each RNAi condition was suspended and counted using a hemacytometer. HCT116 cultures transduced with shRNA's targeting either EBNA1 or Ff-luciferase were confluent by day 5 after seeding.

FIGS. 4A-4C shows Western blot analysis of RPA1 (FIG. 4A), RPA2 (FIG. 4B), and RPA3 (FIG. 4C) in whole cell extracts from HCT116 cells transduced with different hairpins. On day 5 post-infection whole cell extracts (WCE's) were prepared from HCT116 cultures transduced with the noted hairpins. Sample loading on the gel is as follows—lane 1: V2HS_32105 (RPA3) WCE, lane 2: V2HS_32101 (RPA3) WCE, lane 3: V2HS_32160 (RPA1) WCE, lane 4: EBNA1mi1666 WCE (equivalent total protein loaded as the RPA3 and RPA1 RNAi WCE's), lane 5: EBNA1mi1666 WCE diluted 1-to-2, lane 6: EBNA1mi1666 WCE diluted 1-to-4, and lane 7: EBNA1mi1666 WCE diluted 1-to-10. The antibodies used for western blot are RPA1: p70-9, RPA2: p34-20, and RPA3: Abcam ab58317. The asterisk indicates a non-specific band observed in the RPA1 western blot.

Figure 6A:
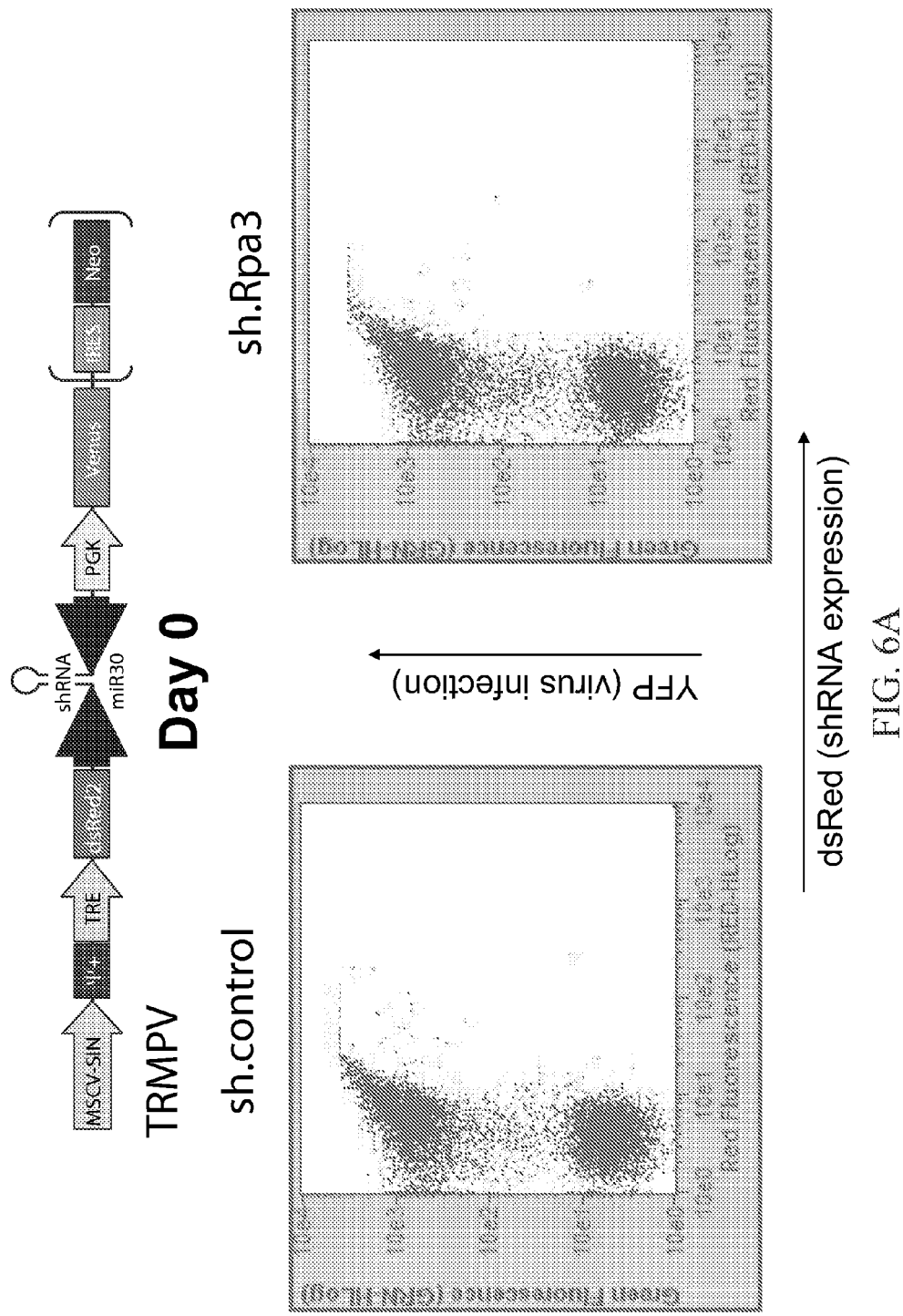
FIG. 6A shows a FACS assay at day 0 of dox treatment of lethal shRNA studies using the TRMPV vector. in vitro.
Figure 6B:
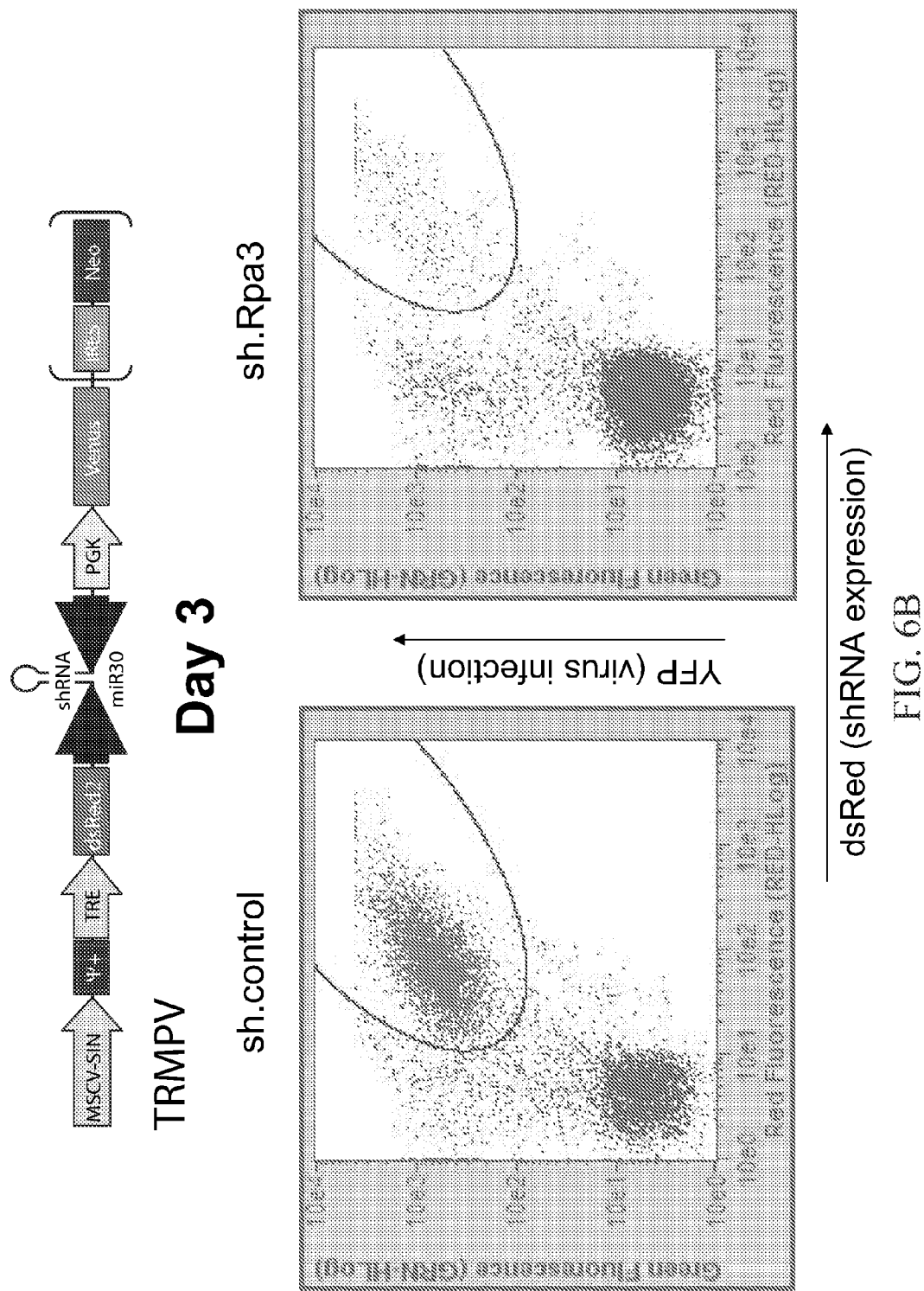
FIG. 6B shows a FACS assay at day 3 of dox treatment of lethal shRNA studies using the TRMPV vector. in vitro. shRNA expressing cells start to deplete for shRpa3.
Figure 6C:
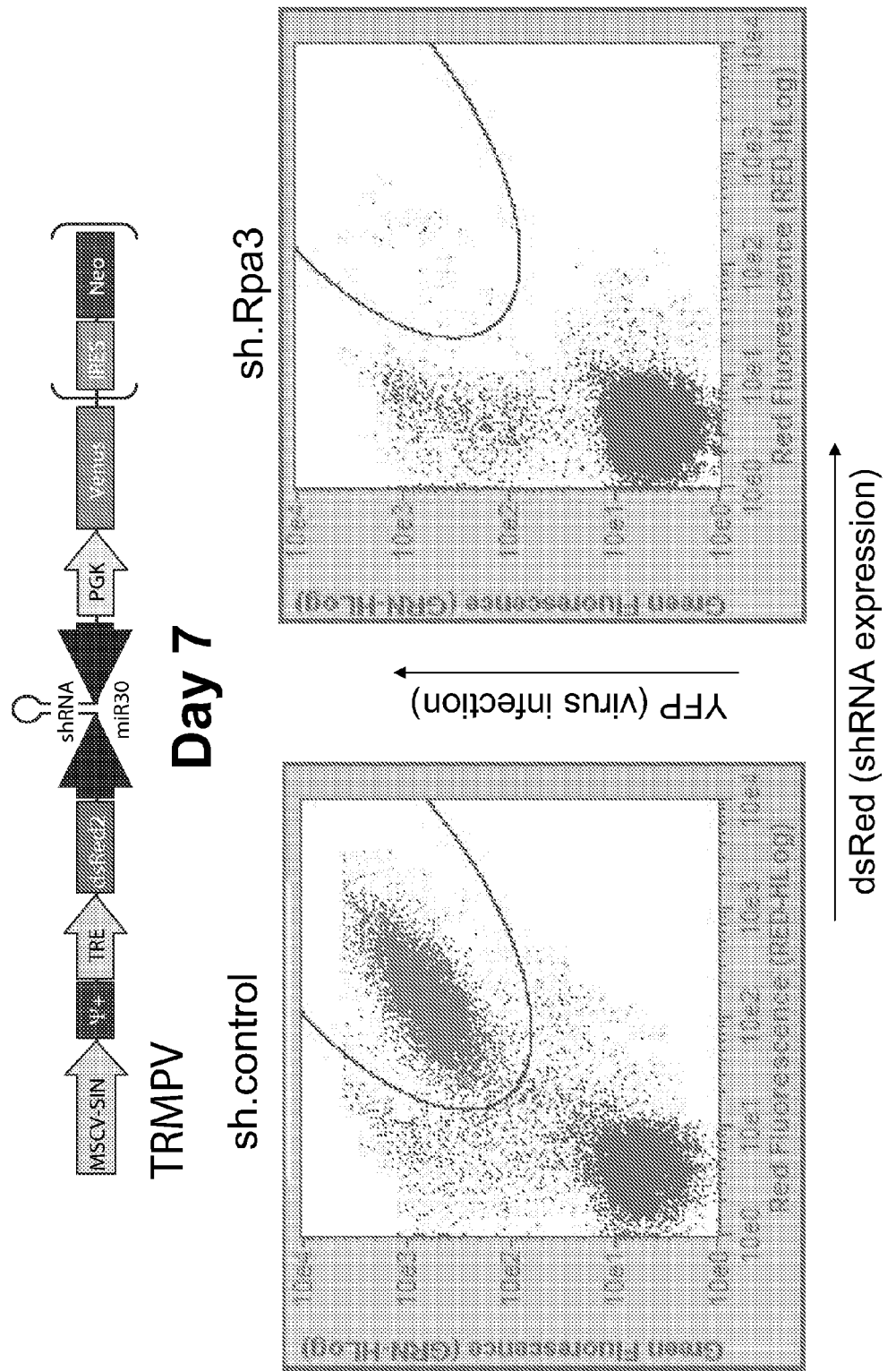

FIG. 6C shows a FACS assay at day 7 of dox treatment of lethal shRNA studies using the TRMPV vector in vitro. Almost complete depletion of shRNA expressing cells in shRpa3 is observed. A few cells fail to induce Rpa3 and grow out (Venus+, dsRed−).

Figure 7:
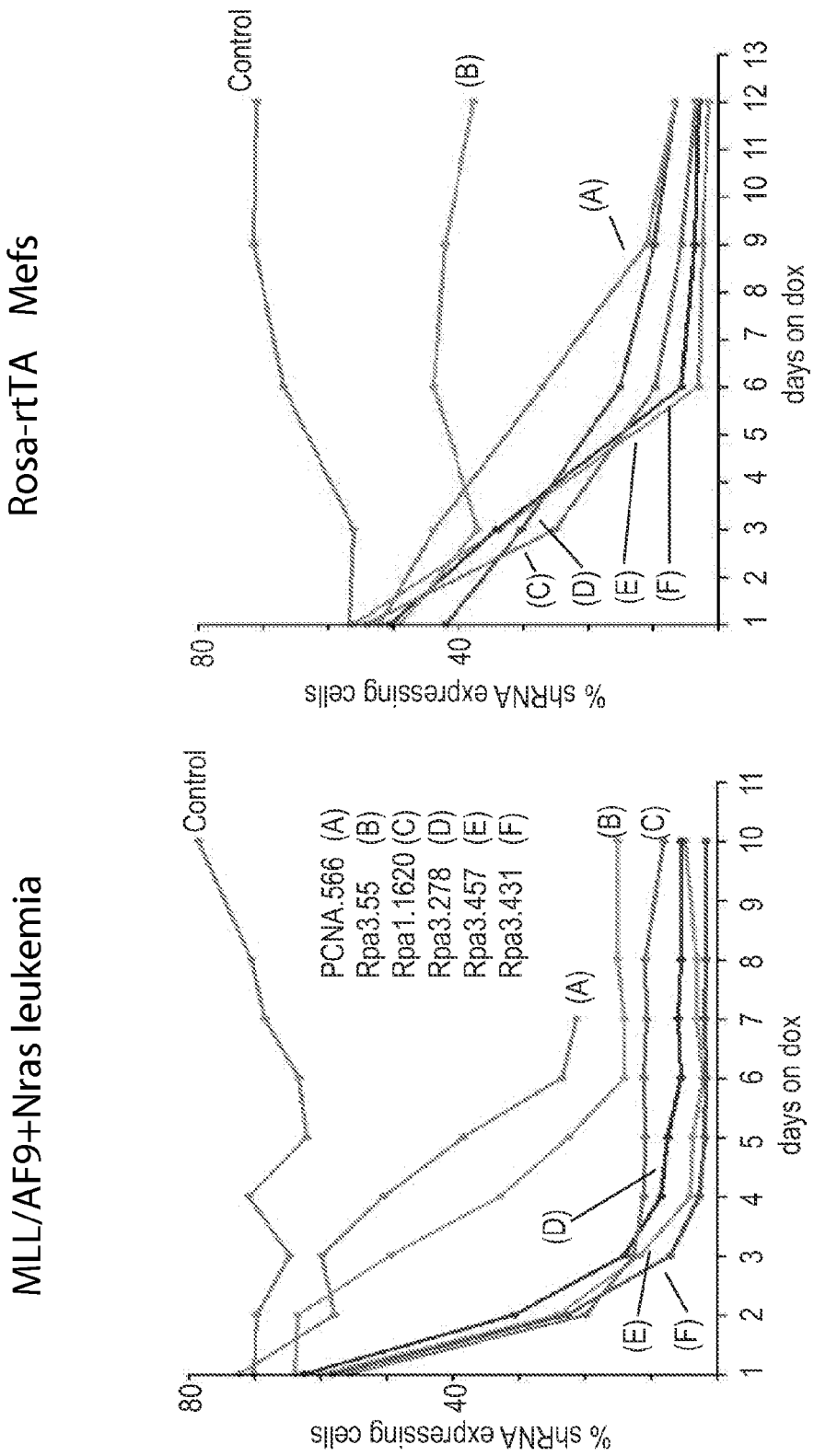

FIG. 7 shows lethal shRNA studies in MLL/AF9+Nras AML.

Figure 8:
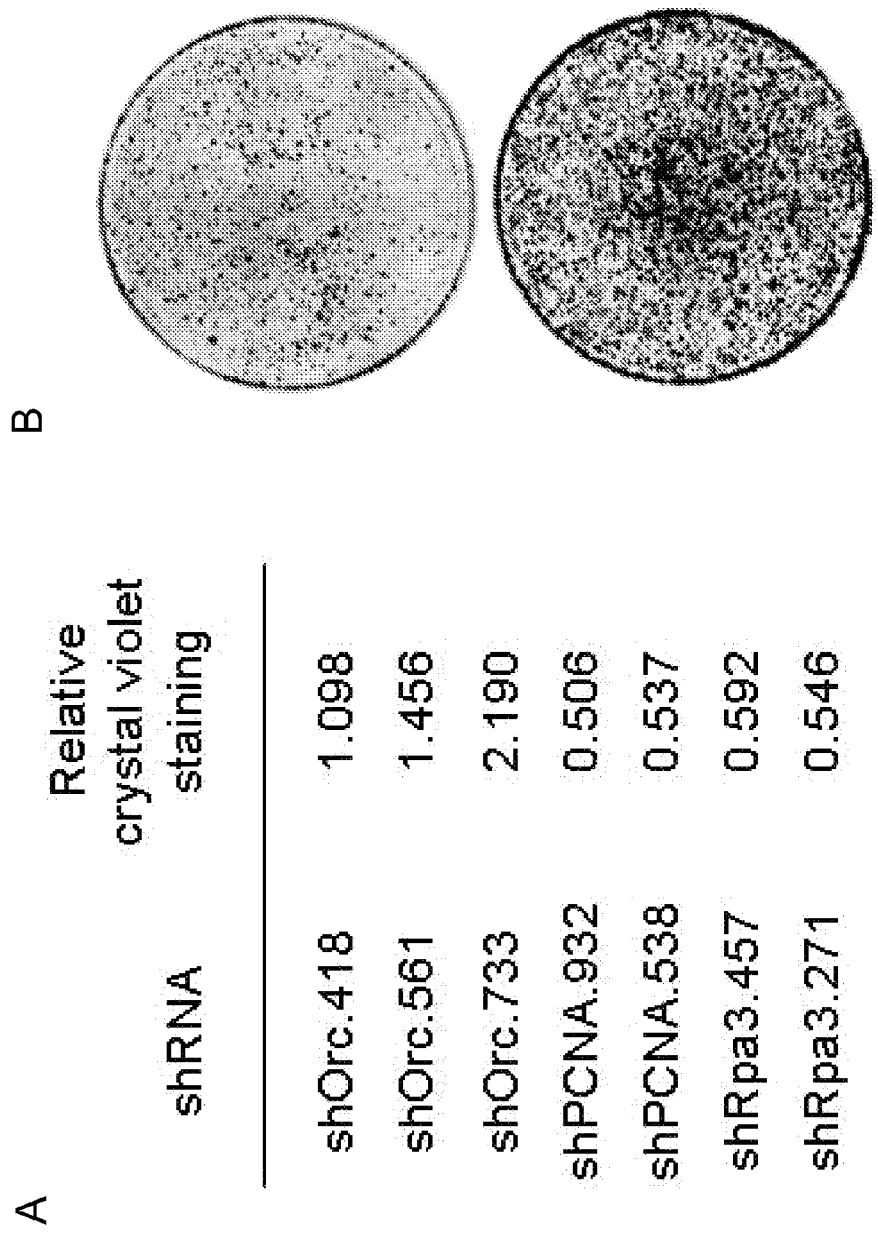

FIG. 8 shows the quantification of Hepa1.6 colony formation assays and representative scans. (FIG. 8A) Mouse hepatocellular carcinoma cells (Hepa1.6) were transduced at high MOI with shRNAs targeting replication genes. Cells were plated at low density, stained with crystal violet, and staining was quantified on a Licor scanner. Values are normalized to empty vector control. (FIG. 8B) Representative scans of colony formation assays of cells infected with an antiproliferative shRNA (top—shRpa3.457) or empty vector control (bottom).

Figure 9:
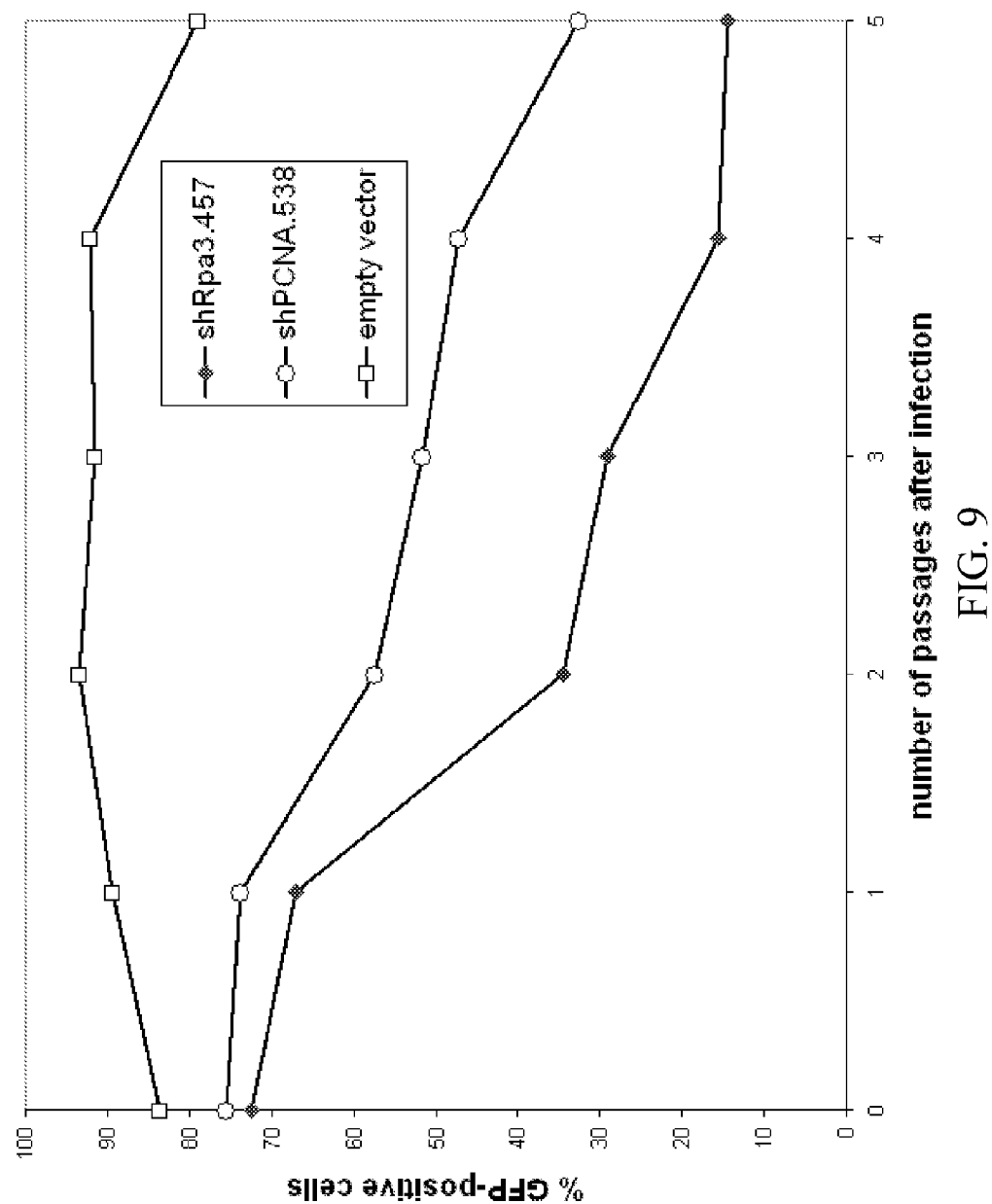

FIG. 9 shows in vitro competition assays in Hepa1.6 cells transduced with shRNA or empty vector. Two days after transduction with a GFP-tagged vector, the number of fluorescent cells was quantified. Cells were passaged 1:8 five times, and the number of GFPpositive transduced cells was quantified at each passage. Cells transduced with an antiproliferative shRNA (shPCNA.538 or shRpa3.457) are outcompeted by uninfected, GFP-negative cells in the population.

FIG. 10 shows in vitro competition assays in MLL leukemia cells. MLL-driven leukemia cells were transduced with inducible hairpins targeting MLL itself, MLL binding partners, and MLL target genes. Cells expressing the inducible shRNA (and its RFP marker) were quantified for 8-11 days after doxycycline induction. In addition to positive controls (FIG. 10A-*shRpa*3, shMLL), only cells expressing an shRNA targeting c-Myb (FIG. 10B) display a strong proliferative disadvantage relative to untransduced cells. Knockdown of other MLL partners and targets do not affect proliferation (FIGS. 10C-F).

FIG. 11 shows identification of shRNAs that affect proliferation of mouse liver carcinoma cells. (FIG. 11A) p53−/− RasV12 liver carcinoma cells were transduced with a library of 2270 shRNAs targeting 1000 genes. Relative shRNA abundance was measured by deep sequencing at 48 hours after transduction and after two more weeks of passaging. Proliferative phenotype of an shRNA was assessed by its change in abundance in the cell population (log ratio of abundance at two weeks of passaging to abundance at 48 hours posttransduction). (FIG. 11B) In vitro competition assays were performed to validate the effect antiproliferative shRNAs (log ratio>>1). In addition to the positive control (shRpa3), shRNAs targeting ribosomal components (shRpl15, shRps4x) confer a proliferative disadvantage to transduced cells relative to untransduced cells.

Figure 12:
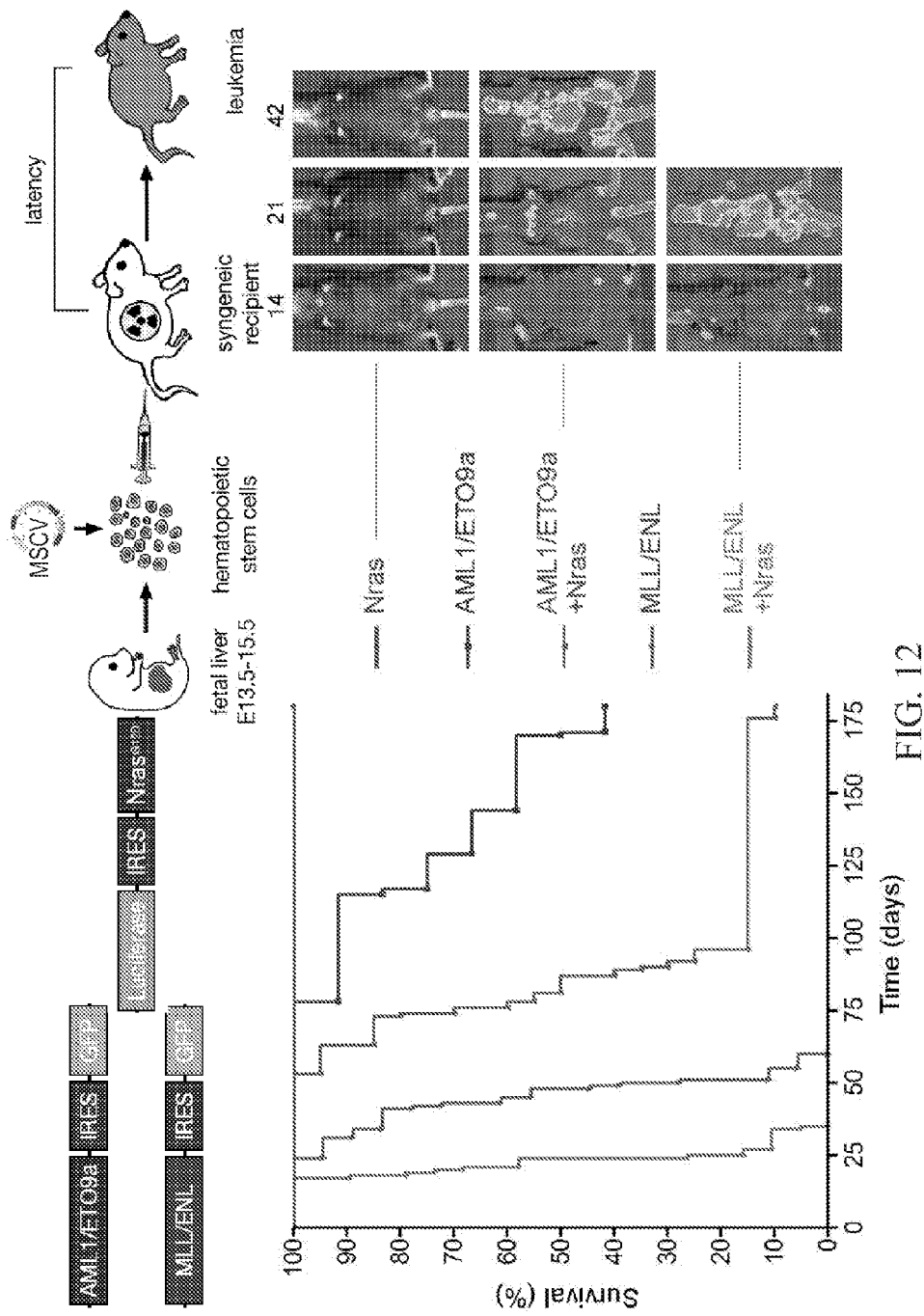

FIG. 12 shows mouse models of AML involving fusion proteins and Nras.

Figure 13:
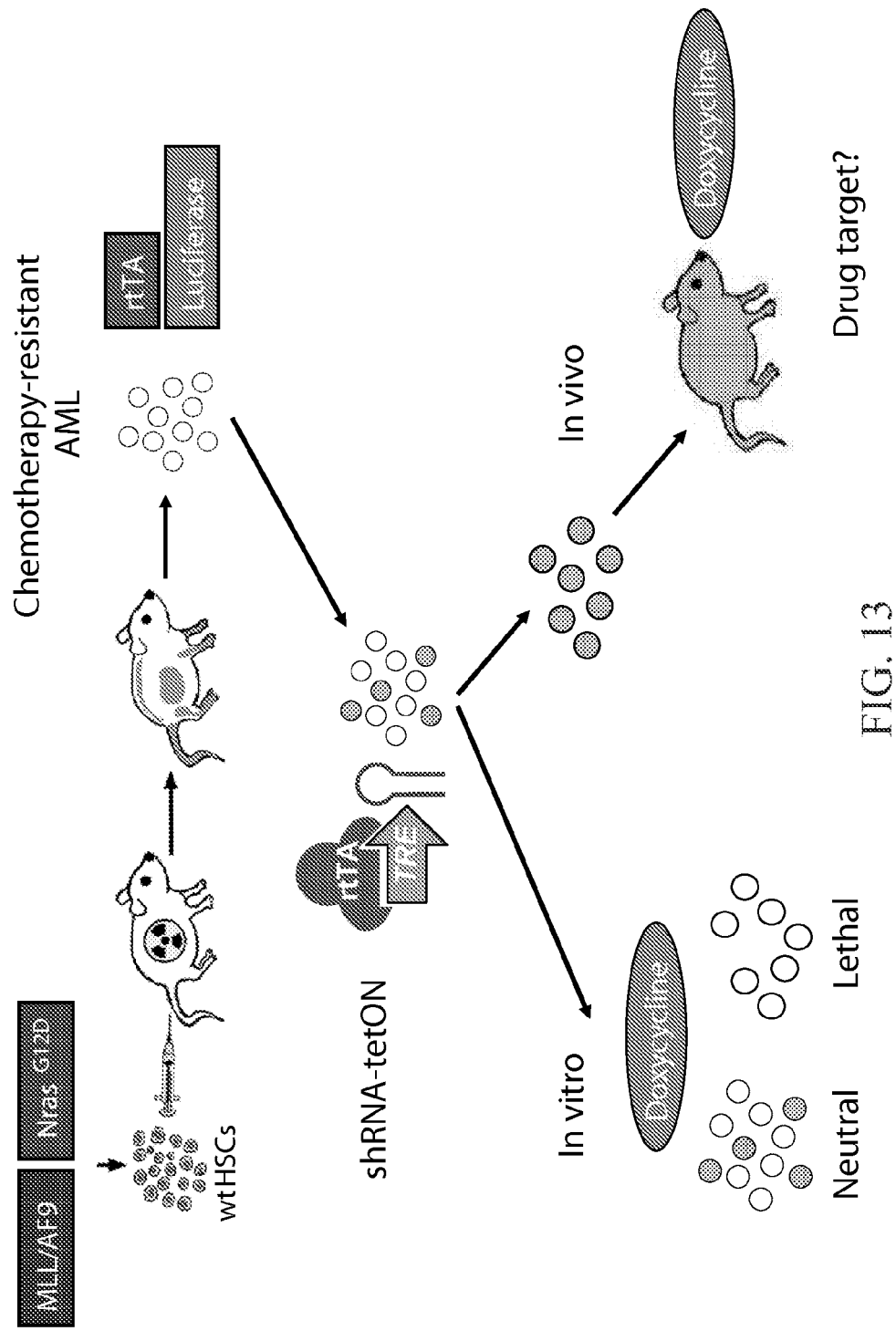

FIG. 13 shows a schematic of a system for negative selection RNAi in leukemia using bicistronic vectors.

Figure 14:
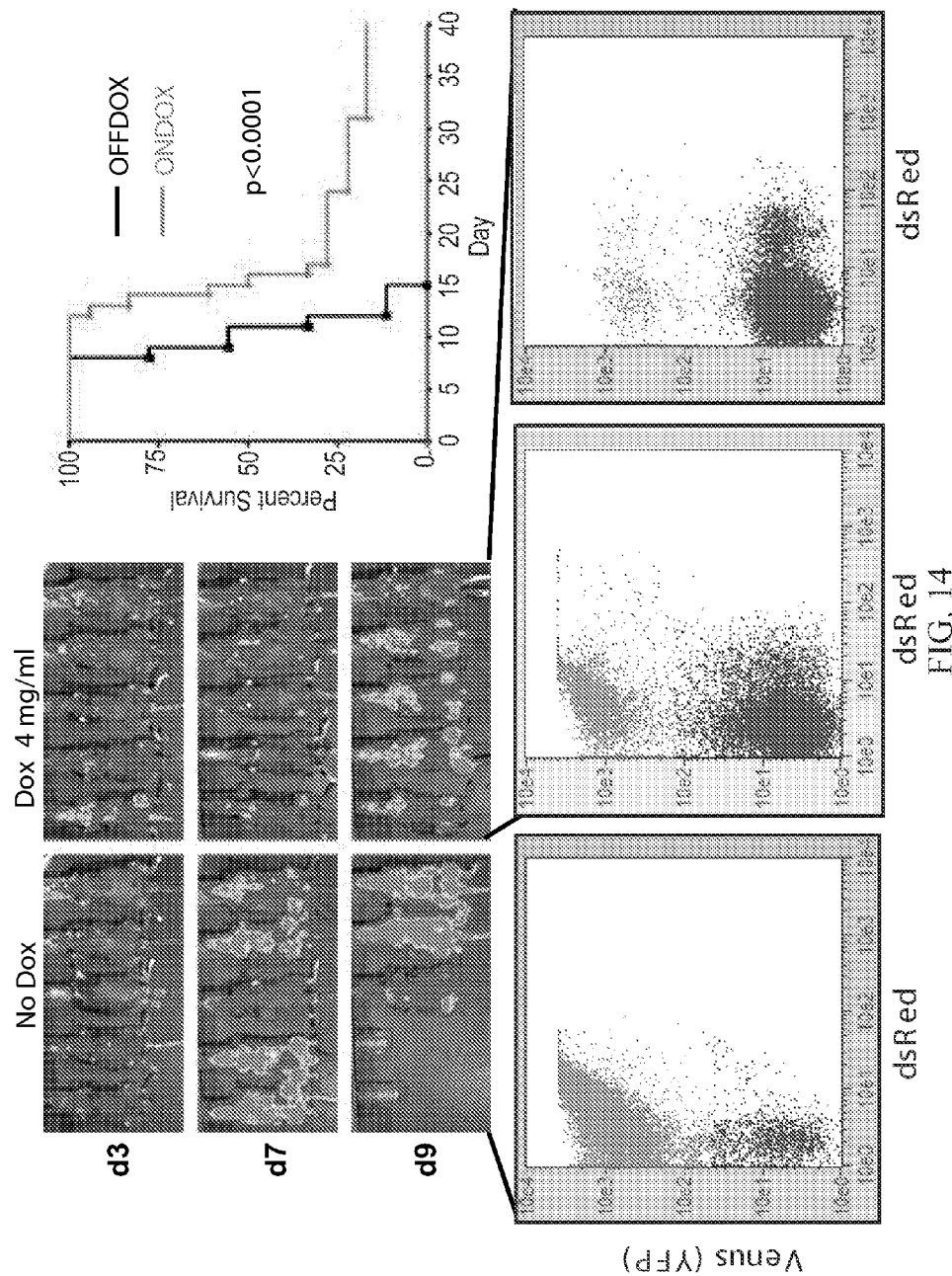

FIG. 14 shows negative selection in vivo using TRMPV in bulk populations. Doxycycline treated mice at a terminal disease stage show no Myb-shRNA expressing cells (double positive for Venus and dsRed fluorescent markers) within the leukemia population indicating the repression of Myb represses leukemia in vivo.

Figure 15:
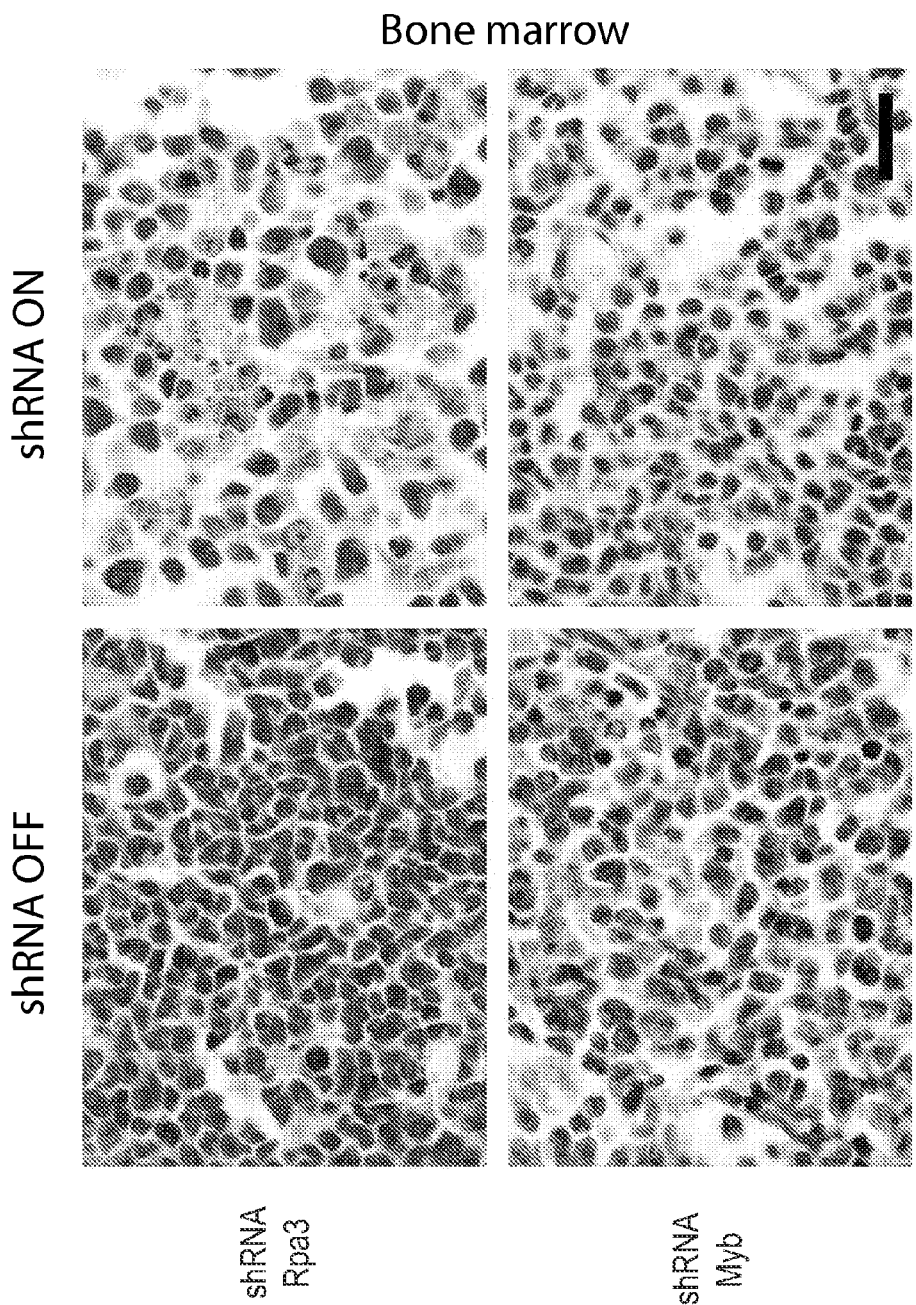

FIG. 15 shows photgraphs of bone marrow histological cross-sections. Rpa3 shRNA or Myb shRNA ameliorates MLL/AF9+Nras AML.

Figure 16:
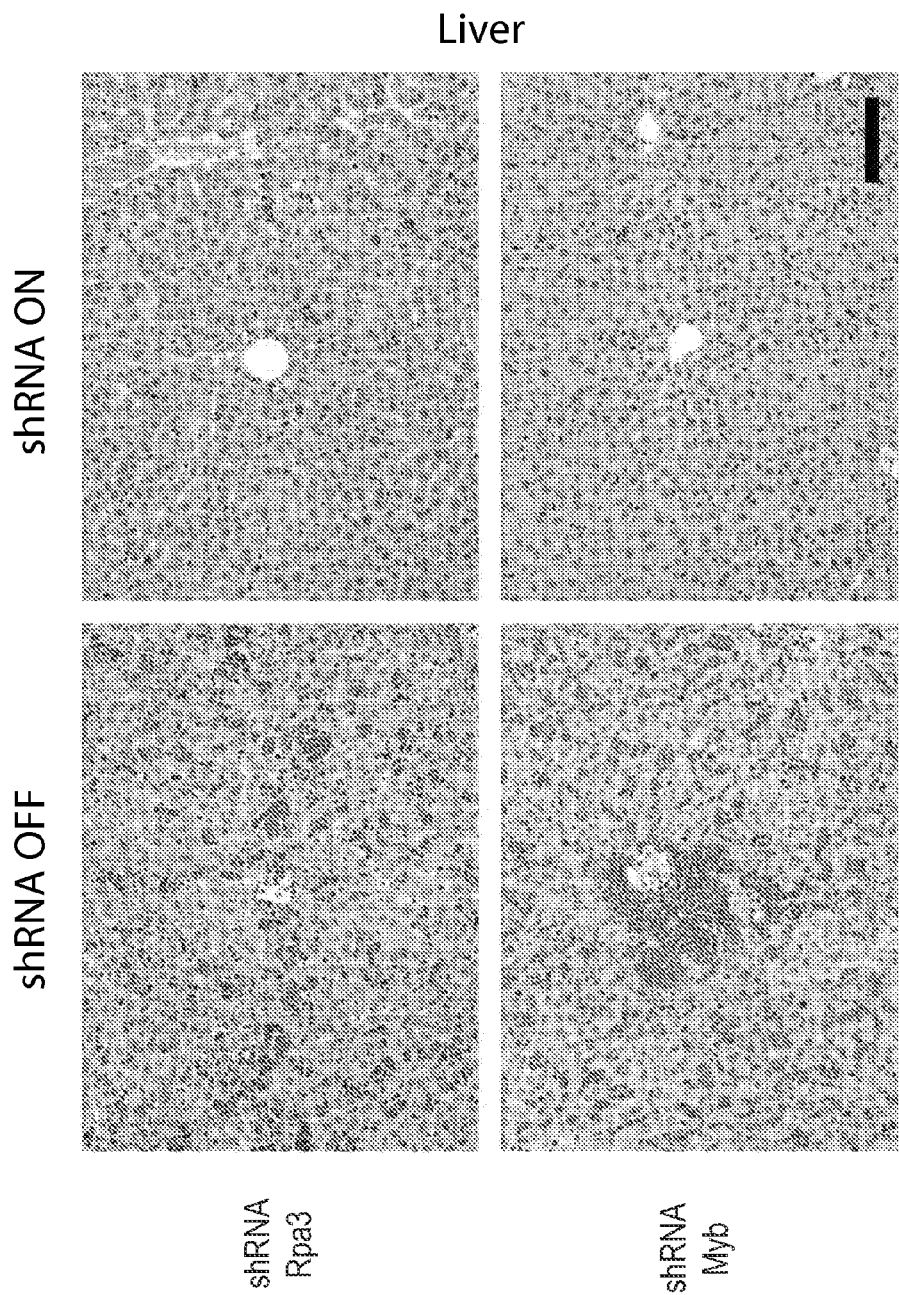

FIG. 16 shows photographs of liver histological cross-sections. Knockdown by Rpa3 shRNA or Myb shRNA ameliorates MLL/AF9+Nras AML.

Figure 17:
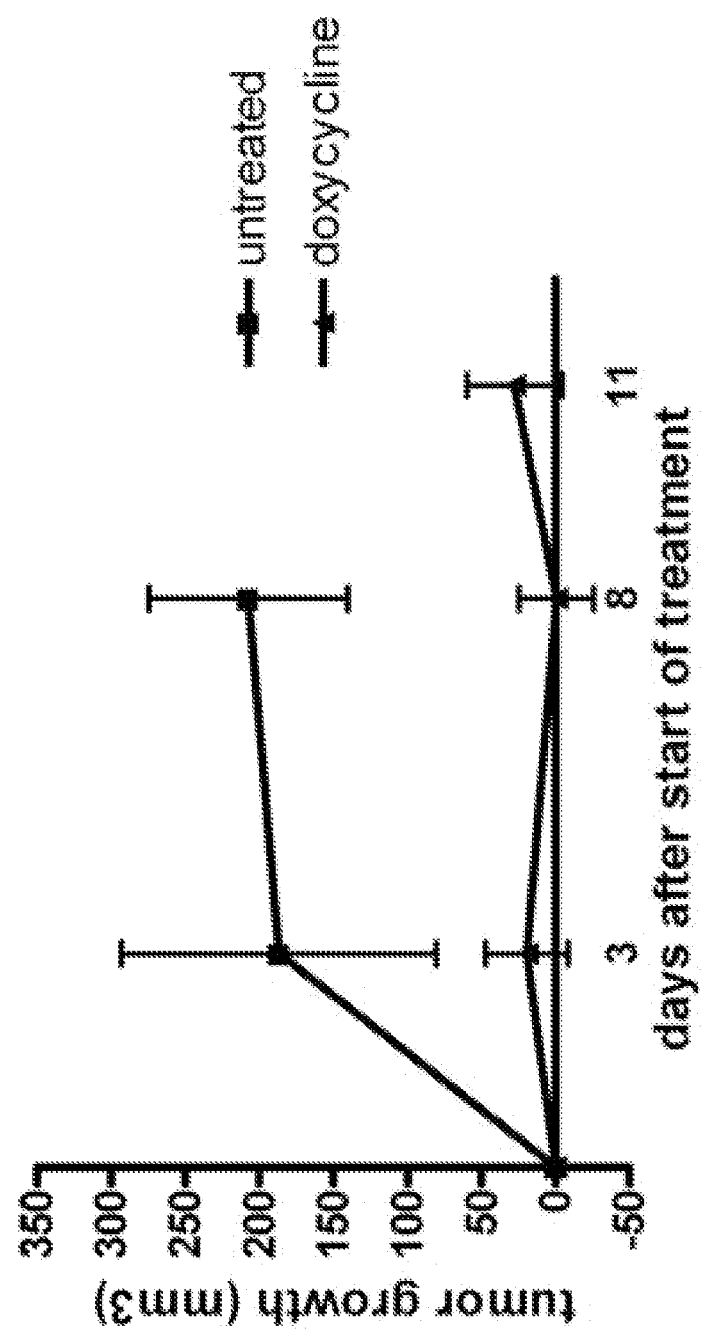

FIG. 17 shows quantification of tumor growth following shRpa3 induction by doxycycline. One million mouse liver carcinoma cells transduced with an inducible shRpa3.457 were injected subcutaneously in nude mice. Two weeks after injection, mice were either treated with doxycycline 2 mg/ml in their drinking water, or left untreated. Change in tumor volumes was measured following treatment. Tumors in which shRpa3 was induced by doxycycline stopped growing or regressed.

Figure 18:
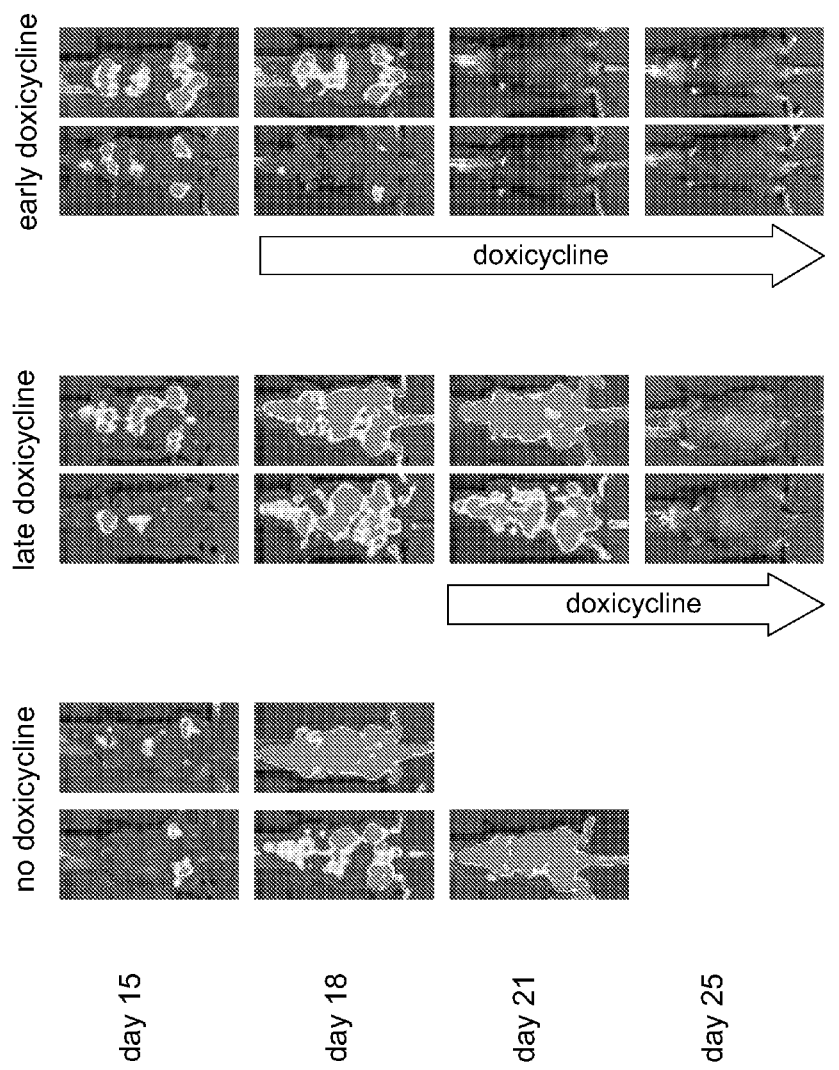

FIG. 18 shows luciferase imaging of leukemic mice harboring inducible shRpa3. Sublethally irradiated recipient mice were transplanted with $1\times10^6$ cells from a luciferase-tagged, chemoresistant leukemia harboring inducible shRpa3. Mice were either left untreated, or treated with doxycycline at an early (day 18 postinjection) or late (day 21) stage of disease progression. While untreated mice succumbed to the disease, shRpa3 induction by doxycycline caused full remission in both early and late treatment groups.

Figure 19A:
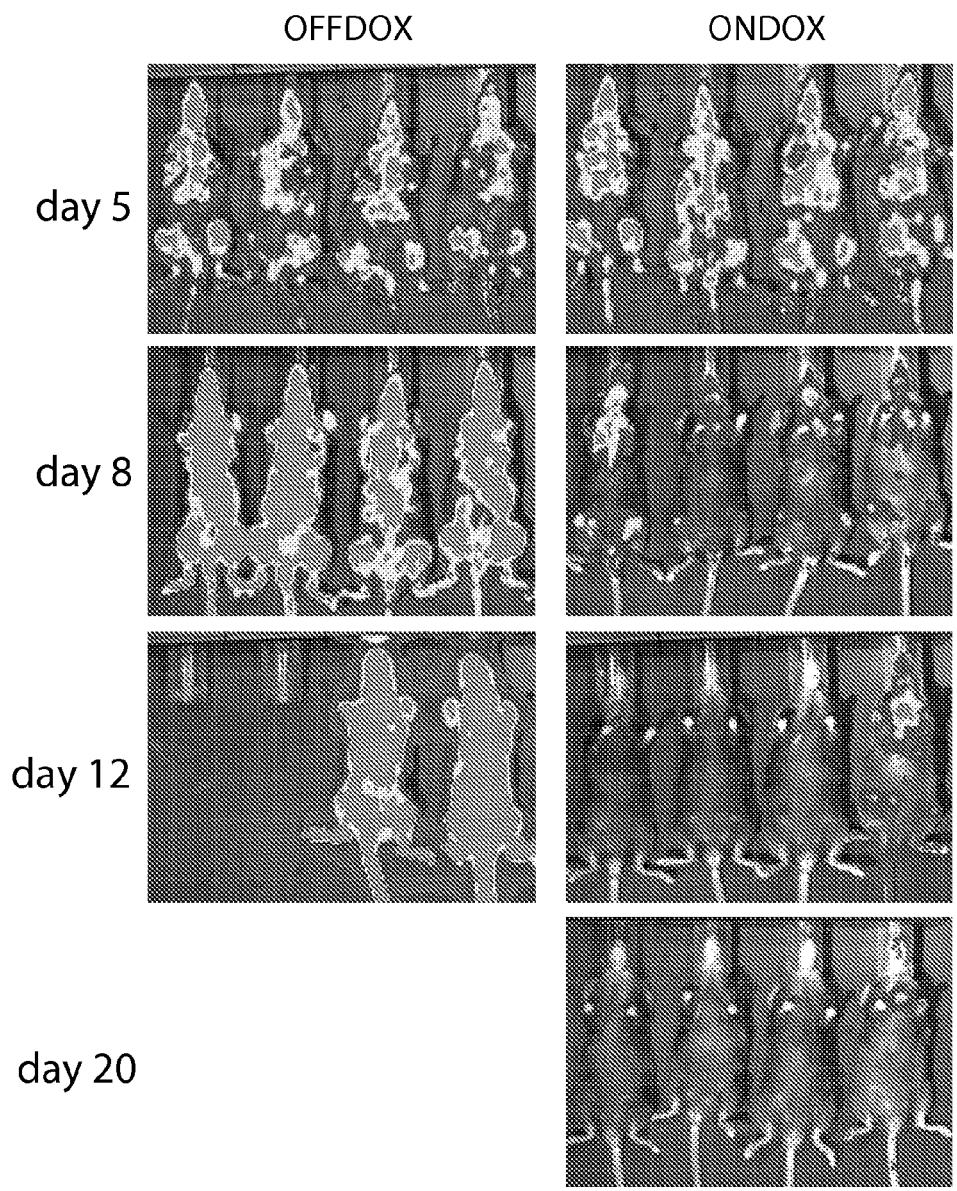
Figure 19B:
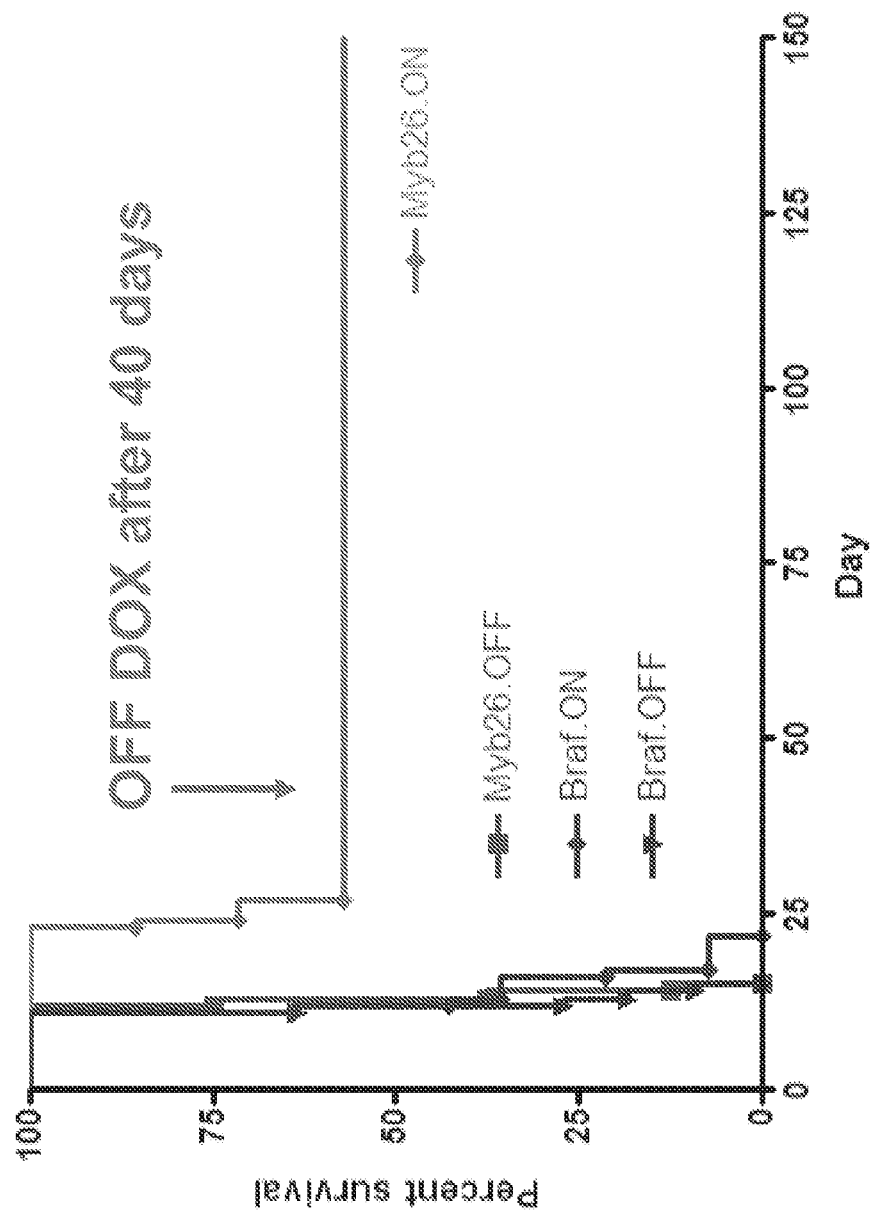

FIG. 19 shows luciferase imaging of leukemic mice with inducible shMyb. Sublethally irradiated recipient mice were transplanted with $1\times10^6$ cells from a luciferase-tagged, chemoresistant MLLdriven leukemia harboring an inducible shRNA targeting c-Myb. Mice were either left untreated, or treated with doxycycline. While untreated mice succumbed to the disease, shMyb induction by doxycycline resulted in to the disease, shMyb induction by doxycycline resulted in full, longterm remission. (FIG. 19A). Kaplan meyer survival curves of mice transplanted with clonal MLL/AF9+Nras induced leukemia harboring shRNAs targeting Myb or Braf. Induction of shRNAs by doxycycline treatment induces long-term survival advantage or cure in mice harboring Myb shRNAs, but has no effect in mice harboring Braf shRNAs. Mice remain disease-free after discontinuing doxycycline treatment after 32 days. (FIG. 19B)

Figure 20:
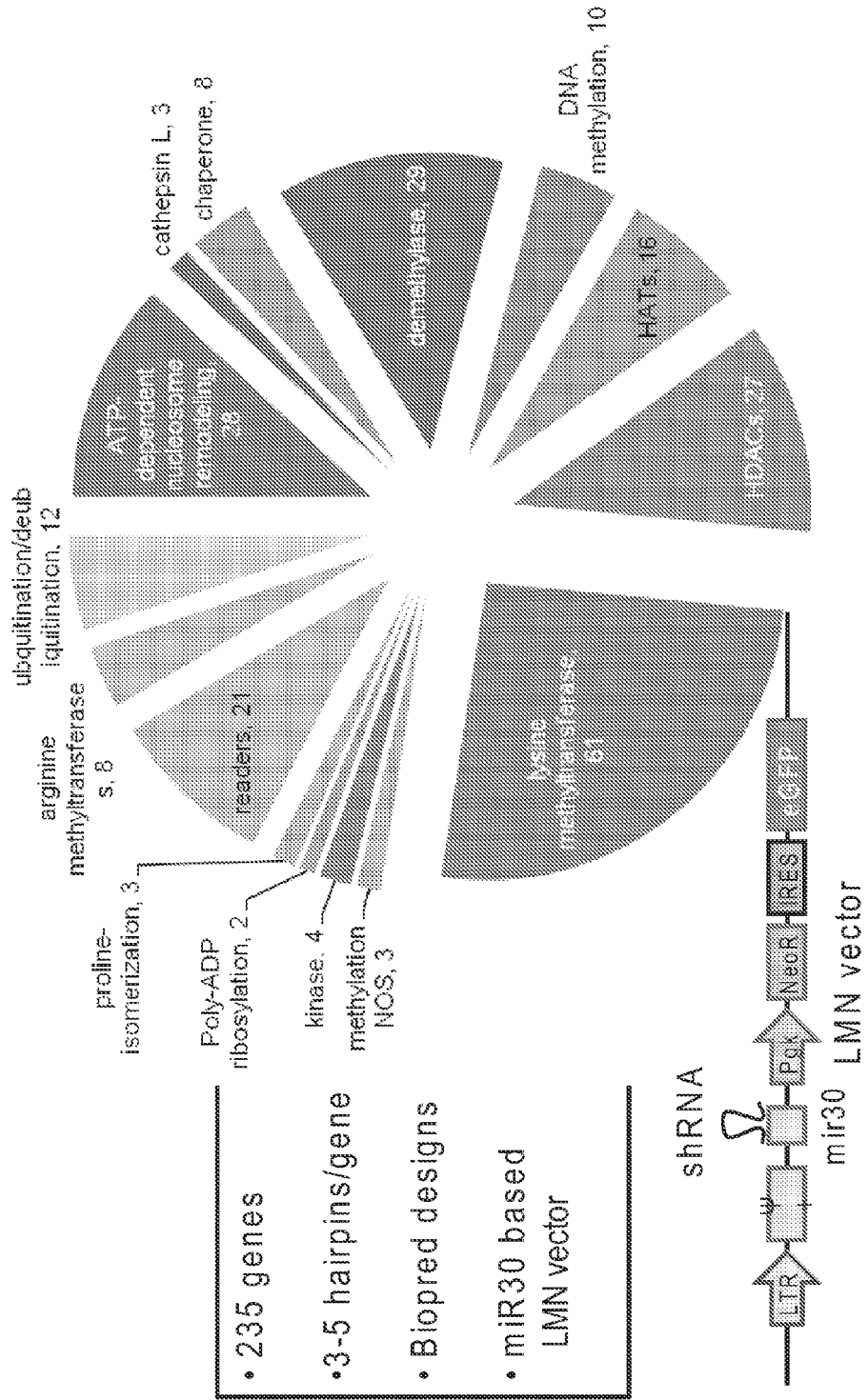

FIG. 20 shows a schematic of a strategy for using negative selection RNAi screening to identify epigenetic modifiers as drug targets for chemotherapy resistant AML using a custom epigenetic library of 1,100 shRNAs targeting genes for 235 known epigenetic regulators. For screening, these shRNAs were cloned into the LMN mir30-embedded shRNA vector.

Figure 21:
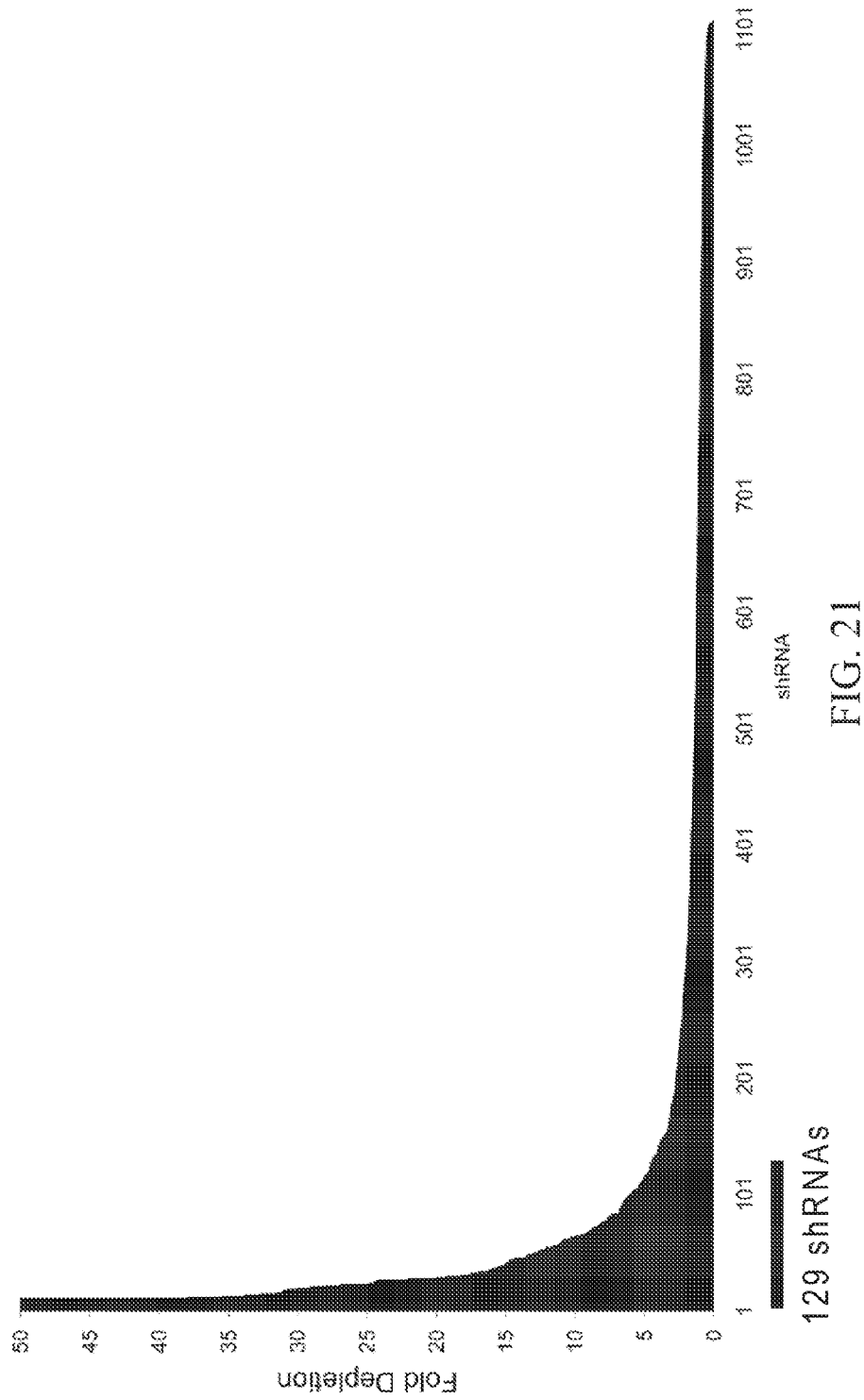

FIG. 21 shows results of a primary screen of each of the 1100 individual shRNAs in the epigenetic library in chemotherapy resistant AML. Each shRNA was monitored for its ability to confer a proliferative disadvantage to MLL-AF9/Nras leukemia cells in vitro. The primary screen identified 35 epigenetic regulators (129 shRNAs) that were required for proliferation of leukemia cells in vitro.

Figure 22:
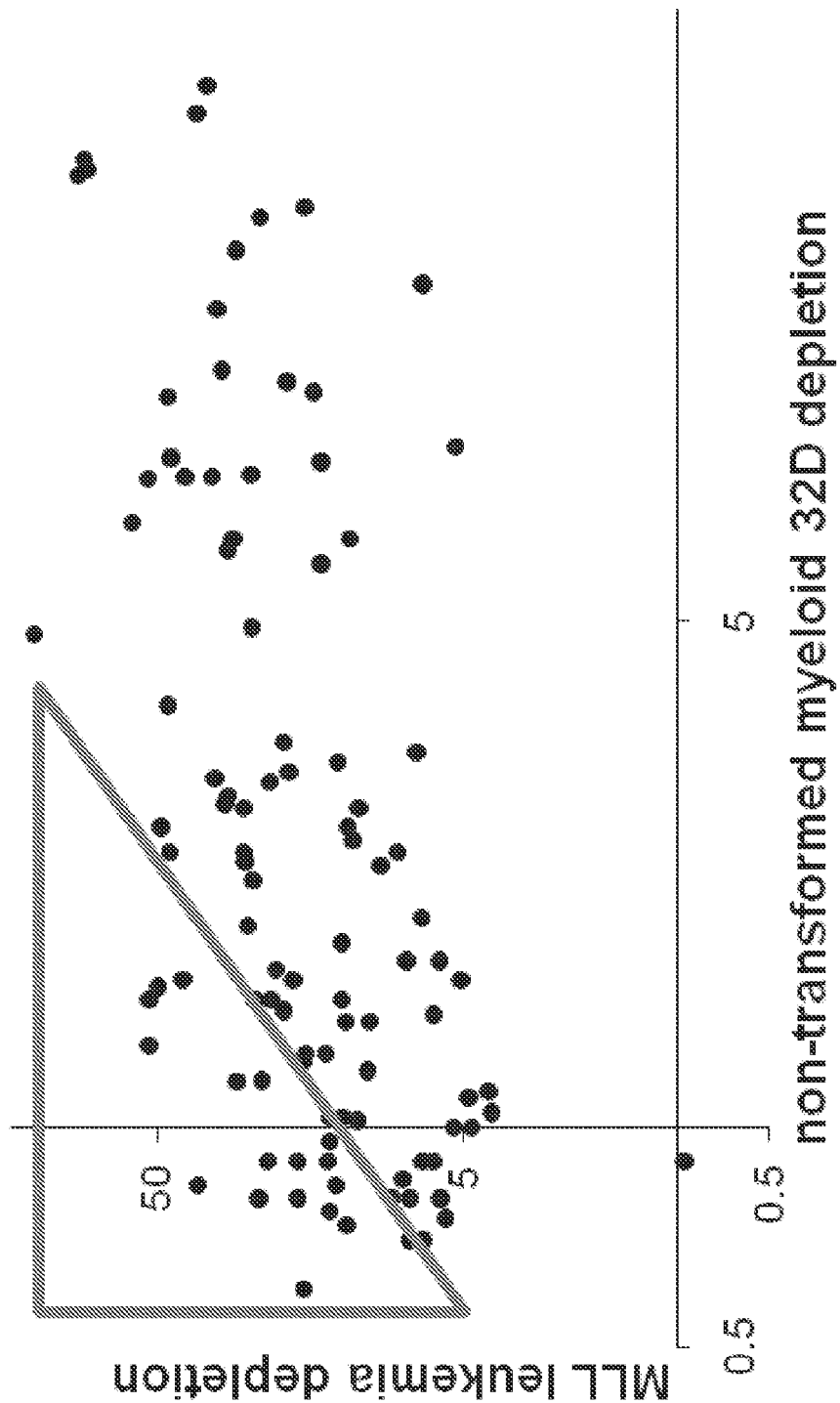

FIG. 22 shows a secondary screen of 129 shRNAs directed against 35 epigentic regulators to determine the ability of the identified shRNAs to selectively inhibit growth of leukemia cells. The screening revealed 8 genes, which leukemias, in contrast to three non-transformed cells, selectively require for their proliferation.

FIG. 23 shows results of a secondary screen identifying 8 genes which leukemias selectively require for their proliferation. The ability of shRNAs directed against these 8 genes, and of shRNAs directed against Rpa3 and Myc genes, to inhibit growth was compared in leukemia cells (FIG. 23A), non-transformed erythroid cells (G1E) (FIG. 23C), non-transformed myeloid cells (32D) (FIG. 23B) and non-transformed stem-like cells (EML) (FIG. 23D).

Figure 24:
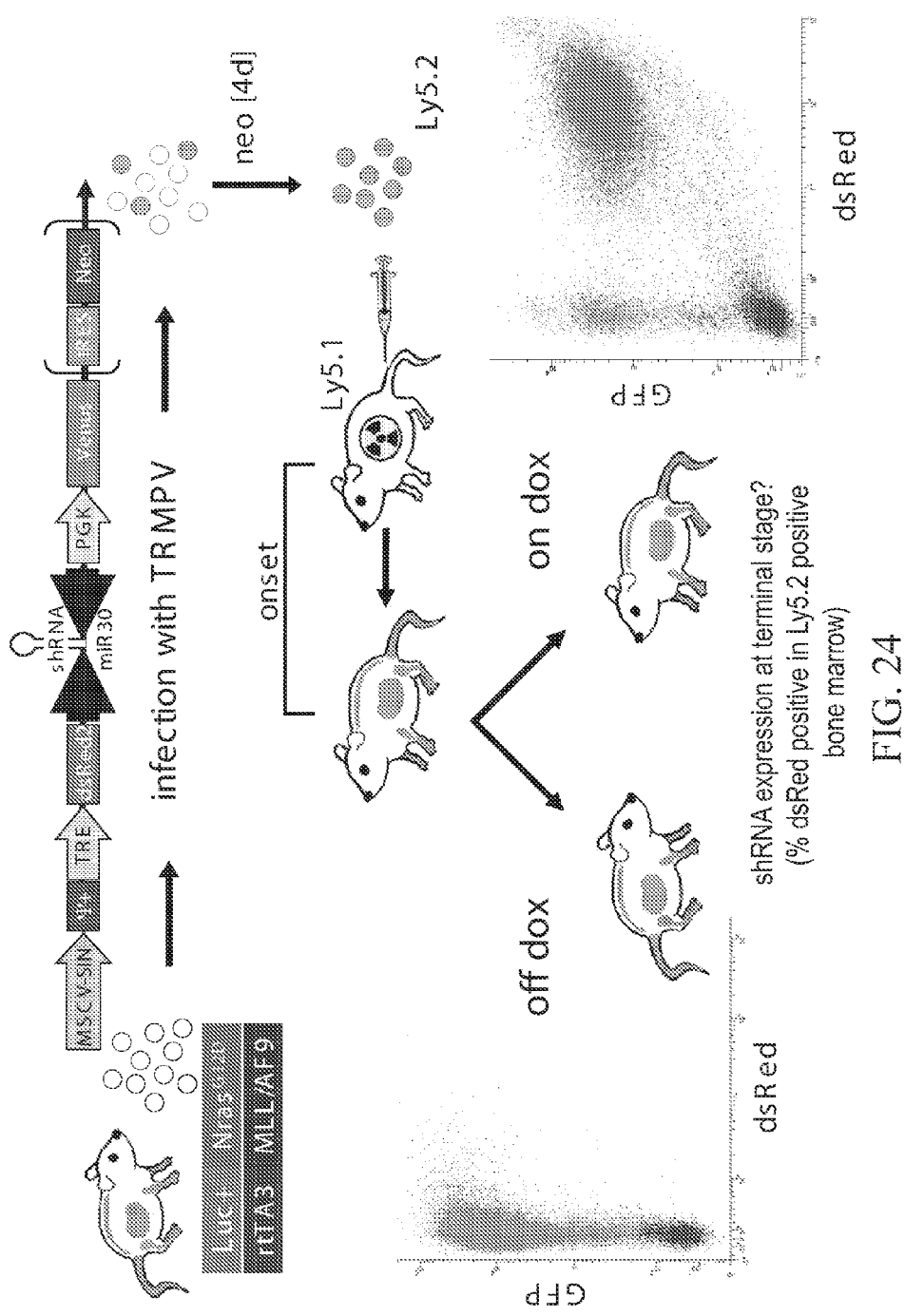

FIG. 24 shows the system and strategy using tet-on competent AML cells and the TRMPV vector to perform negative selection RNAi screening in vivo to validate the therapeutic potential of inhibiting epigenetic modifier genes identified by in vitro screening as required for proliferation of leukemia cells. Each shRNA targeting an epigenetic modifier gene is cloned into the TRMPV vector and introduced into tet-on leukemia cells. Following selection, the leukemia cells were transplanted into recipient mice, which are then treated with Doxycycline 3 days after transplant. The TRMPV//luciferase tagged tet-on AML system facilitates monitoring of shRNA expressing cells in vivo via bioluminescence, providing a rapid and robust assay to assess tumor-inhibitory RNAi effects.

Figure 25:
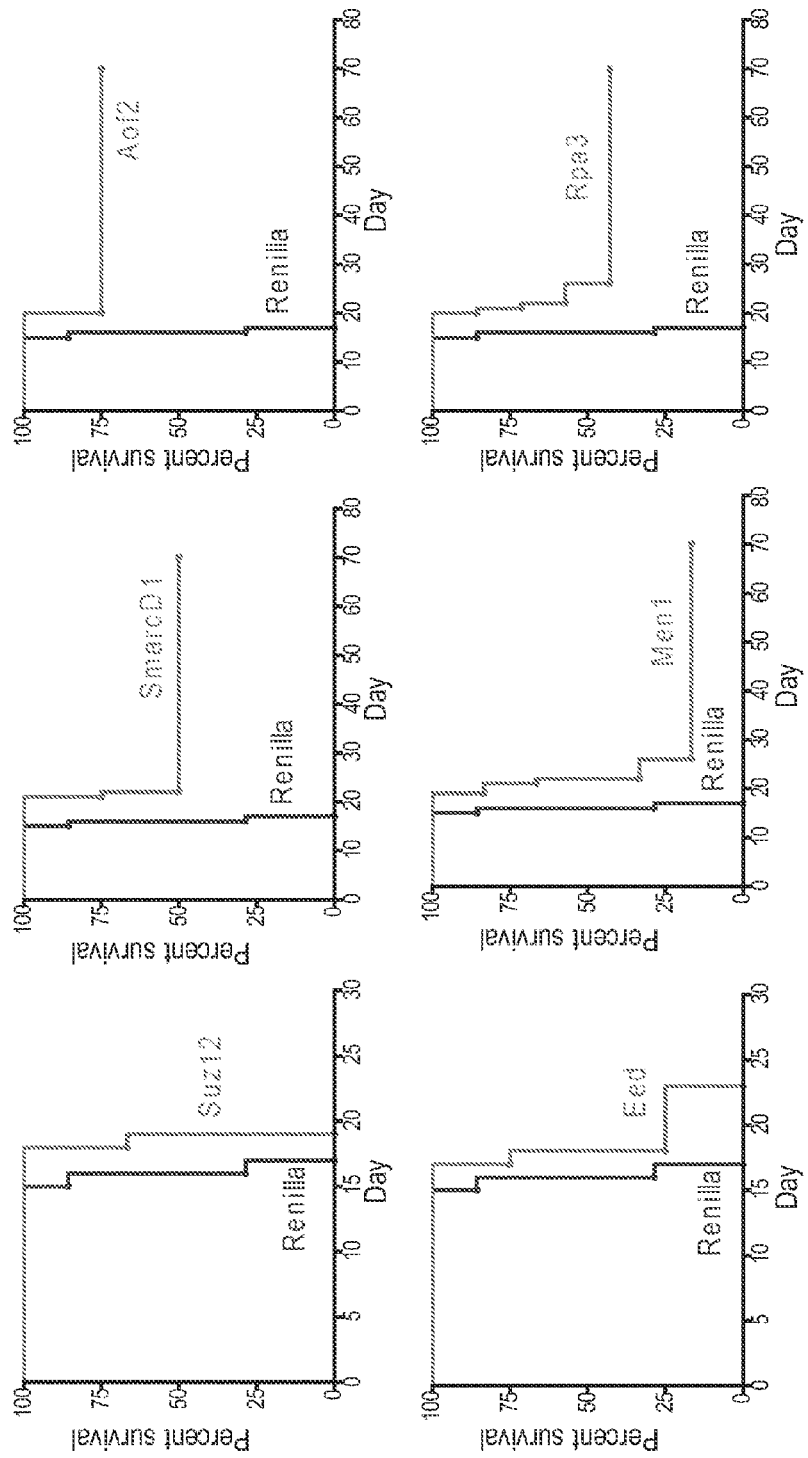

FIG. 25 shows Kaplan-Meyer survival curves of lethally irradiated recipient mice, which were reconstituted with MLL-AF9/Nras tet-on AML cells transduced with tet-inducible shRNAs targeting epigenetic modifier genes (EED, Aof2, Suz12, Men1 and SMARCD1) and Rpa3. Inhibition of these gene targets by these shRNA, as compared to a *Renilla* luciferase control shRNA, revealed a survival benefit or substantial rate of cure in vivo.

Figure 26:
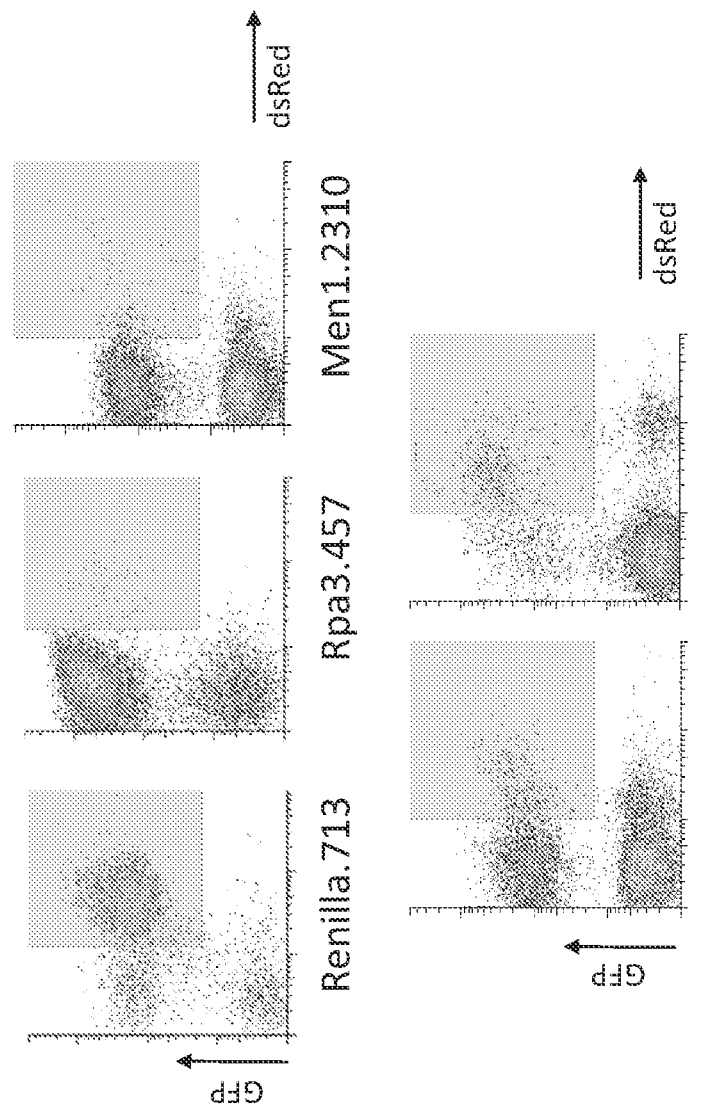

FIG. 26 shows a FACS analysis of shRNA expression in bone marrow at terminal disease stage, demonstrating that shRNAs targeting epigenetic modifier genes (EED, Aof2, Suz12, Men1 and SMARCD1) inhibited proliferation of leukemia cells as the disease developed, compared to a *Renilla* luciferase control.

Figure 27:
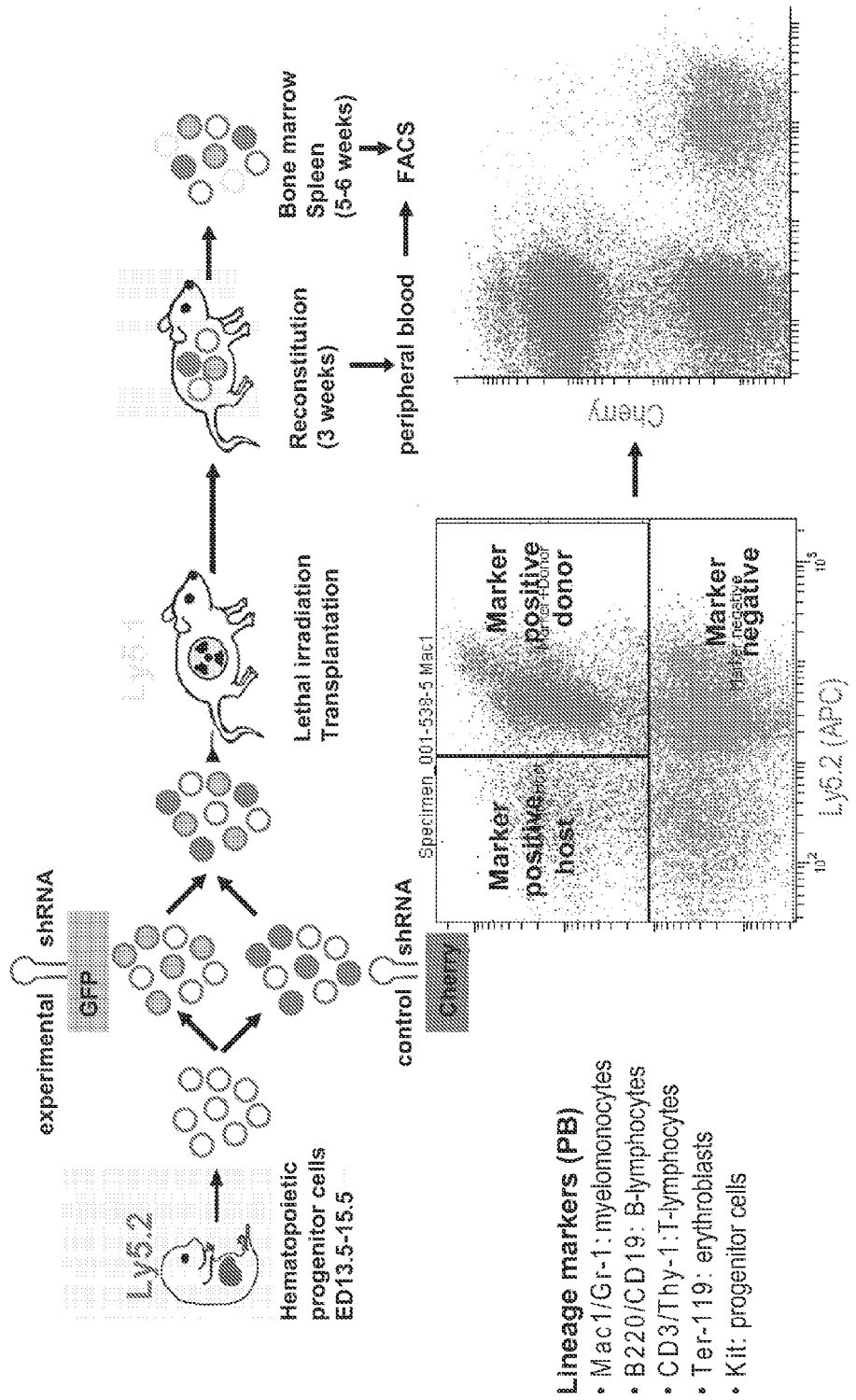

FIG. 27 shows a schematic of a strategy using a dual-color competition assay enabling a direct and robust assessment of shRNA effects in the reconstitution of hematopoieic tissues in vivo. LMN vectors harboring shRNAs are transduced into fetal livers. Infected cells are subsequently transplanted into lethally irradiated recipients. This assay compares the relative contribution of the experimental shRNA (in an LMN vector harboring a GFP marker) to a control, neutral shRNA (in an LMN vector harboring a red fluorescent protein marker (mCherry)). The effect of the experimental shRNA on hematopoesis is assessed by the ratio of these two markers in subsets of peripheral blood cells, or bone marrow or spleen, measured at 4 weeks.

Figure 28:
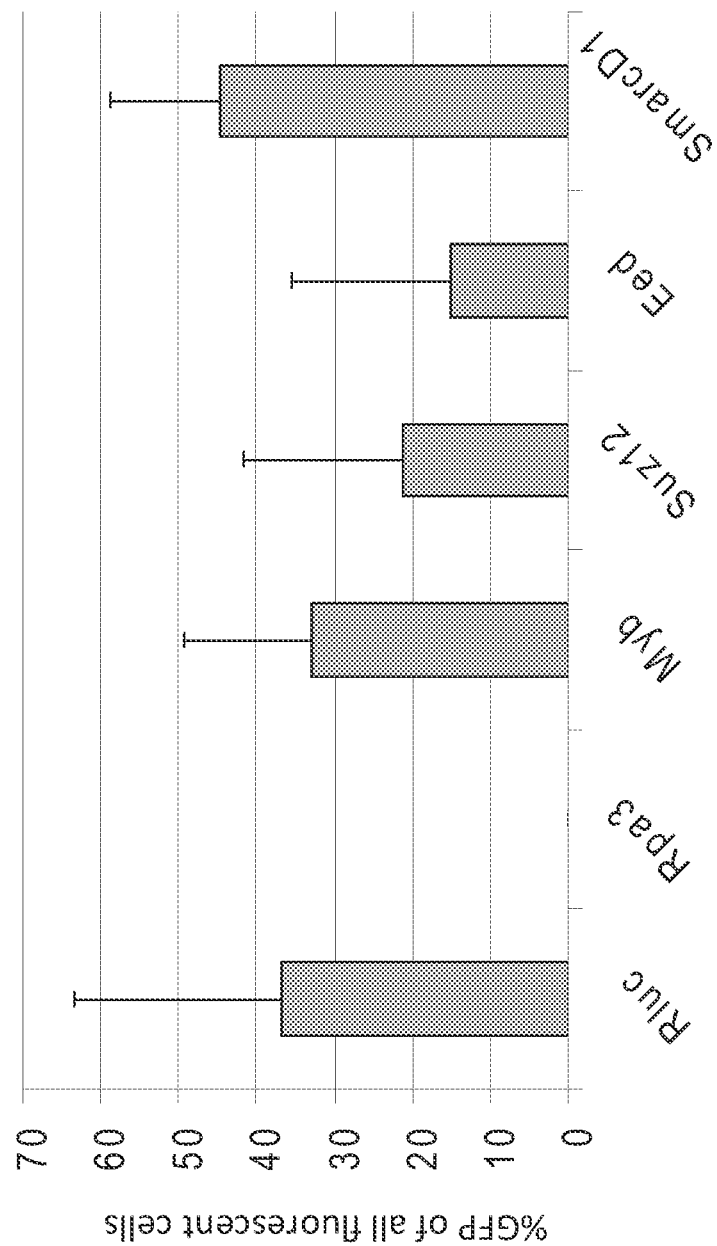

FIG. 28 shows the results of a dual-color competition assay performed to assess the effect of various experimental shRNAs on hematopoiesis in vivo, as compared to a luciferase control shRNA.

Figure 29:
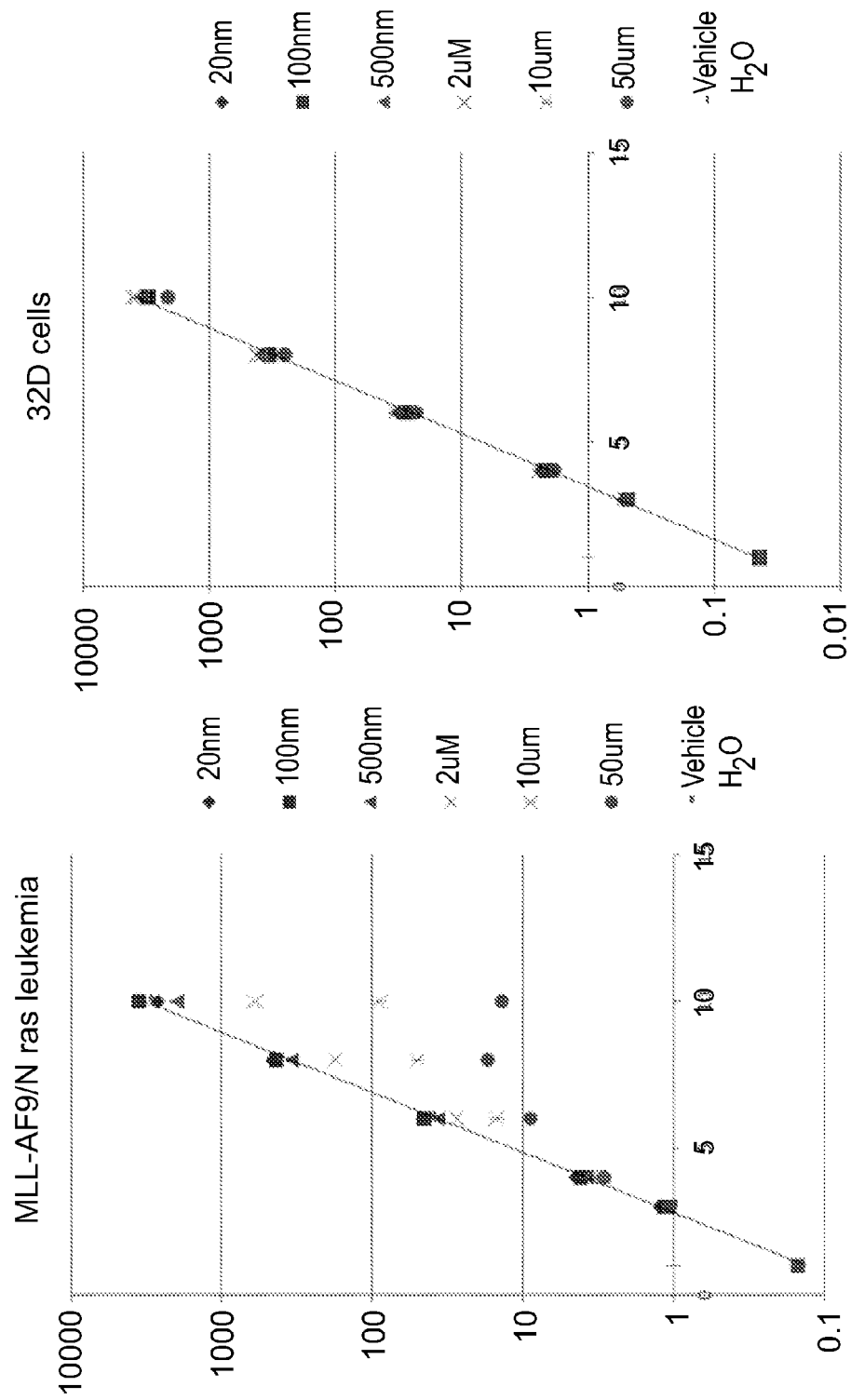

FIG. 29 shows a comparison of the inhibitory effect of different concentrations of tranylcypromine (Aof2 inhibitor) on proliferation of MLL-AF9/Nras leukemia cells other human AML cell lines and a non-transformed myeloid cells (32D) in vitro. The results indicated that tranylcypromine has a selective inhibitory effect on proliferation of AML cells FIG. 30 shows a strategy for generation of genetically defined mosaic mouse models based on common genetic associations in human AML. Frequency of Nras mutations in 111 cases of pediatric AML depending on major karyotype groups. Nras mutations are especially common in concert with core-factor binding translocations (AML1/ETO, CBF-beta/MYH11) and MLL rearrangements. (FIG. 30A). Kaplan-Meier plot showing the overall survival of pediatric AML patients treated after 1998 depending on certain karyotype abnormalities including t(8;21)=AML VETO (n=10), inv(16)/t(16;16)=CBF/MYH11 (n=9), 11q23/MLL rearrangements (n=9) compared to other subtypes (n=22, excluding patients with PML/RAR positive AML). The presence of AML1/ETO and MLL fusion proteins has opposite effects on long-term therapy outcome (FIG. 30B). MSCV-based retroviral constructs used to co-express AML oncogenes with fluorescent and bioluminescent markers (FIG. 30C). Schematic overview of mosaic AML mouse models. Wildtype C57BL/6 fetal liver cells (FLC) isolated at ED 13.5-15.5 were (co-)transduced with oncogenic retroviruses and used to reconstitute the hematopoietic system of lethally irradiated recipient mice (FIG. 30D). Mice reconstituted with FLCs transduced with the indicated transgenes were monitored for illness and died or were euthanized at a terminal disease stage. The data are presented in a Kaplan-Meier format showing the percentage of mouse survival at various times post transplantation (FIG. 30E). Luciferase imaging of recipient mice of FLCs transduced with the indicated genes at 14, 21 and 42 days following transplantation. Transduction of Luciferase-IRES-Nras rapidly induces onset of Luciferase-positive disease only in concert with AML1/ETO9a or MLL/ENL (FIG. 30F). Expression analysis of retroviral oncogenes in wildtype bone marrow (wt bm), and independent primary AMLs (1-3) with indicated genotypes. Expression of human AML1/ETO9a and MLL/ENL transcripts was verified by RT-PCR using fusion-site specific primers. No reverse transcriptase controls were negative in all samples (not shown). Western-blot analysis using pan-Ras and Nras-specific antibodies demonstrating Nras overexpression on leukemia lysates derived from Nras-cotransduced FLCs. Overall Ras levels (pan-Ras) do not show significant elevation (FIG. 30G). Baseline phospho-Erk levels are strongly elevated in leukemias deriving from Nras-cotransduced FLCs. Levels of phosphorylated Erk were measured using phospho-specific flow cytometry in wildtype whole bone marrow and GFP-positive MLL/ENL, MLL/ENL+Nras and AML1/ETO9a+Nras leukemias. Representative histograms are shown (FIG. 30H).

FIG. 31 shows results indicating that defined mosaic AML mouse models have genotype-dependent morphology consistent with human AML. May-Grünwald-Giemsa stained peripheral bloodsmears (20 fold magnification) (FIG. 31A). Wright-Giemsa stained bone marrow cytocentrifugation (100 fold magnification) predominantly show immature blasts in AML1/ETO9a+Nras leukemia, while MLL/ENL+Nras leukemia is characterized by more mature myelomonocytic cells at various differentiation levels (FIG. 31B). Bone marrow immunphenotyping in AML1/ETO9a+Nras leukemic mice shows infiltration of GFP+/c-Kit+/Mac-1−/Gr-1− immature blasts, while MLL/ENL+Nras bone-marrow is dominated by GFP+/c-Kit−/Mac-1+/Gr-1+ myelomonocytic cells (FIG. 31C). Hematoxylin-eosin stained liver sections showing massive leukemic infiltration (20 fold magnification, scale bar 100 um) (FIG. 31D).

Figure 32:
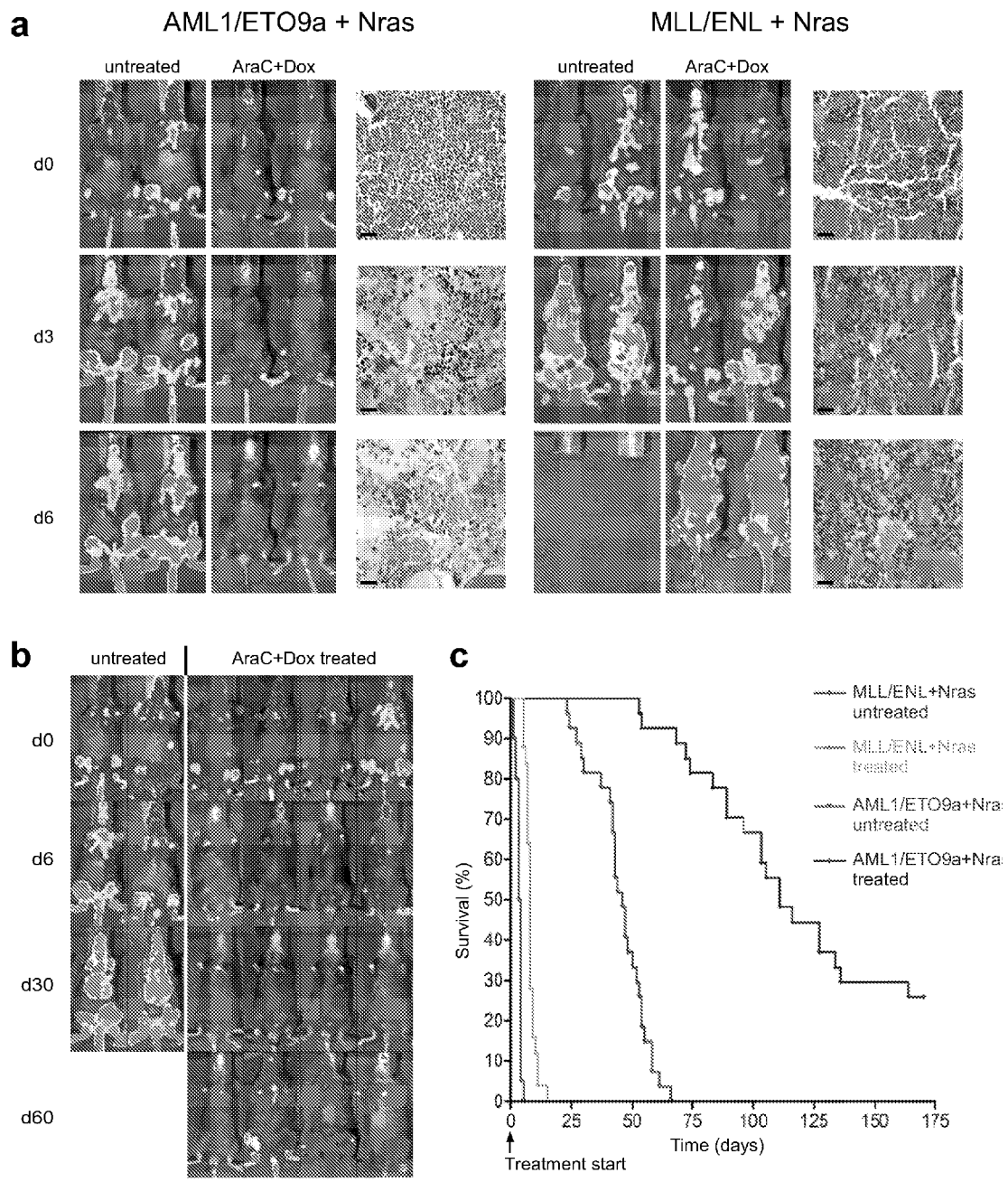

FIG. 32 shows that AML1/ETO9a+Nras and MLL/ENL+Nras AMLs show dramatic differences in their response to combined chemotherapy in vivo. Luciferase-imaging and histological analysis of hematoxylin-eosin stained bone marrow sections before (d0), during (d3) and after 5 days of chemotherapy (d6) show therapy-triggered regression and ultimately complete remission of AML1/ETO9a+Nras leukemia (left panel), while MLL/ENL+Nras leukemia only show decelerated progression, with persistance of blasts in response to treatment (right panel). 40 fold magnification; scale bars 50 um (FIG. 32A). Long-term follow-up luciferase imaging of untreated and treated AML1/ETO9a+Nras leukemia. Treated mice achieve durable remissions lasting at least 30 days (d30). While most mice subsequently relapse, some mice remain in remission following chemotherapy (d60) (FIG. 32B). Kaplan-Meier survival curves of untreated and treated AML1/ETO9a+Nras and MLL/ENL+Nras mice following the initiation of chemotherapy (FIG. 32C).

Figure 33:
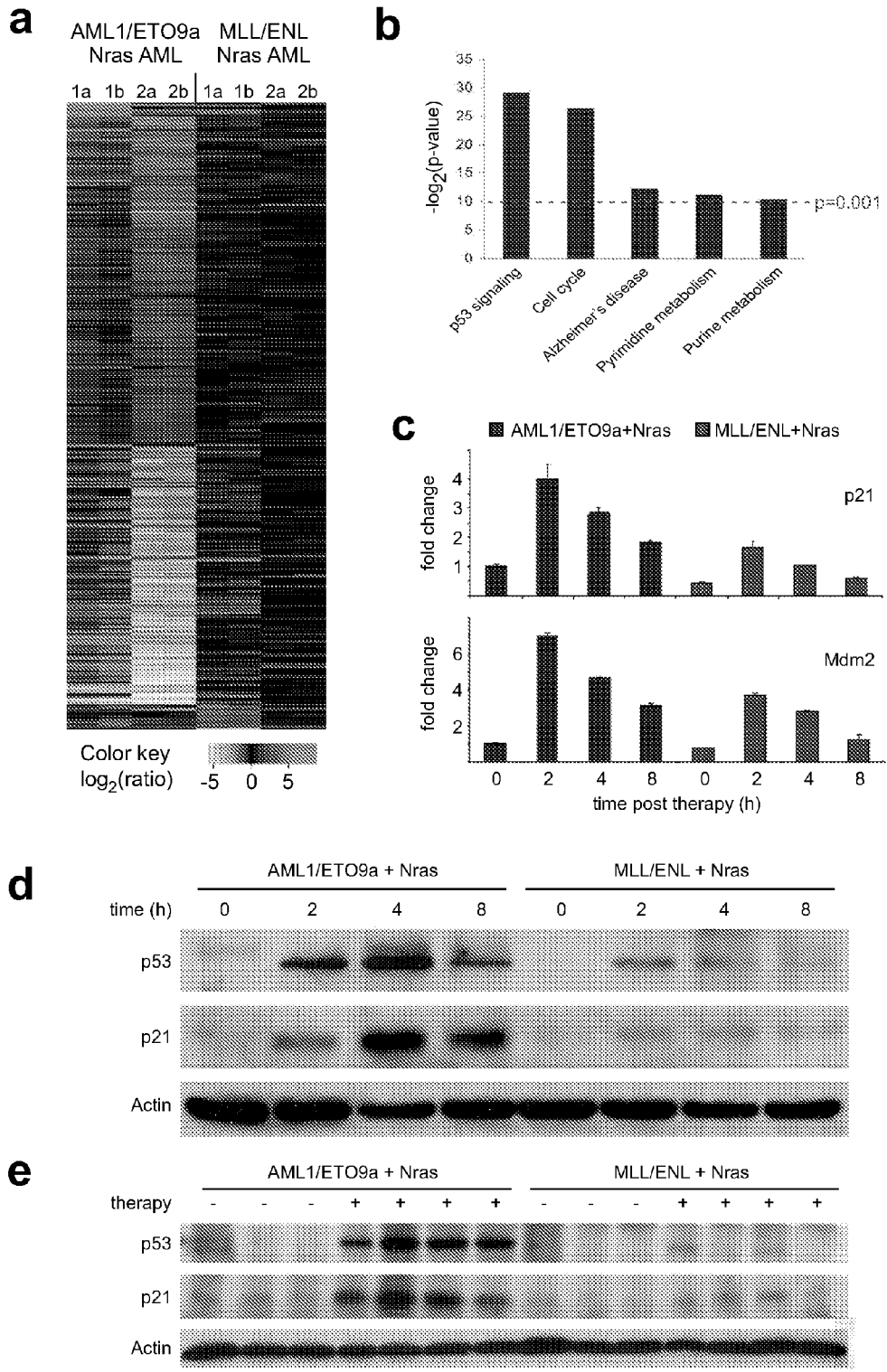

FIG. 33 shows in vivo expression analysis of immediate chemotherapy response programs, which identifies differences in p53 induction between AML1/ETO9a+Nras and MLL/ENL+Nras AMLs. AML1/ETO9a+Nras leukemias show complex gene expression changes in response chemotherapy, while this response profile is blunted in the MLL/ENL+Nras context. For two independent primary leukemias (1,2) of each genotype the expression profile 2 h after combined chemotherapy (a single dose of Ara-C and Doxorubicin i.p.) was compared to this of an untreated control. For each condition microarray profiles were acquired in two technical replicates (a,b). Treatment-induced expression changes were rendered in a green-black-red pseudo color scheme for all genes with an average fold change ≥2.0 in either genotype (FIG. 33A). KEGG pathways analysis of the AML1/ETO9a+Nras specific drug-response signature identifies five pathways with significant alteration and reveals differences in p53 response levels. The 398 most significantly altered genes in treated AML1/ETO9a+Nras leukemia were identified by SAM (FDR 0.2, FC>2) and inferred with KEGG pathways (Ogata et al. 1999) using DAVID (Dennis et al. 2003) (FIG. 33B). Quantitative real-time PCR analysis of p21 and Mdm2 at various time points after chemotherapy in vivo. Baseline expression and induction of both p53 target gene transcripts is attenuated in MLL/ENL+Nras leukemia (FIG. 33C). Western-blot analysis of p53 and p21 in leukemic spleens (>85%

GFP+infiltration) at various time points after i.p. administration of one dose of combined chemotherapy. AML1/ETO9a+ Nras AML show much stronger p53 induction resulting in a stronger and more durable induction of its target p21 (FIG. 33D). Western-blot analysis of p53 and p21 in recipient mice transplanted with independent primary AMLs were either left untreated (−) or were treated with one dose of combined chemotherapy 4 hours prior to sample harvest (+). Individual differences in p53 drug-response programs are dependent on the AML genotype (FIG. 33E).

FIG. 34 shows results of studies in the AML mouse model, indicating that loss of p53 dramatically accelerates AML1/ETO9a, but does not affect MLL/ENL induced leukemogenesis. Kaplan-Meier survival curves of lethally irradiated recipient mice, which were reconstituted with wildtype or p53−/− FLCs transduced with either AML1/ETO9a or MLL/ENL. Loss of p53 accelerates AML1/ETO9a, but not MLL/ENL induced leukemogenesis (FIG. 34A). Bone marrow immunophenotyping of wildtype and p53-deficient AML1/ETO9a and MLL/ENL induced leukemias. Loss of p53 does not affect the typical disease morphology induced by both fusion proteins (FIG. 34B). Kaplan-Meier survival curves of lethally irradiated recipient mice, which were reconstituted with wildtype or p53−/− FLCs co-transduced with AML1/ETO9a and NrasG12D. Loss of p53 also accelerates AMLVETO9a+Nras induced leukemogenesis (FIG. 34C).

Figure 35:
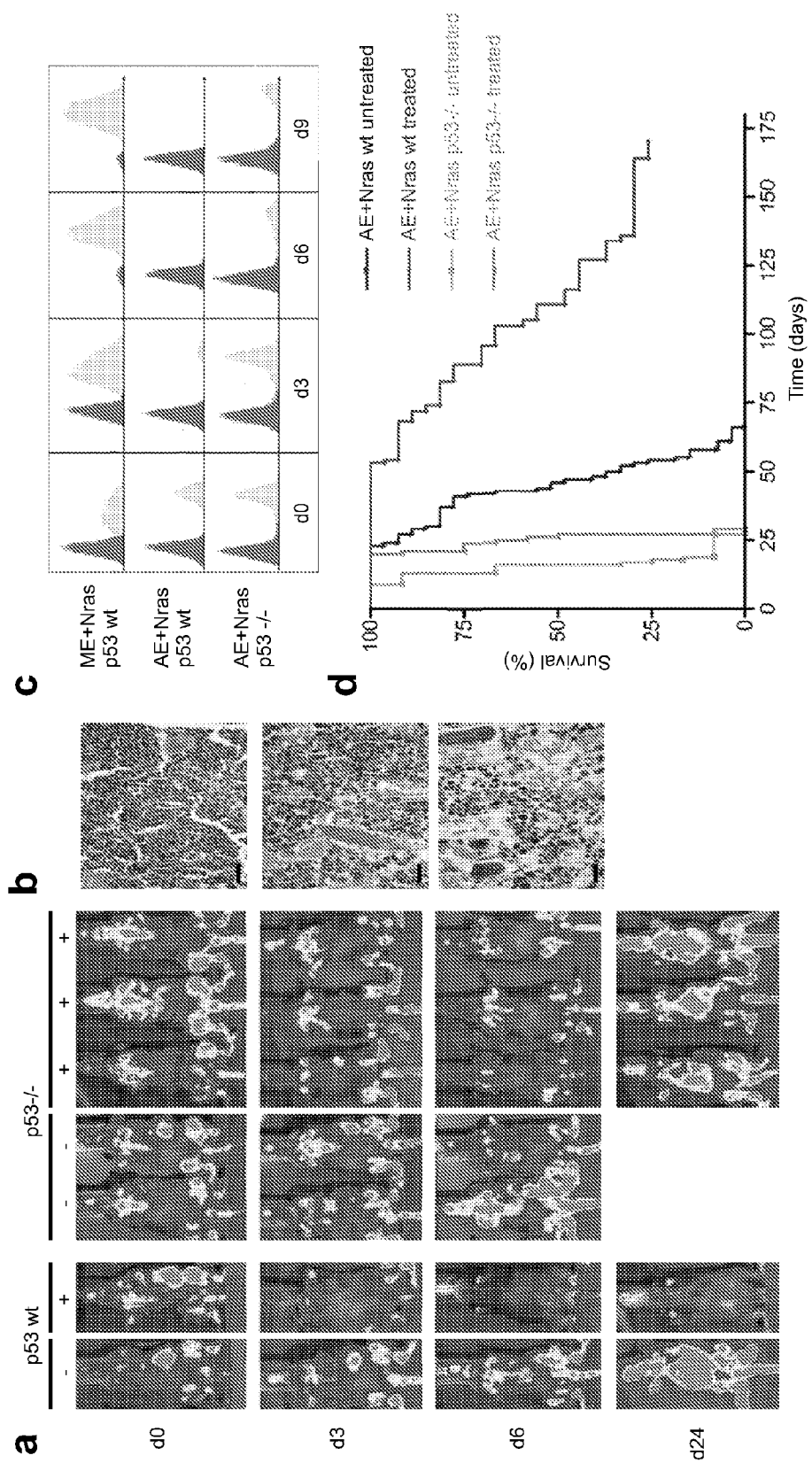

FIG. 35 shows results of studies in the AML mouse model on mechanisms of chemoresistance in AML indicating that loss of p53 induces chemotherapy resistance in AML1/ETO9a+Nras AML. Luciferase imaging of AML1/ETO9a+Nras leukemias generated in wildtype (left panel) or p53−/− (right panel) FLCs before (d0), during (d3) and after chemotherapy (d6, d24). Recipient mice of p53-deficient AMLVETO9a+Nras leukemias retain bioluminescent signal under therapy (FIG. 35A). Hematoxylin-eosin stained bone marrow sections of recipients of p53-deficient AML1/ETO9a+Nras leukemia at various time points following chemotherapy demonstrating blast persistence under chemotherapy (40 fold magnification; scale bars 50 um) (FIG. 35B). GFP histograms of bone marrow flow cytometry before (d0) and at various time points during (d3) and after (d6, d9) chemotherapy. While AMLVETO9a+Nras blasts harboring wildtype p53 (AE+Nras p53 wt) rapidly clear, both MLL/ENL+Nras (ME+Nras p53 wt) and p53-deficient AMLVETO9a+Nras leukemias (AE+Nras p53−/−) show persistence of GFP+ cells in bone marrow (FIG. 35C). Kaplan-Meier survival curves of untreated and treated recipient mice of p53 wildtype and p53-deficient AMLVETO9a+Nras leukemias. Loss of p53 impedes the long-term outcome of chemotherapy (FIG. 35D).

Figure 36:
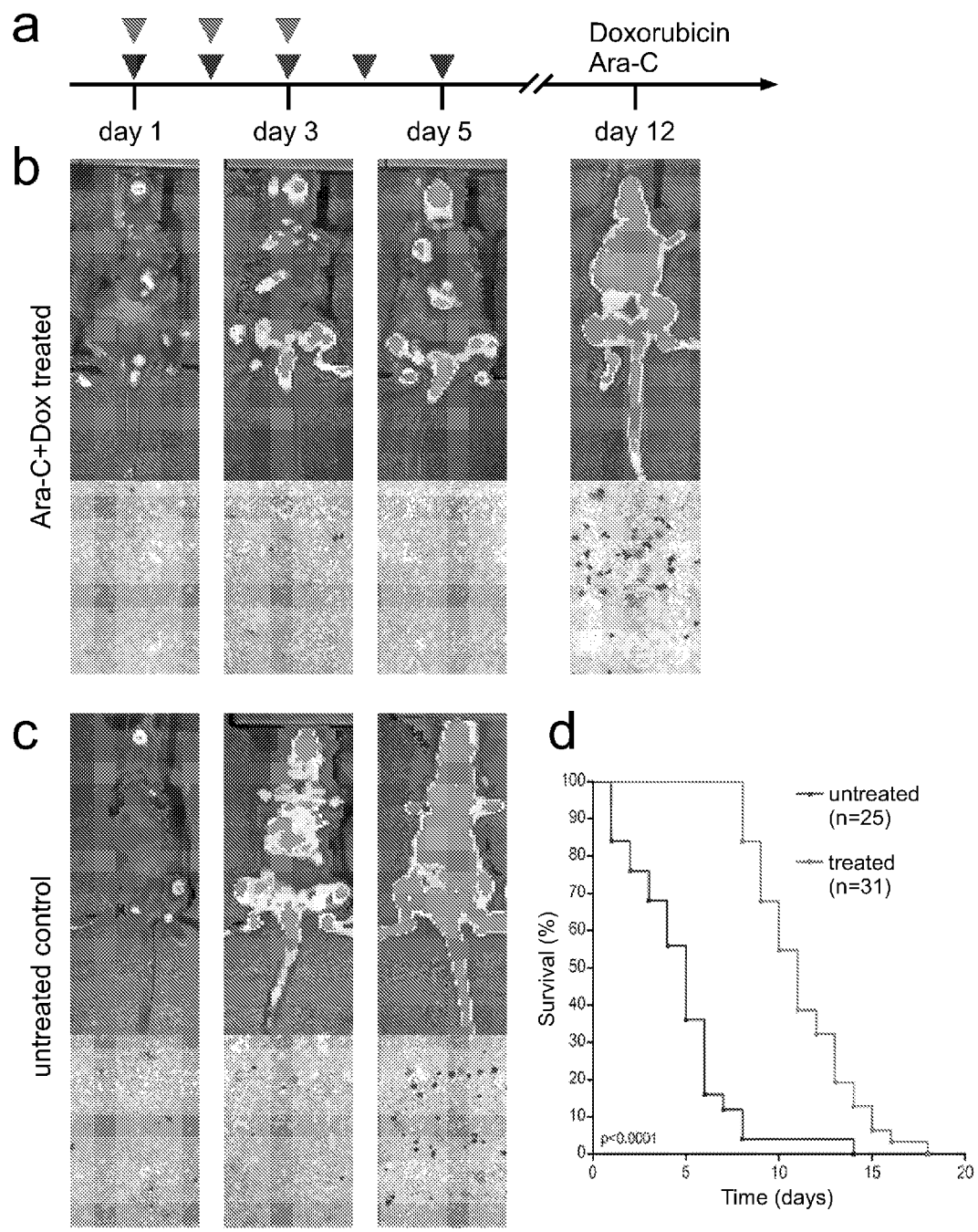

FIG. 36 shows an outline of the strategy used to establish a combined chemotherapy regimen in the mouse AML model modeling clinical AML induction therapy in human patients. Schematic overview of the chemotherapy protocol. The regimen involves daily i.p. injections of Cytarabine (100 mg/kg/d over 5 days) and Doxorubicin (3 mg/kg/d over 3 days) (FIG. 36A). Bioluminescent imaging and peripheral blood smears (May-Grünwald-Giemsa stained) of recipient mice of MLL/ENL-IRES-Luciferase+FLT3-ITD induced AML with and without chemotherapy. Treatment is initiated upon detection of clear signals in pelvis, tail and both femurs and early hepatosplenic infiltration, which was ~5 d before leukemia became detectable in peripheral blood smears. Treatment induces peripheral leucopenia, a deceleration of disease progression, while luciferase imaging demonstrates blast persistence in bone marrow of MLL/ENL+FLT3 AML recipient mice as compared to controls (FIGS. 36B-C). Kaplan-Meier survival curves of untreated and treated recipient mice of MLL/ENL-IRES-Luciferase+FLT3-ITD induced AML (FIG. 36D).

Figure 37:
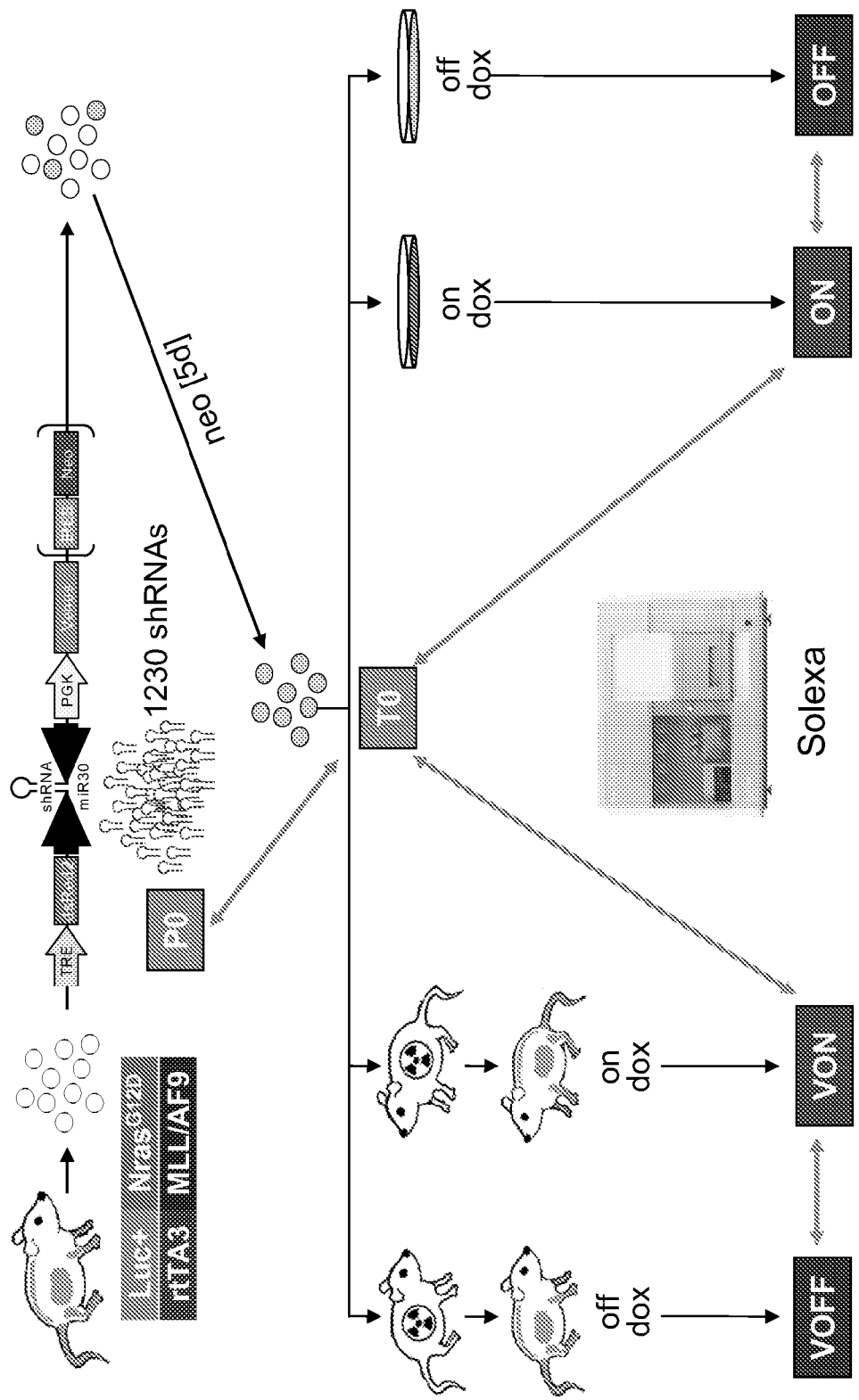

FIG. 37 shows a schematic of pooled negative selection screening in tet-on competent MLL/AF9+Nras AML using a TRMPV shRNA pool comprising 1230 shRNAs (64 controls, 1166 experimental shRNAs). The shRNA representation is analyzed by deep sequencing in the initial plasmid pool (P0), after transduction and drug selection (T0), with or without treatment with doxycycline after passaging in cell culture (ON/OFF) or transplantation and expansion in vivo (VON/VOFF).

Figure 38:
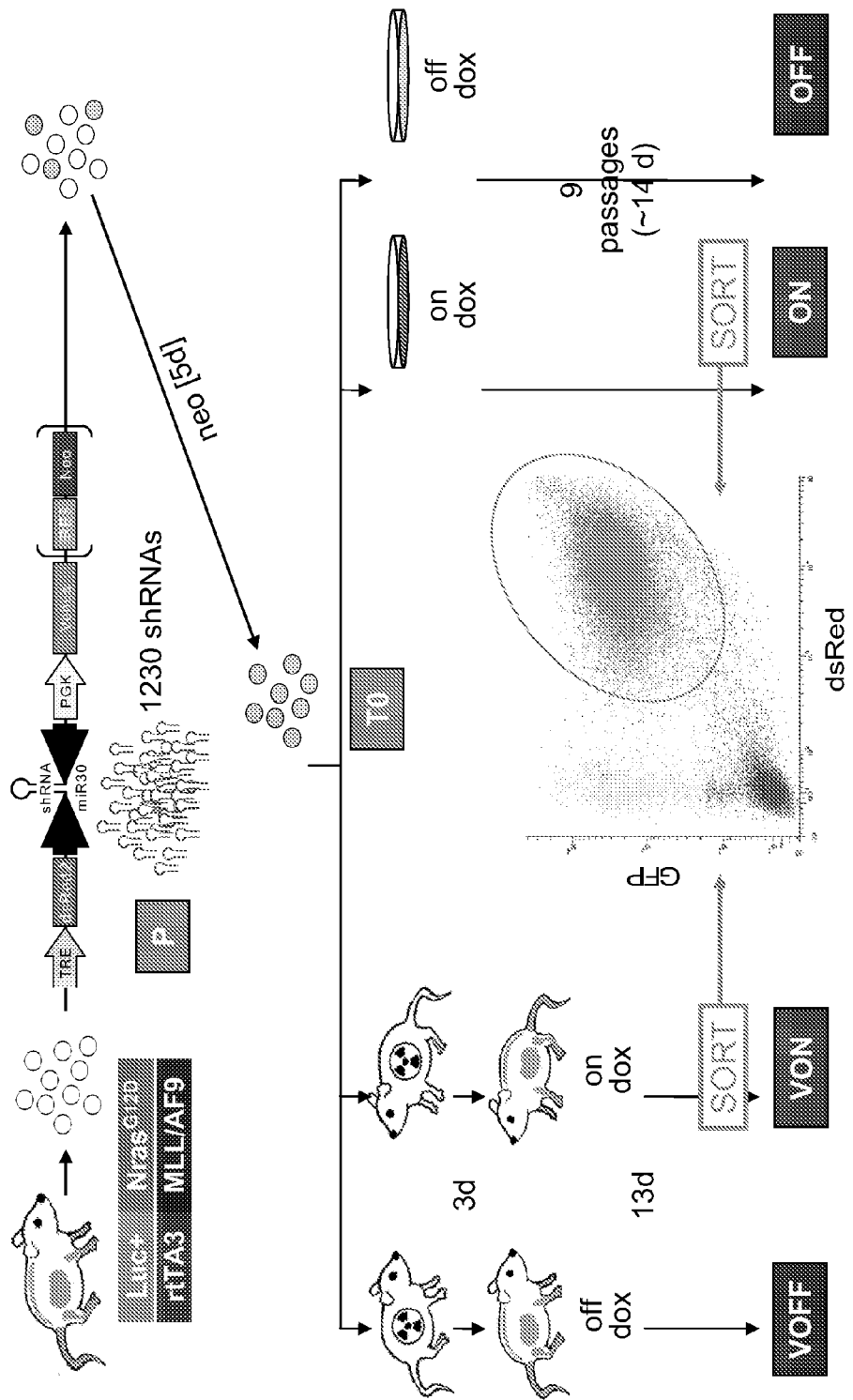

FIG. 38 shows a further schematic of the pooled negative selection screening method. In this method, samples on dox are sorted for shRNA expressing cells (Venus/dsRed double-positive) prior to DNA isolation and PCR to purify for cells that are exposed to specific shRNA effects. This step is critical to the success of screening and is facilitated by the use of TRMPV and tet-on competent cancer models.

Figure 39:
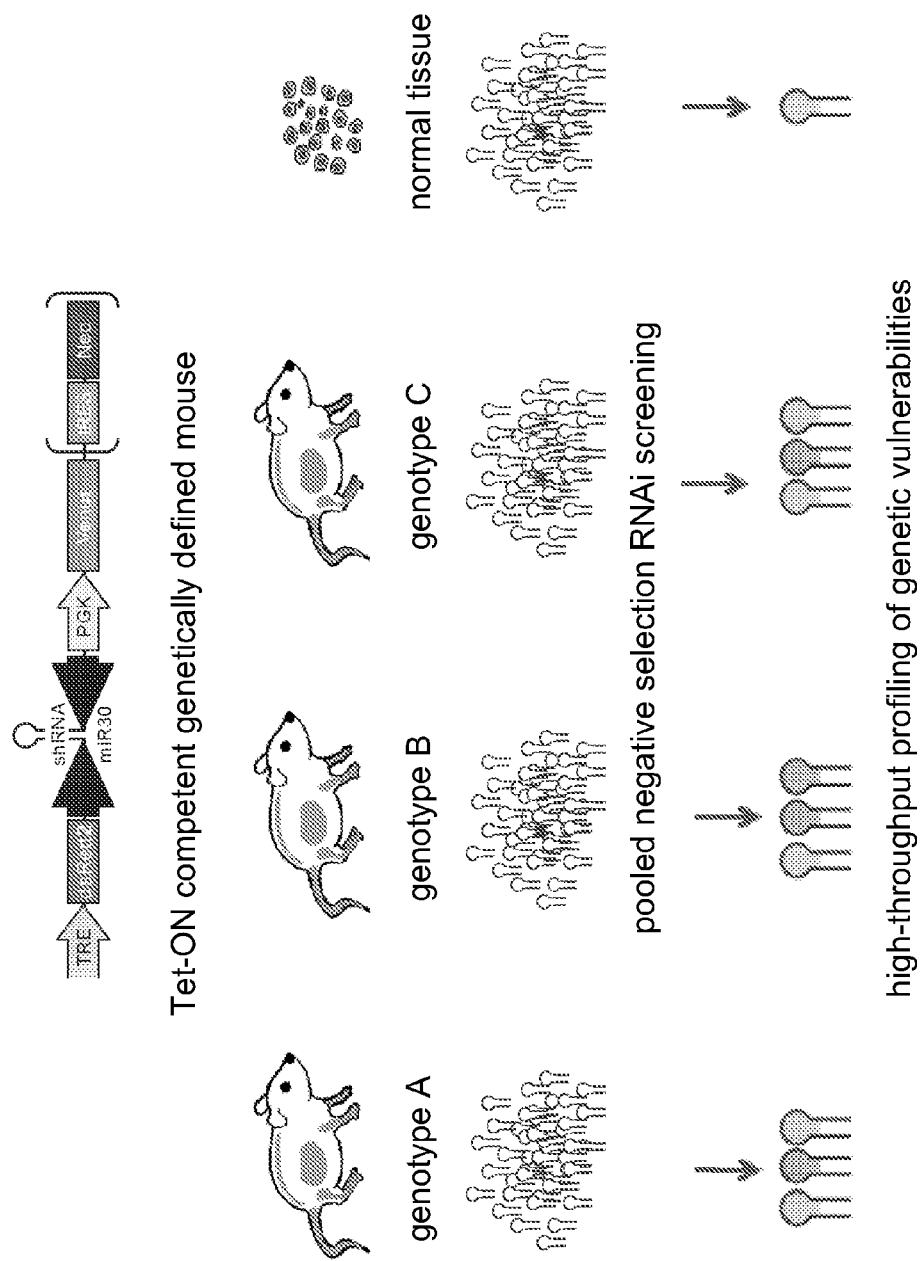

FIG. 39 shows a schematic of parallel pooled negative selection screening in different tet-on competent cancer models and normal reference cells. Such screens are focused on identifying shRNAs that specifically inhibit cancer cells, either generally or in certain genetic contexts.

FIG. 40 shows 64 shRNAs that were previously analyzed for inhibitory effects in MLL/AF9+Nras AML and Mefs and are used in the pooled negative selection screening method as controls.

FIG. 41 shows results of Solexa-deep sequencing of the TRMPV plasmid pool before addition of the 64 control shRNAs.

Figure 42:
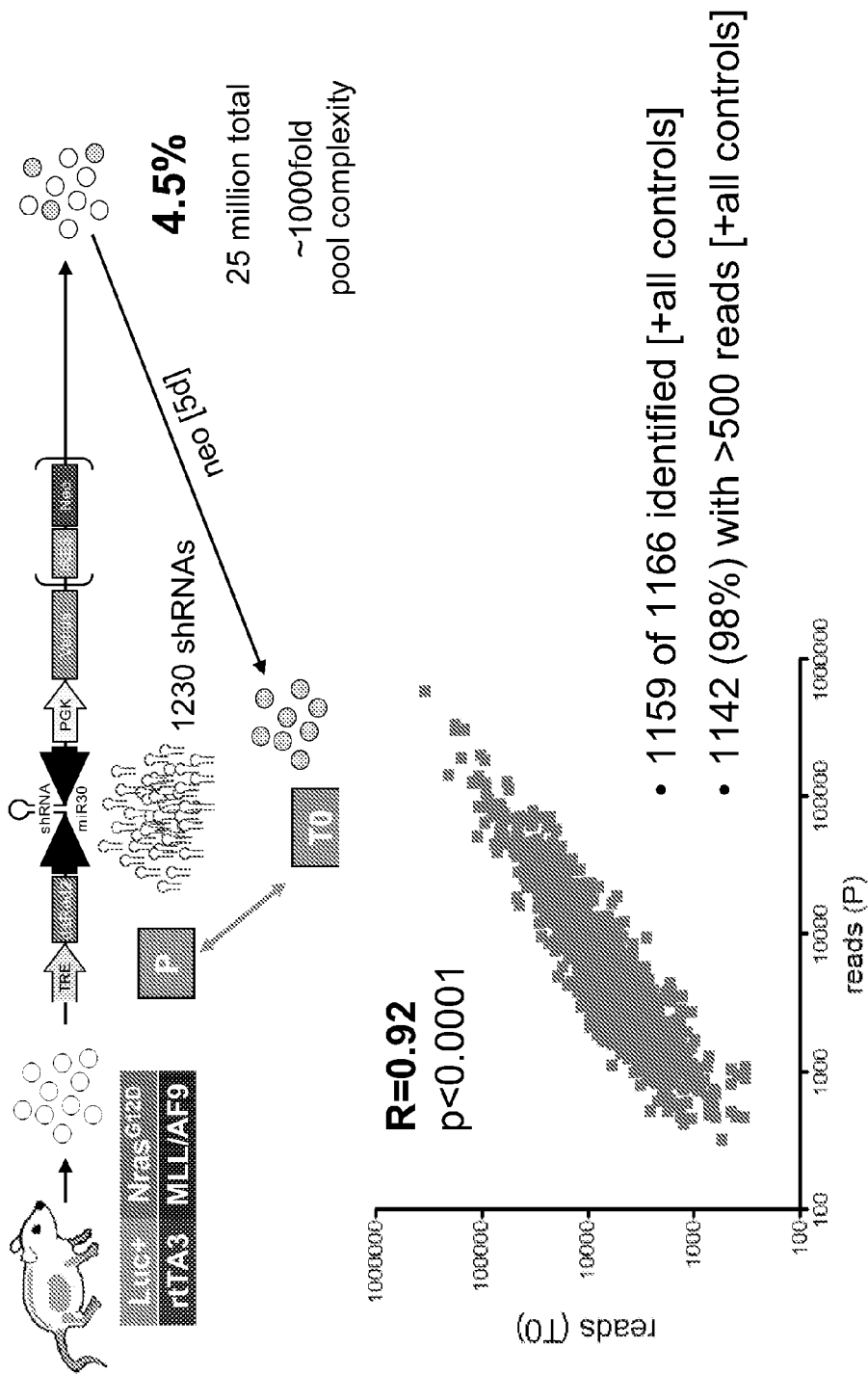

FIG. 42 shows a correlation plot of Solexa deep sequencing reads comparing the representation of individual shRNAs in the plasmid pool (P) and the transduced and selected cell population (T0). R denotes the Pearson product-moment correlation coefficient.

Figure 43:
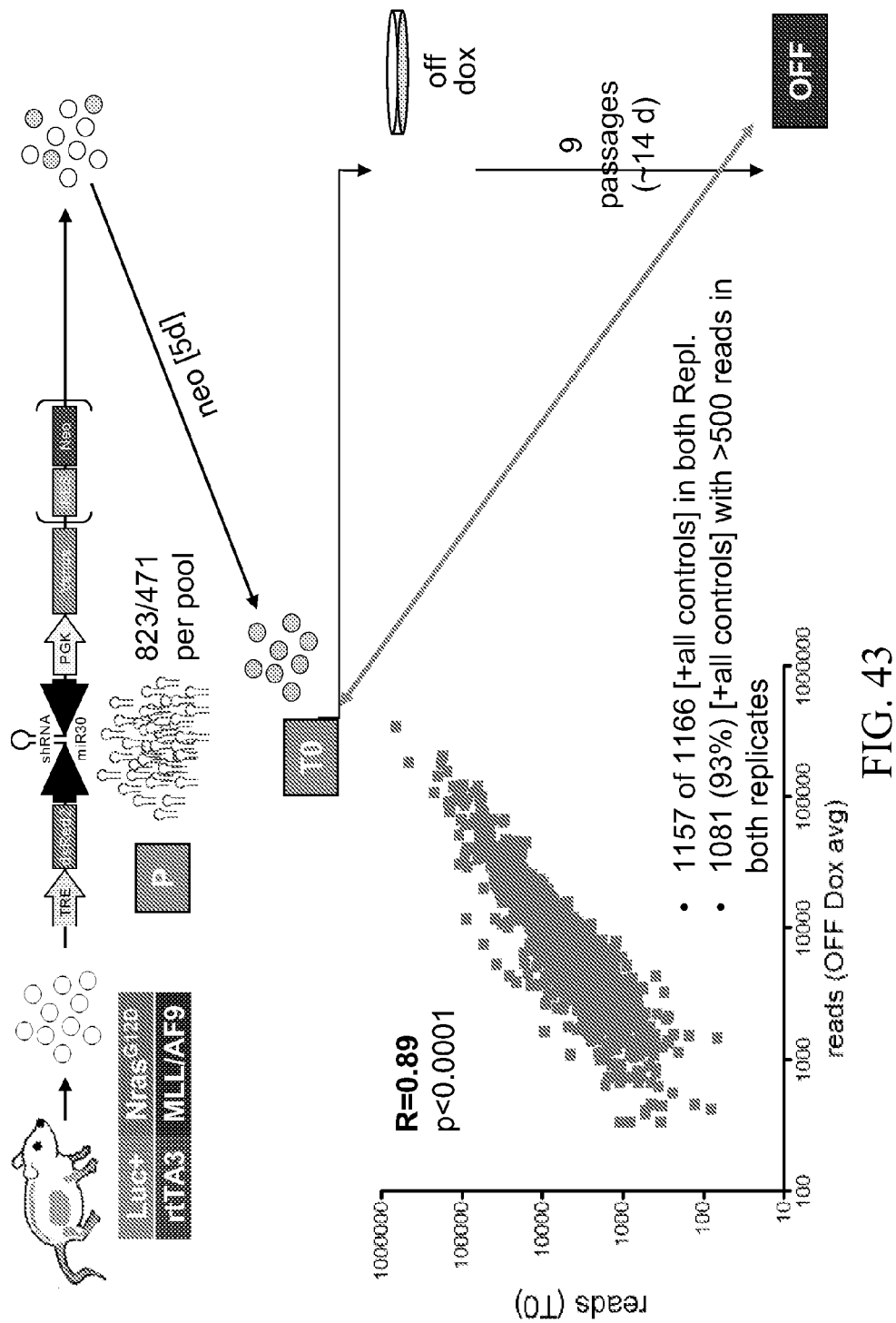

FIG. 43 shows a correlation plot of Solexa deep sequencing reads comparing the representation of individual shRNAs before (T0) and after nine passages in cell culture (OFF). R denotes the Pearson product-moment correlation coefficient.

Figure 44:
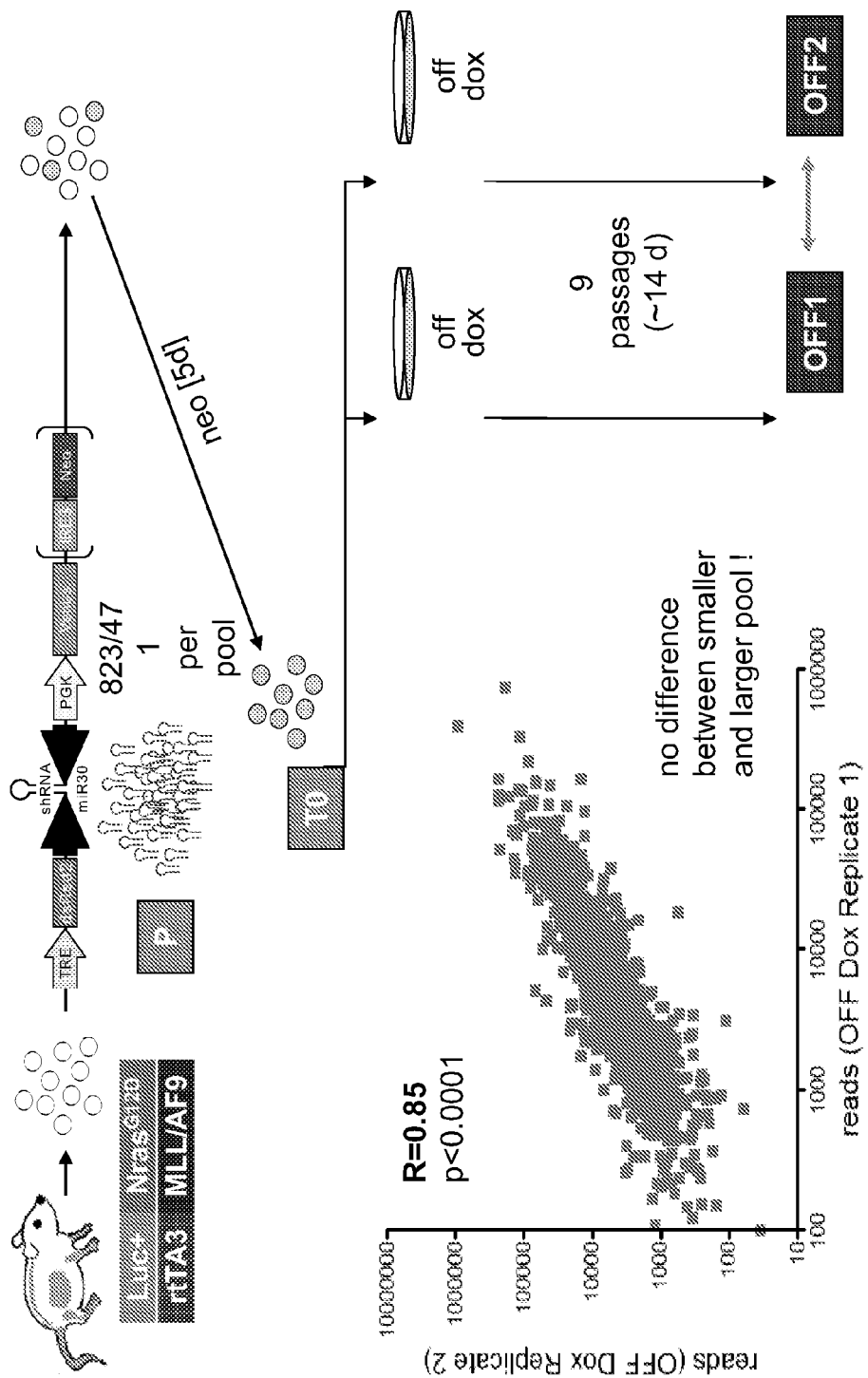

FIG. 44 shows a correlation plot of Solexa deep sequencing reads comparing the representation of individual shRNAs in two independent replicates after nine passages in cell culture (OFF1, OFF2). R denotes the Pearson product-moment correlation coefficient.

Figure 45:
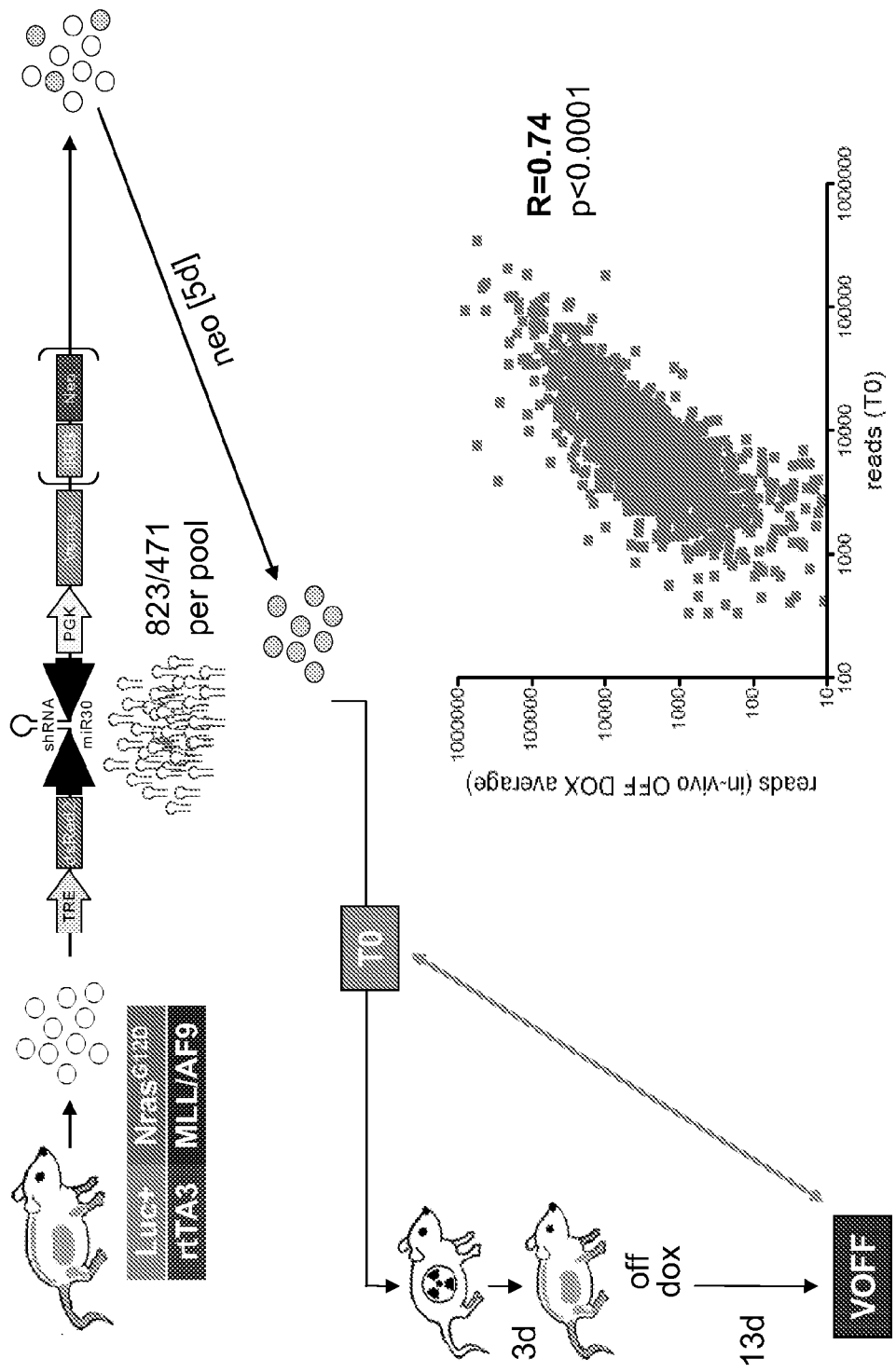

FIG. 45 shows a correlation plot of Solexa deep sequencing reads comparing the representation of individual shRNAs before (T0) and after transplantation into syngeneic recipient mice and leukemia development (VOFF). R denotes the Pearson product-moment correlation coefficient. R denotes the Pearson product-moment correlation coefficient.

Figure 46:
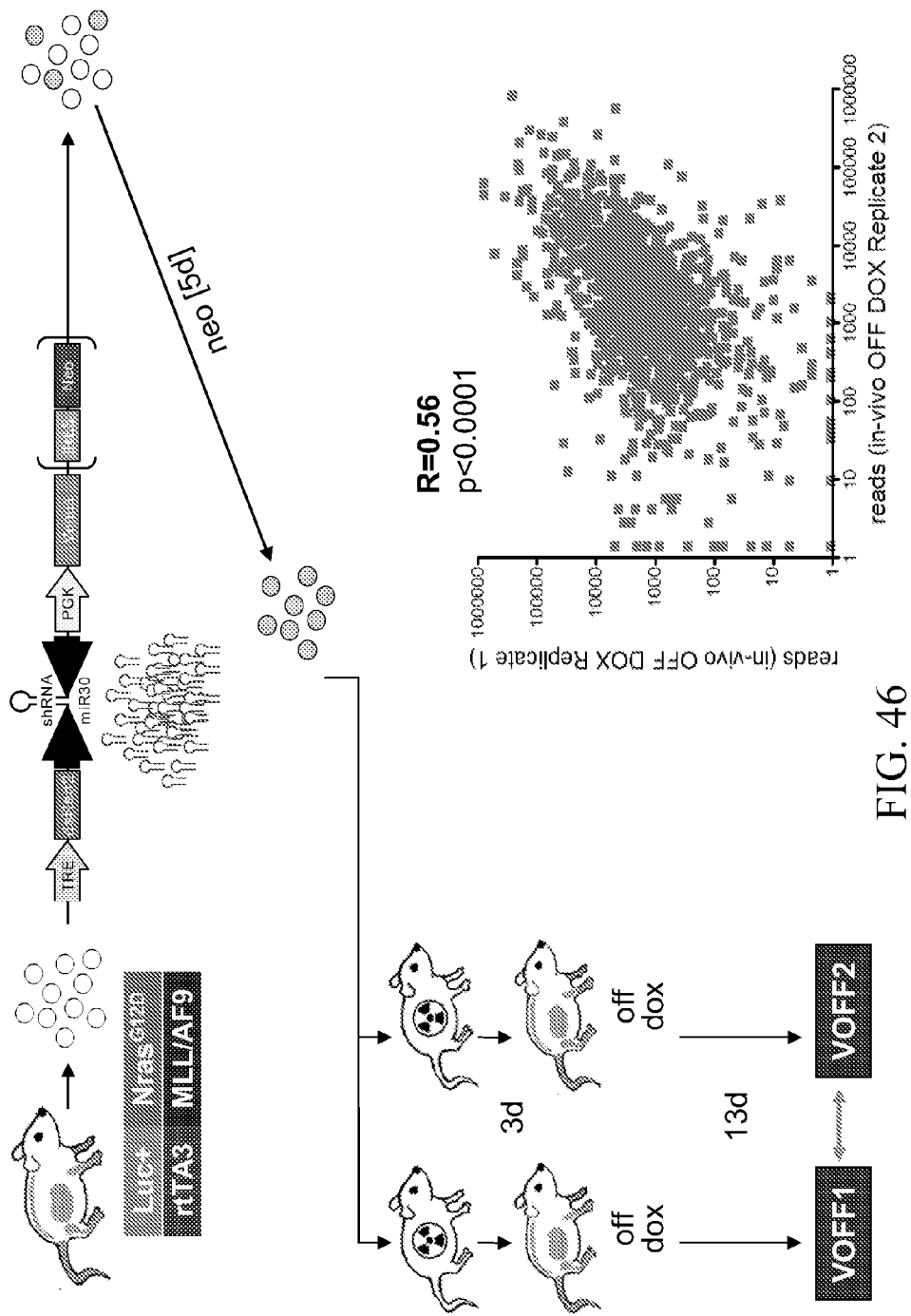

FIG. 46 shows a correlation plot of Solexa deep sequencing reads comparing the representation of individual shRNAs in two independent replicates after transplantation into syngeneic recipient mice and leukemia development (VOFF1, VOFF2). R denotes the Pearson product-moment correlation coefficient.

Figure 47:
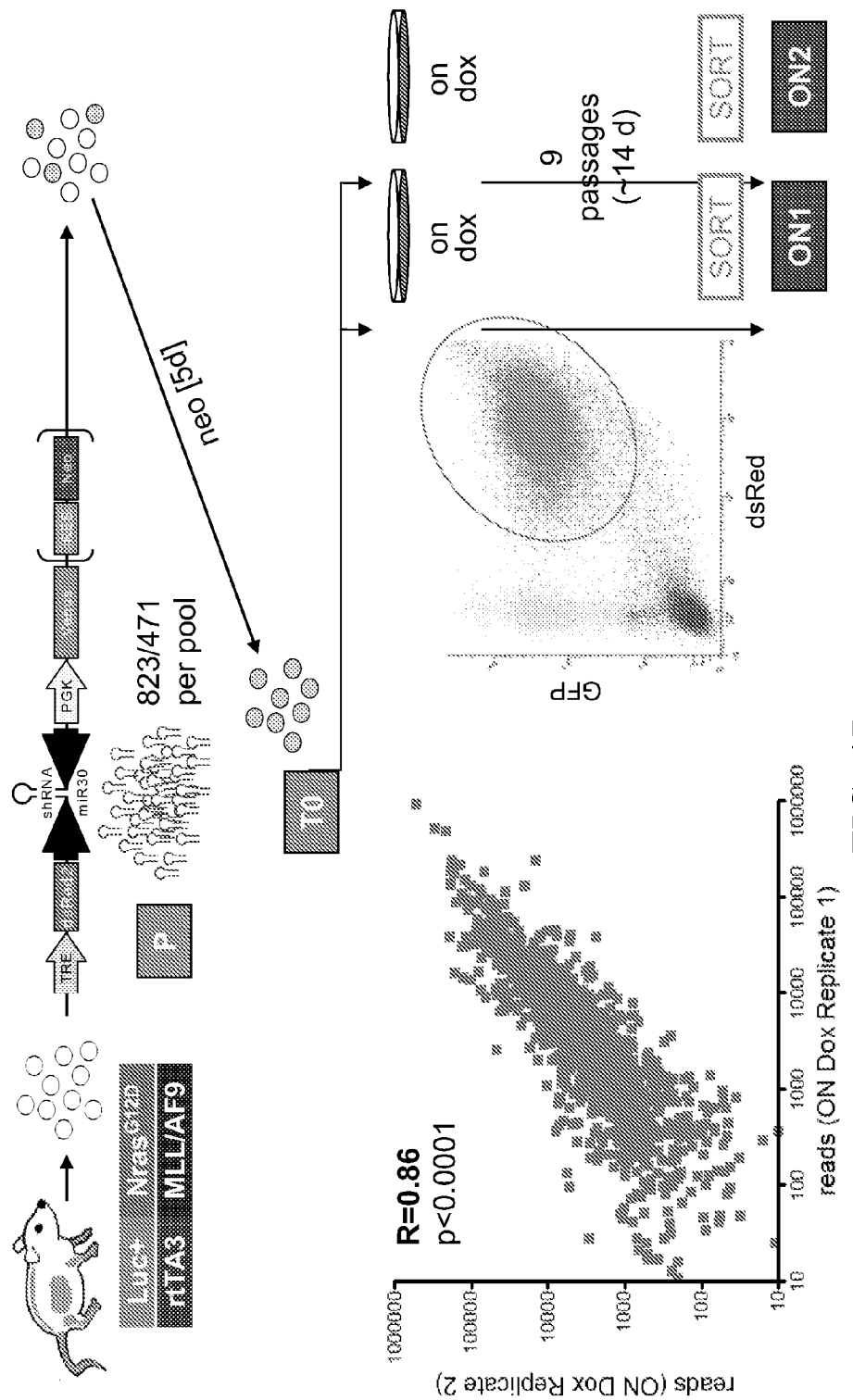

FIG. 47 shows a correlation plot of Solexa deep sequencing reads comparing the representation of individual shRNAs in two independent replicates sorted for shRNA expressing cells after nine passages in cell culture under doxycycline treatment (ON1, ON2). R denotes the Pearson product-moment correlation coefficient.

Figure 48:
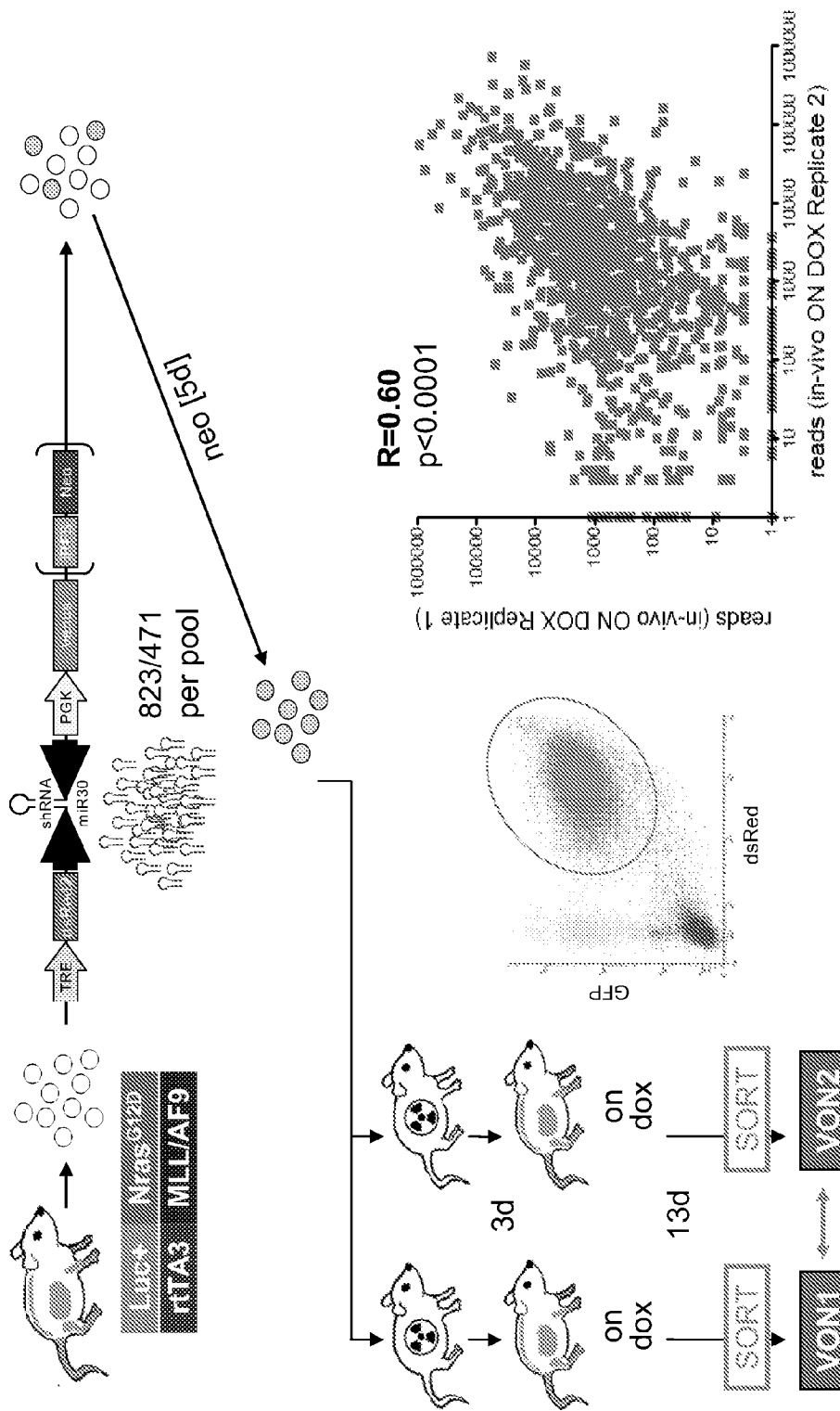

FIG. 48 shows a correlation plot of Solexa deep sequencing reads comparing the representation of individual shRNAs in two independent replicates after transplantation into syngeneic recipient mice, doxycycline treatment and leukemia development (VON1, VON2). Samples were harvested from leukemic mice and sorted for cells with sufficient shRNA expression. R denotes the Pearson product-moment correlation coefficient.

Figure 49:
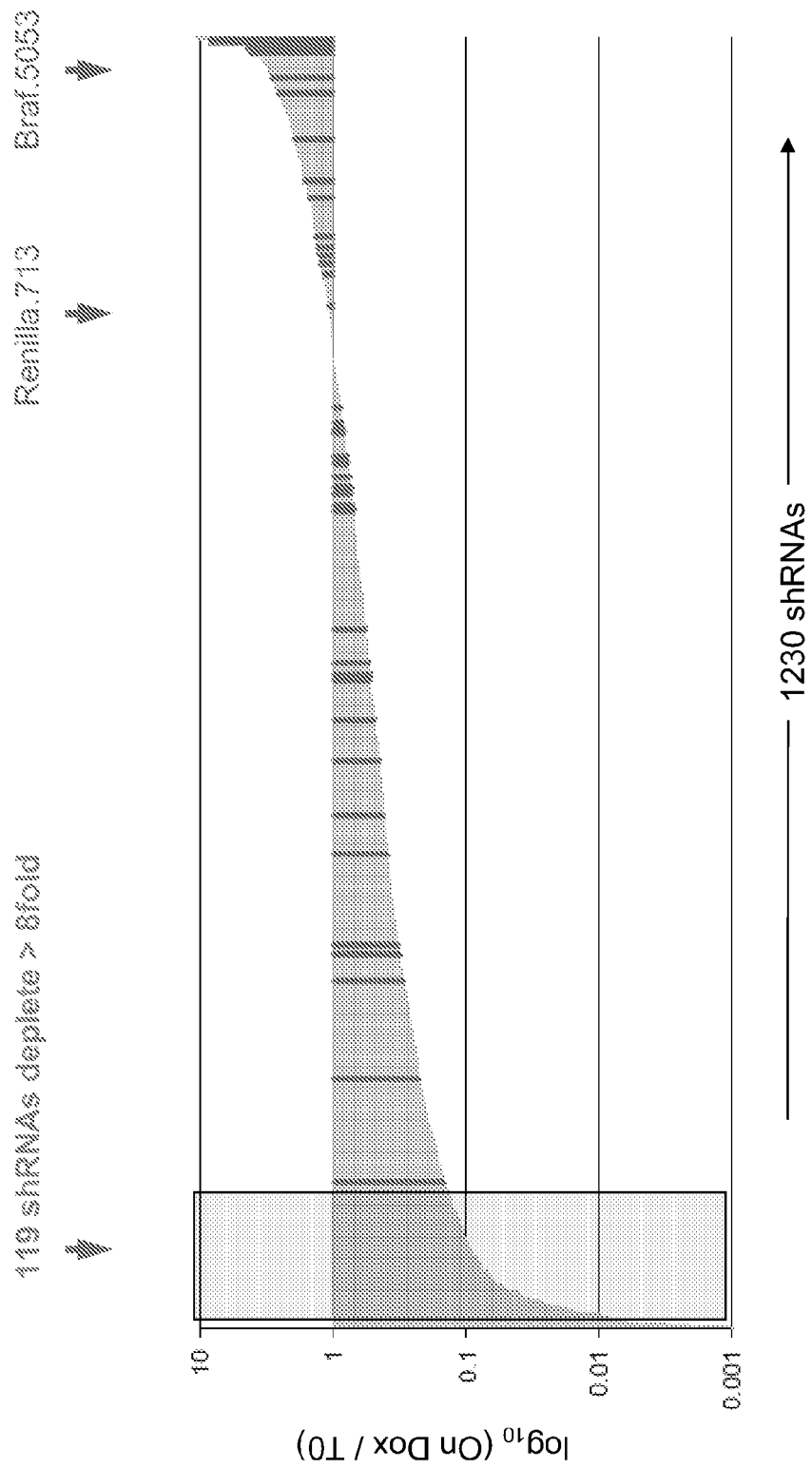

FIG. 49 shows the relative representation (read numbers in Solexa deep sequencing) in doxycycline treated MLL/AF9+ Nras leukemia samples (On Dox) compared to the initial representation (T0). Negative control shRNAs are indicated as dark bars. None of the negative control shRNAs falls into the scoring window of >8 fold depletion.

Figure 50:
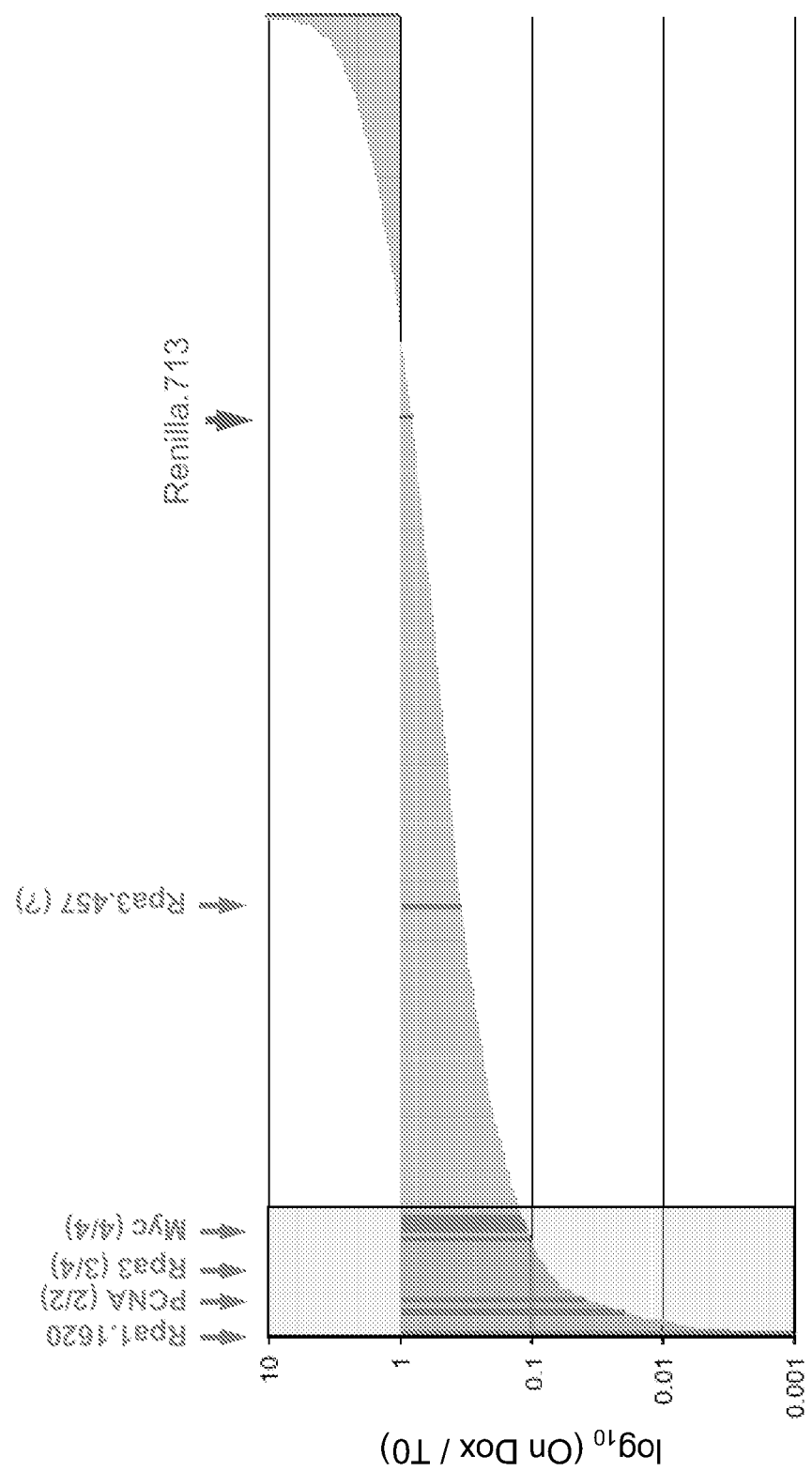

FIG. 50 shows the relative representation of generally lethal control shRNAs in doxycycline treated MLL/AF9+ Nras leukemia samples (On Dox) compared to the initial representation (T0). 10 out of 11 lethal shRNAs are found depleted more than 8 fold.

Figure 51:
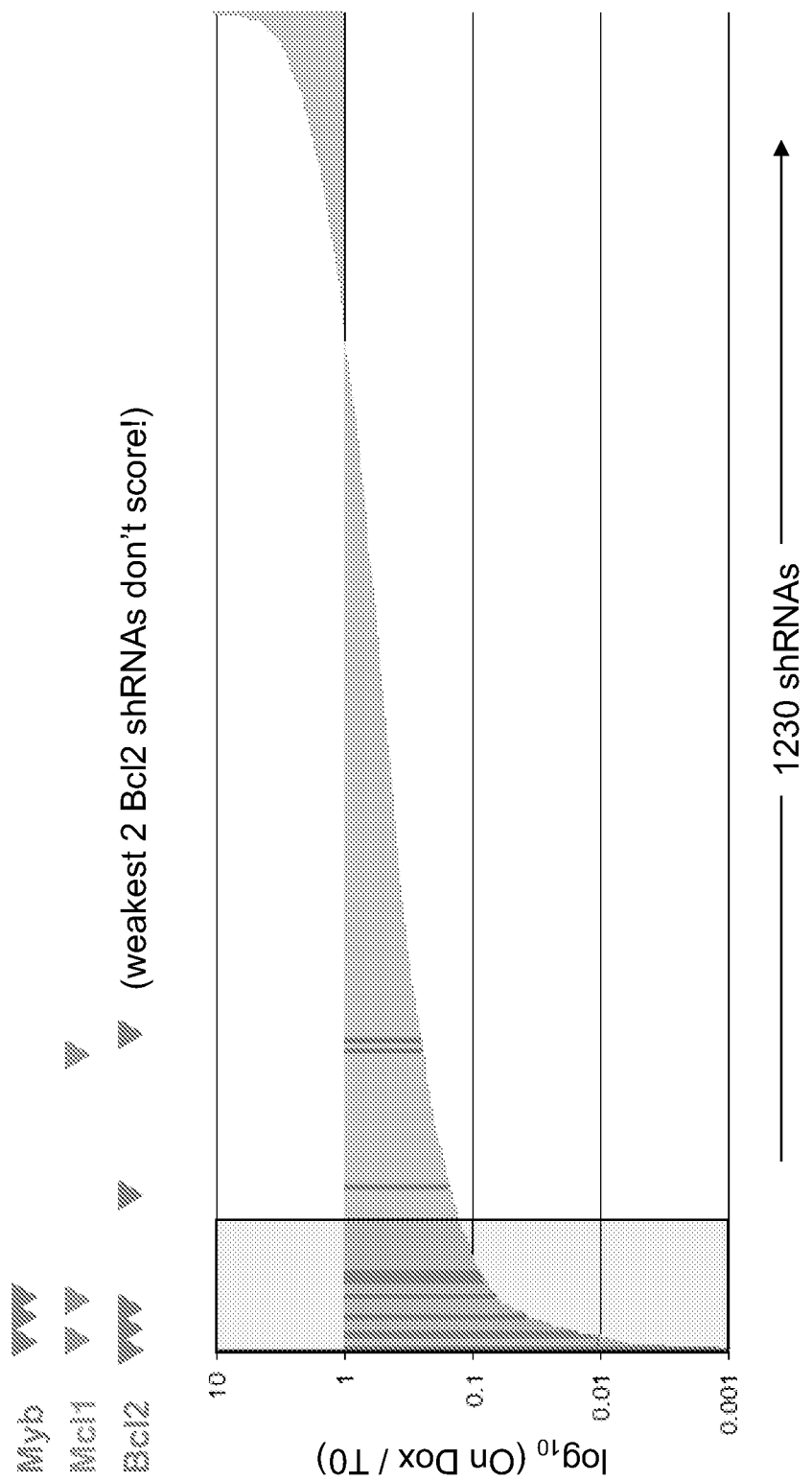

FIG. 51 shows the relative representation of shRNAs known to specifically deplete MLL/AF9+Nras leukemia in doxycycline treated leukemia samples (On Dox) compared to the initial representation (T0). 8 out of 11 of these shRNAs are found depleted more than 8 fold.

4. DETAILED DESCRIPTION OF THE INVENTION

RNAi technology enables specific suppression of the expression of virtually any gene. However, to obtain functional RNAi reagents for clinical applications, it is advantageous to identify a strategy for rational drug design that allows both gene targets and RNAi molecules to be functionally validated in a defined genetic context in vivo that reflects human disease. Here we provide a mouse model that can be used to design rational cancer therapies based on the particular genotype of cancer cells found in human cancers, and in particular, those found in human AML patients. Empirically, this model has demonstrated remarkable similarity with human AML patients in the genotype-response pattern to standard induction chemotherapy, implying that such a system can predict the behavior of therapeutic agents in the clinic.

We additionally provide defined, tet-on competent, mouse leukemia models expressing inducible shRNAs to identify particular RNAi molecules exhibiting the most potent in vivo efficacy for therapeutically curing chemoresistant leukemia. In particular, we apply tet-regulated in vivo RNAi to identify candidate drug target genes and RNAi molecules directed against such drug target genes for therapeutic treatment of chemoresistant AML and other leukemias. We additionally use these systems to further extend observations of in vitro RNAi screens and provide in vivo validation for drug target genes and RNAi molecules identified through such in vitro screens, in particular target genes encoding certain DNA replication proteins.

4.1 General Definitions

A "coding sequence" or a sequence "encoding" a particular molecule is a nucleic acid that is transcribed (in the case of DNA) or translated (in the case of mRNA) into a polypeptide or inhibitory RNA (e.g., an shRNA or an antisense), in vitro or in vitro, when operably linked to an appropriate regulatory sequence. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the coding sequence.

The term "gene" refers to a nucleic acid comprising an open reading frame encoding a polypeptide, including both exon and (optionally) intron sequences. The nucleic acid can also optionally include non-coding sequences such as promoter and/or enhancer sequences.

"Nucleic acid" refers to polynucleotides such as deoxyribonucleic acid (DNA) and ribonucleic acid (RNA). The term can include single-stranded and double-stranded polynucleotides.

"Operably linked" means that the coding sequence is linked to a regulatory sequence in a manner which allows expression of the coding sequence. Regulatory sequences include promoters, enhancers, and other expression control elements that are art-recognized and are selected to direct expression of the coding sequence.

A "small molecule" is a compound having a molecular weight less than about 2500 amu, in particular less than about 2000 amu, even more particular less than about 1500 amu.

In one embodiment, the molecular weight less is less than about 1000 amu, or less than about 750 amu.

A "subject" or "patient" can be a human or non-human animal.

A "transduced cell" is one that has been genetically modified. Genetic modification can be stable or transient. Methods of transduction (i.e., introducing vectors or constructs into cells) include, but are not limited to, liposome fusion (transposomes), viral infection, and routine nucleic acid transfection methods such as electroporation, calcium phosphate precipitation and microinjection. Successful transduction will have an intended effect in the transduced cell, such as gene expression, gene silencing, enhancing a gene target, or triggering target physiological event.

In one embodiment, "treating" means slowing, stopping or reversing the progression of a disease or disorder. "Treating" can also mean amelioration of symptoms associated with a disease or disorder.

"Vector" refers to a vehicle for introducing a nucleic acid into a cell. Vectors include, but are not limited to, plasmids, phagemids, viruses, bacteria, and vehicles derived from viral or bacterial sources. A "plasmid" is a circular, double-stranded DNA molecule. A useful type of vector for use in the present invention is a viral vector, wherein heterologous DNA sequences are inserted into a viral genome that can be modified to delete one or more viral genes or parts thereof. Certain vectors are capable of autonomous replication in a host cell (e.g., vectors having an origin of replication that functions in the host cell). Other vectors can be stably integrated into the genome of a host cell, and are thereby replicated along with the host genome.

4.2 RNAi Mechanism

Investigation of the role of DNA replication genes in modifying human cancer cell proliferation can be facilitated by specifically silencing a particular gene of interest. One such silencing means is through RNA interference (RNAi). RNAi stems from a phenomenon observed in plants and worms, whereby double-stranded RNA (dsRNA) blocks gene expression in a specific and post-transcriptional manner. The dsRNA is cleaved by an RNAse III enzyme "DICER" into a 21-23 nucleotide small interfering RNA (siRNA). These siRNAs are incorporated into an RNA-induced silencing complex (RISC) that identifies and silences RNA complementary to the siRNA. Without being bound by theory, RNAi appears to involve silencing of cytoplasmic mRNA by triggering an endonuclease cleavage, by promoting translation repression, or possibly by accelerating mRNA decapping (Valencia-Sanchez et al., 2006, *Genes & Devel.* 20: 515-524). Biochemical mechanisms of RNAi are currently an active area of research.

Three mechanisms of utilizing RNAi in mammalian cells have been described. The first is cytoplasmic delivery of siRNA molecules, which are either chemically synthesized or generated by DICER-digestion of dsRNA. These siRNAs are introduced into cells using standard transfection methods. The siRNAs enter the RISC to silence target mRNA expression.

The second mechanism is nuclear delivery, via viral vectors, of gene expression cassettes expressing a short hairpin RNA (shRNA). The shRNA is modeled on micro interfering RNA (miRNA), an endogenous trigger of the RNAi pathway (Lu et al., 2005, *Advances in Genetics* 54: 117-142, Fewell et al., 2006, *Drug Discovery Today* 11: 975-982). The endogenous RNAi pathway is comprised of three RNA intermediates: a long, largely single-stranded primary miRNA transcript (pri-mRNA); a precursor miRNA transcript having a stem-and-loop structure and derived from the pri-mRNA (pre-miRNA); and a mature miRNA. The miRNA is transcribed by an RNA polymerase II promoter into the pri-mRNA transcript, which is then cleaved to form the pre-miRNA transcript (Fewell et al., 2006). The pre-miRNA is transported to the cytoplasm and is cleaved by DICER to form mature miRNA. miRNA then interacts with the RISC in the same manner as siRNA. shRNAs, which mimic pre-miRNA, are transcribed by RNA Polymerase II or III as single-stranded molecules that form stem-loop structures. Once produced, they exit the nucleus, are cleaved by DICER, and enter the RISC as siRNAs.

The third mechanism is identical to the second mechanism, except that the shRNA is modeled on primary miRNA (shRNAmir), rather than pre-miRNA transcripts (Fewell et al., 2006). An example is the miR-30 miRNA construct. The use of this transcript produces a more physiological shRNA that reduces toxic effects. The shRNAmir is first cleaved to produce shRNA, and then cleaved again by DICER to produce siRNA. The siRNA is then incorporated into the RISC for target mRNA degradation.

To date, distinct forms of RNA silencing have been found to regulate gene expression, to mediate antiviral responses, to organize chromosomal domains, and to restrain the spread of selfish genetic elements. For example, miRNAs derived from dsRNA precursors regulate gene expression in somatic cells by reducing translation and stability of protein-coding mRNAs.

The primary step in miRNA biogenesis is the nuclear cleavage of the "primary micro RNA" (pri-miRNA), liberating an approximately 70 nucleotide (nt) stem-loop intermediate known as "micro RNA precursor" (pre-miRNA). This processing step is performed by the RNase III endonuclease Drosha, in conjunction with the dsRNA-binding protein "DiGeorge syndrome Critical Region gene 8" (DGCR8) in humans (Pasha in *Drosophila*), leading to 5' monophosphates and ~2 nt 3' overhangs, characteristic for RNase III endonucleases.

The pre-miRNAs are then actively transported to the cytoplasm by Exportin-5 and the Ran-GTP cofactor. Subsequently, the mature miRNAs are excised by another RNase III endonuclease Dicer, acting together with the dsRNA-binding protein tar-binding protein (TRBP) in humans or Loquacious (Logs) in flies. Depending on the species, the resulting short dsRNAs are about 21 to 28 nts in length.

For mRNA degradation, translational repression, or deadenylation, mature miRNAs or siRNAs are loaded into the RNA Induced Silencing Complex (RISC) by the RISC-loading complex (RLC). Subsequently, the guide strand leads the RISC to cognate target mRNAs in a sequence-specific manner and the Slicer component of RISC hydrolyses the phosphodiester bound coupling the target mRNA nucleotides paired to nucleotide 10 and 11 of the RNA guide strand. Slicer forms together with distinct classes of small RNAs the RNAi effector complex, which is the core of RISC. Therefore, the "guide strand" is that portion of the double-stranded RNA that associates with RISC, as opposed to the "passenger strand," which is not associated with RISC. The target sequence contained in a reporter construct of the present invention is at least partially complementary to at least a portion of the guide strand.

To further accelerate the study of cancer genes in vivo, stable RNAi technology has been used to successfully identify and suppress target genes associated with tumorigenesis. For example, expression of microRNA-based shRNA specific to Trp53 produces "potent, stable, and regulatable gene knock-down in cultured cells ... even when present at a single copy in the genome" (Dickins et al., 2005, *Nat. Genet.* 37: 1289-1295). Tumors induced by the p53 knockdown regress upon re-expression of Trp53. (Dickins et al., 2005). The suppression of the Trp53 gene expression by shRNA is also possible in stem cells and reconstituted organs derived from those cells (Hemann et al., 2003, *Nat. Genet.* 33: 396-400). Moreover, the extent of inhibition of p53 function by the shRNA correlates with the type and severity of subsequent lymphomagenesis (Hemann et al., 2003).

RNAi is a powerful tool for in vitro and in vivo studies of gene function and for therapy in both human and veterinary contexts. Depending on the application, any type of RNAi, including but not limited to si- or shRNAs, can be used as RNAi triggers. siRNAs have the advantage of being directly transfectable, chemically synthesized oligonucleotides that circumvent the need for cloning. siRNAs enter the miRNA processing pathway at a later stage, and bypass Drosha processing, Exportin-5 export, and, depending on their size, Dicer cleavage. However, when the objective is therapeutic, it can be useful to use miRNA-based shRNAs as they tend to yield more effective silencing (Chang et al., *Nature Methods*, 2006, 3: 707-714). In addition, the small size of si- and shRNAs, compared with traditional antisense molecules, prevents activation of the dsRNA-inducible interferon system present in mammalian cells. This helps avoid the non-specific phenotypes normally produced by dsRNA larger than 30 base pairs in somatic cells. See, e.g., Elbashir et al., 2002, *Methods Enzymol.* 26: 199-213; McManus and Sharp, 2002, *Nature Reviews* 3: 737-747; Hannon, 2002, *Nature* 418: 244-251; Brummelkamp et al., 2002, *Science* 296: 550-553; Tuschl, 2002, *Nature Biotechnology* 20: 446-448; U.S. Publication No. 2002/0086356; WO 99/32619; WO 01/36646; and WO 01/68836.

As discussed above, RNAi can be achieved using microRNA-based shRNAs that can be potent triggers of the RNAi machinery and are capable of efficiently suppressing gene expression when expressed from a single copy in the genome (Dickins et al., 2005; Silva et al., 2005, *Nat. Genet.* 37: 1281-1288). This technology has been used in the mosaic mouse model of hepatocellular carcinoma (HCC) to show that stable knockdown of the Trp53 tumor suppressor by RNAi can mimic Trp53 gene loss in vivo (Zender et al., 2005), and that regulated RNAi can reversibly modulate endogenous p53 expression to implicate the role of p53 loss in tumor maintenance (Xue et al., 2007, *Nature* 445: 656-660). Similar approaches have been used to rapidly validate Deleted in Liver Cancer 1 (DLC1) as a potent tumor suppressor gene (Xue et al., 2008, *Genes Devel.* 22: 1439-1444).

RNAi is possible via direct introduction of siRNA into the cell, or by gene expression cassettes expressing shRNA or shRNAmir. shRNA and shRNAmir are modeled on intermediate constructs of miRNA. Both are cleaved by DICER to form siRNAs and interact with the RISC complex in the same manner as siRNA.

4.3 RNAi Molecules

Interfering RNA or small inhibitory RNA (RNAi) molecules include short interfering RNAs (siRNAs), repeat-associated siRNAs (rasiRNAs), and micro-RNAs (miRNAs) in all stages of processing, including shRNAs, pri-miRNAs, and pre-miRNAs. These molecules have different origins: siRNAs are processed from double-stranded precursors (dsRNAs) with two distinct strands of base-paired RNA; siRNAs that are derived from repetitive sequences in the genome are called rasiRNAs; miRNAs are derived from a single transcript that forms base-paired hairpins. Base pairing of siRNAs and miRNAs can be perfect (i.e., completely complementary) or imperfect, including bulges in the duplex region.

RNAi molecules useful in this invention can be, without limitation, shRNA, siRNA, piwi-interacting RNA (piRNA), micro RNA (miRNA), double-stranded RNA (dsRNA), antisense RNA, or any other RNA species that can be cleaved inside a cell to form interfering RNAs. As used herein, siRNAs useful in this invention include, without limitation, modified siRNAs, including siRNAs with enhanced stability in vivo. Modified siRNAs include molecules containing nucleotide analogues, including those molecules having additions, deletions, and/or substitutions in the nucleobase, sugar, or backbone; and molecules that are cross-linked or otherwise chemically modified. (See Crooke, U.S. Pat. Nos. 6,107,094 and 5,898,031; Elmen et al., U.S. Publication Nos. 2008/0249039 and 2007/0191294; Manoharan et al., U.S. Publication No. 2008/0213891; MacLachlan et al., U.S. Publication No. 2007/0135372; and Rana, U.S. Publication No. 2005/0020521; all of which are hereby incorporated by reference.)

As used herein, an "shRNA molecule" includes a conventional stem-loop shRNA, which forms a precursor miRNA (pre-miRNA). "shRNA" also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. When transcribed, an shRNA forms a primary miRNA (pri-miRNA) or a structure very similar to a natural pri-miRNA. The pri-miRNA is subsequently processed by Drosha and its cofactors into pre-miRNA. Therefore, the term "shRNA" includes pri-miRNA (shRNA-mir) molecules and pre-miRNA molecules.

A "stem-loop structure" refers to a nucleic acid having a secondary structure that includes a region of nucleotides which are known or predicted to form a double strand or duplex (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches.

In some instances the precursor miRNA molecule can include more than one stem-loop structure. The multiple stem-loop structures can be linked to one another through a linker, such as, for example, a nucleic acid linker, a miRNA flanking sequence, other molecule, or some combination thereof.

MicroRNAs are endogenously encoded RNA molecules that are about 22-nucleotides long and generally expressed in a highly tissue- or developmental-stage-specific fashion and that post-transcriptionally regulate target genes. More than 200 distinct miRNAs have been identified in plants and animals. These small regulatory RNAs are believed to serve important biological functions by two prevailing modes of action: (1) by repressing the translation of target mRNAs, and (2) through RNA interference (RNAi), that is, cleavage and degradation of mRNAs. In the latter case, miRNAs function analogously to small interfering RNAs (siRNAs). The highly tissue-specific or developmentally regulated expression of miRNAs is likely key to their predicted roles in eukaryotic development and differentiation. Analysis of the endogenous role of miRNAs is facilitated by techniques that allow the regulated over-expression or inappropriate expression of authentic miRNAs in vivo. The ability to regulate the expression of siRNAs will greatly increase their utility both in cultured cells and in vivo. Thus, one can design and express artificial miRNAs based on the features of existing miRNA genes.

Short hairpin RNAs can be designed to mimic endogenous miRNAs. Many miRNA intermediates can be used as models for shRNA or shRNAmir, including without limitation a miRNA comprising a backbone design of miR-15a, -16, -19b, -20, -23a, -27b, -29a, -30b, -30c, -104, -132s, -181, -191, -223 (see U.S. Publication No. 2005/0075492). The miR-30 natural configuration has proven especially beneficial in producing mature synthetic miRNAs. miR30-based shRNAs and shRNAmirs have complex folds, and, compared with simpler stem/loop style shRNAs, are more potent at inhibiting gene expression in transient assays. Moreover, they are associated with less toxic effects in cells.

In a certain embodiment, shRNA molecules are designed based on the human miR-30 sequence, redesigned to allow expression of artificial shRNAs by substituting the stem sequences of the pri-miR-30 with unrelated base-paired sequences (Siolas et al., 2005, *Nat. Biotech.* 23: 227-231; Silva et al., 2005, *Nat. Genet.* 37: 1281-1288); Zeng et al. (2002), *Molec. Cell* 9: 1327-1333). The natural stem sequence of the miR-30 can be replaced with a stem sequence from about 16 to about 29 nucleotides in length, in particular from about 19 to 29 nucleotides in length. The loop sequence can be altered such that the length is from about 3 to about 23 nucleotides. In one embodiment, the stem of the shRNA molecule is about 22 nucleotides in length. In another embodiment, the stem is about 29 nucleotides in length. Thus, the invention can be practiced using shRNAs that are synthetically produced, as well as microRNA (miRNA) molecules that are found in nature and can be remodeled to function as synthetic silencing short hairpin RNAs.

"RNAi-expressing construct" or "RNAi construct" is a generic term that includes nucleic acid preparations designed to achieve an RNA interference effect. An RNAi-expressing construct comprises an RNAi molecule that can be cleaved in vivo to form an siRNA. For example, an RNAi construct is an expression vector capable of giving rise to an siRNA in vivo. Exemplary methods of making and delivering long or short RNAi constructs can be found, for example, in WO01/68836 and WO01/75164.

In certain embodiments of the invention, such as those directed to therapeutic applications, it may be desirable to use siRNAs, including modified siRNAs, based on the sequences of the shRNA sequences disclosed herein. For example, it may be desirable to use an siRNA that binds to the same target sequence as the shRNA sequences disclosed herein. One of skill in the art can readily design such siRNAs, for example basing the siRNA sequence on any or all parts of the shRNA sequence that is complementary to or binds to the target sequence.

4.4 Vectors

The vectors described in International application no. PCT/US2008/081193 and methods of making and using the vectors are incorporated herein by reference.

shRNAs can be expressed from vectors to provide sustained silencing and high yield delivery into almost any cell type. In a certain embodiment, the vector is a viral vector. Exemplary viral vectors include retroviral, including lentiviral, adenoviral, baculoviral and avian viral vectors. The use of viral vector-based RNAi delivery not only allows for stable single-copy genomic integrations but also avoids the non-sequence specific response via cell-surface toll-like receptor 3 (TLR3), which has raised many concerns for the specificity of siRNA mediated effects. In one embodiment of the present invention, a pool of shRNAs is introduced into murine HSCs using a vector known in the art.

Retroviruses from which the retroviral plasmid vectors can be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector can be employed to transduce packaging cell lines to form producer cell lines. Examples of packaging cells which can be transfected include, but are not limited to, the PE501, PA317, R-2, R-AM, PA12, T19-14x, VT-19-17-H2, RCRE, RCRIP, GP+E-86, GP+envAm12, and DAN cell lines as described in Miller, Human Gene Therapy 1:5-14 (1990), which is incorporated herein by reference in its entirety. The vector can transduce the packaging cells through any means known in the art. A producer cell line generates infectious retroviral vector particles which include polynucleotide encoding a DNA replpication protein. Such retroviral vector particles then can be employed, to transduce eukaryotic cells, either in vitro or in vivo. The transduced eukaryotic cells will express a DNA replpication protein.

In certain embodiments, cells can be engineered using an adeno-associated virus (AAV). AAVs are naturally occurring defective vimses that require helper viruses to produce infectious particles (Muzyczka, N., Curr. Topics in Microbiol. Immunol. 158:97 (1992)). It is also one of the few viruses that can integrate its DNA into nondividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377. For example, an AAV vector can include all the sequences necessary for DNA replication, encapsidation, and host-cell integration. The recombinant AAV vector can be transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct. These viral particles are then used to transduce eukaryotic cells.

Essentially any method for introducing a nucleic acid construct into cells can be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle can be used to accomplish both efficient introduction of an expression construct into the cell and transcription of the encoded shRNA. Other methods known in the art for introducing nucleic acids to cells can be used, such as lipid-mediated carrier transport, chemical mediated transport, such as calcium phosphate, and the like. Thus the shRNA-encoding nucleic acid construct can be introduced along with components that perform one or more of the following activities: enhance RNA uptake by the cell, promote annealing of the duplex strands, stabilize the annealed strands, or otherwise increase inhibition of the target gene.

Expression of endogenous miRNAs is controlled by RNA polymerase II (Pol II) promoters. It has been shown that shRNAs are also most efficiently driven by Pol II promoters, as compared to RNA polymerase III promoters (Dickins et al., 2005, Nat. Genet. 39: 914-921). Therefore, in a certain embodiment, the coding sequence of the RNAi molecule is controlled by an inducible promoter or a conditional expression system, including, without limitation, RNA polymerase type II promoters. Examples of useful promoters in the context of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types. A certain embodiment uses tetracycline-responsive promoters, one of the most effective conditional gene expression systems in in vitro and in vivo studies. See International Patent Application PCT/US2003/030901 (Publication No. WO 2004-029219 A2) and Fewell et al., 2006, Drug Discovery Today 11: 975-982, for a description of inducible shRNA.

Tetracycline (Tet)-responsive promoters can be used for in vitro and in vivo studies. Tet-On is a variation of the Tet-Off system (Gossen and Bujard, (1992), Proc. Natl. Acad. Sci. USA, 89:5547-5551), and features a modified Tet repressor that has reversed DNA binding properties when compared to the wild-type Tet-repressor (tetR) encoded in the Tn10 Tet-resistance operon of E. coli. The reverse tetracycline-controlled transactivator (rtTA) is made from a Tet-repressor fused to the activating domain of virion protein 16 (VP16) of herpes simplex virus (HSV). In contrast to the Tet-Off system, the Tet-On system is optimized for induction by the Tet-analogue doxycycline (Dox) only.

Expression of rtTA can be driven by a constitutive promoter of choice. When rtTA is expressed, the presence of Dox leads to a conformational change and binding of rtTA-Dox to the Tet operator sequence (tetO) of the Tet-resistance operon. The rtTA3 is an improved variant of the reverse tet-trans activator, showing a more sigmoidal induction curve, which is a result of less background activity Off-Dox (tet-On system) and full induction of transgene expression at lower doxycycline (Dox) concentrations (Urlinger et al., (2000), Proc. Natl. Acad. Sci. U.S.A. 97, 7963-7968). Seven serial tetO sequences were fused to a minimal cytomegalovirus (CMV) promoter and termed the Tet-responsive element (TRE). The binding of rtTA-Dox, therefore, induces the expression of a gene of interest from the minimal CMV promoter. Thus, by placing an shRNA under the control of the TRE, the expression of the RNAi molecule is inducible by the addition of Dox.

To facilitate the monitoring of the target gene knockdown and the formation and progression of a cancer, cells harboring the RNAi-expressing construct can additionally comprise a marker or reporter construct, such as a fluorescent construct. The reporter construct can express a marker, such as green fluorescent protein (GFP), enhanced green fluorescent protein (EGFP), *Renilla Reniformis* green fluorescent protein, GFPmut2, GFPuv4, yellow fluorescent protein (YFP), such as VENUS, enhanced yellow fluorescent protein (EYFP), cyan fluorescent protein (CFP), enhanced cyan fluorescent protein (ECFP), blue fluorescent protein (BFP), enhanced blue fluorescent protein (EBFP), citrine and red fluorescent protein from discosoma (dsRED). Other suitable detectable markers include chloramphenicol acetyltransferase (CAT), luminescent proteins such as luciferase lacZ (β-galactosidase) and horseradish peroxidase (HRP), nopaline synthase (NOS), octopine synthase (OCS), and alkaline phosphatase. The marker gene can be separately introduced into the cell harboring the shRNA construct (e.g., co-transfected, etc.). Alternatively, the marker gene can be on the shRNA construct, and the marker gene expression can be controlled by the same or a separate translation unit, for example, by an IRES (internal ribosomal entry site). In a certain embodiment, the marker is a yellow fluorescent protein (VENUS). In some embodiments, the vector can be an RNAi vector (e.g., TRMPV) shown in FIG. 5.

Reporters can also be those that confer resistance to a drug, such as neomycin, ampicillin, bleomycin, chloramphenicol, gentamycin, hygromycin, kanamycin, lincomycin, methotrexate, phosphinothricin, puromycin, doxycycline, and tetracyclin. Reporters can also be lethal genes, such as herpes simplex virus-thymidine kinase (HSV-TK) sequences, as well as sequences encoding various toxins including the diphtheria toxin, the tetanus toxin, the cholera toxin and the pertussis toxin. A further negative selection marker is the hypoxanthine-guanine phosphoribosyl transferase (HPRT) gene for negative selection in 6-thioguanine.

To facilitate the quantification of specific shRNAs in a complex population of cells infected with a library of shRNAs, each shRNA construct can additionally comprise a barcode. A barcode is a unique nucleotide sequence (generally a 19-mer), linked to each shRNA. The barcode can be used to monitor the abundance of each shRNA via micoarray hybridization (Fewell et al., 2006, *Drug Discovery Today* 11: 975-982). In a certain embodiment, each shRNA construct also comprises a unique barcode. For more information on the use of barcodes in shRNA pooled analyses, see WO 04/029219, Bernards et al., 2006, *Nature Methods* 3: 701-706, and Chang et al., 2006, *Nature Methods* 3: 707-714.

The efficacy of RNAi depends on its sequence and on that of its target site. In a conventional approach, the potency of RNAi sequences are tested by expressing the molecule and testing the suppression of the target mRNA (e.g., QRT-PCR, Northern blot) or its protein product (e.g., Western blot).

In one embodiment, the expression of a given shRNA from the Tet-inducible promoter (or other promoter) can knockdown the cognate reporter-target mRNA construct expressed from an independent promoter cloned into the same vector. In this embodiment, cells expressing a potent RNAi lose expression of the fluorescent marker upon induction of the Tet-inducible promoter (addition of doxycycline in a Tet-On system) due to RNA interference. Cells expressing a weak RNAi molecule retain expression of the fluorescent marker due to the lack of a potent RNAi response. This differential expression of the fluorescent marker provides a way of distinguishing RNAi molecules exhibiting varying knock-down efficacy.

Cells expressing different levels of fluorescence (or no fluorescence) can be gated and sorted by flow cytometry. Potent knockdown cells (no fluorescence) can be differentially isolated from intermediate, weak, and no-knockdown populations. These populations can be expanded such that PCR can be performed to clone out the shRNA sequences into other plasmids, such as bacterial plasmids, which can be used to transform bacteria. In this manner, individual colonies contain a single RNAi sequence, and thus, each individual RNAi sequence can be analyzed. For larger pools, identification of individual RNAi sequences can be performed by other methods, such as hybridization on custom arrays.

4.5 RNAi Design and Libraries si- and shRNAs targeting genes of interest can be chosen from various sources. In one embodiment, the RNAi sequences are selected from existing libraries. For example, Silva et al. (2005, *Nat. Genet.* 37: 1281-1288), have described extensive libraries of pri-miR-30-based retroviral expression vectors that can be used to down-regulate almost all known human (at least 28,000) and mouse (at least 25,000) genes. (See RNAi CODEX, a single database that curates publicly available RNAi resources, and provides the most complete access to this growing resource, allowing investigators to see not only released clones but also those that are soon to be released, available at the Cold Spring Harbor Laboratories website). Pools of shRNAs useful to practice methods of the invention can be from the "the Cancer 1000" library, which was constructed by Steve Elledge and Greg Hannon. The "Cancer 1000" shRNA library includes a mixture of well characterized oncogenes and tumor suppressor genes in addition to many poorly-characterized genes somehow related to cancer, across many ontological groups, as compiled by literature mining. In another embodiment, the pools of shRNA useful to practice the method of the invention come from a cDNA library that includes a mixture of DNA replication genes. A similar library design rationale can be easily applied to construct RNAi libraries targeting genomes of other organisms, such as the human. Negative controls can include shRNAs to genes not present in the organism's genome or empty vectors.

In another embodiment, si- and shRNAs can be designed de novo. The sequence coding for an RNAi molecule is referred to as an RNAi coding sequence. The coding sequence can be, for example, a sequence that encodes an shRNA molecule. Coding sequences for shRNA molecules can be designed according to the teachings expressed in Hannon et al. (US Publication No. 2006/0135456), Hannon et al. (International Publication No. WO2006/073601), and Dickens et al., (US Publication No. 2007/0044164), the contents of which are hereby expressly incorporated by reference. The choice of the right primary sequence has an important role in determining the efficacy and specificity of the resulting RNAi response. Current features of design rules for RNAi molecules include the thermodynamic asymmetry of the RNA duplex, sequence homology of the seed sequence to its cognate target mRNA but not to other mRNAs, and a set of empirical single nucleotide position preferences. The thermodynamic asymmetry is important since only the strand with the less stable 5' end is favorable or exclusively loaded into the RISC and will therefore serve as the guide strand. The seed sequence comprises nucleotide positions 2-8 of the guide strand and has been show to be the major specificity determinant of si- and shRNAs. Single nucleotide positional preferences include, for example, the A or U at position 10 of the guide strand that can promote catalytic RISC-mediated passenger strand and substrate cleavage.

In certain embodiments, useful interfering RNAs can be designed with a number of software programs, e.g., the OligoEngine siRNA design tool. Algorithms for in silenco prediction, or alorithms based on an empirically trained neural network, such as BIOPREDsi, can be used. Birmingham et al. (2007, *Nat. Protocols* 2: 2068-2078) provide a comprehensive overview of prediction algorithms.

In certain embodiments of the invention, such as those directed to therapeutic applications, it may be desirable to use siRNAs, including modified siRNAs, based on the sequences of the shRNA sequences disclosed herein. For example, it may be desirable to use an siRNA that binds to the same target sequence as the shRNA sequences disclosed herein. One of skill in the art can readily design such siRNAs, for example basing the siRNA sequence on any or all parts of the shRNA sequence that is complementary to or binds to the target sequence.

The siRNAs for use in this invention can have a double-stranded region of about 16 to 29 base pairs, in particular 19 to 29 base pairs in length. In a certain embodiment, the duplex region is 21, 22, or 23 base pairs in length. In one aspect, the siRNA comprises a 3' overhang of 1 to 4 nucleotides, in particular 2 nucleotides. Useful siRNAs are highly specific for a region of the target gene and can comprise a 19 to 29 base pair sequence of the mRNA of a target gene, with at least one, but in particular two or three, base pair mismatches with a non-target gene-related sequence. In some embodiments, the siRNAs do not bind to RNAs having more than three base pair mismatches with the target region. siRNAs can be prepared extracellularly and intracellularly using a variety of known methods, including chemical synthesis, in vitro transcription, siRNA expression vectors, and PCR expression cassettes.

Other methods of RNAi can also be used in the practice of this invention. See, e.g., International Patent Application PCT/US2003/030901 (Publication No. WO 2004-029219 A2) and Fewell et al., 2006, *Drug Discovery Today* 11: 975-982, for a description of inducible shRNA, in which the vector does not express the shRNA unless a specific reagent is added. Several studies investigating the function of essential genes using RNAi rely on inducible shRNA. For example, shRNAmir constructs can be created based on a tetracycline-responsive promotor system, such that shRNA expression is regulated by changing doxycycline levels.

In some embodiments, effective RNAi molecules against a target gene may be designed through the Target Sensor assay, according to the teachings expressed in Fellmann et al. (International Publication No. WO2009/055724)(PCT/US08/81193), the contents of which are hereby expressly incorporated by reference. In further aspects of this invention, most potent siRNA or shRNA against a target gene (e.g., having the most effect in inhibiting cell proliferation or eliminating cancer cells in vivo) may be identified through use of tet-regulated in vivo RNAi screening (Example 6).

4.6 In Vivo Mouse Models

The methods of the invention use a genetically defined mosaic mouse model for leukemia, such as the acute myeloid leukemia (AML) model or the myeloid/lymphoid leukemia (MLL) model. Individual cases of human leukemia are often associated with certain specific categories of recurring genetic abnormalities, such as rearrangements or mutations of specific gene loci. For example the MLL gene is fused to a large variety of more than 50 different partner genes in AML. (Schoch et al., 2003, *Blood* 102:2395-2402). Some subcategories, for example, 11q23/MLL rearrangements in AML, are associated with poor outcome and resistance to conventional chemotherapies.

As a mouse model of such human leukemias, we generated mice harboring leukemias with genetic alterations reflecting genetic alterations found in chemoresistant AML. MLL rearrangements in human AML are commonly associated with activating mutations in Nras. To model chemoresistant human AML involving MLL translocations, we generated mouse leukemias co-expressing an MLL gene fusion variant together with oncogenic Nras. We applied a "mosaic" approach involving retroviral transduction of oncogenes into hematopoietic stem- and progenitor cells, followed by re-transplantation of the genetically-altered cells into syngeneic recipients (FIG. 12). This strategy enables multiple oncogenes and reporter elements to be introduced in a one-step procedure, thereby facilitating disease monitoring and reducing the animal husbandry associated with germline transgenic mice. The resulting primary leukemias can be isolated and transplanted into secondary recipient mice to assess response to chemotherapy treatment or to evaluate RNAi targets.

In one embodiment, the hematopoetic stem- and progenitor cells are fetal liver cells (FLCs) derived from mouse embryos (e.g., E13.5-15.5 embryos). In another embodiment, the hematopoetic stem- and progentor cells are derived from bone marrow. In one embodiment, an MLL gene fusion variant associated with a particularly poor prognosis, MLL/AF9 and MLL/ENL (Schoch et al. 2003) can be used, alone or together with an activated Nras (e.g., $Nras^{G12D}$). In another embodiment, gene alterations associated with less aggressive AML (e.g., AML1/ETO9a) can be used, alone or together with an activated Nras (e.g., $Nras^{G12D}$). In a further embodiment, the MLL fusion gene is co-expressed with a reporter gene (marker protein) (e.g., enhanced green fluorescent protein (EGFP)) in a bicistronic construct (FIG. 12). In a further embodiment, oncogenic $Nras^{G12D}$ is co-expressed with a marker protein (e.g., luciferase) that enables imaging of the resulting leukemias by bioluminescence. In a further embodiment, $Nras^{G12D}$ is cloned downstream of an internal ribosomal entry site (IRES), which reduces expression of the ectopic Nras gene to near physiological levels (Parikh et al. 2006).

In another embodiment, primary leukemia cells are isolated from diseased animals, transplanted in recipient animals and development of leukemias in the recipient animals is monitored by bioluminescent imaging, using one or more co-expressed marker proteins (e.g., luciferase co-expressed with oncogenic $Nras^{G12D}$).

In another embodiment, a tet transactivator protein (e.g., rtTA3, a potent and non-toxic rtTA variant) together with the oncogene responsible for maintaining a malignant phenotype, (e.g. MLL/AF9), is expressed from one promotor (e.g. LTR) in a bicistronic vector, wherein resulting primary leukemias arising in the animals are comprised of "tet-on competent" leukemia cells.

4.6.1 "Tet-on Competent" shRNA Screening In Vivo

We developed a robust method for in vivo screening using "tet-on competent" vectors to identify siRNA molecules with therapeutic efficacy against chemoresistant leukemias using transplantable primary leukemias generated through our mosiac mouse model. In particular, we directed this approach to identify siRNA targets in leukemias involving specific genetic alterations reflecting those observed in human AML, such as rearrangements of the MLL gene. The tet-on competent vector comprises three critical elements that allow for efficient and robust evalutation and/or screening in vivo of shRNAs expressed in transplanted primary leukemias: (1) inducible expression of shRNA controlled by an inducible tet-responsive promoter, (2) a marker gene, (e.g., dsRed2) co-expressed from the same transcript comprising the shRNA allowing monitoring of shRNA expression, (3) separate selection marker (e.g., Venus=yellow fluorescent protein) expressed from a separate promoter that allows for separate monitoring of vector integration (e.g., Venus) and shRNA expression (e.g., dsRed2).

Importantly, we determined that in using the tet-on competent vector to identify therapeutically potent shRNAs, as a critical prerequisite, it is essential to maintain stable, robust expression of a tet transactivator protein in all transplanted leukemic cells. Otherwise, outgrowth of clones in which shRNA expression is no longer inducible (for example, through selective pressure against expression of therapeutically active shRNAs) severely compromises success of screening or evaluation of shRNA activity. As an additional critical element of the screening method, we modified our mosaic mouse model by co-expressing a tet transactivator protein (e.g., rtTA3, a potent and non-toxic rtTA variant) together with the oncogene responsible for maintaining the leukemic phenotype, (e.g. MLL/AF9), from one promotor (e.g. LTR) in a bicistronic vector, ensuring that stable, robust rtTA expression and inducibility of shRNA expression is maintained in all transplanted cells, and independently of the identity of the particular shRNA being expressed.

In one embodiment of the invention, primary tet-on competent leukemia cells are isolated from diseased animals, transduced with a "tet-on competent" vector and transplanted in recipient animals. In a further embodiment, the tet-on competent vector comprises a sequence encoding an shRNA that is complementary to at least a portion of a target gene. In another embodiment, primary tet-on competent leukemia cells are isolated from diseased animals and transduced with a plurality of tet-on competent vectors, each comprising a sequence encoding a representative shRNA from an shRNA library, and transduced cells are transplanted into recipient animals. In a further embodiment, shRNA expression in transplanted cells is monitored by expression of a selection marker (marker protein, reporter gene, e.g., dsRed2) co-expressed from the same transcript comprising the shRNA. In a further embodiment, integration of the tet-on competent vector in transplanted cells is monitored by expression of a separate selection marker (marker protein, reporter gene, e.g., Venus=yellow fluorescent protein) expressed from a separate promoter that allows for separate monitoring of vector integration (e.g., Venus) and shRNA expression (e.g., dsRed2).

Bicistronic vectors, such as the pIRES2 Vectors from Clonetech (Mountain View, Calif.) and the Bicep Vectors from Sigma-Aldrich (St. Louis, Mo.), can be obtained commercially.

Mice harboring a tet-responsive RNA polymerase II promoter can drive the targeting of a microRNA-based short hairpin RNA to a DNA replication protein. rtTA transactivators ("tet-on") can be activated by tetracycline or its analog doxycycline. Thus, RNA polymerase II promoters, including the tet-responsive TRE promoter, can be used to express shRNAs complementary to a nucleotide sequence of a target gene based on microRNA precursors. In one embodiment, shRNAs are targeted to a DNA replication protein. Non-limiting example of DNA replication proteins include replication protein A3 (RPA3), ribonucleotide reductase M1 (RRM1), cell division cycle 45 (CDC45) and pescadillo 1 (PEST). In certain embodiments, the shRNA can be or comprise a sequence selected from one of SEQ ID NOs: 8-14. In other embodiments, shRNAs are targeted to a gene encoding a protein shown in Table 1, Table 2, Table 3, or Table 4. Non-limiting examples of specific shRNAs are listed in Tables 1, 2, 3, and 4.

4.7 Additional Methods of Screening

The tet-on competent screening systems, along with siRNA targets identified herein, are useful for screening candidate therapeutic agents in vivo, in particular candidate agents capable of enhancing the therapeutic activity of a particular siRNA in eliminating or otherwise inhibiting proliferation or survival of tumor cells (e.g., AML and other leukemias).

The tet-on competent screening systems, in combination with shRNA libraries, are useful in screening for siRNA targets that enhance the sensitivity of tumor cells (e.g., AML or other leukemias) to a chemotherapeutic agent. In one embodiment, the method comprises introducing a plurality of transduced into a recipient mouse In another embodiment, the tet-on competent screening systems, along with siRNA targets identified herein, are useful to identify therapeutic agents that modulate downstream substrates or signaling pathway components of such siRNA targets.

One aspect of the invention is directed to methods for identifying compounds that inhibit cell proliferation, and in particular proliferation of tumor cells (e.g., therapy-resistant AML and other leukemias). In one embodiment, the method comprises (1) introducing into a cancer cell an RNAi molecule that is complementary to a nucleotide sequence of a target gene, wherein the target gene encodes a DNA replication protein or an epigenetic modifier (e.g., an enzyme that modifies chromatin); (2) contacting the cancer cell with a candidate compound; and (3) determining whether the candidate compound inhibits cell proliferation. In another embodiment, the method further comprises: administering an effective amount of the compound to a non-human animal having a tumor; and monitoring tumor growth in the non-human animal. In certain embodiments, the method further comprises comparing tumor growth in the non-human animal treated with the compound to tumor growth in the non-human animal not treated with the compound. Monitoring tumor growth can be carried out according to methods known in the art and can comprise evaluating the size of the cells comprising the tumor, measuring cell viability, or a carrying out a combination of monitoring modes described.

A further aspect of the invention is a method for testing a cancer arising from an Nras$^{G12D}$/shRNA tumor oncogene-transformed cancer for sensitivity to a treatment. Another aspect of this invention is a method for testing a chemotherapy-resistant AML (e.g., human AML harboring an MLL-fusion oncogene, AML arising from hematopoietic stem- and progenitor cells transduced with an MLL-fusion+ oncogenic Nras, see e.g., Example 6). Cancer cells, such as leukemia cells, can be cultured in vitro. The cells are subsequently contacted with a candidate treatment and monitored for growth (e.g., by observing cell number, confluence in flasks, staining to distinguish viable from nonviable cells). Failure to increase in viable cell number, slower rate of increase in cell number, or a decline in viable cell number, compared to cells which are untreated or mock-treated, is an indication of sensitivity to the treatment. The treatment to be tested can be one or more substances, for example, those compounds identified in the screen of the invention, a known anti-cancer agent (e.g., a chemotherapy drug), such as adriamycin, cylophosphamide, prednisone, vincristine, or a radioactive source. The treatment can also be exposure to various kinds of energy or particles, such as gamma-irradiation, or can be a combination of approaches. In some cases, the treatment can also be administration of one or more substances or exposure to conditions, or a combination of both, wherein the effects of the treatment as anti-cancer therapy are unknown. In addition, candidate compounds can be selected based on their effect on proteins that bind or interact with DNA replication proteins.

Candidate compounds can be further tested in leukemias or leukemia-related tumors in situ in a mouse. Animals can be tested essentially as described in U.S. Pat. No. 6,583,333.

A compound that inhibits cell proliferation can be a small molecule that binds to and disrupts or inhibits the function of DNA replication proteins. A compound that inhibits an epigenetic pathway can be a small molecule that binds to and disrupts or inhibits the enzymatic function of an epigenetic modifier (e.g., an enzyme that modifies chromatin). Small molecules are a diverse group of synthetic and natural substances generally having low molecular weights. They can be isolated from natural sources (for example, plants, fungi, microbes and the like), obtained commercially and/or available as libraries or collections, or synthesized. Candidate small molecules that disrupt the function of DNA replication proteins or epigenetic modifiers can be identified via in silico screening or high-through-put (HTP) screening of combinatorial libraries. Most conventional pharmaceuticals, such as aspirin, penicillin, and many chemotherapeutics, are small molecules, and can be obtained commercially, can be chemically synthesized, or can be obtained from random or combinatorial libraries as described below (Werner et al., (2006) *Brief Funct. Genomic Proteomic* 5(1):32-6).

Knowledge of the primary sequence of a molecule of interest, such as DNA replication proteins or epigenetic modifiers discussed herein, can provide information as to the inhibitors or antagonists of the protein of interest in addition to agonists. Identification and screening of agonists and antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Test compounds, such as cell proliferation inhibitors (e.g., inhibitors of DNA replication proteins) or epigenetic modifiers (e.g., enzymes that modify chromatin), can be screened from large libraries of synthetic or natural compounds (see Wang et al., (2007) *Curr Med Chem*, 14(2):133-55; Mannhold (2006) *Curr Top Med Chem*, 6 (10):1031-47; and Hensen (2006) *Curr Med Chem* 13(4):361-76). Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available, e.g. from Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) *Tib Tech* 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized to contain non-peptide synthetic moieties, which are less subject to enzymatic degradation compared to their naturally-occurring counterparts. Libraries are also meant to include, for example, but are not limited to, peptide-on-plasmid libraries, polysome libraries, aptamer libraries, synthetic peptide libraries, synthetic small molecule libraries, neurotransmitter libraries, and chemical libraries. The libraries can also comprise cyclic carbon or heterocyclic structure and/or aromatic or polyaromatic structures substituted with one or more of the functional groups described herein.

Small molecule combinatorial libraries can also be generated and screened. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A compound array can be a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding published PCT application, WO95/18972, and in U.S. Pat. No. 5,712,171 g and its corresponding published PCT application, WO96/22529, which are hereby incorporated by reference.

Examples of chemically synthesized libraries are described in Fodor et al., (1991) *Science* 251:767-773; Houghten et al., (1991) *Nature* 354:84-86; Lam et al., (1991) *Nature* 354:82-84; Medynski, (1994) *BioTechnology* 12:709-710; Gallop et al., (1994) *J. Medicinal Chemistry* 37(9):1233-1251; Ohlmeyer et al., (1993) *Proc. Natl. Acad. Sci. USA* 90:10922-10926; Erb et al., (1994) *Proc. Natl. Acad. Sci. USA* 91:11422-11426; Houghten et al., (1992) *Biotechniques* 13:412; Jayawickreme et al., (1994) *Proc. Natl. Acad. Sci. USA* 91:1614-1618; Salmon et al., (1993) *Proc. Natl. Acad. Sci. USA* 90:11708-11712; PCT Publication No. WO 93/20242, dated Oct. 14, 1993; and Brenner et al., (1992) *Proc. Natl. Acad. Sci. USA* 89:5381-5383.

In one non-limiting example, non-peptide libraries, such as a benzodiazepine library (see e.g., Bunin et al., (1994) *Proc. Natl. Acad. Sci. USA* 91:4708-4712), can be screened. Peptoid libraries, such as that described by Simon et al., (1992) *Proc. Natl. Acad. Sci. USA* 89:9367-9371, can also be used. Another example of a library that can be used, in which the amide functionalities in peptides have been permethylated to generate a chemically transformed combinatorial library, is described by Ostresh et al. (1994), *Proc. Natl. Acad. Sci. USA* 91:11138-11142.

Screening the libraries can be accomplished by any variety of commonly known methods. See, for example, the following references, which disclose screening of peptide libraries: Parmley and Smith, (1989) *Adv. Exp. Med. Biol.* 251:215-218; Scott and Smith, (1990) *Science* 249:386-390; Fowlkes et al., (1992) *BioTechniques* 13:422-427; Oldenburg et al., (1992) *Proc. Natl. Acad. Sci. USA* 89:5393-5397; Yu et al., (1994) *Cell* 76:933-945; Staudt et al., (1988) *Science* 241: 577-580; Bock et al., (1992) *Nature* 355:564-566; Tuerk et al., (1992) *Proc. Natl. Acad. Sci. USA* 89:6988-6992; Ellington et al., (1992) *Nature* 355:850-852; U.S. Pat. Nos. 5,096, 815; 5,223,409; and 5,198,346, all to Ladner et al.; Rebar et al., (1993) *Science* 263:671-673; and PCT Pub. WO 94/18318.

4.8 Methods of Treatment

Another aspect of the invention is a method of treating cancer by inhibiting cancer cell proliferation through the downregulation of a target gene identified through the methods of the invention as a gene whose expression is necessary for survival of the cancer cell. In some aspects, the target gene encodes a DNA replication protein. In other aspects, the target gene encodes an epigenetic modifier. The protein encoded by the target gene can be downregulated directly, by introducing into a cancer cell an RNAi molecule against the DNA replication protein, or indirectly, by targeting an upstream factor that regulates expression, inhibition or activation of the target protein. The invention provides methods of treating a cancer in a subject by introducing into cells a pharmaceutical composition comprising a therapeutic agent, such therapeutic agent comprising an shRNA expression construct, an siRNA or another RNAi molecule. In certain embodiments of the invention, such as those directed to therapeutic applications, it may be desirable to use siRNAs, including modified siRNAs, based on the sequences of the shRNA sequences disclosed herein. For example, it may be desirable to use an siRNA that binds to the same target sequence as the shRNA sequences disclosed herein. One of skill in the art can readily design such siRNAs, for example basing the siRNA sequence on any or all parts of the shRNA sequence that is complementary to or binds to the target sequence.

For example, the shRNA can be reliably expressed in vivo in a variety of cell types. In certain embodiments the cells are administered in order to treat a condition. There are a variety of mechanisms by which shRNA expressing cells can be useful for treating cancer. For example, a condition can be caused, in part, by a population of cells expressing an undesirable gene. These cells can be ablated and replaced with administered cells comprising shRNA that decreases expression of the undesirable gene. An shRNA can be targeted to essentially any gene, the decreased expression of which can be helpful in treating cancer.

In one embodiment, the invention can be a method for treating cancer comprising identifying in a cancer cell increased expression or copy number of at least one gene that encodes a DNA replication protein or epigenetic modifier as compared with that in a normal cell and inhibiting the DNA replication protein or epigenetic modifier. Non-limiting examples of DNA replication proteins include replication protein A3 (RPA3), ribonucleotide reductase M1 (RRM1), cell division cycle 45 (CDC45) and pescadillo 1 (PES1). shRNAs that are complementary to a nucleotide sequence of a gene encoding a protein shown in Table 1 provides additional examples of DNA replication proteins. Non-limiting examples of epigenetic modifiers include AOF2, EED, HDAC, MEN1, SMARCA4, SMARCD1, SUZ12 and WHSC111.

In another embodiment, the invention can be a method for inhibiting proliferation of a cancer cell by introducing into the cancer cell a small interfering RNA (siRNA) comprising a nucleic acid sequence that is complementary to a nucleotide sequence of a target gene. The target gene encodes a DNA replication protein, wherein the DNA replication protein is selected from the group consisting of replication protein A3 (RPA3), ribonucleotide reductase M1 (RRM1), cell division cycle 45 (CDC45), and pescadillo 1 (PES1). In another aspect, the target gene encodes an epigenetic modifier, wherein the epigenetic modifier is selected from the group consisting of AOF2, EED, HDAC, MEN1, SMARCA4, SMARCD1, SUZ12 and WHSC111.

In a further embodiment, the invention can be a method for inhibiting proliferation of a cancer cell by introducing into the cancer cell an expression vector comprising a nucleic acid sequence encoding a short hairpin RNA (shRNA) operably linked to a RNA polymerase promoter. The shRNA comprises a loop and a duplex region, wherein the duplex region comprises a sequence that is complementary to a nucleotide sequence of a target gene. The target gene encodes a DNA replication protein, wherein the DNA replication protein is selected from the group consisting of replication protein A3 (RPA3), ribonucleotide reductase M1 (RRM1), cell division cycle 45 (CDC45) and pescadillo 1 (PES1) thereby inhibiting proliferation of a cancer cell upon expression of the shRNA. In another aspect, the target gene encodes an epigenetic modifier, wherein the epigenetic modifier is selected from the group consisting of AOF2, EED, HDAC, MEN1, SMARCA4, SMARCD1, SUZ12 and WHSC111, thereby inhibiting proliferation of a cancer cell upon expression of the shRNA.

In some embodiments, the methods for treating cancer and for inhibiting proliferation of a cancer cell can further comprise administering a chemotherapy drug to the cancer cell. Cytotoxic drugs (for example, chemotherapy drugs) that interfere with critical cellular processes including DNA, RNA, and protein synthesis, can also be administered in combination with the introduction of an RNAi molecule. Some non-limiting examples of chemotherapy drugs include: aminoglutethimide, amsacrine, asparaginase, bcg, anastrozole, bleomycin, buserelin, bicalutamide, busulfan, capecitabine, carboplatin, camptothecin, chlorambucil, cisplatin, carmustine, cladribine, colchicine, cyclophosphamide, cytarabine, dacarbazine, cyproterone, clodronate, daunorubicin, diethylstilbestrol, docetaxel, dactinomycin, doxorubicin, dienestrol, etoposide, exemestane, filgrastim, fluorouracil, fludarabine, fludrocortisone, epirubicin, estradiol, gemcitabine, genistein, estramustine, fluoxymesterone, flutamide, goserelin, leuprolide, hydroxyurea, idarubicin, levamisole, imatinib, lomustine, ifosfamide, megestrol, melphalan, interferon, irinotecan, letrozole, leucovorin, ironotecan, mitoxantrone, nilutamide, medroxyprogesterone, mechlorethamine, mercaptopurine, mitotane, nocodazole, octreotide, methotrexate, mitomycin, paclitaxel, oxaliplatin, temozolomide, pentostatin, plicamycin, suramin, tamoxifen, porfimer, mesna, pamidronate, streptozocin, teniposide, procarbazine, titanocene dichloride, raltitrexed, rituximab, testosterone, thioguanine, vincristine, vindesine, thiotepa, topotecan, tretinoin, vinblastine, trastuzumab, and vinorelbine.

In one embodiment, the chemotherapy drug is an alkylating agent, a nitrosourea, an anti-metabolite, a topoisomerase inhibitor, a mitotic inhibitor, an anthracycline, a corticosteroid hormone, or a sex hormone.

An alkylating agent works directly on DNA to prevent the cancer cell from propagating. These agents are not specific to any particular phase of the cell cycle. In one embodiment, alkylating agents can be selected from busulfan, cisplatin, carboplatin, chlorambucil, cyclophosphamide, ifosfamide, dacarbazine (DTIC), mechlorethamine (nitrogen mustard), melphalan, and temozolomide.

An antimetabolite makes up the class of drugs that interfere with DNA and RNA synthesis. These agents work during the S phase of the cell cycle and are commonly used to treat leukemias, tumors of the breast, ovary, and the gastrointestinal tract, as well as other cancers. In one embodiment, an antimetabolite can be 5-fluorouracil, capecitabine, 6-mercaptopurine, methotrexate, gemcitabine, cytarabine (ara-C), fludarabine, or pemetrexed.

Topoisomerase inhibitors are drugs that interfere with the topoisomerase enzymes that are important in DNA replication. Some examples of topoisomerase I inhibitors include topotecan and irinotecan while some representative examples of topoisomerase II inhibitors include etoposide (VP-16) and teniposide.

Anthracyclines are chemotherapy drugs that also interfere with enzymes involved in DNA replication. These agents work in all phases of the cell cycle and thus, are widely used as a treatment for a variety of cancers. In one embodiment, an anthracycline used with respect to the invention can be daunorubicin, doxorubicin (Adriamycin), epirubicin, idarubicin, or mitoxantrone.

Non-limiting examples of cancers that can be treated according to the methods of the invention include, for example, leukemias, acute lymphocytic leukemia, myeloid/lymphoid or mixed lineage leukemia (MLL), chronic lymphocytic leukemia, lynphomas, B cell lymphoma, T cell lymphoma, non-Hodgkins lymphoma, Hodgkins lymphoma, myeloma, hematopoietic neoplasias, thymoma, lymphoma, sarcoma, lung cancer, liver cancer, colon cancer, renal cancer, breast cancer, bladder cancer, uterine cancer, cervical cancer and other soft tissue and solid tumor cancers, and including chemotherapy-resistant and radiation therapy-resistant cancers.

The cancer cell can be a human cancer cell. The cancer cell can also be a mammalian cancer cell including, but not limited to, a non-primate cancer cell (e.g., a cow, pig, bird, sheep, goat, horse, cat, dog, rat, and mouse) and a primate cancer cell (e.g., a monkey, such as a cynomolgous monkey, a chimpanzee, and a human). The cancer cell can also be a non-human cancer cell, such as from a bird (e.g., a quail, chicken, or turkey), a farm animal (e.g., a cow, horse, pig, or sheep), a pet (e.g., a cat, dog, or guinea pig), or laboratory animal (e.g., an animal model for a disorder or disease).

4.9 Pharmaceutical Compositions and Administration

Another aspect of the invention is a pharmaceutical composition comprising a therapeutic agent for the treatment of cancer (for example, leukemias such as AML or MLL). The composition has specific utility to treat a cancer by targeting a gene identified through the methods of the invention as a gene whose expression is necessary for survival of the cancer cell. Such a gene can be a gene encoding a DNA replication protein described herein. In one aspect, the pharmaceutical composition can be used for the treatment of cancer in which the activity or expression of a protein encoded by the target gene is greater in the cancer cell than in normal tissue. An embodiment of this invention can be practiced using inhibitors directed to the DNA replication proteins listed in Table 1. A further embodiment of this invention can be practiced using inhibitors directed to epigenetic modifier proteins identified through the methods of this invention as novel therapeutic targets for chemotherapy-resistant AML, in particular Eed, Suz12, Aof2, Smarca4, Smarcd1, Men1, Hdac3, and Whs111.

In one aspect of this invention, inhibitors directed to the identified therapeutic targets described herein, including compounds that inhibit or disrupt the function of the target gene and also siRNAs or modified siRNAs, are administered in therapeutically effective amounts. In treating disease, a therapeutically effective amount ("effective amount") is a dose administered to a patient that is sufficient to provide a medically desirable result. For example, a therapeutically effective amount is an amount that inhibits or halts the progression of the particular disease, for example, progression of a chemotherapy resistant cancer. In treating cancer, an effective amount of an inhibitor is for example, an amount necessary to restore sensitivity to another chemotherapeutic agent, inhibit cancer cell replication, increase apoptosis in cancer cells, regress the cancer, reduce cancer cell load, suppress further growth of the cancer or reduce one or more signs or symptoms of the cancer. In some embodiments, inhibitors directed to the identified therapeutic targets described herein are adminstered as a combination drug therapy. In some aspects, combination therapy will include administration of the inhibitor in combination with an existing chemotherapy drug.

Methods of the invention provide for the administration of an RNAi molecule or for compounds identified in the screening methods above that inhibit cellular proliferation or eliminate cancer cells in vivo. In some embodiments, a method comprises introducing into a subject a transfected stem cell comprising a siRNA or a nucleic acid construct encoding an shRNA. The siRNA or the shRNA is complementary to at least a portion of a target gene, wherein the transfected stem cell exhibits decreased expression of the target gene, and wherein the transfected stem cell gives rise to a transfected tumor cell in vivo. The target gene can encode a DNA replication protein, wherein the DNA replication protein is selected from the group consisting of replication protein A3 (RPA3), ribonucleotide reductase M1 (RRM1), cell division cycle 45 (CDC45) and pescadillo 1 (PEST) thereby inhibiting proliferation of a cancer cell. In another aspect, the target gene encodes an epigenetic modifier, wherein the epigenetic modifier is selected from the group consisting of AOF2, EED, HDAC, MEN1, SMARCA4, SMARCD1, SUZ12 and WHSC111. For example, the stem cell can be derived from an animal that has a genetic predisposition to tumorigenesis, such as an oncogene over-expressing animal (e.g. E-myc mice) or a tumor suppressor knockout (e.g., p53−/− animal). Alternatively, an animal comprising the stem cells can be exposed to carcinogenic conditions such that tumors comprising cells derived from the stem cells are generated. An animal having tumors can be treated with a chemotherapeutic or other anti-tumor regimen, and the effect of this regimen on cells expressing the shRNA can be evaluated.

In certain embodiments, the invention provides a composition formulated for administration to a subject, such as a human or veterinary subject. A composition so formulated can comprise a stem cell comprising a nucleic acid construct encoding an shRNA designed to decrease the expression of a target gene. A composition can also comprise a pharmaceutically acceptable excipient. Any suitable cell can be used. For example, cells to be transfected can be essentially any type of cell for implantation into in a subject. The cell having the target gene can be germ line or somatic, totipotent or pluripotent, dividing or non-dividing, parenchymal or epithelial, immortalized or transformed, or the like. The cell can be a stem cell or a differentiated cell. After transfection, stem cells can be administered to a subject, or cultured to form differentiated stem cells (e.g., embryonic stem cells cultured to form neural, hematopoietic or pancreatic stem cells) or cultured to form differentiated cells.

Stem cells can be stem cells recently obtained from a donor, and in certain embodiments, the stem cells are autologous stem cells. Stem cells can also be from an established stem cell line that is propagated in vitro. Suitable stem cells include embryonic stems and adult stem cells, whether totipotent, pluripotent, multipotent or of lesser developmental capacity. Stem cells can be derived from mammals, such as rodents (e.g. mouse or rat), primates (e.g. monkeys, chimpanzees or humans), pigs, or ruminants (e.g. cows, sheep and goats). Examples of mouse embryonic stem cells include: the JM1 ES cell line described in M. Qiu et al., Genes Dev 9, 2523 (1995), and the ROSA line described in G. Friedrich, P. Soriano, Genes Dev 5, 1513 (1991), and mouse ES cells described in U.S. Pat. No. 6,190,910. Many other mouse ES lines are available from Jackson Laboratories (Bar Harbor, Me.). Examples of human embryonic stem cells include those available through the following suppliers: Arcos Bioscience, Inc., Foster City, Calif.; CyThera, Inc., San Diego, Calif.; BresaGen, Inc., Athens, Ga.; ES Cell International, Melbourne, Australia; Geron Corporation, Menlo Park, Calif.; University of California, San Francisco, Calif.; and Wisconsin Alumni Research Foundation, Madison, Wis. In addition, examples of embryonic stem cells are described in the following U.S. patents and published patent applications: U.S. Pat. Nos. 6,245,566; 6,200,806; 6,090,622; 6,331,406; 6,090,622; 5,843,780; 20020045259; 20020068045. In certain embodiments, the human ES cells are selected from the list of approved cell lines provided by the National Institutes of Health. Examples of human adult stem cells include those described in the following U.S. patents and patent applications: U.S. Pat. Nos. 5,486,359; 5,766,948; 5,789,246; 5,914,108; 5,928,947; 5,958,767; 5,968,829; 6,129,911; 6,184,035; 6,242,252; 6,265,175; 6,387,367; 20020016002; 20020076400; 20020098584; and, for example, in PCT publication WO 01/11011. In certain embodiments, a suitable stem cell can be derived from a cell fusion or dedifferentiation process, such as described in U.S. patent application 20020090722, in PCT publications WO 02/38741, WO 01/51611, WO 99/63061, and WO 96/07732.

In some embodiments, stem cells can be hematopoietic or mesenchymal stem cells, such as stem cell populations derived from adult human bone marrow. Recent studies suggest that marrow-derived hematopoietic (HSCs) and mesenchymal stem cells (MSCs), which are readily isolated, have a broader differentiation potential than previously recognized. Many purified HSCs not only give rise to all cells in blood, but can also develop into cells normally derived from endoderm, like hepatocytes (Krause et al., 2001, Cell 105: 369-77; Lagasse et al., 2000 Nat Med 6: 1229-34). In at least one report (Lagasse et al, 2000 Nat Med 6: 1229-34), the possibility of somatic cell fusion was ruled out. MSCs appear to be similarly multipotent, producing progeny that can, for example, express neural cell markers (Pittenger et al., 1999 Science 284: 143-7; Zhao et al., 2002 Exp Neural 174: 11-20).

In other embodiments, stem cells are derived from an autologous source or an HLA-type matched source. For example, HSCs can be obtained from the bone marrow of a subject in need of ex vivo cell therapy and cultured by a method described herein to generate an autologous cell composition. Other sources of stem cells are easily obtained from a subject, such as stem cells from muscle tissue, stem cells from skin (dermis or epidermis) and stem cells from fat. Stem cell compositions can also be derived from banked stem cell sources, such as banked amniotic epithelial stem cells or banked umbilical cord blood cells.

Transfected cells can also be used in the manufacture of a medicament for the treatment of subjects. Examples of pharmaceutically acceptable excipients include matrices, scaffolds, or other substrates to which cells can attach (optionally formed as solid or hollow beads, tubes, or membranes), as well as reagents that are useful in facilitating administration (e.g. buffers and salts), preserving the cells (e.g. chelators such as sorbates, EDTA, EGTA, or quaternary amines or other antibiotics), or promoting engraftment. Cells can be encapsulated in a membrane or in a microcapsule. Cells can be placed in microcapsules composed of alginate or polyacrylates. (Lim et al. (1980) Science 210:908; O'Shea et al. (1984) Biochim. Biochys. Acta. 840:133; Sugamori et at (1989) Trans. Am. Soc. Artif. Intern. Organs 35:791; Levesque et al. (1992) Endocrinology 130:644; and Lim et al. (1992) Transplantation 53:1180).

Additional methods for encapsulating cells are known in the art. (Aebischer et al. U.S. Pat. No. 4,892,538; Aebischer et al. U.S. Pat. No. 5,106,627; Hoffman et al. (1990) Expt. Neurobiol. 110:39-44; Jaeger et al. (1990) Prog. Brain Res. 82:4146; and Aebischer et al. (1991) J. Biomech. Eng. 113: 178-183, U.S. Pat. No. 4,391,909; U.S. Pat. No. 4,353,888; Sugamori et al. (1989) Trans. Am. Artif. Intern. Organs 35:791-799; Sefton et al. (1987) Biotehnol. Bioeng. 29:1135-1143; and Aebischer et al. (1991) Biomaterials 12:50-55).

The site of implantation of cell compositions can be selected by one of skill in the art depending on the type of cell and the therapeutic objective. Exemplary implantation sites include intravenous or intraarterial administration, administration to the liver (via portal vein injection), the peritoneal cavity, the kidney capsule or the bone marrow.

In other embodiments, the invention provides a composition formulated for administration to a subject, such as a human or veterinary subject, comprising an RNAi molecule identified according to the screening methods described above. The RNAi molecule or the candidate compound identified according to the screening methods described above can be administered to a human or non-human animal, for example, a veterinary subject such as a non-human primate, a rodent (e.g., a mouse or rat), a lagomorph (e.g., a rabbit), a canid (e.g. a domestic dog), a feline (e.g., a domestic cat), an equine (e.g., a horse), or a bovine, (e.g., a cow). In general, animals with complete or near complete genome projects are useful.

Modification and delivery of RNAi molecules in vivo can be accomplished as described in U.S. Pat. Nos. 6,627,616, 6,897,068, 6,379,966; in U.S. Patent Application Publication Nos. US 2007/0281900 (Dec. 6, 2007) and US 2007/0293449 (Dec. 20, 2007); and in Vorhies and Nemunaitis J J, Methods Mol. Biol. 2009; 480:11-29, López-Fraga M et al., Infect Disord Drug Targets. 2008 December; 8(4):262-73, Watts et al., Drug Discov Today. 2008 October; 13(19-20):842-55, Lu and Woodle, Methods Mol. Biol. 2008; 437:93-107, de Fougerolles, Hum Gene Ther. 2008 February; 19(2):125-32, Rossi J J, Hum Gene Ther. 2008 April; 19(4):313-7, Belting M and Wittrup A. Methods Mol. Biol. 2009; 480:1-10, Pushparaj et al., J DENT RES 2008; 87: 992-1003, Shrivastava and Srivastava, Biotechnol J. 2008 March; 3(3):339-53, and Raemdonck K, et al., Drug Discov Today. 2008 November; 13(21-22):917-31, Castanotto D & Rossi J J, Nature 2009 January; 457:426-433, Davis M et al., Nature advance online publication (21 Mar. 2010) doi:10.1038/nature08956, each of which are incorporated by reference in their entireties.

The candidate compound identified according to the screening methods described above can be administered by subcutaneous, intra-muscular, intra-peritoneal, or intravenous injection; infusion; oral, nasal, or topical delivery; or a combination thereof.

Compounds can be incorporated into pharmaceutical compositions suitable for administration. Such compositions can comprise a compound identified in further screens described above (for example, a cell proliferation inhibitor such as a compound that disrupts the function of a DNA replication protein) and a pharmaceutically acceptable carrier.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

5. EXAMPLES OF THE INVENTION

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

5.1 Example 1

In Vitro Screening Assay for RNAi Target Identification 5.1.1 Construction of pLM-Puro Plasmid and Subcloning of shRNAs The mir30-based shRNAs used in this invention are most effective in knocking down expression of their target gene if they are under the transcriptional control of a Pol II promoter. shRNAs, with the exception of EBNA1mi1666, Lucifmi203, ORC1mi550, ORC2mi1903, and ORC2mi1981, were purchased from Open Biosystems, which provided the shRNAs in the pSM2 plasmid, containing a Pol III promoter (U6 promoter). All shRNAs were sub-cloned from pSM2 to the pLM-puro plasmid, where shRNA expression is regulated by an upstream LTR element that functions as a Pol II promoter.

The pLM-puro plasmid was constructed as follows. The pMSCV plasmid (obtained from Clontech) was linearized with EcoRI (unique restriction site in the multiple cloning site of pMSCV) and the following short duplex was ligated into pMSCV:

```
                                        (SEQ ID NO: 15)
         aattcgtaaaacgcgtacgacggcct (SEQ ID NO: 16)
              gcatttt gcgcatgctgccgga ttaa
```

This insert encodes a single MluI restriction site and has sticky ends compatible for ligation into the pMSCV plasmid. The result is the addition of a unique MluI restriction site into the multiple cloning site of pMSCV, which was named pMSCV-MluI. A functional EcoRI restriction site in pMSCV-MluI is retained at the 5' end of the insert, however the EcoRI site at the 3' end of the insert is rendered non-functional by the substitution of the C in GAATTC with an A to yield GAATTA.

Next, construction of pLM-puro was completed by sub-cloning the SalI-MfeI fragment from the pSM2 plasmid into the compatible XhoI/EcoRI sites in the multiple cloning site of pMSCV-MluI. The SalI-MfeI fragment from pSM2 encodes the 5' Mir30 flanking sequence, cloning site for inserting the shRNA sequence, and the 3' Mir30 flanking sequence. This ligation results in loss of the XhoI and EcoRI sites from the multiple cloning site of pMSCV-MluI. The pLM-puro plasmid derives from its pMSCV backbone functional LTR sequences required for expression of the inserted shRNA, as well as sequences necessary for packaging of the shRNA expression construct into viral particles formed after transfection of the plasmid into a packaging cell line. The pLM-puro plasmid also derives from its pMSCV backbone expression of a puromycin resistance marker that enables selection of human cells stably transduced with the shRNA expression cassette.

shRNAs were subcloned from pSM2 into pLM-puro by digesting both plasmids with XhoI and MluI. This resulted in a fragment encoding the shRNA, 3' Mir30 flanking sequence, and a short DNA sequence that is unique in composition for each shRNA and termed a barcode. The barcode can be used in array-based high throughput assay systems. This fragment was then ligated into the unique XhoI site of pLM-puro that is just downstream of the 5' Mir30 flanking sequence and the unique MluI site in pLM-puro downstream of the 3' Mir30 flanking sequence.

5.1.2 Preparation of pLM-Puro Plasmids Encoding shRNAs not in pSM2

The shRNAs against ORC1, ORC2, EBNA1, and Ff-luciferase used in this work were generated as follows. The following 97-mer oligonucleotides were purchased:

```
ORC1mi550:
                                              (SEQ ID NO: 17)
TGCTGTTGACAGTGAGCGCGGAAATATTCTGGTATGATTATAGTGAAGCC

ACAGATGTATAATCATACCAGAATATTTCCTTGCCTACTGCCTCGGA

ORC2mi1903:
                                              (SEQ ID NO: 18)
TGCTGTTGACAGTGAGCGAGGAACTGATGGAGTAGAGTATTAGTGAAGCC

ACAGATGTAATACTCTACTCCATCAGTTCCCTGCCTACTGCCTCGGA

ORC2mi1981:
                                              (SEQ ID NO: 19)
TGCTGTTGACAGTGAGCGAGAGGCTTGAAGCTTTCCTTTATAGTGAAGCC

ACAGATGTATAAAGGAAAGCTTCAAGCCTCCTGCCTACTGCCTCGGA

EBNA1mi1666:
                                              (SEQ ID NO: 20)
TGCTGTTGACAGTGAGCGCGTCCATTGTCTGTTATTTCATTAGTGAAGCC

ACAGATGTAATGAAATAACAGACAATGGACTTGCCTACTGCCTCGGA

Lucifmi203:
                                              (SEQ ID NO: 21)
TGCTGTTGACAGTGAGCGCCGATATGGGCTGAATACAAATTAGTGAAGCC

ACAGATGTAATTTGTATTCAGCCCATATCGTTGCCTACTGCCTCGGA
```

A PCR amplification was then performed using the above 97mers as templates and the following oligonucleotides as primers:

```
5' Primer:
                                              (SEQ ID NO: 22)
CAGAAGGCTCGAGAAGGTATATTGCTGTTGACAGTGAGCG 3' Primer:
                                              (SEQ ID NO: 23)
CTAAAGTAGCCCCTTGAATTCCGAGGCAGTAGGCA
```

The resulting PCR product was then digested with XhoI and EcoRI and inserted into the unique XhoI and EcoRI sites of pLM-puro located between the 5' Mir30 and 3'Mir30 flanking sequences. These plasmids do not encode unique barcode sequences for the respective shRNAs.

The sequence of the inserts for each shRNA are as follows. The nucleotides encoding the shRNA sequences that target each respective mRNA for destruction are underlined.

```
ORC1mi550:
                                              (SEQ ID NO: 24)
CTCGAGAAGGTATATTGCTGTTGACAGTGAGCGCGGAAATATTCTGGTAT

GATTATAGTGAAGCCACAGATGTATAATCATACCAGAATATTTCCTTGCC

TACTGCCTCGGAATTC

ORC2mi1903:
                                              (SEQ ID NO: 25)
CTCGAGAAGGTATATTGCTGTTGACAGTGAGCGAGGAACTGATGGAGTAG

AGTATTAGTGAAGCCACAGATGTAATACTCTACTCCATCAGTTCCCTGCC

TACTGCCTCGGAATTC

ORC2mi1981:
                                              (SEQ ID NO: 26)
CTCGAGAAGGTATATTGCTGTTGACAGTGAGCGAGAGGCTTGAAGCTTTC

CTTTATAGTGAAGCCACAGATGTATAAAGGAAAGCTTCAAGCCTCCTGCC

TACTGCCTCGGAATTC

EBNA1mi1666:
                                              (SEQ ID NO: 27)
CTCGAGAAGGTATATTGCTGTTGACAGTGAGCGCGTCCATTGTCTGTTAT

TTCATTAGTGAAGCCACAGATGTAATGAAATAACAGACAATGGACTTGCC

TACTGCCTCGGAATTC

Lucifmi203:
                                              (SEQ ID NO: 28)
CTCGAGAAGGTATATTGCTGTTGACAGTGAGCGCCGATATGGGCTGAATA

CAAATTAGTGAAGCCACAGATGTAATTTGTATTCAGCCCATATCGTTGCC

TACTGCCTCGGAATTC
```

5.1.3 Preparation of VSVG-Pseudotyped Amphotrophic Retrovirus

One million four hundred thousand Phoenix-amphotrophic packaging cells (cell line kindly provided by Gary Nolan) were seeded per well of 6-well plates in 2 mL DMEM+10% fetal bovine serum (FBS). After allowing ~24 hours for cells to attach to wells, each culture was co-transfected using lipofectamine 2000 (Invitrogen) with pHelper plasmid, pVSVG plasmid, and a pLM-puro plasmid encoding a particular shRNA. The pHelper and pVSVG plasmids were added to improve infection efficiency of HCT116 cultures. At ~24 hours post-transfection, the transfection media on each culture was aspirated and replaced with DMEM media+10% FBS. At ~36 hours post-transfection, media containing virus was collected from each packaging cell culture and filtered through a 0.45 micron filter using a 3 mL syringe. Two milliliters DMEM+10% FBS was then added back to each culture of packaging cells. At ~42-48 hours post-transfection, media containing virus was again collected from each packaging cell culture and filtered through a 0.45 micron filter using a 3 mL syringe. Packaging cultures were then bleached and discarded according to standard BL2+ safety protocol for disposal of infectious waste.

5.1.4 Infection and Selection of HCT116 Cultures

About 24 hours prior to infection, 150,000 HCT116 cells were seeded per well of a 24-well plate in 0.4 mL DMEM+ 10% FBS. At the time of the first round of infection, culture media was aspirated from each HCT116 culture and 0.5 mL media containing virus, obtained from ~36-hour post-transfection packaging cell culture as described above, was added to each HCT116 culture. Each HCT116 culture was infected with virus encoding a particular shRNA. The cultures were returned to the incubator, and ~8-12 hours later, the media containing virus was aspirated from each culture and replaced with media containing virus encoding the same shRNA, which was obtained from the ~42-48-hours post-transfection packaging cell cultures. Thus each HCT116 culture underwent two rounds of infection with virus encoding a particular shRNA.

About 24 hours after the second round of infection of the HCT116 cultures, cells from each culture were suspended and seeded to 6-well plates in 2 mL DMEM+10% FBS+1.5 µg/mL puromycin per well. Following two days of growth, cells in each culture were suspended in 3 mL DMEM+FBS+ 1.5 µg/mL puromycin. Two milliliters of each suspension were seeded to 6-well plates. Following two more days of growth (day 5 post-infection), cells in each culture were suspended in complete DMEM and cell numbers per culture were counted using a hemacytometer.

5.1.5 Normalization of Results for Experimental RNAi Cultures

Results from the counting described above for 255 HCT116 cultures transduced with different shRNAs were generated from multiple experiments. In each experiment, the impact of 36-48 different shRNAs on HCT116 proliferation was tested.

In each experiment, HCT116 cells were also transduced with hairpins against EBNA1 (EBNA1mi1666) and Ff-luciferase (lucifmi203). 2-3 HCT116 cultures were infected with virus encoding EBNA1mi1666; another 2-3 HCT116 cultures were infected with virus encoding Lucifmi203. Neither EBNA1 nor Ff-luciferase is encoded in the genome of HCT116 cells; therefore shRNAs targeting these genes should not impair HCT116 proliferation. A BLAST search for sequences in the human genome that match the sequences of these shRNAs was performed to verify that these shRNAs would not target endogenous transcripts for degradation. Similar to cultures transduced with other shRNAs, on day 5 post-infection, HCT116 cells in cultures transduced with either EBNA1mi1666 or Lucifmi203 were suspended and counted using a hemacytometer. HCT116 cultures transduced with either EBNA1mi1666 or Lucifmi203 contained similar numbers of cells by day 5 post-infection, supporting the conclusion that neither shRNA impaired HCT116 proliferation.

Figure 1:
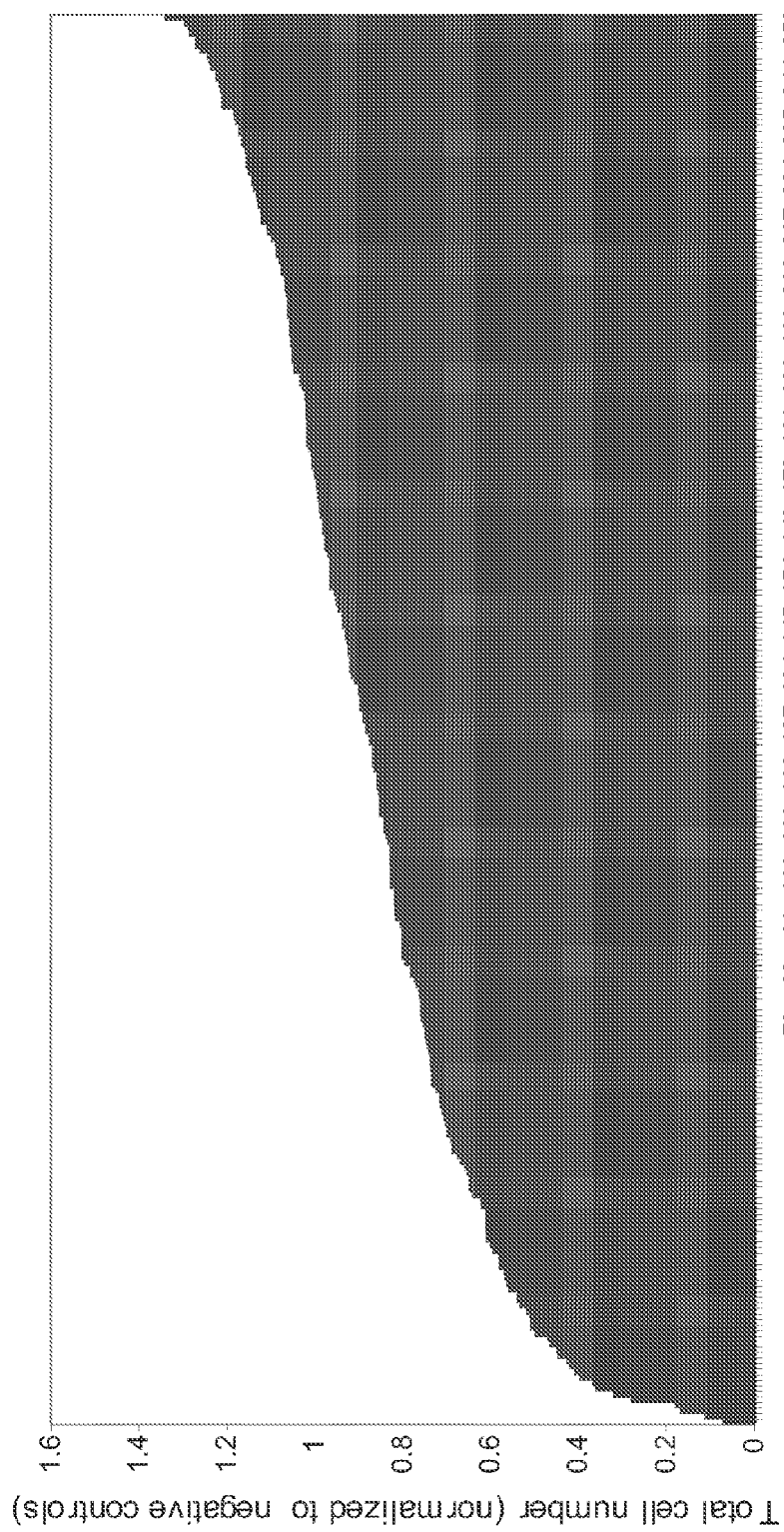

The average cell number in HCT116 cultures transduced with EBNA1mi1666 and Lucifmi203 was calculated for each experiment and cell numbers in cultures transduced with the other shRNAs in the given experiment were normalized to this value. These results are presented in FIG. 1. Since all results are normalized to the average cell number observed in cultures transduced with EBNA1mi1666 and Lucifmi203, results for these negative control cultures have a value of 1.0 and are not presented on the plot.

5.2 Example 2

Cytotoxicity of shRNAs in Human Cancer Cells

Figures 3A, 3B:
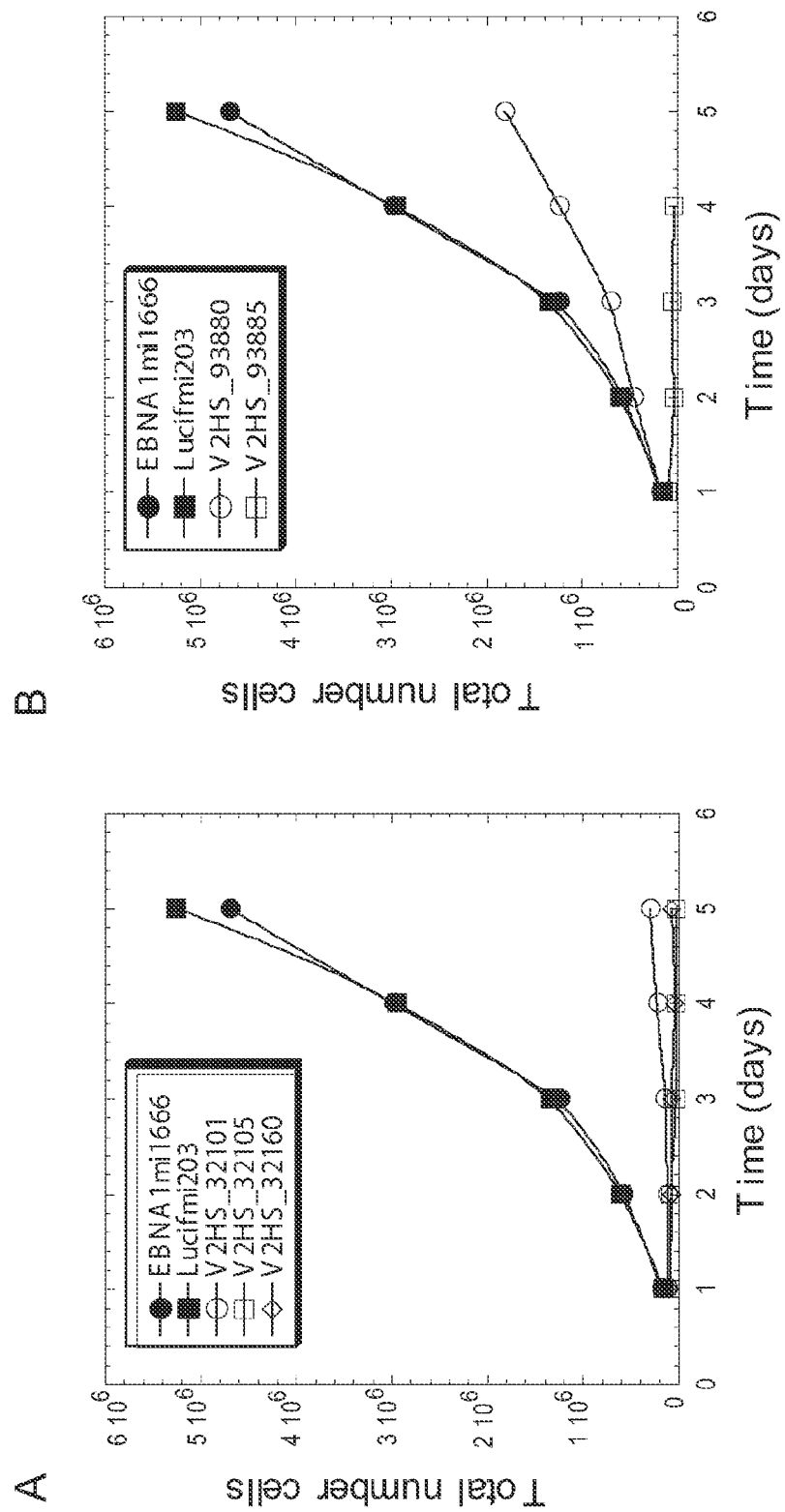
Figure 3C:
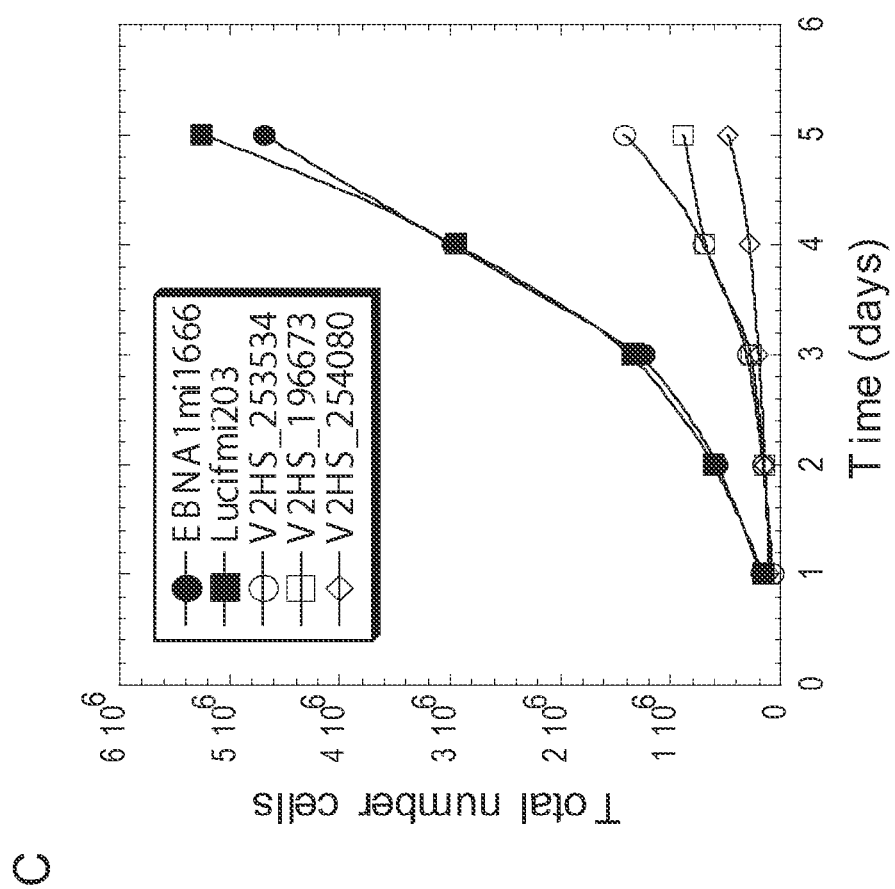
Figure 4:
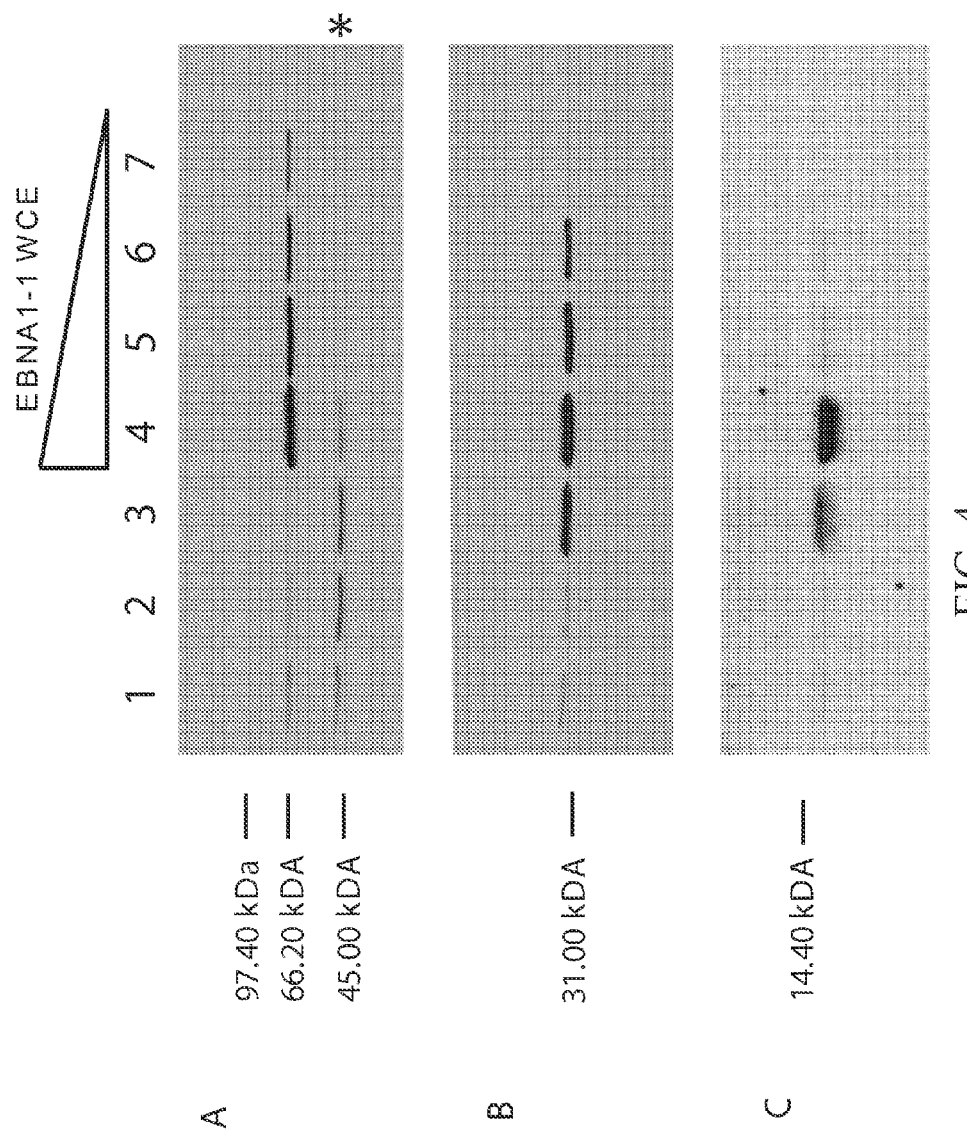

The assay described in Example 1 was used to identify shRNAs against DNA replication proteins that had the greatest anti-proliferative effect on HCT116 cell cultures. FIG. 2 shows those hairpins with greater than two-fold inhibition of proliferation. shRNAs targeting RRM1, RPA1, RPA3, and PEST were effective. See FIG. 2 and FIG. 3. FIG. 4 shows a Western blot analysis of expression of RPA subunits in HCT116 cultures transformed with RNAi molecules against RPA3 and RPA1. RPA3 expression is abolished by two shRNAs targeting RPA3.

TABLE 1

Cell numbers in experimental shRNA transduced cultures at 5 days post-infection (normalized to average of cells counted in negative control shRNA transduced cultures)

| Gene | shRNA ID | Cell # in culture/average cell number in negative control cultures |
|---|---|---|
| RRM1 | V2HS_93885 | 0.06872852 |
| RPA1 | V2HS_32160 | 0.10996564 |
| RPA3 | V2HS_32105 | 0.16494845 |
| PES1 | V2HS_254080 | 0.17721519 |
| PES1 | V2HS_196673 | 0.27848101 |
| RPA3 | V2HS_32101 | 0.3161512 |
| PCNA | V2HS_152708 | 0.35738832 |
| CDCA5 | V2HS_70809 | 0.36426513 |
| PES1 | V2HS_253534 | 0.39240506 |
| DDX5 | V2HS_24065 | 0.40506329 |
| C8ORF1 | V2HS_15119 | 0.41772152 |
| dkfzp434b168 | V2HS_96517 | 0.42268041 |
| C8ORF1 | V2HS_15118 | 0.44303797 |
| MCM5 | V2HS_84917 | 0.44620253 |
| FLJ10154 | V2HS_135540 | 0.46017699 |
| SLD5 | V2HS_138608 | 0.46518987 |
| C9orf76 | V2HS_176960 | 0.49484536 |
| dkfzp313a243 | V2HS_122245 | 0.50515464 |
| ELLS1 | V2HS_37210 | 0.50515464 |
| FLJ20530 | V2HS_174204 | 0.50737463 |
| FLJ20516 | V2HS_220099 | 0.51327434 |
| FLJ25416 | V2HS_29799 | 0.53097345 |
| TYMS | V2HS_229638 | 0.53608247 |
| dkfzp313a243 | V2HS_111231 | 0.53608247 |
| KIAA1614 | V2HS_59045 | 0.55457227 |
| SLD5 | V2HS_236484 | 0.56012658 |
| TYMS | V2HS_94107 | 0.56357388 |
| ZNF183 | V2HS_95049 | 0.56701031 |
| PCNA | V2HS_152710 | 0.57731959 |
| c14orf130 | V2HS_203406 | 0.57731959 |
| RHOBTB3 | V2HS_95943 | 0.57911392 |
| RAMP | V2HS_225424 | 0.59106529 |
| USP53 | V2HS_19252 | 0.59810127 |
| CDC45 | V2HS_172575 | 0.604811 |
| ELLS1 | V2HS_37208 | 0.604811 |
| C8ORF1 | V2HS_15117 | 0.60759494 |
| MCM5 | V2HS_84918 | 0.60759494 |
| MCM10 | V2HS_175971 | 0.60759494 |
| PSF1 | V2HS_34186 | 0.60759494 |
| ORC5 | V2HS_152497 | 0.61708861 |
| RRM1 | V2HS_93880 | 0.6185567 |
| FLJ20516 | V2HS_222044 | 0.63716814 |
| MCM3 | V2HS_151629 | 0.64556962 |
| RAMP | V2HS_115868 | 0.64604811 |
| CDCA7 | V2HS_57684 | 0.64604811 |
| MGC40214 | V2HS_21213 | 0.64948454 |
| PSF1 | V2HS_34187 | 0.65506329 |
| Luzp5 | V2HS_173669 | 0.66475645 |
| KIAA1614 | V2HS_248717 | 0.67256637 |
| FLJ10154 | V2HS_237686 | 0.68436578 |
| CDCA5 | V2HS_70812 | 0.68472622 |
| dkfzp434b168 | V2HS_96520 | 0.68728522 |
| FLJ25416 | V2HS_29802 | 0.69616519 |
| MYCBP2 | V2HS_254277 | 0.69620253 |
| C6orf72 | V2HS_205077 | 0.6991404 |
| MGC2610 | V2HS_111372 | 0.70103093 |
| TTC14 | V2HS_85344 | 0.7054755 |
| ORC2 | Orc2mi1903 | 0.71150436 |
| MCM5 | V2HS_84920 | 0.71202532 |
| MCM10 | V2HS_175970 | 0.71202532 |
| FLJ20105 | V2HS_155113 | 0.72206304 |
| RHOBTB3 | V2HS_95941 | 0.73101266 |
| MCM3 | V2HS_151632 | 0.73101266 |
| MCM10 | V2HS_221770 | 0.73101266 |
| MGC2610 | V2HS_111373 | 0.73195876 |
| MYCBP2 | V2HS_200448 | 0.73417722 |

TABLE 1-continued

Cell numbers in experimental shRNA transduced cultures at 5 days post-infection (normalized to average of cells counted in negative control shRNA transduced cultures)

| Gene | shRNA ID | Cell # in culture/average cell number in negative control cultures |
|---|---|---|
| DDX5 | V2HS_24063 | 0.73417722 |
| CANP | V2HS_285907 | 0.73775216 |
| MGC2610 | V2HS_246266 | 0.74226804 |
| Luzp5 | V2HS_173665 | 0.74269341 |
| C6orf72 | V2HS_205290 | 0.74498567 |
| WDHD1 | V2HS_199940 | 0.74498567 |
| RHOBTB3 | V2HS_95944 | 0.75 |
| ORC3 | V2HS_48977 | 0.75398223 |
| KIAA1598 | V2HS_175062 | 0.75516224 |
| TIMELESS | V2HS_47526 | 0.75601375 |
| C9orf76 | V2HS_176963 | 0.75601375 |
| USP53 | V2HS_19254 | 0.75949367 |
| KDELC1 | V2HS_98989 | 0.76103152 |
| KIAA1529 | V2HS_19447 | 0.76696165 |
| c14orf130 | V2HS_203155 | 0.76975945 |
| SLD5 | V2HS_138603 | 0.77848101 |
| Luzp5 | V2HS_277726 | 0.77936963 |
| C6orf72 | V2HS_250508 | 0.79083095 |
| RBBP4 | V2HS_57091 | 0.79725086 |
| KIAA0701 | V2HS_50916 | 0.79725086 |
| KIAA0738 | V2HS_260627 | 0.79725086 |
| CDC6 | V2HS_112878 | 0.79725086 |
| C1orf63 | V2HS_39946 | 0.79725086 |
| USP53 | V2HS_19251 | 0.79746835 |
| FLJ10154 | V2HS_135542 | 0.80235988 |
| NT5C2L1 | V2HS_38659 | 0.81152738 |
| kiaa008 | V2HS_95173 | 0.81375358 |
| DC13 | V2HS_50978 | 0.81375358 |
| KIAA1529 | V2HS_19475 | 0.81415929 |
| KIAA1614 | V2HS_249384 | 0.81415929 |
| FLJ20530 | V2HS_174203 | 0.81415929 |
| FLJ11806 | V2HS_158009 | 0.82474227 |
| c14orf130 | V2HS_202843 | 0.82474227 |
| C1orf63 | V2HS_39943 | 0.82474227 |
| dkfzp434b168 | V2HS_96521 | 0.82474227 |
| KDELC1 | V2HS_231665 | 0.8252149 |
| KDELC1 | V2HS_98994 | 0.8252149 |
| FLJ13231 | V2HS_82233 | 0.8259587 |
| FLJ13231 | V2HS_256796 | 0.8259587 |
| CANP | V2HS_285266 | 0.82997118 |
| dkfzp313a243 | V2HS_122242 | 0.83505155 |
| FLJ20530 | V2HS_174199 | 0.83775811 |
| FLJ11127 | V2HS_176291 | 0.83775811 |
| KIAA1586 | V2HS_102262 | 0.83775811 |
| FLJ20105 | V2HS_155116 | 0.84813754 |
| ORC2 | Orc2mil981 | 0.84955745 |
| ORC4 | V2HS_152488 | 0.84955745 |
| KIAA1598 | V2HS_222689 | 0.84955752 |
| RBBP4 | V2HS_247612 | 0.85223368 |
| MCM3 | V2HS_262054 | 0.85443038 |
| SLD5 | V2HS_138605 | 0.85443038 |
| FBXL20 | V2HS_263207 | 0.8556701 |
| FLJ20530 | V2HS_223307 | 0.86135693 |
| C9orf76 | V2HS_276972 | 0.86597938 |
| dkfzp313a243 | V2HS_225310 | 0.86597938 |
| ZNF183 | V2HS_95052 | 0.86597938 |
| ZNF183 | V2HS_95051 | 0.86597938 |
| ORC1 | mi550 | 0.87187265 |
| MYCBP2 | V2HS_251405 | 0.87341772 |
| MGC2610 | V2HS_111370 | 0.87972509 |
| C1orf63 | V2HS_39941 | 0.87972509 |
| ABHD10 | V2HS_175389 | 0.88760807 |
| ABHD10 | V2HS_175391 | 0.88760807 |
| DC13 | V2HS_50979 | 0.89398281 |
| WDHD1 | V2HS_196383 | 0.89398281 |
| FIGNL1 | V2HS_201768 | 0.89398281 |
| KIAA1529 | V2HS_19426 | 0.89675516 |
| FLJ11127 | V2HS_277435 | 0.89675516 |
| XM_066946 | V2HS_23889 | 0.90855457 |
| ORC3 | V2HS_48972 | 0.91327426 |
| KDELC1 | V2HS_98993 | 0.91690544 |
| kiaa008 | V2HS_232596 | 0.91690544 |
| RBBP4 | V2HS_57090 | 0.91752577 |
| KIAA1529 | V2HS_19402 | 0.92035398 |
| XM_066946 | V2HS_23890 | 0.92035398 |
| NUP43 | V2HS_157038 | 0.9221902 |
| FLJ20105 | V2HS_155115 | 0.92836676 |
| PARP16 | V2HS_174138 | 0.92836676 |
| FLJ25416 | V2HS_29798 | 0.93215339 |
| KIAA1586 | V2HS_102265 | 0.93215339 |
| ABHD10 | V2HS_175390 | 0.93371758 |
| FLJ13231 | V2HS_82234 | 0.9439528 |
| ELLS1 | V2HS_37211 | 0.94845361 |
| ORC5 | V2HS_152494 | 0.94936709 |
| UHRF1 | V2HS_249046 | 0.9512894 |
| PCNA | V2HS_261970 | 0.96219931 |
| CDC45 | V2HS_172574 | 0.96219931 |
| CDCA7 | V2HS_57686 | 0.96219931 |
| FIGNL1 | V2HS_201915 | 0.96275072 |
| PARP16 | V2HS_174136 | 0.96275072 |
| PARP16 | V2HS_174137 | 0.96275072 |
| ORC3 | V2HS_246135 | 0.9663716 |
| kiaa0008 | V2HS_95176 | 0.97421203 |
| C10orf70 | V2HS_221723 | 0.97421203 |
| FIGNL1 | V2HS_201952 | 0.97421203 |
| KIAA1598 | V2HS_223530 | 0.97935103 |
| FLJ29771 | V2HS_29771 | 0.97935103 |
| NT5C2L1 | V2HS_38658 | 0.97982709 |
| UHRF1 | V2HS_70516 | 0.98567335 |
| ORC4 | V2HS_152489 | 0.98761053 |
| ORC6 | V2HS_199171 | 0.98761053 |
| CDC6 | V2HS_112875 | 0.98969072 |
| CDCA7 | V2HS_57682 | 0.98969072 |
| FLJ35740 | V2HS_47350 | 0.99115044 |
| FLJ11127 | V2HS_220725 | 0.99115044 |
| DDX11 | V2HS_24008 | 0.99713467 |
| NME1 | V2HS_76045 | 1 |
| COMMD7 | V2HS_88587 | 1.00288184 |
| XM_066946 | V2HS_23885 | 1.00294985 |
| MGC2610 | V2HS_49352 | 1.00343643 |
| NME1 | V2HS_76050 | 1.01030928 |
| FBXO30 | V2HS_202750 | 1.01440922 |
| NT5C2L1 | V2HS_159134 | 1.01440922 |
| KIAA1529 | V2HS_19427 | 1.01474926 |
| FLJ20516 | V2HS_174169 | 1.01474926 |
| FLJ13231 | V2HS_82235 | 1.01474926 |
| MGC40214 | V2HS_21211 | 1.01718213 |
| MGC2610 | V2HS_111371 | 1.01718213 |
| C1orf63 | V2HS_39942 | 1.01718213 |
| WDHD1 | V2HS_6044 | 1.02005731 |
| WDHD1 | V2HS_198756 | 1.02005731 |
| COMMD7 | V2HS_259262 | 1.0259366 |
| PCNA | V2HS_152712 | 1.03092784 |
| CDC45 | V2HS_172579 | 1.03092784 |
| Luzp5 | V2HS_173668 | 1.04297994 |
| FLJ12973 | V2HS_176783 | 1.04467354 |
| CANP | V2HS_285579 | 1.04899135 |
| ATAD2 | V2HS_54362 | 1.04899135 |
| NT5C2L1 | V2HS_159132 | 1.04899135 |
| KIAA0101 | V2HS_73018 | 1.05063291 |
| HBOI | V2HS_197280 | 1.05063291 |
| CROP | V2HS_65519 | 1.05444126 |
| DC13 | V2HS_50982 | 1.05444126 |
| C10orf70 | V2HS_276497 | 1.05444126 |
| FLJ12973 | V2HS_176782 | 1.05841924 |
| MGC40214 | V2HS_21212 | 1.05841924 |
| dkfzp313a243 | V2HS_111235 | 1.05841924 |
| RAMP | V2HS_115869 | 1.05841924 |
| KIAA1529 | V2HS_19423 | 1.0619469 |
| HBOI | V2HS_48974 | 1.06329114 |
| CROP | V2HS_65523 | 1.06361032 |
| DDX11 | V2HS_24005 | 1.06590258 |
| LMO4 | V2HS_84510 | 1.07204611 |
| c14orf130 | V2HS_255281 | 1.07216495 |

TABLE 1-continued

Cell numbers in experimental shRNA transduced cultures at 5 days post-infection (normalized to average of cells counted in negative control shRNA transduced cultures)

| Gene | shRNA ID | Cell # in culture/average cell number in negative control cultures |
|---|---|---|
| DDX11 | V2HS_242050 | 1.0773639 |
| FBXO30 | V2HS_202507 | 1.08357349 |
| NUP43 | V2HS_157040 | 1.08357349 |
| CDC6 | V2HS_112873 | 1.08591065 |
| COMMD7 | V2HS_259596 | 1.09510086 |
| FBXL20 | V2HS_195454 | 1.10309278 |
| ORC6 | V2HS_12700 | 1.10442468 |
| ATAD2 | V2HS_54361 | 1.11815562 |
| LMO4 | V2HS_84513 | 1.11815562 |
| FLJ35740 | V2HS_206342 | 1.12094395 |
| ORC4 | V2HS_235462 | 1.12566362 |
| FLJ12973 | V2HS_176779 | 1.12714777 |
| LMO4 | V2HS_256362 | 1.129683 |
| ORC6 | V2HS_198092 | 1.13628309 |
| ACD | V2HS_116355 | 1.14121037 |
| NUP43 | V2HS_157037 | 1.14121037 |
| FIGNL1 | V2HS_202276 | 1.14613181 |
| FBXO30 | V2HS_262021 | 1.15273775 |
| FBXO30 | V2HS_203571 | 1.15273775 |
| DDX17 | V2HS_203066 | 1.15273775 |
| FBXL20 | V2HS_262023 | 1.15463918 |
| CDCA5 | V2HS_70776 | 1.16426513 |
| DDX17 | V2HS_238845 | 1.16426513 |
| dkfzp313a243 | V2HS_111234 | 1.16838488 |
| C10orf70 | V2HS_221836 | 1.16905444 |
| ACD | V2HS_116356 | 1.17579251 |
| FLJ20516 | V2HS_174170 | 1.179941 |
| ACD | V2HS_116352 | 1.18040346 |
| KIAA0701 | V2HS_50917 | 1.20962199 |
| KIAA0701 | V2HS_50914 | 1.20962199 |
| KIAA0738 | V2HS_73695 | 1.20962199 |
| TTC14 | V2HS_85339 | 1.21037464 |
| HBOI | V2HS_197676 | 1.21518987 |
| ORC6 | V2HS_199450 | 1.22123883 |
| DDX17 | V2HS_203274 | 1.22190202 |
| FBXO30 | V2HS_202575 | 1.23342939 |
| dkfzp313a243 | V2HS_111232 | 1.2371134 |
| KIAA0101 | V2HS_73015 | 1.24050633 |
| NT5C2L1 | V2HS_38657 | 1.25648415 |
| FBXO30 | V2HS_262218 | 1.26801153 |
| TTC14 | V2HS_85343 | 1.26801153 |
| NT5C2L1 | V2HS_38656 | 1.2795389 |
| WDHD1 | V2HS_196266 | 1.28366762 |
| FLJ11806 | V2HS_158008 | 1.29209622 |
| ATAD2 | V2HS_54364 | 1.33717579 |

5.3 Example 3

Cytotoxicity of siRNAs in Human Cancer Cells siRNAs derived from the shRNAs of Example 2 were all highly cytotoxic to HCT116 cells. The siRNA sequences and shRNAs from which they were derived are shown below RPA3
(SEQ ID NO: 1)
RPA3si1417: CAUCUUAUGUCCAGUUUAA (v2HS_32101)

(SEQ ID NO: 2)
RPA3si1403: CACCAUCUUGUGUACAUCU (v2HS_32105)

RRM1
(SEQ ID NO: 3)
RRM1si1820: CAGAUCUUUGAAACUAUUU (v2HS_93885)

CDC45
(SEQ ID NO: 4)
CDC45si384: CAGUCAAUGUCGUCAAUGUAU (v2HS_172575)

The numbers refer to the location in the cDNA sequences for the respective genes that these sequences initiate. In parenthesis are the Codex and Open Biosystems catalog numbers for the shRNAs from which these siRNAs were derived.

Cytotoxicity was determined by the reduction in culture confluency over time after transfection of the siRNA relative to negative control RNAi cultures. Interestingly, in the shRNA context V2HS_32105 was more cytotoxic than V2HS_32101. However in the siRNA context the opposite was the case, where RPA3si1417 was more cytotoxic than RPA3si1403.

Using a slightly different assay, we observed about a 5-fold reduction in the ability of HCT116 cells transduced with V2HS_172575 (targeting CDC45) to form colonies compared to cells transduced with the negative control shRNAs, which was interpreted as a significant reduction in HCT116 proliferation. After selecting for puromycin resistant HCT116 cells transduced with the shRNA, cultures were split and seeded 5,000 cells into a well of a 12-well plate in media containing puromycin. Cultures were allowed to grow for 8 days, at which time puromycin resistant colonies were apparent. Wells were then stained with crystal violet allowing visualization of any effect of the shRNA on colony formation in comparison to control cell transduced with shRNAs against either Ff-luciferase or EBNA1. Crystal violet was destained off the colonies and the amount of stain taken up by the well was measured, allowing quantitatation of the amount of colony formation in different wells. Western blots of cells transduced with CDC45 shRNAs showed a correlation between cytotoxicity and knockdown of CDC45 expression, with V2HS_172575 being the most cytotoxic.

5.4 Example 4

RNAi Against DNA Replication Genes in Mouse Cells

An assay similar to that described in Example 1 was used to test the effect of RNAi molecules against genes encoding DNA replication proteins in mouse cancer cells (Hepa1.6). Similar results in mouse cells were observed as compared to human cells (FIG. 8 and FIG. 9). For example, mouse tumors regress upon induction of RNAi against Rpa3 (FIG. 17).

Results also showed that inducible RNAi targeted against Rpa3 causes regression in a genetically defined mosaic mouse model of human AML (FIG. 18).

Figure 5:
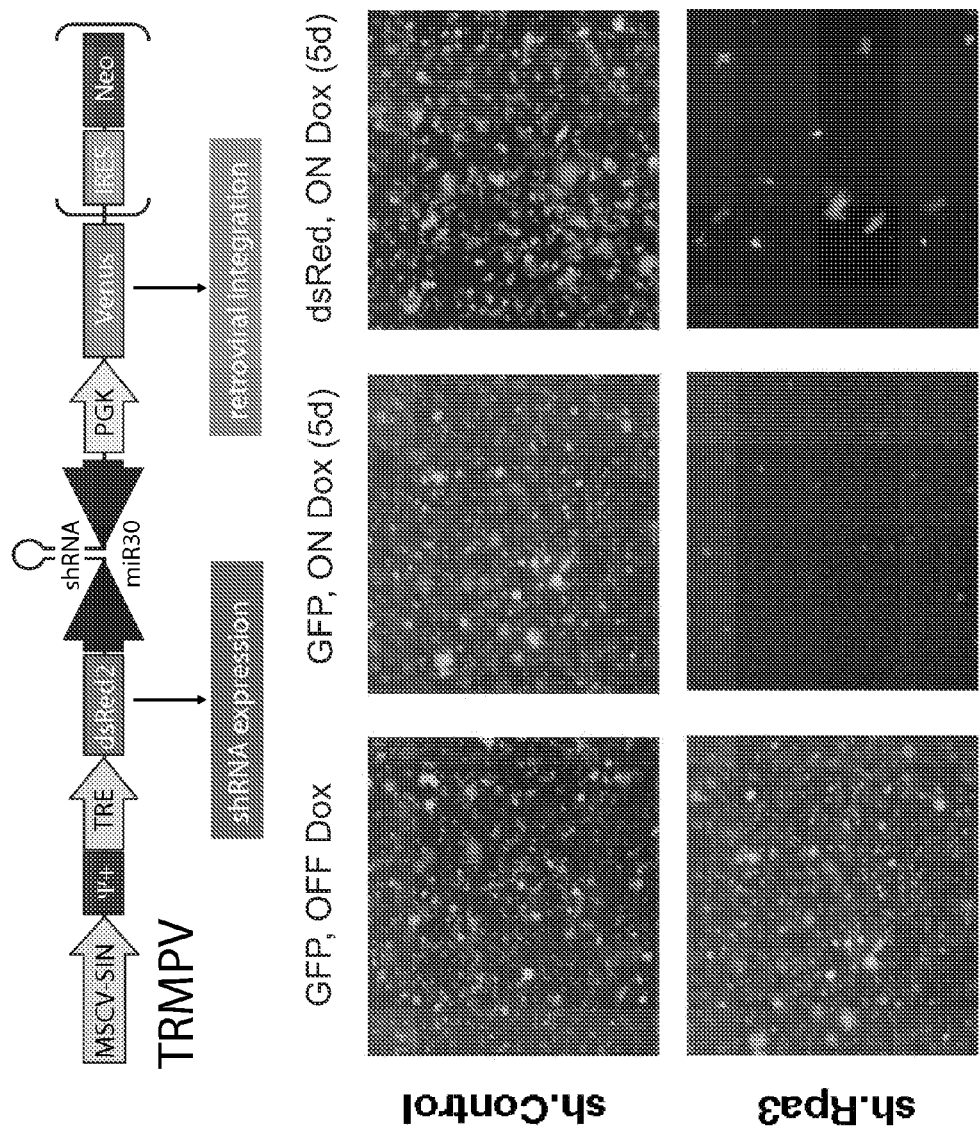
FIG. 5 shows an in vivo negative selection RNAi vector (TRMPV) that allows for separate monitoring of retroviral integration (Venus=YFP) and shRNA expression (dsRed).

Recipient cells expressing a shRNA against a target gene (for example, RPA3) are sorted based on a selectable marker whose expression substantially matches the expression of the RNAi molecule (FIG. 5). Depletion for the target gene RPA3 is observed (for example, see FIGS. 6A-C and FIG. 7).

5.5 Example 5

Additional Screens

A large-scale screen of cancer-related genes for modifiers of proliferation in a mouse model of liver carcinoma identified a small number of anti-proliferative shRNAs targeting ribosomal proteins (Rp115, Rps4x) (FIGS. 11A-B). This result echoes the identification of ribosomal biogenesis gene pescadillo in the human replication gene screen (FIG. 2 and FIG. 3).

RNAi screening as described herein followed by in vivo validation, as described below, to confirm the potency of therapeutic effect of a particular RNAi molecule in vivo can be used to identify drug targets for cancer therapy. For example, a screen of Mixed Lineage Leukemia (MLL) pathway genes for modifiers of proliferation in an MLL-driven mouse leukemia showed that shRNAs targeting c-Myb were strongly antiproliferative (FIGS. 10A-F). Inducible RNAi against Myb causes regression of this aggressive, chemoresistant leukemia in vivo (FIG. 19).

5.6 Example 6

AML Mouse Model

We developed AML mouse models to reflect common genetic themes in human AML. We used mice harboring leukemias that accurately reflect the genetics and pathology of human AML as tractable models to study the impact of cancer heterogeneity on therapy response and to explore the molecular basis for variable leukemia behavior. We see that leukemias expressing the AML1/ETO9a oncoprotein (mimicking translocation (8;21) in humans) respond well to conventional chemotherapy, whereas those expressing MLL/ENL (recapitulating translocation (11;19) in humans) show a particularly dismal response. Remarkably, the response patterns of these two leukemia subtypes accurately mimic what is observed in human patients with the same genetic lesions.

To rapidly generate mice harboring leukemias with various genetic alterations we applied a "mosaic" approach involving retroviral transduction of oncogenes into hematopoietic stem- and progenitor cells, followed by re-transplantation of the genetically-altered cells into syngeneic recipients (FIG. 30D). This strategy enables multiple oncogenes and reporter elements to be introduced in a one-step procedure, thereby facilitating disease monitoring and reducing the animal husbandry associated with germline transgenic mice. To model translocation (8;21) we choose to express the AML1/ETO9a splice variant that is expressed in the majority of t(8;21) patients and has increased leukemogenic potential in mice (Yan et al. 2006; Lafiura et al. 2008). To model MLL translocations, we used the MLL/ENL variant which is among the most common and associated with a particularly poor prognosis (Schoch et al. 2003). Both fusion genes were co-expressed with enhanced green fluorescent protein (EGFP) in bicistronic constructs (FIG. 30C). Oncogenic Nras$^{G12D}$ was co-expressed with luciferase to enable imaging of the resulting leukemias by bioluminescence. Of note, Nras$^{G12D}$ was cloned downstream of an internal ribosomal entry site (IRES), which reduces expression of the ectopic Nras gene to near physiological levels (Parikh et al. 2006).

Each oncogene was introduced alone or in combination into fetal liver cells (FLCs) derived from E13.5-15.5 embryos, and the infected populations—which are highly enriched for hematopoietic stem and progenitor cells (Morrison et al. 1995)—were used to reconstitute the hematopoietic compartment of lethally-irradiated syngeneic recipient mice (FIG. 30D). Recipient animals were then monitored for disease onset by analysis of peripheral blood and bioluminescence for the transduced luciferase reporter. As expected, mice receiving FLCs expressing AML1/ETO9a or MLL/ENL alone eventually developed GFP-positive leukocytosis consistent with peripheral leukemia. The survival of these animals was similar to previous reports, with AML1/ETO9a inducing leukemia with a longer latency and reduced penetrance compared to MLL/ENL (170 vs. 48 days median survival, p<0.0001).

Retroviral Constructs

All retroviruses were constructed in the MSCV backbone (Clontech). MSCV-IRES-Luciferase was generated by replacing GFP in MSCV-IRES-GFP with an NcoI/SalI fragment from pGL3-Basic (Promega) after excision of the 3' polyA-signal. Mouse Nras$^{G12D}$ was amplified and mutated by PCR from IMAGE clone 6475312 (Invitrogen) and cloned downstream of the internal ribosomal entry site (IRES); subsequently Luciferase was cloned upstream of the IRES. The AML1/ETO9a cDNA was generated by PCR from full-length human AML1/ETO-IRES-GFP and subcloned into MSCV-IRES-GFP. Human MLL/ENL was subcloned from MLL/ENL-PGK-Neo (generously provided by Irving L. Weissman) into MSCV-IRES-GFP and MSCV-IRES-Luciferase.

MSCV-5'LTR-rtTA3-IRES-MLL/AF9 was constructed with the MSCV backbone (Clontech) with a standard EMCV (Encephalomyocarditis virus)-IRES (internal ribosomal entry site) to allow for bicistronic transgene expression. A reverse tet-transactivator, rtTA3 (Das, et al., *JBC*, 2004), was cloned directly after the packaging signal and is driven by the retroviral MSCV-LTR promoter assuring high expression levels. MLL/AF9 is a fusion oncogene isolated from a patient carrying a t(9;11) translocation. It also is expressed from the LTR-transcript and uses IRES as a secondary translational start. MSCV-5'LTR-Luciferase-IRES-Nras(G12D) was also constructed the MSCV backbone (Clontech) with a standard EMCV (Encephalomyocarditis virus)-IRES (internal ribosomal entry site) to allow for bicistronic transgene expression and comprises a Luciferase insert cloned from pGL-Prom (Promega) and mouse oncogenic Nras(G12D), which was cloned and mutated from a full-length cDNA clone (Invitrogen).

Although Nras$^{G12D}$ was not oncogenic on its own, it cooperated with both AML1/ETO9a and MLL/ENL to accelerate leukemia onset and reduce overall survival (FIG. 30E), 170 to 84 days for AML1/ETO9a, p=0.0026; 48 to 24 days for MLL/ENL, p<0.0001). Of note, leukemias arising from FLCs transduced with both retroviral vectors were invariably positive for both luciferase (FIG. 30F) and GFP, suggesting a strong selective advantage for cells harboring a fusion protein together with Nras. Indeed, the resulting leukemias expressed the expected transgenes (FIG. 30G), and those harboring activated Nras displayed hyperactive Mitogen Activated Protein Kinase (MAPK) signaling as assessed by flow cytometry for phospho-Erk (a downstream Ras effector in the MAPK cascade) (FIG. 30H). Thus, lesions that occur together in human AML cooperate to rapidly generate leukemia in mice.

Fetal Liver Cell Isolation, Retroviral Transduction and Transplantation

E13.5-15.5 fetal liver cells from wild-type C57BL/6 mice were isolated, cultured and retrovirally transduced as previously described (Schmitt et al. 2002). Retroviral cotransduction was carried out by mixing viral supernatants from independent transfections of Phoenix packaging cells in a 1:1 ratio. Retroviral transduction of GFP expressing constructs was assessed 24 h after the last infection by flow cytometry (Guava EasyCyte, Guava Technologies); typically demonstrating transduction of about 20% of fetal liver cells. Transduction of luciferase expressing constructs was confirmed qualitatively (IVIS100, Caliper LifeSciences). About 1×10$^6$ cells were transplanted by tail vein injection of 6-8 week old lethally irradiated C57BL/6 recipient mice (9.0 Gy as single dose administered 24 h prior to transplantation). The Cold Spring Harbor Animal Care and Use Committee approved all mouse experiments included in this work.

Monitoring and Characterization of Primary Leukemias

Bioluminescent imaging was performed using an IVIS100 imaging system (Caliper LifeSciences). Mice were injected intraperitoneally with 150 mg/kg D-Luciferin (Caliper LifeSciences), anesthetized with isoflurane and imaged for 1 minute after a 5 minute incubation following injection. Primary FLC recipient mice were sacrificed at terminal disease stage (whole body signal in bioluminescent imaging, severe leukocytosis in peripheral blood smears, moribund appearance) by $CO_2$ euthanasia. Leukemia cells were harvested from bone marrow (by flushing tibias and femurs with DMEM) and spleen (by gently meshing enlarged spleens between two glass slides), filtered through a nylon screen (35 μm) to obtain single-cell suspensions and cryopreserved in fetal bovine serum (FBS) containing 10% DMSO. Peripheral blood smears and bone marrow cytospins were stained with Wright-Giemsa (Sigma); tissue specimens were fixed in 10% formalin and stained with hematoxylin and eosin (Sigma) using standard protocols.

For immunophenotyping, single-cell suspensions of bone marrow and spleen were incubated in ACK red cell lysis buffer (150 mM $NH_4Cl$, 10 mM $KHCO_3$, 0.1 mM EDTA) for 5 minutes, resuspended in FACS buffer (PBS, 5% FBS, 0.1% $NaN_3$) and preincubated with anti-CD16/CD32 ($F_c$-block, 1:1000, BD Pharmingen). Aliquots of ~0.5×10$^6$ cells were stained for 20 minutes on ice with phycoerythrin-Cy5-conjugated monoclonal antibodies specific for Mac-1, Gr-1, F4/80, CD45, CD3, CD19, B220, TER119, CD117, Sca-1 and a phycoerythrin-conjugated Ly-6C antibody (all 1:100, Biolegend). Data were collected on a LSR-II flow cytometer (BD Biosciences) and analyzed using FACSDiva (BD Biosciences) and FlowJo (Treestar) software. Statistical evaluation of overall survival was based on the log-rank (Mantel-Cox) test for comparison of the Kaplan-Meier event-time format.

5.7 Example 7

Murine Leukemias Display Pathological Features of Human AML

In human patients, AML is characterized by the appearance of malignant myeloid progenitors, which rapidly accumulate in bone marrow and aggressively infiltrate extramedullary tissues. Mice harboring leukemias co-expressing either AML1/ETO9a or MLL/ENL together with oncogenic Nras displayed progressive anemia and leukocytosis (See FIG. 31A), with extensive hepatosplenomegaly. Upon reaching a terminal stage, GFP-positive cells dominated their peripheral blood, bone marrow, spleen and liver (FIGS. 31C-D). Immunophenotyping, cytologic and histologic analyses revealed that AML1/ETO9a+Nras leukemias predominantly contain immature blasts (Mac1$^-$, Gr1$^-$, Ly-6C$^-$, F4/80$^{-/lo}$, CD45$^{lo}$, CD3$^-$, CD19$^-$, B220$^-$, TER119$^-$, CD117$^+$, Sca-1$^-$; FIGS. 31B-C), which parallels observations in other models of corefactor binding AML (Yan et al. 2004; Kuo et al. 2006). Although such purely immature subtypes are seen in t(8;21)-positive AML, most human cases show a significant granulocytic maturation besides immature myeloblasts, which was absent in murine AML1/ETO9a+Nras AML.

In contrast, MLL/ENL+Nras leukemias predominantly consisted of more differentiated myeloid cells (Mac1$^+$, Gr1$^{+/lo}$, Ly-6C$^+$, F4/80$^{+/lo}$, CD45$^+$, CD3$^-$, CD19$^-$, B220$^-$, TER119$^-$, CD117$^{lo/-}$, Sca-1$^-$, FIGS. 31B-C) and involve the monocytic lineage—a typical feature of human 11q23-rearranged AML. Similar to previous MLL fusion-based mouse models (Cozzio et al. 2003), the morphology resembles myelomonocytic and monocytic subtypes, which are seen in ~42% of human cases of 11q23-rearranged AML (Schoch et al. 2003). Despite its potent effects on leukemia onset, Nras did not appear to influence leukemia morphology, since leukemias induced by AML1/ETO9a or MLL/ENL alone were similar to those co-expressing Nras. In summary, mosaic mouse models based on cooperation of Nras with either fusion protein recapitulate common genetic and pathologic features of human AML.

5.8 Example 8

Establishment of Murine Chemotherapy Regimen that Mimics Clinical AML Induction Therapy To study factors that influence the outcome of conventional AML therapy in mice, we established a simple chemotherapy regimen involving intraperitoneal injection of cytarabine (100 mg/kg over 5 days) and doxorubicin (3 mg/kg over 3 days; FIG. 36A), which mimics the standard induction therapy used to treat AML in human patients. Of note, in our studies, doxorubicin was used over the more commonly used anthracycline daunorubicin, which showed high toxicity in mice if applied intraperitoneally. Efficacy and safety of this regimen were initially evaluated in a previously described model based on co-transduction of MLL/ENL and FLT3-ITD (Ono et al. 2005). In order to rapidly generate homogenous treatment cohorts we harvested bone marrow and spleen from terminally ill primary FLC recipient mice and transplanted 1 million leukemia cells into 20-30 secondary recipients. In initial studies, we noted that this combination therapy was not tolerated in mice when treatment was initiated based on a high leukemia burden in the peripheral blood; although the peripheral disease disappeared within two days, animals died shortly thereafter with peripheral leukopenia.

To better monitor leukemia progression and treat animals at an earlier stage of disease, we took advantage of the luciferase reporter, which we linked to MLL/ENL in a bicistronic retrovirus. Bioluminescent imaging allowed detection of MLL/ENL+FLT3-ITD leukemic cells in bone marrow, spleen and liver approximately 10 days after transplantation into secondary recipients, which corresponded to approximately 30% infiltration in bone-marrow and spleen in pathologic analysis, while the disease became apparent in peripheral bloodsmears about 5-7 days later (FIG. 36A). When mice were treated when disease was detected by bioluminescent imaging, most showed some response to therapy (FIG. 36B), while untreated controls progressed rapidly (FIG. 36C). Although most responses were only partial (median survival benefit of 7 days, p<0.0001; FIG. 36D), none of the animals appeared to succumb to treatment toxicity, but instead from advancing leukemia. These studies demonstrate the utility of bioluminescence monitoring for treatment studies and establish an effective and safe combined chemotherapy regimen that mirrors AML induction therapy.

Transplantation and In-Vivo Treatment Studies

For treatment studies each primary leukemia was transplanted into 20-30 6-8 weeks old sublethally irradiated recipient mice (4.5 Gy, 24 h prior to transplantation) by tail-vein injection of 1×10$^6$ viable GFP+ cells/recipient. Viability was assayed by propidium iodide (PI) staining; GFP+/PI− cells were counted using a Guava EasyCyte flow cytometer (Guava Technologies). Recipient mice were monitored by bioluminescent imaging every 4 days starting 10 days after transplantation. Treatment was initiated upon detection of clear signals in pelvis, tail and both femurs and initial stage of hepatosplenic infiltration, which correlated with 30-60% bone marrow infiltration as assessed by flow cytometry. Mice were treated for five consecutive days every 24 h with intraperitoneal (i.p.) injections of 100 mg/kg Cytarabine (Bedford Laboratories); during the first three days 3 mg/kg Doxorubicin (Bedford Laboratories) was administered in a separate i.p. injection. Immediate response and long-term treatment effects were monitored by weekly luciferase imaging starting the first day after treatment and by histopathological analysis of representative mice at various time points.

Gene Expression Analysis (Quantitative Real-Time PCR, Microarrays, Immunoblotting)

For drug-response studies, diseased mice were treated with a single dose of Cytarabine (100 mg/kg) and Doxorubicin (3 mg/kg) i.p. at various time points prior to harvest. Samples were obtained from enlarged spleens predominantly containing leukemia cells; infiltration of >85% GFP+ cells was confirmed by flow cytometry. Following ACK-lysis of single cell suspensions, RNA was extracted using RNAeasy columns (Qiagen) and cDNA was synthesized using TaqMan reverse transcriptase reaction (Applied Bosystems) according to the manufacturer's protocols. Quantitative PCR analysis was performed on an iCycler mounted with an iQ5 multicolor real time PCR detection system (Biorad). Primers used were specific for MLL/ENL (MLLf 5'-TCCCGCCTCAGCCAC-CTACTACAG (SEQ ID NO: 29), ENLr 5'-CGTG-GTGGGCTTCTTGCGCAGTT (SEQ ID NO: 30)), AML1/ETO9a (AML1f 5'-CTACCGAGCCATGAAGAACC (SEQ ID NO: 31), ETOr 5'-AGAGGAAGGCCCATTGCTGAA (SEQ ID NO: 32)), Cdkn1a (p21f 5'-GTTCCGCACAGGAG-CAAAGT (SEQ ID NO: 33), p21r 5'-ACGGCGCAACT-GCTCAC (SEQ ID NO: 34)) and Mdm2 (Mdm2f 5'-CTCA-CAGATTCCAGCTTCGGA (SEQ ID NO: 35), Mdm2r 5'-TGCGCTCCAACGGACTTTA (SEQ ID NO: 36)). Parallel reactions were done with primers specific for beta-actin (actbf 5'-CTCTGTGTGGATCGGTGGCT (SEQ ID NO: 37), actbr 5'-GCTGATCCACATCTGCTGGAAA (SEQ ID NO: 38)). Expression data were normalized against actin controls. Microarray experiments were performed on Mouse Genome 430A 2.0 arrays (Affymetrix) according to manufacturer's instructions.

For Western blot analysis, ACK-treated samples were lysed in Laemmli buffer, separated by SDS-PAGE and transferred to Immobilon PVDF membrane (Millipore). We used antibodies against p53 (IMX25, Leica Microsystems, 1:1000), p21 (C-19, Santa Cruz Biotechnology, 1:500), Nras (F155, Santa Cruz Biotechnology, 1:300), pan-Ras (Ras10, Upstate Biotechnology, 1:1000) and Actin (AC-15, Abcam, 1:5000). Flow cytometric analysis of phospho-Erk in bone marrow was performed using anti-pERK (#9101, Cell Signaling, 1:100) as previously described (Van Meter et al. 2007). To assess baseline phospho-Erk levels, cells were starved in the serum-free harvesting medium at 37° C. for 30 min. and then fixed and analyzed without cytokine stimulation.

5.9 Example 9

AMLs Expressing AML1/ETO9a or MLL/ENL Display Differences in Response to Conventional Chemotherapy To determine whether defined AML genotypes display distinct treatment sensitivities, we transplanted multiple primary AML1/ETO9a+Nras and MLL/ENL+Nras leukemias and treated secondary recipient mice upon bioluminescent disease detection in bone marrow and spleen. Leukemias coexpressing AML1/ETO9a and Nras rapidly regressed under combined chemotherapy leading to complete remissions. Thus, by 6 days after initiating treatment, luciferase signals disappeared completely, and histological analyses and flow cytometry revealed that the bone marrow and spleen were leukemia-free (FIGS. 32A and 35B). In most instances, mice harboring these leukemias remained in remission for at least 30 days (FIG. 32B), showing an overall survival benefit of 69 days (p<0.0001; FIG. 32C). Although 80% of the treated mice eventually relapsed, often emanating from focal regions in the bone or spleen, the rest remained leukemia free for even one year. Such behavior is reminiscent of the generally effective action of induction therapy in patients.

In stark contrast, MLL/ENL+Nras induced AML persisted under chemotherapy. Bioluminescent imaging merely showed a decelerated progression, while histology and flow cytometry revealed refractory leukemic infiltrates in the bone marrow (FIGS. 32A and 35B). After this minor stagnation in disease acceleration, animals progressed rapidly and died with only a minor survival benefit (5 days compared to untreated controls, p<0.0001; FIG. 32C). Hence, the MLL/ENL fusion protein produced leukemias that showed a very poor therapeutic response.

Our studies find a remarkable similarity in the genotype-response pattern of mouse AML models and human AML patients to standard induction chemotherapy, implying that such systems can predict the behavior of therapeutic agents in the clinic. Therefore, these and similar mouse models provide relevant systems for further studies on drug action and drug resistance and, by extrapolation, predictive test systems for characterizing potential new drug targets or testing new therapies for their efficacy at treating otherwise refractory malignancies.

5.10 Example 10

Screening and Evaluation of RNAi Targets

We applied tet-regulated in vivo RNAi to evaluate the role of candidate drug target genes in established MLL-fusion leukemia. These results have characterized seven genes as essential for the survival of established MLL/AF9 induced AML, amongst them four MLL-associated genes (MLL, Men1, Meis1, Myb) that are dispensable in Mefs. These studies demonstrate the power of tet-regulated RNAi to identify and evaluate genetic Achilles' heels in chemotherapy-resistant leukemia. To facilitate these studies we used the bioluminescent tet-on competent AML mouse model based on cooperation of an MLL-fusion oncogene (MLL/AF9) and oncogenic Nras, which reflects a common genetic association in human AML. Coexpression of MLL/AF9 and Nras$^{G12D}$ resulted in aggressive myelomonocytic leukemias (mean survival 21 days), which are refractory to combined chemotherapy (see FIG. 12).

An especially advantageous feature of the tet-on competent AML mouse model is in the use of tet-on competent leukemia cells, wherein said tet-on competent leukemia cells carry a bicistronic nucleic acid construct comprising a promoter operably linked to a fusion gene associated with chemotherapy-resistant leukemia, and a sequence encoding a reverse tet-transactivator protein, such that both coding sequences are co-expressed from said promoter. Importantly, we determined that in using inducible shRNA vectors for negative selection RNAi screening, as a critical prerequisite, it is essential to maintain stable, robust expression of a tet transactivator protein in all transplanted leukemic cells. Otherwise, outgrowth of clones in which shRNA expression is no longer inducible (for example, through selective pressure against expression of therapeutically active shRNAs) severely compromises success of screening or evaluation of shRNA activity.

A critical feature of mosaic mouse model for negative selection RNAi screening (see Examples 6-7) is the co-expression of a tet transactivator protein (e.g., rtTA3, a potent and non-toxic rtTA variant) together with the oncogene responsible for maintaining the leukemic phenotype, (e.g. MLL/AF9), from one promotor (e.g. LTR) in a bicistronic vector, ensuring that stable, robust rtTA expression and inducibility of shRNA expression is maintained in all transplanted cells, and independently of the identity of the particular shRNA being expressed.

Retroviral Constructs and Isolation of Tet-on AML Cells

SCV-5'LTR-rtTA3-IRES-MLL/AF9 was constructed with the MSCV backbone (Clontech) with a standard EMCV (Encephalomyocarditis virus)-IRES (internal ribosomal entry site) to allow for bicistronic transgene expression. A reverse tet-transactivator, rtTA3 (Das, et al., JBC, 2004), was cloned directly after the packaging signal and is driven by the retroviral MSCV-LTR promotor assuring high expression levels. MLL/AF9 is a fusion oncogene isolated from a patient carrying a t(9;11) translocation. It also is expressed from the LTR-transcript and uses IRES as a secondary translational start. MSCV-5'LTR-Luciferase-IRES-Nras(G12D) was also constructed in the MSCV backbone (Clontech) with a standard EMCV (Encephalomyocarditis virus)-IRES (internal ribosomal entry site) to allow for bicistronic transgene expression and comprises a Luciferase insert cloned from pGL-Prom (Promega) and mouse oncogenic Nras(G12D), which was cloned and mutated from a full-length cDNA clone (Invitrogen).

Tet-on leukemia (MLL/AF9+Nras AML) cells were obtained from a mouse transplanted with fetal liver cells derived from mouse embryos (e.g., E13.5-15.5 embryos) and stably transformed with the bicistronic tet-on construct SCV-5'LTR-rtTA3-IRES-MLL/AF9. Fetal liver cell isolation, retroviral isolation, retroviral transduction and transplantation were essentially carried out as above (see Examples 6-8).

To evaluate the potency of single-gene directed approaches in these therapy resistant AMLs, tumor cells were isolated from mice and transduced with a series of tet-regulatable shRNAs targeting (i) essential genes involved in DNA replication [Rpa1, Rpa3, PCNA], (ii) MLL associated genes [MLL, HoxA9, Meis1, Men1, Dot1L, Myb] and (iii) other controls [Luciferase, Braf]. Effects of doxycycline-induced shRNA expression in vitro and in vivo were studied using a dual-color tet-shRNA vector that allows precise tracking of shRNA expressing cells. TRMPV was constructed in the pQCXIX self-inactivating retroviral backbone (Clontech, Palo Alto, Calif.) by inserting the Tet-responsive element (TRE), dsRed, the miR30 context and a PGK-Venus expression cassette using standard cloning techniques (FIG. 5). In some experiments, variants of the vector an IRES-Neomycin (TRMPVIN) or IRES-Hygromycin (TRMPVIH) cassette were introduced downstream of Venus to facilitate drug selection. To construct TRMPVIR Neomycin in TRMPVIN was exchanged to rtTA3 (Das et al. 2004) and the TRE promoter was replaced by the TREtight variant (Clontech 2003). After selection, the tet-on cells (MLL/AF9+Nras AML) now carrying tet-inducible shRNAs were transplanted into secondary recipient mice. (see FIGS. 13-14). Following leukemia onset as evidenced through bioluminescent imaging mice were treated with oral doxycycline to induce expression of these shRNAs in the recipient mice.

In results of these experiments potent antileukemic effects were observed for multiple shRNAs targeting Rpa1, Rpa3, PCNA and certain MLL associated genes (MLL itself, Meis1, Men1, Myb). For example, in some experiments, mice were transplanted with AML cells carrying tet-inducible Rpa3 and Myb shRNAs. Following leukemia onset as evidenced through bioluminescent imaging, treatment of mice with oral doxycycline induced rapid and durable remissions upon induction of Rpa3 and Myb shRNAs. Histological analysis of the bone marrow and liver showed that shRNAs targeting Rpa3 or Myb ameliorated MLL/AF9-Nras leukemia (FIG. 15 and FIG. 16). In contrast, mice transplanted with MLL/AF9+ Nras AML cells expressing Braf control shRNAs suffered from continued progression of leukemia under doxycycline treatment. In particular, these results demonstrate that chemotherapy-resistant MLL/AF9-Nras leukemia can be ameliorated by tet-inducible shRNAs targeting Rpa3 (and others components of the replication machinery) (FIG. 18), as well as Myb (see FIG. 19). In parallel assays using tet-on competent Mefs we show that the antileukemic effects of shRNAs targeting MLL-associated genes are not due to general cytotoxicity.

The shRNAs identified as having potent antileukemic effects are directly useful in various embodiments of the invention. Additionally, modified shRNA molecules and siRNA molecules directed against the targeted genes and derived from these shRNAs according to the disclosures herein (for example, as exemplified in sections 4.3-4.5, Example 3) are useful in other embodiments of the invention, and in particular, in the therapeutic use of such siRNA molecules to treat therapy resistant cancers. shRNA that exhibited particularly potent antileukemic effects are shown below:

```
Bcl2.1132:
                                      (SEQ ID NO: 40)
TGCTGTTGACAGTGAGCGCGACTGATATTAACAAAGCTTATAGTGAAGC
CACAGATGTATAAGCTTTGTTAATATCAGTCTTGCCTACTGCCTCGGA

Bcl2.1422:
                                      (SEQ ID NO: 41)
TGCTGTTGACAGTGAGCGACCGGGAGAACAGGGTATGATATAGTGAAGC
CACAGATGTATATCATACCCTGTTCTCCCGGCTGCCTACTGCCTCGGA

Bcl2.2169:
                                      (SEQ ID NO: 42)
TGCTGTTGACAGTGAGCGACAGTAGAAATTATATGCATTATAGTGAAGC
CACAGATGTATAATGCATATAATTTCTACTGCTGCCTACTGCCTCGGA

Mcl1.1334:
                                      (SEQ ID NO: 43)
TGCTGTTGACAGTGAGCGAAAGAGTCACTGTCTGAATGAATAGTGAAGC
CACAGATGTATTCATTCAGACAGTGACTCTTCTGCCTACTGCCTCGGA

Mcl1.1792:
                                      (SEQ ID NO: 44)
TGCTGTTGACAGTGAGCGAAACAGCCTCGATTTTTAAGAATAGTGAAGC
CACAGATGTATTCTTAAAAATCGAGGCTGTTCTGCCTACTGCCTCGGA

Mcl1.2018:
                                      (SEQ ID NO: 45)
TGCTGTTGACAGTGAGCGCGGACTGGTTATAGATTTATAATAGTGAAGC
CACAGATGTATTATAAATCTATAACCAGTCCATGCCTACTGCCTCGGA

Meis1.1045:
                                      (SEQ ID NO: 46)
TGCTGTTGACAGTGAGCGAAAGATGTAACAAGATCAGCAATAGTGAAGC
CACAGATGTATTGCTGATCTTGTTACATCTTCTGCCTACTGCCTCGGA Meis1.2095:
                                      (SEQ ID NO: 47)
TGCTGTTGACAGTGAGCGCTACGTTGTTTCTTATAGATTTTAGTGAAGC
CACAGATGTAAAATCTATAAGAAACAACGTAATGCCTACTGCCTCGGA
```

-continued

Meis1.2775:
(SEQ ID NO: 48)
TGCTGTTGACAGTGAGCGCTATGTAGACATTGTAAATAAATAGTGAAGC
CACAGATGTATTTATTTACAATGTCTACATAATGCCTACTGCCTCGGA Men1.219:
(SEQ ID NO: 49)
TGCTGTTGACAGTGAGCGACGGAATTGTAAGGAACTAGAATAGTGAAGC
CACAGATGTATTCTAGTTCCTTACAATTCCGGTGCCTACTGCCTCGGA Men1.2310:
(SEQ ID NO: 50)
TGCTGTTGACAGTGAGCGCCACCCTCATCCTCTAATTCAATAGTGAAGC
CACAGATGTATTGAATTAGAGGATGAGGGTGATGCCTACTGCCTCGGA Men1.2707:
(SEQ ID NO: 51)
TGCTGTTGACAGTGAGCGACTGCCCGAATTTGGAAATCTTTAGTGAAGC
CACAGATGTAAAGATTTCCAAATTCGGGCAGCTGCCTACTGCCTCGGA Myb.2572:
(SEQ ID NO: 52)
TGCTGTTGACAGTGAGCGCTCCATGTATCTCAGTCACTAATAGTGAAGC
CACAGATGTATTAGTGACTGAGATACATGGAATGCCTACTGCCTCGGA Myb.2652:
(SEQ ID NO: 53)
TGCTGTTGACAGTGAGCGCCCCAAGTAATACTTAATGCAATAGTGAAGC
CACAGATGTATTGCATTAAGTATTACTTGGGATGCCTACTGCCTCGGA Myb.670:
(SEQ ID NO: 54)
TGCTGTTGACAGTGAGCGACACAACCATTTGAATCCAGAATAGTGAAGC
CACAGATGTATTCTGGATTCAAATGGTTGTGCTGCCTACTGCCTCGGA Pcna.1216:
(SEQ ID NO: 55)
TGCTGTTGACAGTGAGCGCAAGAAATATTGTTCAATTTAATAGTGAAGC
CACAGATGTATTAAATTGAACAATATTTCTTATGCCTACTGCCTCGGA Pcna.538:
(SEQ ID NO: 56)
TGCTGTTGACAGTGAGCGCGGAGTACAGCTGTGTAATAAATAGTGAAGC
CACAGATGTATTTATTACACAGCTGTACTCCTTGCCTACTGCCTCGGA Rpa1.1620:
(SEQ ID NO: 57)
TGCTGTTGACAGTGAGCGCCCGCATGATCTTATCGGCAAATAGTGAAGC
CACAGATGTATTTGCCGATAAGATCATGCGGTTGCCTACTGCCTCGGA Rpa3.278:
(SEQ ID NO: 58)
TGCTGTTGACAGTGAGCGCAAGGAAGATACTAATCGCTTTTAGTGAAGC
CACAGATGTAAAAGCGATTAGTATCTTCCTTATGCCTACTGCCTCGGA Rpa3.431:
(SEQ ID NO: 59)
TGCTGTTGACAGTGAGCGCAAGGAAGACTCCTGCAGTTTATAGTGAAGC
CACAGATGTATAAACTGCAGGAGTCTTCCTTATGCCTACTGCCTCGGA Rpa3.457:
(SEQ ID NO: 60)
TGCTGTTGACAGTGAGCGCGCGACTCCTATAATTTCTAATTAGTGAAGC
CACAGATGTAATTAGAAATTATAGGAGTCGCTTGCCTACTGCCTCGGA Rpa3.561:
(SEQ ID NO: 61)
TGCTGTTGACAGTGAGCGCAAAAGTGATACTTCAATATATTAGTGAAGC
CACAGATGTAATATATTGAAGTATCACTTTTATGCCTACTGCCTCGGA

5.11 Example 11

An Epigenetics RNAi Screen for Novel Therapeutic Targets in Chemotherapy-Resistant AML As described above, in one non-limiting embodiment, shRNAs are complementary to a nucleotide sequence of a DNA replication protein. Non-limiting example of DNA replication proteins include replication protein A3 (RPA3), ribonucleotide reductase M1 (RRM1), cell division cycle 45 (CDC45) and pescadillo 1 (PEST). In another non-limiting embodiment, shRNAs are complementary to a nucleotide sequence of epigenetic modifier genes. Here, we also applied tet-regulated in vivo RNAi in our MLL-fusion leukemia model to evaluate the role of epigenetic modifier genes as candidate drug targets. To identify novel therapeutic targets for chemotherapy-resistant AML, we established a screening method that utilizes a combination of in vitro and in vivo RNAi technologies. We specifically investigated other enzymes that modify chromatin (epigenetic modifiers) as potential new drug targets in this disease. A custom library of 1,100 shRNAs was constructed that targets all known epigenetic regulators that have been identified to date, amounting to 235 genes (FIG. 20). These shRNAs were cloned into the LMN mir30-embedded shRNA vector driven by constitutive retroviral LTR promoter. A downstream Pgk promoter drives expression of Neomycin resistance cassette and eGFP separated by an internal ribosomal entry site. The choice of neomycin resistance was to allow subsequent in vivo testing in the final stage of validation, as other drug resistance markers are rejected by an immune response in mice.

The primary screen was performed by systematically profiling each of the 1100 individual shRNAs in the epigenetics library for its ability to confer a proliferative disadvantage to MLL-AF9/Nras leukemia cell growth in vitro (FIG. 21). This was monitored by measuring the relative loss of the shRNA+/GFP+population over 10 days following transduction of the leukemia cells. Each shRNA was scored by this method, which identified 35 epigenetic regulators that were required for proliferation of leukemia cell in vitro (based on a cutoff of 5-fold depletion and >2 shRNAs identified per gene). To gain insight into whether the requirement for these genes was unique to leukemia cells or was a general feature of all non-transformed hematopoietic cells, we compared the ability of the identified shRNAs to inhibit growth of leukemia cells, non-transformed erythroid cells (G1E), non-transformed myeloid cells (32D), and non-transformed stem-like cells (EML). The result of this multi-parameter testing revealed 8 genes that leukemias require for their proliferation but is dispensable for growth of all other hematopoietic cell lines tested (FIGS. 22-23). The findings are in contrast to the Rpa3 and Myc genes, which were required in all 4 cell types for growth in vitro (FIG. 23). The identified genes are Eed, Suz12, Aof2, Smarca4, Smarcd1, Men1, Hdac3, and Whs111.

The sequence of the shRNAs from the library targeting these genes are listed below as the oligo sequence. The knockdown efficiency of each shRNA was tested and correlated with the relative inhibition of leukemia cell proliferation (data not shown). These shRNAs, identified as having potent and specific antileukemic effects are directly useful in various embodiments of the invention. Additionally, modified shRNA molecules and siRNA molecules directed against the targeted genes and derived from these shRNAs according to the disclosures herein (for example, as exemplified in sections 4.3-4.5, Example 3) are useful in other embodiments of the invention, and in particular, in the therapeutic use of such siRNA molecules to treat therapy resistant cancers.

shRNA Sequences for AOF2:

Aof2.2435:
(SEQ ID NO: 39)
TGCTGTTGACAGTGAGCGCCTGGAAATGACTATGATTTAATAGTGAA
GCCACAGATGTATTAAATCATAGTCATTTCCAGATGCCTACTGCCTC
GGA

Aof2.1153:
(SEQ ID NO: 218)
TGCTGTTGACAGTGAGCGAATGGCTGTCGTCAGCAAACAATAGTGAA
GCCACAGATGTATTGTTTGCTGACGACAGCCATGTGCCTACTGCCTC
GGA

Aof2.1869:
(SEQ ID NO: 219)
TGCTGTTGACAGTGAGCGCAGGCTTGGACATTAAACTGAATAGTGAA
GCCACAGATGTATTCAGTTTAATGTCCAAGCCTTTGCCTACTGCCTC
GGA

Aof2.2857:
(SEQ ID NO: 220)
TGCTGTTGACAGTGAGCGCTTGGAAGTACAGCTCCATAAATAGTGAA
GCCACAGATGTATTTATGGAGCTGTACTTCCAAATGCCTACTGCCTC
GGA

Aof2.1956
(SEQ ID NO: 221)
TGCTGTTGACAGTGAGCGACACAAGTCAAACCTTTATTTATAGTGAA
GCCACAGATGTATAAATAAAGGTTTGACTTGTGGTGCCTACTGCCTC
GGA

Aof2.2741
(SEQ ID NO: 222)
TGCTGTTGACAGTGAGCGACAAGCTCTTCTAGCAATACTATAGTGAA
GCCACAGATGTATAGTATTGCTAGAAGAGCTTGCTGCCTACTGCCTC
GGA shRNA Sequences for EED:

Eed.949:
(SEQ ID NO: 223)
TGCTGTTGACAGTGAGCGACTGGATCTAGAGGCATTATAATAGTGAAGCC
ACAGATGTATTATAATGCCTCTAGATCCAGCTGCCTACTGCCTCGGA

Eed.710:
(SEQ ID NO: 224)
TGCTGTTGACAGTGAGCGCCAGCCTCAAGGAAGATCATAATAGTGAAGCC
ACAGATGTATTATGATCTTCCTTGAGGCTGTTGCCTACTGCCTCGGA

Eed.1397:
(SEQ ID NO: 225)
TGCTGTTGACAGTGAGCGCAGGCGATTTGATACTTTCCAATAGTGAAGCC
ACAGATGTATTGGAAAGTATCAAATCGCCTATGCCTACTGCCTCGGA

Eed.1083:
(SEQ ID NO: 226)
TGCTGTTGACAGTGAGCGCAAAGATCATGCTTTACGGTTATAGTGAAGCC
ACAGATGTATAACCGTAAAGCATGATCTTTATGCCTACTGCCTCGGA

Eed.1820:
(SEQ ID NO: 227)
TGCTGTTGACAGTGAGCGCTAGAAGTAATGTATCTTGCTATAGTGAAGCC
ACAGATGTATAGCAAGATACATTACTTCTATTGCCTACTGCCTCGGA

Eed.1765:
(SEQ ID NO: 228)
TGCTGTTGACAGTGAGCGAATCGACTTCGATAAACTATTTTAGTGAAGCC
ACAGATGTAAAATAGTTTATCGAAGTCGATCTGCCTACTGCCTCGGA shRNA Sequences for HDAC:

Hdac3.987:
(SEQ ID NO: 229)
TGCTGTTGACAGTGAGCGACCCGGTGTTGGACATATGAAATAGTGAA
GCCACAGATGTATTTCATATGTCCAACACCGGGCTGCCTACTGCCTC
GGA Hdac3.161:
(SEQ ID NO: 230)
TGCTGTTGACAGTGAGCGACTGGCATTGACTCATAGCCTATAGTGAA
GCCACAGATGTATAGGCTATGAGTCAATGCCAGGTGCCTACTGCCTC
GGA Hdac3.854:
(SEQ ID NO: 231)
TGCTGTTGACAGTGAGCGATCCCTGGGCTGTGATCGATTATAGTGAA
GCCACAGATGTATAATCGATCACAGCCCAGGGAGTGCCTACTGCCTC
GGA Hdac3.1037:
(SEQ ID NO: 232)
TGCTGTTGACAGTGAGCGCGAGGAACTTCCCTATAGTGAATAGTGAA
GCCACAGATGTATTCACTATAGGGAAGTTCCTCATGCCTACTGCCTC
GGA Hdac3.1491:
(SEQ ID NO: 233)
TGCTGTTGACAGTGAGCGCCCATATGTGGTTCTAGAATTATAGTGAA
GCCACAGATGTATAATTCTAGAACCACATATGGTTGCCTACTGCCTC
GGA Hdac3.506:
(SEQ ID NO: 234)
TGCTGTTGACAGTGAGCGATTCTGCTATGTCAATGACATATAGTGAA
GCCACAGATGTATATGTCATTGACATAGCAGAAGTGCCTACTGCCTC
GGA shRNA Sequences for MEN1:

Men1.2310:
(SEQ ID NO: 235)
TGCTGTTGACAGTGAGCGCCACCCTCATCCTCTAATTCAATAGTGAA
GCCACAGATGTATTGAATTAGAGGATGAGGGTGATGCCTACTGCCTC
GGA

Men1.219:
(SEQ ID NO: 236)
TGCTGTTGACAGTGAGCGACGGAATTGTAAGGAACTAGAATAGTGAA
GCCACAGATGTATTCTAGTTCCTTACAATTCCGGTGCCTACTGCCTC
GGA

Men1.1457:
(SEQ ID NO: 237)
TGCTGTTGACAGTGAGCGACACTGTTATCCAAGACTACAATAGTGAA
GCCACAGATGTATTGTAGTCTTGGATAACAGTGGTGCCTACTGCCTC
GGA

Men1.2707:
(SEQ ID NO: 238)
TGCTGTTGACAGTGAGCGACTGCCCGAATTTGGAAATCTTTAGTGAA
GCCACAGATGTAAAGATTTCCAAATTCGGGCAGCTGCCTACTGCCTC
GGA

Men1.228:
(SEQ ID NO: 239)
TGCTGTTGACAGTGAGCGCAAGGAACTAGAAGGCCCTATATAGTGAA
GCCACAGATGTATATAGGGCCTTCTAGTTCCTTATGCCTACTGCCTC
GGA

Men1.218:
(SEQ ID NO: 62)
TGCTGTTGACAGTGAGCGACCGGAATTGTAAGGAACTAGATAGTGAA
GCCACAGATGTATCTAGTTCCTTACAATTCCGGGTGCCTACTGCCTC
GGA shRNA Sequences for SMARCA4

Smarca4.3232:
(SEQ ID NO: 63)
TGCTGTTGACAGTGAGCGAAAGGTAGAGTATGTCATCAAATAGTGAA
GCCACAGATGTATTTGATGACATACTCTACCTTCTGCCTACTGCCTC
GGA Smarca4.5466:
(SEQ ID NO: 64)
TGCTGTTGACAGTGAGCGCCTGGAGTCAGACAGTAATAAATAGTGAA
GCCACAGATGTATTTATTACTGTCTGACTCCAGTTGCCTACTGCCTC
GGA Smarca4.4935:
(SEQ ID NO: 65)
TGCTGTTGACAGTGAGCGACTCCGTCAAGGTGAAGATCAATAGTGAA
GCCACAGATGTATTGATCTTCACCTTGACGGAGCTGCCTACTGCCTC
GGA Smarca4.3364:
(SEQ ID NO: 66)
TGCTGTTGACAGTGAGCGCCTGATGAACACTATTATGCAATAGTGAA
GCCACAGATGTATTGCATAATAGTGTTCATCAGTTGCCTACTGCCTC
GGA Smarca4.3633:
(SEQ ID NO: 67)
TGCTGTTGACAGTGAGCGCCAGGCTTGATGGAACCACAAATAGTGAA
GCCACAGATGTATTTGTGGTTCCATCAAGCCTGATGCCTACTGCCTC
GGA Smarca4.4299:
(SEQ ID NO: 68)
TGCTGTTGACAGTGAGCGCCAGCGACTCACTGACAGAGAATAGTGAA
GCCACAGATGTATTCTCTGTCAGTGAGTCGCTGTTGCCTACTGCCTC
GGA shRNA Sequences for SMARCD1

Smarcd1.986:
(SEQ ID NO: 69)
TGCTGTTGACAGTGAGCGAAAGCACTGTGGCAGTATATTATAGTGAA
GCCACAGATGTATAATATACTGCCACAGTGCTTGTGCCTACTGCCTC
GGA Smarcd1.1858:
(SEQ ID NO: 70)
TGCTGTTGACAGTGAGCGCTAGGACCTCTAGATAGTGTTATAGTGAA
GCCACAGATGTATAACACTATCTAGAGGTCCTATTGCCTACTGCCTC
GGA Smarcd1.690:
(SEQ ID NO: 71)
TGCTGTTGACAGTGAGCGCCGCGGCCTTGTCCAAATATGATAGTGAA
GCCACAGATGTATCATATTTGGACAAGGCCGCGTTGCCTACTGCCTC
GGA Smarcd1.1738:
(SEQ ID NO: 72)
TGCTGTTGACAGTGAGCGCCACCTGTTATCCCGTCCTGTATAGTGAA
GCCACAGATGTATACAGGACGGGATAACAGGTGATGCCTACTGCCTC
GGA Smarcd1.2668:
(SEQ ID NO: 73)
TGCTGTTGACAGTGAGCGACAGGTTTGTCACCCGGAGTTATAGTGAA
GCCACAGATGTATAACTCCGGGTGACAAACCTGGTGCCTACTGCCTC
GGA Smarcd1.1702:
(SEQ ID NO: 74)
TGCTGTTGACAGTGAGCGCCACAATGAAGAGGGTGTCACATAGTGAA
GCCACAGATGTATGTGACACCCTCTTCATTGTGATGCCTACTGCCTC
GGA shRNA Sequences for SUZ12

Suz12.1676:
(SEQ ID NO: 75)
TGCTGTTGACAGTGAGCGATAGGATAGATGTTTCAATCAATAGTGAA
GCCACAGATGTATTGATTGAAACATCTATCCTAGTGCCTACTGCCTC
GGA

Suz12.909:
(SEQ ID NO: 76)
TGCTGTTGACAGTGAGCGACTGGCAGTTTCCAGTAATGAATAGTGAA
GCCACAGATGTATTCATTACTGGAAACTGCCAGGTGCCTACTGCCTC
GGA

Suz12.1842:
(SEQ ID NO: 77)
TGCTGTTGACAGTGAGCGATCGGAGTTTCTTGAATCTGAATAGTGAA
GCCACAGATGTATTCAGATTCAAGAAACTCCGACTGCCTACTGCCTC
GGA

Suz12.3979:
(SEQ ID NO: 78)
TGCTGTTGACAGTGAGCGATAGGTGTAGAATTATTGCTTATAGTGAA
GCCACAGATGTATAAGCAATAATTCTACACCTACTGCCTACTGCCTC
GGA

Suz12.4300:
(SEQ ID NO: 79)
TGCTGTTGACAGTGAGCGCTAAATGTTTATTTGAAATCAATAGTGAA
GCCACAGATGTATTGATTTCAAATAAACATTTAATGCCTACTGCCTC
GGA

Suz12.419:
(SEQ ID NO: 80)
TGCTGTTGACAGTGAGCGACGCGGTGTTGCCGGTGAAGAATAGTGAA
GCCACAGATGTATTCTTCACCGGCAACACCGCGGTGCCTACTGCCTC
GGA shRNA Sequences for WHSC1l1

Whsc1l1.1653:
(SEQ ID NO: 81)
TGCTGTTGACAGTGAGCGCACGAAGGGTATTGGTAACAAATAGTGAA
GCCACAGATGTATTTGTTACCAATACCCTTCGTTTGCCTACTGCCTC
GGA Whsc1l1.524:
(SEQ ID NO: 82)
TGCTGTTGACAGTGAGCGACTCACCCGAGATTAAACTAAATAGTGAA
GCCACAGATGTATTTAGTTTAATCTCGGGTGAGCTGCCTACTGCCTC
GGA Whsc1l1.276:
(SEQ ID NO: 83)
TGCTGTTGACAGTGAGCGCATCAGCTTGTATGAAACTCAATAGTGAA
GCCACAGATGTATTGAGTTTCATACAAGCTGATTTGCCTACTGCCTC
GGA Whsc1l1.373:
(SEQ ID NO: 84)
TGCTGTTGACAGTGAGCGCCTGACTATTACCATTCAGAAATAGTGAA
GCCACAGATGTATTTCTGAATGGTAATAGTCAGTTGCCTACTGCCTC
GGA Whsc1l1.1307:
(SEQ ID NO: 85)
TGCTGTTGACAGTGAGCGCTACCTCTAAGACGGAAGTCAATAGTGAA
GCCACAGATGTATTGACTTCCGTCTTAGAGGTAATGCCTACTGCCTC
GGA Whsc1l1.1059:
(SEQ ID NO: 86)
TGCTGTTGACAGTGAGCGCCGGGAATACAAAGGTCATGAATAGTGAA
GCCACAGATGTATTCATGACCTTTGTATTCCCGTTGCCTACTGCCTC
GGA To confirm that inhibiting the genes identified in our screen would have therapeutic potential when inhibited in vivo, subsequent validation was performed using a conditional, Tet-On RNAi vector (TRMPV) (FIG. 24). Using this approach, the mir30-embedded shRNA is cloned downstream of the Tet-responsive promoter (TRE). A downstream Pgk promoter drives Venus and Neo-resistance cassette. To allow stable efficient Tet-inducible activation, the rtTA3 (Tet-activator) gene is expressed from the same retroviral vector as the MLL-Af9 oncogene, separated by an IRES sequence. This manipulation of the retroviral vectors ensures that all MLL-AF9 transformed cells will be competent for induction of the shRNA via doxycylcine (a tetracycline analog) treatment. Each shRNA targeting the epigenetic regulator is cloned into the TRMPV vector and introduced into tet-on leukemia lines. Following neomycin selection, the leukemia cells are transplanted into recipient mice, which are then treated with Doxycyline after day 3 of transplant (after the disease has initiated). Disease was monitored via bioluminescence, overall survival benefit, and relative contribution of dsRed+/shRNA+ cells to the final disease burden when the mice succumb to the disease.

This analysis was performed for the shRNAs targeting Eed, Aof2, Suz12, Men1, and Smarcd1, which revealed a survival benefit to mice, which for some genes resulted in significant rates of cure in vivo (FIG. 25). In addition, all shRNAs inhibited proliferation of leukemia cells as the disease developed, as compare to a *Renilla* luciferase control shRNA (FIG. 26). These findings validate that addictions of leukemia cells to epigenetic pathways, as identified by using an in vitro RNAi screen, can be exploited for therapeutic benefit in vivo.

As an additional verification that therapy resistant AML leukemias harbor a unique sensitivity to inhibition of the identified epigenetic pathways, the influence of the epigenetics shRNAs on normal hematopoiesis was also examined in vivo following retroviral transduction of LMN (MSCV-miR30/shRNA-PGK-Neo-IRES-GFP; constructed by inserting a miR30-cassette and a PGK-NeomycinR-IRES-GFP cassette in the MSCV-backbone (Clontech)) into E13.5 fetal livers and subsequent transplantation of infected cells into lethally irradiated recipients (FIG. 27). This assay compares the relative contribution of the experimental shRNA vector (linked with GFP) to control, neutral shRNA LMN vector that harbors the red fluorescent protein (mCherry). At 4 weeks following transplantation of the mixed GFP+ and mCherry+ cells into recipient animals, the ratio of these two colors is measured in subsets of peripheral blood cells of various hematopoietic lineages or in bone marrow and spleens by co-staining with surface markers (e.g. Mac1, Gr1 for myeloid, B220 for B-lymphoid). Transduction with the Rpa3 shRNA in the LMN-GFP vector is entirely depleted from normal hematopoietic cells after 4 weeks of transplantation. In contrast, the shRNAs targeting the epigenetic regulators Suz12.1676, Eed.1829, and Smarcd1.1858 have little, if any impact on proliferation of normal hematopoietic cells in vivo (FIG. 28). This approach further demonstrates that the epigenetics RNAi screen has identified unique hypersensitivities of the therapy-resistant AML leukemia cells.

5.12 Example 12

Use of Inhibitors of Epigenetic Gene Targets as Novel Therapies for Chemotherapy Resistant AML An important feature of the proteins encoded by the gene targets identified from the above screen (Example 11) is their demonstrated enzymatic activity, identifying these proteins as attractive drug targets. As a further aspect of this invention, such drug targets may be used in subsequent chemical screens to identify compounds able to inhibit their respective enzymatic activities. Compounds identified through such screening may provide for reasonable therapeutic strategies in treatment of therapy-resistant AML leukemia.

As another aspect of this invention, known inhibitors of those proteins are used for treatment of therapy-resistant AML leukemias. Compounds useful in the invention include Dznep and other Eed inhibitors, hydroximates (such as SAHA, TSA and CBHA) and other HDAC inhibitors, and MAO-inhibitors and other inhibitors with activity against Aof2 (lysine-specific demethylase-1/LSD1). (Tan J et al., Genes Dev. 2007 May 1; 21(9):1050-63, Lane A A et al., J Clin Oncol. 2009 Nov. 10; 27(32):5459-68, Miller et al., J. Med. Chem. 2003; 46: 5097-5116, Lee M G et al., Chem. Biol. 2006 June; 13(6):563-7, Ueda R et al., J. Am. Chem. Soc. 2009 Dec. 9; 131(48):17536-7).

As an initial investigation of the applicability of these compounds in therapy-resistant AML leukemia, we tested whether tranylcypromine (an FDA-approved MAO inhibitor that has inhibitory activity towards Aof2) impacted proliferation of MLL-leukemia cells in vitro. (FIG. 29). We observed a dose-dependent inhibition of MLL-leukemia cell proliferation upon exposing leukemia cells to tranylcypromine. In contrast, exposure to tranylcypromine had no impact on growth of the non-transformed 32D cell line. We also observed an effect on growth of several human AML cell lines (HL60, Kasumi1, Molm13), but not others (KG1). These findings indicate that use of small molecules that target the epigenetic enzymes identified in our screen may provide reasonable therapeutic strategies for this otherwise therapy-resistant disease.

5.13 Example 13

Screening and Evaluation of RNAi Targets by Pooled Negative Selection RNAi Screening In Vitro and In Vivo In addition to the analysis of single shRNAs for inhibitory effects in vitro and in vivo, the combination of tet-on competent cancer models and tet-regulatable shRNA expression vectors allowing for monitoring shRNA expression through fluorescent and other reporter genes (e.g. TRMPV and derivates) facilitates pooled shRNA negative selection screening (FIG. 37). In such approaches a pool of over 1,000 shRNAs are retrovirally transduced into tet-on competent cancer models (here MLL/AF9+Nras AML) and selected for shRNA containing cells by either drug selection (e.g. G418) or fluorescence-activated cell sorting (FACS). Selected cell populations harboring a library of shRNAs then can be cultured in the absence or presence of doxycyline (off dox and on dox, respectively) or injected into syngeneic recipient mice that are either treated with doxycyline or left untreated.

The representation of each shRNA within the pool can be effectively assessed by deep sequencing of shRNA cassettes in a given cell population. For this, genomic DNA is extracted from leukemia cells containing the shRNA pool, and the shRNA guide or passenger strand (21-22 target gene specific nucleotides of the shRNA) by PCR using primers specific for common sequences flanking the gene specific part of the shRNA (e.g. miR30 19 nt loop and miR30 common 3' sequence). The primers also contain 5'-adapters required for deep sequencing (e.g. for Illumina/Solexa sequencing primers are p5+mir3: 5'-AATGATACGGCGACCACCGAC-TAAAGTAGCCCCTTGAATTC-3' (SEQ ID NO: 215) and p7+Loop: 5'-CAAGCAGAAGACGGCATACGATAGT-GAAGCCACAGATGTA-3' (SEQ ID NO: 216)). Deep sequencing is subsequently performed using a primer binding the flanking nucleotide sequence next to the target gene specific part of the shRNA (for Illumina/Solexa platforms the primer is mir30EcoR1Seq: 5'-TAGCCCCTTGAATTCCGA GGCAGTAGGCA-3' (SEQ ID NO: 217)).

The use of shRNA vectors that allow for monitoring of shRNA expression through fluorescent and other reporter genes (e.g. TRMPV) in combination with tet-on competent mouse models facilitates the isolation of pure shRNA expressing cell populations (e.g. by FACS, for TRMPV by sorting of Venus/dsRed double positive cells (FIG. 38). This selection of shRNA expressing cells prior to DNA isolation strongly reduces the background caused by cell populations with insufficient shRNA induction, which are predicted to contain genomic representation of the whole shRNA library without shRNA specific shifts in representation. The final readout is based on the comparison of shRNA representation (i.e. deep sequencing read numbers) before the assay (t0) or from cell populations left without doxycycline treatment (off dox) to those where shRNA were induced and cells subsequently sorted for shRNA expressing cells (on dox). shRNA with inhibitory effects are predicted to loose representation (show less reads) on dox compared to t0 and off dox.

This pooled is RNAi screening strategy can be applied to rapidly survey inhibitory effects of large pools of shRNAs (~1000 at a time) in different tet-on competent cancer models and normal control cells (FIG. 39). For example, a pool of 1166 shRNAs targeting 836 predominantly druggable genes associated with MLL fusion proteins in human leukemia and mouse models of MLL/AF9-induced AML (MLL cure library) was analyzed in pooled negative selection screening in tet-on competent MLL/AF9+Nras AML and immortalized murine embryonic fibroblasts (Mef) in parallel. To establish and validate this screening approach, the pool also contained 64 control shRNAs each of which have been previously analyzed for inhibitory effects in both AML cells and Mefs using the same experimental system (FIG. 40).

After pooling of 1166 experimental and 64 control shRNAs the presence of shRNAs was verified by deep sequencing of shRNAs within the plasmid vector pool (FIG. 41). The library of 1230 shRNAs was then retrovirally transduced into target cells at predominantly single copy integration (data not shown) into approximately 1000 target cells for each shRNA (1000 fold library representation). The successful transduction of the whole shRNA library was confirmed by deep sequencing from infected cells following selection, which demonstrated a high correlation of shRNA reads in the plasmid vector pool and the infected/selected cell population (FIG. 42).

In addition we demonstrate that the library representation can be maintained during prolonged periods of passaging in cell culture (FIGS. 43-44) as well as after transplantation into syngeneic recipient mice (FIGS. 45-46). Furthermore, independent biological replicates of on dox samples show a high correlation of shRNA representation both in vitro and in vivo indicating that shRNA-mediated effects and consequent changes in library representation are specific and not random (FIGS. 47-48).

After analysis of deep sequencing a total of 119 shRNAs were consistently found more than 8-fold depleted in MLL/AF9+Nras induced AML in independent biological replicates in vitro and in vivo. None of the 44 neutral control shRNAs showed this level of depletion (FIG. 49), while 18 out of 22 inhibitory control shRNAs were found more than 8 fold reduced in representation (FIGS. 50-51). Importantly, for each control gene known to be required for maintenance of MLL/AF9+Nras leukemia (Rpa1, Rpa3, PCNA, Myc, Myb, Bcl2, Mcl1 and Telo2) at least, mostly multiple shRNAs were identified as more than 8-fold depleted indicating that this pooled screening approach can efficiently and specifically identify genes required for cancer cell survival. Out of 101 depleted non-control shRNAs 88 showed specific depletion in MLL/AF9+Nras leukemia and were not significantly altered in Mefs.

Thus, these shRNAs point out genes that are specifically required in MLL/AF9+Nras leukemia maintenance, but dispensable for survival of normal Mef cells. These genes are Acpp, Acs1, Adam23, Apls2, Arf3, Aspa, Atp6v0d1, AU018778, Cacna1f, Casp1, Ccr1, Cd6, Cdc42ep1, Cdc42ep3, Centa1, Centd3, Cerk, Cpd, Ctbs, Cx3cr1, Dio2, Dnajc10, Dsp, EG277089, EG408196, F10, Fas, Fgd4, Flot2, Fn1, Fn3k, Fosb, Fpr1, Gab3, Gart, Gas1, Gdi1, Hexa, Hpgd, Htatip2, Kcnh7, Klf5, Klrb1b, L1cam, Lima1, Mef2c, Mgst1, Myo7a, Ncf1, Nln, Nmur1, Nrg4, Nrp1, Ntrk3, Ogg1, Park2, Pctk1, Pde1b, Pdgfrb, Pgam1, Pitpnm1, Pkm2, Plcb2, Plod3, Ptpn18, Pyg1, Rbks, Rgs6, Rock2, S100a9, Slc11a1, Slc12a5, Slc15a3, Slc22a4, Slc6a13, Smpd2, Syt17, Tex14, Thyn1, Tnfsf12, Trpm4, Vnn3 and Wnt10b.

TABLE 2 shRNAs specifically depleted in MLL/AF9 + Nras leukemia cells as compared to Mef cells (shRNAs specifically inhibiting MLL/AF9 induced AML, but not Mefs)

| shRNA | Fold depletion in AML | Fold depletion in Mef |
|---|---|---|
| Hexa.1510 | 1,777.36 | 2.13 |
| Ccr1.733 | 472.15 | 1.18 |
| Cdc42ep3.1922 | 315.30 | 0.38 |
| Dsp.6155 | 242.96 | 0.60 |
| Gart.2470 | 146.15 | 0.67 |
| Thyn1.315 | 145.53 | 1.04 |
| Gas1.2159 | 132.34 | 0.81 |
| Pctk1.948 | 123.76 | 0.27 |
| Pygl.1463 | 118.65 | 1.94 |
| Fn3k.298 | 103.54 | 2.82 |
| Arf3.1357 | 94.96 | 0.86 |
| Mef2c.1872 | 63.15 | 0.77 |
| Pitpnm1.561 | 60.72 | 0.27 |
| Apls2.2744 | 57.84 | 2.31 |
| Cpd.1693 | 50.07 | 3.91 |
| Slc22a4.2223 | 41.21 | 3.41 |
| Adam23.5211 | 40.11 | 0.30 |
| Fn1.4143 | 36.54 | 0.84 |
| Tnfsf12.1204 | 36.03 | 0.93 |
| L1cam.5255 | 31.42 | 1.26 |
| Cd6.520 | 28.66 | 2.28 |
| Cerk.4466 | 27.79 | 0.61 |
| Fgd4.821 | 25.66 | 2.12 |
| Fosb.1165 | 13.12 | 3.61 |
| Cx3cr1.1223 | 12.98 | 0.69 |
| Slc12a5.3582 | 12.58 | 2.21 |
| Cacna1f.3314 | 12.52 | 2.14 |
| Plod3.2501 | 12.30 | 2.62 |
| Atp6v0d1.481 | 12.03 | 1.90 |
| Centa1.1387 | 11.44 | 0.77 |
| Park2.2222 | 11.36 | 1.32 |
| Flot2.1039 | 10.89 | 2.72 |
| Plcb2.3742 | 10.81 | 2.25 |
| Kcnh7.2642 | 10.58 | 0.92 |
| F10.1044 | 10.52 | 1.25 |
| Hpgd.1070 | 10.43 | 1.10 |
| Slc15a3.1086 | 10.29 | 2.32 |
| Syt17.721 | 10.25 | 0.86 |
| Gab3.527 | 10.22 | 0.46 |
| Vnn3.345 | 10.19 | 2.59 |
| Acsl1.3559 | 10.18 | 1.45 |
| Ncf1.2370 | 10.06 | 2.33 |
| Gdi1.2355 | 9.92 | 2.86 |
| Slc6a13.1196 | 9.77 | 1.52 |
| EG277089.605 | 25.37 | 2.02 |
| Gdi1.1120 | 24.81 | 1.98 |
| Plod3.3138 | 21.28 | 0.71 |
| EG408196.85 | 20.79 | 0.25 |
| Trpm4.2813 | 20.52 | 2.33 |
| Dio2.2087 | 20.52 | 2.52 |
| Pgam1.1811 | 20.18 | 0.17 |
| Nmur1.7 | 19.45 | 2.58 |
| Ctbs.796 | 19.44 | 0.19 |
| Rbks.337 | 17.02 | 1.07 |
| Lima1.3235 | 16.44 | 0.56 |
| Casp1.248 | 16.16 | 3.84 |
| Pdgfrb.1028 | 16.16 | 2.15 |
| Htatip2.575 | 15.74 | 1.08 |
| Wnt10b.1717 | 15.69 | 1.35 |
| Pde1b.2027 | 15.12 | 1.31 |
| Cdc42ep1.317 | 14.91 | 1.47 |
| Myo7a.618 | 14.79 | 4.42 |
| Rgs6.896 | 14.33 | 1.99 |
| Nrp1.2022 | 13.60 | 1.80 |
| Centd3.3993 | 13.37 | 1.77 |
| Aspa.996 | 13.25 | 0.68 |

TABLE 2-continued shRNAs specifically depleted in MLL/AF9 + Nras leukemia cells as compared to Mef cells (shRNAs specifically inhibiting MLL/AF9 induced AML, but not Mefs)

| shRNA | Fold depletion in AML | Fold depletion in Mef |
|---|---|---|
| S100a9.148 | 13.18 | 2.68 |
| Klrb1b.845 | 9.74 | 0.43 |
| Fpr1.375 | 9.66 | 3.07 |
| Pkm2.2154 | 9.63 | 1.92 |
| Tex14.3976 | 9.60 | 1.90 |
| Slc11a1.307 | 9.52 | 0.41 |
| Klf5.581 | 9.37 | 1.01 |
| Mgst1.549 | 9.14 | 1.09 |
| Acpp.818 | 9.00 | 0.85 |
| Dnajc10.2057 | 8.99 | 1.47 |
| Ntrk3.167 | 8.88 | 1.76 |
| Gart.2713 | 8.73 | 2.22 |
| Ogg1.395 | 8.69 | 1.44 |
| Smpd2.592 | 8.63 | 2.89 |
| Fas.1344 | 8.57 | 1.36 |
| AU018778.350 | 8.45 | 1.18 |
| Centa1.940 | 8.24 | 1.13 |
| Nrp1.479 | 8.19 | 0.83 |
| Ptpn18.247 | 8.13 | 0.21 |
| Nrg4.1358 | 8.11 | 0.54 |
| Rock2.3898 | 8.10 | 1.04 |
| Nln.1429 | 8.03 | 1.61 |

TABLE 3

MLL/AF9 specific control shRNAs (shRNAs inhibiting MLL/AF9 induced AML, but not Mefs)

| shRNA | Fold depletion in AML | Fold depletion in Mef |
|---|---|---|
| Bcl2.1422 | 1,686.19 | 2.71 |
| Bcl2.2169 | 12.61 | 1.62 |
| Bcl2.906 | 12.28 | 0.98 |
| Mcl1.1334 | 104.03 | 3.00 |
| Mcl1.2018 | 11.48 | 3.02 |
| Myb.2572 | 67.47 | 0.92 |
| Myb.2652 | 15.46 | 1.14 |
| Myb.670 | 26.46 | 1.28 |

TABLE 4 shRNAs inihibiting both MLL/AF9 induced AML and Mefs.

| shRNA | Fold depletion in AML | Fold depletion in Mef |
|---|---|---|
| Myc.1888 | 8.48 | 3.83 |
| Myc.1891 | 9.05 | 4.62 |
| Myc.2105 | 9.19 | 11.70 |
| Pcna.1186 | 51.94 | 11.42 |
| Pcna.566 | 9.89 | 6.15 |
| Rpa1.1620 | 2,891.47 | 10.23 |
| Rpa3.561 | 8.81 | 10.63 |

TABLE 5

Neutral control shRNAs (functional shRNAs that do not inhibit MLL/AF9 induced AML and Mefs)

| shRNA | Fold depletion in AML | Fold depletion in Mef |
|---|---|---|
| BRAF.3750 | 0.76 | 1.08 |
| BRAF.3826 | 0.92 | 0.87 |
| BRAF.5053 | 0.66 | 0.33 |
| Kit.1241 | 1.88 | 0.99 |
| Kit.2021 | 1.92 | 1.61 |
| Kit.221 | 1.19 | 0.69 |
| Kit.4813 | 0.81 | 0.84 |

TABLE 5-continued

Neutral control shRNAs (functional shRNAs that do not inhibit MLL/AF9 induced AML and Mefs)

| shRNA | Fold depletion in AML | Fold depletion in Mef |
|---|---|---|
| Lin28.2180 | 1.15 | 0.80 |
| Lin28.2186 | 1.43 | 1.55 |
| Lin28.2270 | 0.22 | 1.10 |
| Lin28.2430 | 1.37 | 0.89 |
| Luciferase.1309 | 1.22 | 0.52 |
| Map2k1.1200 | 2.26 | 1.24 |
| Map2k1.2337 | 0.24 | 0.68 |
| Mn1.1403 | 1.94 | 0.77 |
| Mn1.2545 | 0.81 | 0.29 |
| Mn1.5760 | 0.38 | 0.91 |
| Mn1.5864 | 0.61 | 1.09 |
| Ptgs2.1082 | 0.51 | 0.51 |
| Ptgs2.2058 | 1.78 | 1.27 |
| Ptgs2.284 | 0.34 | 1.21 |
| Ptgs2.3711 | 1.38 | 1.46 |
| Renilla.713 | 1.29 | 1.02 |
| Trp53.1224 | 0.10 | 0.84 |

The shRNAs of Table 2-4, identified as having potent anti-leukemic effects, and in particular specific antileukemic effects (Tables 2-3) are directly useful in various embodiments of the invention. Additionally, it should be appreciated that modified shRNA molecules and siRNA molecules directed against the targeted genes and derived from these shRNAs according to the disclosures herein (for example, as exemplified in sections 4.3-4.5, Example 3) are useful in other embodiments of the invention, and in particular, in the therapeutic use of such siRNA molecules to treat therapy resistant cancers.

The sequences of the shRNAs listed in Tables 2-4 are listed below as the oligo sequence:

```
Acpp.818:
                                 (SEQ ID NO: 87)
TGCTGTTGACAGTGAGCGAAAAGAGAAATCTCGACTCCAATAGTGA
AGCCACAGATGTATTGGAGTCGAGATTTCTCTTTCTGCCTACTGCC
TCGGA Acsl1.3559:
                                 (SEQ ID NO: 88)
TGCTGTTGACAGTGAGCGCCAGCATTTCACTTTACTGCAATAGTGA
AGCCACAGATGTATTGCAGTAAAGTGAAATGCTGTTGCCTACTGCC
TCGGA Adam23.5211:
                                 (SEQ ID NO: 89)
TGCTGTTGACAGTGAGCGCTACGACCACGTCAGTTACAAATAGTGA
AGCCACAGATGTATTTGTAACTGACGTGGTCGTATTGCCTACTGCC
TCGGA Ap1s2.2744:
                                 (SEQ ID NO: 90)
TGCTGTTGACAGTGAGCGACAGGAGCAAGATGAGTTACTATAGTGA
AGCCACAGATGTATAGTAACTCATCTTGCTCCTGCTGCCTACTGCC
TCGGA Arf3.1357:
                                 (SEQ ID NO: 91)
TGCTGTTGACAGTGAGCGACCCTTCTGTGTTGGTGAGATATAGTGA
AGCCACAGATGTATATCTCACCAACACAGAAGGGCTGCCTACTGCC
TCGGA Aspa.996:
                                 (SEQ ID NO: 92)
TGCTGTTGACAGTGAGCGCATGAAGCTGCATATTATGAAATAGTGA
AGCCACAGATGTATTTCATAATATGCAGCTTCATTTGCCTACTGCC
TCGGA
```

-continued

Atp6v0d1.481:
(SEQ ID NO: 93)
TGCTGTTGACAGTGAGCGACACCAGCGTTCAATAGCTGAATAGTGA
AGCCACAGATGTATTCAGCTATTGAACGCTGGTGCTGCCTACTGCC
TCGGA

AU018778.350:
(SEQ ID NO: 94)
TGCTGTTGACAGTGAGCGCCTGAAGATTGCCTGTACCTAATAGTGA
AGCCACAGATGTATTAGGTACAGGCAATCTTCAGATGCCTACTGCC
TCGGA

Bcl2.1422:
(SEQ ID NO: 95)
TGCTGTTGACAGTGAGCGACCGGGAGAACAGGGTATGATATAGTGA
AGCCACAGATGTATATCATACCCTGTTCTCCCGGCTGCCTACTGCC
TCGGA

Bcl2.2169:
(SEQ ID NO: 96)
TGCTGTTGACAGTGAGCGACAGTAGAAATTATATGCATTATAGTGA
AGCCACAGATGTATAATGCATATAATTTCTACTGCTGCCTACTGCC
TCGGA

Bcl2.757:
(SEQ ID NO: 97)
TGCTGTTGACAGTGAGCGCCCCGATTCATTGCAAGTTGTATAGTGA
AGCCACAGATGTATACAACTTGCAATGAATCGGGATGCCTACTGCC
TCGGA

Bcl2.906:
(SEQ ID NO: 98)
TGCTGTTGACAGTGAGCGCGCACAGGAATTTTGTTTAATATAGTGA
AGCCACAGATGTATATTAAACAAAATTCCTGTGCATGCCTACTGCC
TCGGA

Cacna1f.3314:
(SEQ ID NO: 99)
TGCTGTTGACAGTGAGCGACTGGCCTGCGCTACTATACAATAGTGA
AGCCACAGATGTATTGTATAGTAGCGCAGGCCAGCTGCCTACTGCC
TCGGA Casp1.248:
(SEQ ID NO: 100)
TGCTGTTGACAGTGAGCGCCAGTGAGTATAGGGACAATAATAGTGA
AGCCACAGATGTATTATTGTCCCTATACTCACTGATGCCTACTGCC
TCGGA Ccr1.733:
(SEQ ID NO: 101)
TGCTGTTGACAGTGAGCGCCTGGATTGACTACAAGTTGAATAGTGA
AGCCACAGATGTATTCAACTTGTAGTCAATCCAGATGCCTACTGCC
TCGGA Cd6.520:
(SEQ ID NO: 102)
TGCTGTTGACAGTGAGCGAGAGCCACTTCTGGGAACACAATAGTGA
AGCCACAGATGTATTGTGTTCCCAGAAGTGGCTCCTGCCTACTGCC
TCGGA Cdc42ep1.317:
(SEQ ID NO: 103)
TGCTGTTGACAGTGAGCGCCTAGCAGTTGTAAGCAATCAATAGTGA
AGCCACAGATGTATTGATTGCTTACAACTGCTAGTTGCCTACTGCC
TCGGA Cdc42ep3.1922:
(SEQ ID NO: 104)
TGCTGTTGACAGTGAGCGCAACAAGCAAGGTATTACTGTATAGTGA
AGCCACAGATGTATACAGTAATACCTTGCTTGTTTTGCCTACTGCC
TCGGA Centa1.1387:
(SEQ ID NO: 105)
TGCTGTTGACAGTGAGCGCCAGAACCTCATTAAAGTTGAATAGTGA
AGCCACAGATGTATTCAACTTTAATGAGGTTCTGATGCCTACTGCC
TCGGA Centa1.940:
(SEQ ID NO: 106)
TGCTGTTGACAGTGAGCGCCCGAAGGCTCATGTACTTCAATAGTGA
AGCCACAGATGTATTGAAGTACATGAGCCTTCGGTTGCCTACTGCC
TCGGA Centd3.3993:
(SEQ ID NO: 107)
TGCTGTTGACAGTGAGCGCCTGGACCACAAGCATCCTTAATAGTGA
AGCCACAGATGTATTAAGGATGCTTGTGGTCCAGTTGCCTACTGCC
TCGGA Cerk.4466:
(SEQ ID NO: 108)
TGCTGTTGACAGTGAGCGCCTGGTATATTTGAGAAGCAATAGTGA
AGCCACAGATGTATTGTCTTCTCAAATATACCAGATGCCTACTGCC
TCGGA Cpd.1693:
(SEQ ID NO: 109)
TGCTGTTGACAGTGAGCGCACCAGGTGAACCAGAATTTAATAGTGA
AGCCACAGATGTATTAAATTCTGGTTCACCTGGTTTGCCTACTGCC
TCGGA Ctbs.796:
(SEQ ID NO: 110)
TGCTGTTGACAGTGAGCGCCCCACAGAGCATCTCACTAAATAGTGA
AGCCACAGATGTATTTAGTGAGATGCTCTGTGGGTTGCCTACTGCC
TCGGA Cx3cr1.1223:
(SEQ ID NO: 111)
TGCTGTTGACAGTGAGCGACTGCATCTTATGTGCAAGAATAGTGA
AGCCACAGATGTATTTCTTGCACATAAGATGCAGGTGCCTACTGCC
TCGGA Dio2.2087:
(SEQ ID NO: 112)
TGCTGTTGACAGTGAGCGCCAGGAATTTGGTTAAATGGAATAGTGA
AGCCACAGATGTATTCCATTTAACCAAATTCCTGTTGCCTACTGCC
TCGGA Dnajc10.2057:
(SEQ ID NO: 113)
TGCTGTTGACAGTGAGCGCTCCAACGACAGTGGTATTCAATAGTGA
AGCCACAGATGTATTGAATACCACTGTCGTTGGATTGCCTACTGCC
TCGGA Dsp.6155:
(SEQ ID NO: 114)
TGCTGTTGACAGTGAGCGCCAGGAAGTTCTTCGATCAATATAGTGA
AGCCACAGATGTATATTGATCGAAGAACTTCCTGTTGCCTACTGCC
TCGGA EG277089.605:
(SEQ ID NO: 115)
TGCTGTTGACAGTGAGCGCCTCAATCTCATTGGTGGCTTATAGTGA
AGCCACAGATGTATAAGCCACCAATGAGATTGAGATGCCTACTGCC
TCGGA EG408196.85:
(SEQ ID NO: 116)
TGCTGTTGACAGTGAGCGCAGCGAGAACCAGTGAGAAATATAGTGA
AGCCACAGATGTATATTTCTCACTGGTTCTCGCTTTGCCTACTGCC
TCGGA F10.1044:
(SEQ ID NO: 117)
TGCTGTTGACAGTGAGCGACACCATCTTGAATGAGTTCTATAGTGA
AGCCACAGATGTATAGAACTCATTCAAGATGGTGCTGCCTACTGCC
TCGGA Fas.1344:
(SEQ ID NO: 118)
TGCTGTTGACAGTGAGCGCGAGGAGAATTATAAACTGAATAGTGA
AGCCACAGATGTATTTCAGTTTATAATTCTCCTCATGCCTACTGCC
TCGGA Fgd4.821:
(SEQ ID NO: 119)
TGCTGTTGACAGTGAGCGAAAGGAGACTAATGAACAGAAATAGTGA
AGCCACAGATGTATTTCTGTTCATTAGTCTCCTTCTGCCTACTGCC
TCGGA Flot2.1039:
(SEQ ID NO: 120)
TGCTGTTGACAGTGAGCGACAAGGTGACATCAGAAGTAAATAGTGA
AGCCACAGATGTATTTACTTCTGATGTCACCTTGCTGCCTACTGCC
TCGGA Fn1.4143:
(SEQ ID NO: 121)
TGCTGTTGACAGTGAGCGCCAGTAGGATACTACACAGTTATAGTGA
AGCCACAGATGTATAACTGTGTAGTATCCTACTGATGCCTACTGCC
TCGGA Fn3k.298:
(SEQ ID NO: 122)
TGCTGTTGACAGTGAGCGAAAGAGCCTTAGCAGTCAGGCATAGTGA
AGCCACAGATGTATGCCTGACTGCTAAGGCTCTTCTGCCTACTGCC
TCGGA Fosb.1165:
(SEQ ID NO: 123)
TGCTGTTGACAGTGAGCGCCAGGCGGAAACTGATCAGCTTTAGTGA
AGCCACAGATGTAAAGCTGATCAGTTTCCGCCTGATGCCTACTGCC
TCGGA Fpr1.375:
(SEQ ID NO: 124)
TGCTGTTGACAGTGAGCGATTGGTTCATGTGCAAATTCATTAGTGA
AGCCACAGATGTAATGAATTTGCACATGAACCAACTGCCTACTGCC
TCGGA Gab3.527:
(SEQ ID NO: 125)
TGCTGTTGACAGTGAGCGCGACGGAAACACTAATAGTGTATAGTGA
AGCCACAGATGTATACACTATTAGTGTTTCCGTCATGCCTACTGCC
TCGGA Gart.2470:
(SEQ ID NO: 126)
TGCTGTTGACAGTGAGCGCAAGAATCTGATTGAAACCATATAGTGA
AGCCACAGATGTATATGGTTTCAATCAGATTCTTATGCCTACTGCC
TCGGA Gart.2713:
(SEQ ID NO: 127)
TGCTGTTGACAGTGAGCGAACCAGGGTAATTAATCACAAATAGTGA
AGCCACAGATGTATTTGTGATTAATTACCCTGGTGTGCCTACTGCC
TCGGA Gas1.2159:
(SEQ ID NO: 128)
TGCTGTTGACAGTGAGCGACCCGAAATTACAACTGCATTATAGTGA
AGCCACAGATGTATAATGCAGTTGTAATTTCGGGGTGCCTACTGCC
TCGGA Gdi1.1120:
(SEQ ID NO: 129)
TGCTGTTGACAGTGAGCGCCAACAGGAAGTCAGACATCTATAGTGA
AGCCACAGATGTATAGATGTCTGACTTCCTGTTGATGCCTACTGCC
TCGGA Gdi1.2355:
(SEQ ID NO: 130)
TGCTGTTGACAGTGAGCGACTCTAGTATATTTCACAGAAATAGTGA
AGCCACAGATGTATTTCTGTGAAATATACTAGAGCTGCCTACTGCC
TCGGA Hexa.1510:
(SEQ ID NO: 131)
TGCTGTTGACAGTGAGCGAGAGCAGTAACCTGACAACTAATAGTGA
AGCCACAGATGTATTAGTTGTCAGGTTACTGCTCCTGCCTACTGCC
TCGGA Hpgd.1070:
(SEQ ID NO: 132)
TGCTGTTGACAGTGAGCGCAAACTAGGTTATAACCTATAATAGTGA
AGCCACAGATGTATTATAGGTTATAACCTAGTTTTGCCTACTGCC
TCGGA Htatip2.575:
(SEQ ID NO: 133)
TGCTGTTGACAGTGAGCGACAGCAGTTTCTTATACCTACATAGTGA
AGCCACAGATGTATGTAGGTATAAGAAACTGCTGGTGCCTACTGCC
TCGGA Kcnh7.2642:
(SEQ ID NO: 134)
TGCTGTTGACAGTGAGCGCATGGTTCATCTTTATGCCAAATAGTGA
AGCCACAGATGTATTTGGCATAAAGATGAACCATTTGCCTACTGCC
TCGGA Klf5.581:
(SEQ ID NO: 135)
TGCTGTTGACAGTGAGCGCTCCGATAATTTCAGAGCATAATAGTGA
AGCCACAGATGTATTATGCTCTGAAATTATCGGAATGCCTACTGCC
TCGGA Klrb1b.845:
(SEQ ID NO: 136)
TGCTGTTGACAGTGAGCGCCAGATTCTTCATTGTATAAATTAGTGA
AGCCACAGATGTAATTTATACAATGAAGAATCTGTTGCCTACTGCC
TCGGA L1cam.5255:
(SEQ ID NO: 137)
TGCTGTTGACAGTGAGCGCCAGAATTATAACAGGCAAATATAGTGA
AGCCACAGATGTATATTTGCCTGTTATAATTCTGATGCCTACTGCC
TCGGA Lima1.3235:
(SEQ ID NO: 138)
TGCTGTTGACAGTGAGCGAACGGACATTGTACCCAGATAATAGTGA
AGCCACAGATGTATTATCTGGGTACAATGTCCGTCTGCCTACTGCC
TCGGA Mcl1.1334:
(SEQ ID NO: 139)
TGCTGTTGACAGTGAGCGAAAGAGTCACTGTCTGAATGATAGTGA
AGCCACAGATGTATTCATTCAGACAGTGACTCTTCTGCCTACTGCC
TCGGA Mcl1.2018:
(SEQ ID NO: 140)
TGCTGTTGACAGTGAGCGCGGACTGGTTATAGATTTATAATAGTGA
AGCCACAGATGTATTATAAATCTATAACCAGTCCATGCCTACTGCC
TCGGA Mef2c.1872:
(SEQ ID NO: 141)
TGCTGTTGACAGTGAGCGCTGCCTCAGTGATACAGTATAATAGTGA
AGCCACAGATGTATTATACTGTATCACTGAGGCAATGCCTACTGCC
TCGGA Mgst1.549:
(SEQ ID NO: 142)
TGCTGTTGACAGTGAGCGCAAGGAGCAGACTGTACTTGTATAGTGA
AGCCACAGATGTATACAAGTACAGTCTGCTCCTTATGCCTACTGCC
TCGGA Myb.2572:
(SEQ ID NO: 143)
TGCTGTTGACAGTGAGCGCTCCATGTATCTCAGTCACTAATAGTGA
AGCCACAGATGTATTAGTGACTGAGATACATGGAATGCCTACTGCC
TCGGA Myb.2652:
(SEQ ID NO: 144)
TGCTGTTGACAGTGAGCGCCCCAAGTAATACTTAATGCAATAGTGA
AGCCACAGATGTATTGCATTAAGTATTACTTGGGATGCCTACTGCC
TCGGA Myb.670:
(SEQ ID NO: 145)
TGCTGTTGACAGTGAGCGACACAACCATTTGAATCCAGAATAGTGA
AGCCACAGATGTATTCTGGATTCAAATGGTTGTGCTGCCTACTGCC
TCGGA Myc.1888:
(SEQ ID NO: 146)
TGCTGTTGACAGTGAGCGAGAAACGACGAGAACAGTTGAATAGTGA
AGCCACAGATGTATTCAACTGTTCTCGTCGTTTCCTGCCTACTGCC
TCGGA Myc.1891:
(SEQ ID NO: 147)
TGCTGTTGACAGTGAGCGCACGACGAGAACAGTTGAAACATAGTGA
AGCCACAGATGTATGTTTCAACTGTTCTCGTCGTTTGCCTACTGCC
TCGGA Myc.2105:
(SEQ ID NO: 148)
TGCTGTTGACAGTGAGCGCCTGCCTCAAACTTAAATAGTATAGTGA
AGCCACAGATGTATACTATTTAAGTTTGAGGCAGTTGCCTACTGCC
TCGGA Myo7a.618:
(SEQ ID NO: 149)
TGCTGTTGACAGTGAGCGCCCGCCAGTACACCAACAAGAATAGTGA
AGCCACAGATGTATTCTTGTTGGTGTACTGGCGGATGCCTACTGCC
TCGGA Ncf1.2370:
(SEQ ID NO: 150)
TGCTGTTGACAGTGAGCGCCAGAAGATCAATGCACATAAATAGTGA
AGCCACAGATGTATTTATGTGCATTGATCTTCTGTTGCCTACTGCC
TCGGA Nln.1429:
(SEQ ID NO: 151)
TGCTGTTGACAGTGAGCGAAAGGATAAAGCTACTGGAGAATAGTGA
AGCCACAGATGTATTCTCCAGTAGCTTTATCCTTCTGCCTACTGCC
TCGGA Nmur1.7:
(SEQ ID NO: 152)
TGCTGTTGACAGTGAGCGCCTGCAATATCAGTGAGTTCAATAGTGA
AGCCACAGATGTATTGAACTCACTGATATTGCAGATGCCTACTGCC
TCGGA Nrg4.1358:
(SEQ ID NO: 153)
TGCTGTTGACAGTGAGCGCCAGACATGTTGAAGTGAATAATAGTGA
AGCCACAGATGTATTATTCACTTCAACATGTCTGTTGCCTACTGCC
TCGGA Nrp1.2022:
(SEQ ID NO: 154)
TGCTGTTGACAGTGAGCGACACAAGGTTCATCAGGATCTATAGTGA
AGCCACAGATGTATAGATCCTGATGAACCTTGTGGTGCCTACTGCC
TCGGA Nrp1.479:
(SEQ ID NO: 155)
TGCTGTTGACAGTGAGCGCACCCTCATTCTTACCATCCAATAGTGA
AGCCACAGATGTATTGGATGGTAAGAATGAGGGTATGCCTACTGCC
TCGGA Ntrk3.167:
(SEQ ID NO: 156)
TGCTGTTGACAGTGAGCGCCTGCAGCAAGACTGAGATCAATAGTGA
AGCCACAGATGTATTGATCTCAGTCTTGCTGCAGATGCCTACTGCC
TCGGA Ogg1.395:
(SEQ ID NO: 157)
TGCTGTTGACAGTGAGCGACAGATCAAGTATGGACACTGATAGTGA
AGCCACAGATGTATCAGTGTCCATACTTGATCTGCTGCCTACTGCC
TCGGA Park2.2222:
(SEQ ID NO: 158)
TGCTGTTGACAGTGAGCGCAACAGAGAAAGTGCCTATAAATAGTGA
AGCCACAGATGTATTTATAGGCACTTTCTCTGTTATGCCTACTGCC
TCGGA Pcna.1186:
(SEQ ID NO: 159)
TGCTGTTGACAGTGAGCGAATCAATGATCTTGACGCTAAATAGTGA
AGCCACAGATGTATTTAGCGTCAAGATCATTGATGTGCCTACTGCC
TCGGA Pcna.566:
(SEQ ID NO: 160)
TGCTGTTGACAGTGAGCGATCGGGTGAATTTGCACGTATATAGTGA
AGCCACAGATGTATATACGTGCAAATTCACCCGACTGCCTACTGCC
TCGGA Pctk1.948:
(SEQ ID NO: 161)
TGCTGTTGACAGTGAGCGCCCGGGAAGTATCCCTGCTTAATAGTGA
AGCCACAGATGTATTAAGCAGGGATACTTCCCGGATGCCTACTGCC
TCGGA Pde1b.2027:
(SEQ ID NO: 162)
TGCTGTTGACAGTGAGCGCTGCCTCCAAGTTTCTAAGCAATAGTGA
AGCCACAGATGTATTGCTTAGAAACTTGGAGGCAATGCCTACTGCC
TCGGA Pdgfrb.1028:
(SEQ ID NO: 163)
TGCTGTTGACAGTGAGCGAAACGACCATGGCGATGAGAAATAGTGA
AGCCACAGATGTATTTCTCATCGCCATGGTCGTTCTGCCTACTGCC
TCGGA Pgam1.1811:
(SEQ ID NO: 164)
TGCTGTTGACAGTGAGCGCAAGGAGTGATGTGCAATACTTTAGTGA
AGCCACAGATGTAAAGTATTGCACATCACTCCTTTTGCCTACTGCC
TCGGA Pitpnm1.561:
(SEQ ID NO: 165)
TGCTGTTGACAGTGAGCGCCAGGATGCTTATCAAGGAGTATAGTGA
AGCCACAGATGTATACTCCTTGATAAGCATCCTGATGCCTACTGCC
TCGGA Pkm2.2154:
(SEQ ID NO: 166)
TGCTGTTGACAGTGAGCGCGCCCACCTGAATGTCAATAAATAGTGA
AGCCACAGATGTATTTATTGACATTCAGGTGGGCATGCCTACTGCC
TCGGA Plcb2.3742:
(SEQ ID NO: 167)
TGCTGTTGACAGTGAGCGCAGGGACCTTAATACTCAGATATAGTGA
AGCCACAGATGTATATCTGAGTATTAAGGTCCCTTTGCCTACTGCC
TCGGA Plod3.2501:
(SEQ ID NO: 168)
TGCTGTTGACAGTGAGCGAACCGTTGATATCCACATGAAATAGTGA
AGCCACAGATGTATTTCATGTGGATATCAACGGTGTGCCTACTGCC
TCGGA Plod3.3138:
(SEQ ID NO: 169)
TGCTGTTGACAGTGAGCGACTCAGCCTCACTTTCAATAAATAGTGA
AGCCACAGATGTATTTATTGAAAGTGAGGCTGAGGTGCCTACTGCC
TCGGA Ptpn18.247:
(SEQ ID NO: 170)
TGCTGTTGACAGTGAGCGCCACGAACAAGAACCGCTACAATAGTGA
AGCCACAGATGTATTGTAGCGGTTCTTGTTCGTGTTGCCTACTGCC
TCGGA -continued Pyg1.1463:
(SEQ ID NO: 171)
TGCTGTTGACAGTGAGCGCACCAGACAAGTTCCAGAATAATAGTGA
AGCCACAGATGTATTATTCTGGAACTTGTCTGGTTTGCCTACTGCC
TCGGA Rbks.337:
(SEQ ID NO: 172)
TGCTGTTGACAGTGAGCGAAGCCTCCATAATTGTCAATAATAGTGA
AGCCACAGATGTATTATTGACAATTATGGAGGCTGTGCCTACTGCC
TCGGA Rgs6.896:
(SEQ ID NO: 173)
TGCTGTTGACAGTGAGCGCCAAGTGAAGATTGACCGGAAATAGTGA
AGCCACAGATGTATTTCCGGTCAATCTTCACTTGTTGCCTACTGCC
TCGGA Rock2.3898:
(SEQ ID NO: 174)
TGCTGTTGACAGTGAGCGCCAGATTCTATATGCCAATGAATAGTGA
AGCCACAGATGTATTCATTGGCATATAGAATCTGATGCCTACTGCC
TCGGA Rpa1.1620:
(SEQ ID NO: 175)
TGCTGTTGACAGTGAGCGCCCGCATGATCTTATCGGCAAATAGTGA
AGCCACAGATGTATTTGCCGATAAGATCATGCGGTTGCCTACTGCC
TCGGA Rpa3.561:
(SEQ ID NO: 176)
TGCTGTTGACAGTGAGCGCAAAAGTGATACTTCAATATATTAGTGA
AGCCACAGATGTAATATATTGAAGTATCACTTTTATGCCTACTGCC
TCGGA S100a9.148:
(SEQ ID NO: 177)
TGCTGTTGACAGTGAGCGCCAGACAAATGGTGGAAGCACATAGTGA
AGCCACAGATGTATGTGCTTCCACCATTTGTCTGATGCCTACTGCC
TCGGA Slc11a1.307:
(SEQ ID NO: 178)
TGCTGTTGACAGTGAGCGCAACATTGAGTCCGACCTTCAATAGTGA
AGCCACAGATGTATTGAAGGTCGGACTCAATGTTTTGCCTACTGCC
TCGGA Slc12a5.3582:
(SEQ ID NO: 179)
TGCTGTTGACAGTGAGCGAAACGAGGTCATCGTGAATAAATAGTGA
AGCCACAGATGTATTTATTCACGATGACCTCGTTCTGCCTACTGCC
TCGGA Slc15a3.1086:
(SEQ ID NO: 180)
TGCTGTTGACAGTGAGCGCCTGGTTCTATTGGAGCATCAATAGTGA
AGCCACAGATGTATTGATGCTCCAATAGAACCAGTTGCCTACTGCC
TCGGA Slc22a4.2223:
(SEQ ID NO: 181)
TGCTGTTGACAGTGAGCGCAAACGTATAAATGCTATCCAATAGTGA
AGCCACAGATGTATTGGATAGCATTTATACGTTTATGCCTACTGCC
TCGGA Slc6a13.1196:
(SEQ ID NO: 182)
TGCTGTTGACAGTGAGCGACTGGGACTAGATAGCCAGTTTTAGTGA
AGCCACAGATGTAAAACTGGCTATCTAGTCCCAGGTGCCTACTGCC
TCGGA Smpd2.592:
(SEQ ID NO: 183)
TGCTGTTGACAGTGAGCGACAGCATGTCTACAGTCTGAATTAGTGA
AGCCACAGATGTAATTCAGACTGTAGACATGCTGGTGCCTACTGCC
TCGGA Syt17.721:
(SEQ ID NO: 184)
TGCTGTTGACAGTGAGCGCCGAGGAGATCATGTCCAAGTATAGTGA
AGCCACAGATGTATACTTGGACATGATCTCCTCGTTGCCTACTGCC
TCGGA Tex14.3976:
(SEQ ID NO: 185)
TGCTGTTGACAGTGAGCGCCAGGAGCTACTTGATGAAATTTAGTGA
AGCCACAGATGTAAATTTCATCAAGTAGCTCCTGATGCCTACTGCC
TCGGA Thyn1.315:
(SEQ ID NO: 186)
TGCTGTTGACAGTGAGCGCAAGCAACTACTGGCTGATGAATAGTGA
AGCCACAGATGTATTCATCAGCCAGTAGTTGCTTATGCCTACTGCC
TCGGA Tnfsf12.1204:
(SEQ ID NO: 187)
TGCTGTTGACAGTGAGCGCAATGGATATTAAAGAGAATAATAGTGA
AGCCACAGATGTATTATTCTCTTTAATATCCATTTTGCCTACTGCC
TCGGA Trpm4.2813:
(SEQ ID NO: 188)
TGCTGTTGACAGTGAGCGACAAGATTGTCATAGTGAGCAATAGTGA
AGCCACAGATGTATTGCTCACTATGACAATCTTGGTGCCTACTGCC
TCGGA Vnn3.345:
(SEQ ID NO: 189)
TGCTGTTGACAGTGAGCGAACGCCAGAAGATGGAATCTATTAGTGA
AGCCACAGATGTAATAGATTCCATCTTCTGGCGTCTGCCTACTGCC
TCGGA Wnt10b.1717:
(SEQ ID NO: 190)
TGCTGTTGACAGTGAGCGCCTCGAATAGACTAAGATGAAATAGTGA
AGCCACAGATGTATTTCATCTTAGTCTATTCGAGTTGCCTACTGCC
TCGGA BRAF.3750:
(SEQ ID NO: 191)
TGCTGTTGACAGTGAGCGCTAGCATAATGACAATTATTTATAGTGA
AGCCACAGATGTATAAATAATTGTCATTATGCTAATGCCTACTGCC
TCGGA BRAF.3826:
(SEQ ID NO: 192)
TGCTGTTGACAGTGAGCGCCCCATTGTTTCTTCCAACTTATAGTGA
AGCCACAGATGTATAAGTTGGAAGAAACAATGGGATGCCTACTGCC
TCGGA BRAF.5053:
(SEQ ID NO: 193)
TGCTGTTGACAGTGAGCGCTAGGGTGATGTCTCACTTGAATAGTGA
AGCCACAGATGTATTCAAGTGAGACATCACCCTATTGCCTACTGCC
TCGGA Kit.1241:
(SEQ ID NO: 194)
TGCTGTTGACAGTGAGCGATTCCGTGACATTCAACGTTTATAGTGA
AGCCACAGATGTATAAACGTTGAATGTCACGGAAGTGCCTACTGCC
TCGGA Kit.2021:
(SEQ ID NO: 195)
TGCTGTTGACAGTGAGCGACACCCTGGTCATTACAGAATATAGTGA
AGCCACAGATGTATATTCTGTAATGACCAGGGTGGTGCCTACTGCC
TCGGA Kit.221:
(SEQ ID NO: 196)
TGCTGTTGACAGTGAGCGCCAGATGGACTTTCAAGACCTATAGTGA
AGCCACAGATGTATAGGTCTTGAAAGTCCATCTGATGCCTACTGCC
TCGGA Kit.4813:
(SEQ ID NO: 197)
TGCTGTTGACAGTGAGCGATTGGATATTCTTGAAAGTTTATAGTGA
AGCCACAGATGTATAAACTTTCAAGAATATCCAAGTGCCTACTGCC
TCGGA Lin28.2180:
(SEQ ID NO: 198)
TGCTGTTGACAGTGAGCGCAGCGTGATGGTTGATAGCTAATAGTGA
AGCCACAGATGTATTAGCTATCAACCATCACGCTATGCCTACTGCC
TCGGA Lin28.2186:
(SEQ ID NO: 199)
TGCTGTTGACAGTGAGCGAATGGTTGATAGCTAAAGGAAATAGTGA
AGCCACAGATGTATTTCCTTTAGCTATCAACCATCTGCCTACTGCC
TCGGA Lin28.2270:
(SEQ ID NO: 200)
TGCTGTTGACAGTGAGCGCAACGGGACAAATGCAATAGAATAGTGA
AGCCACAGATGTATTCTATTGCATTTGTCCCGTTTTGCCTACTGCC
TCGGA Lin28.2430:
(SEQ ID NO: 201)
TGCTGTTGACAGTGAGCGATGGCCTAGTTGTGTAAATATATAGTGA
AGCCACAGATGTATATATTTACACAACTAGGCCACTGCCTACTGCC
TCGGA Luciferase.1309:
(SEQ ID NO: 202)
TGCTGTTGACAGTGAGCGCCCGCCTGAAGTCTCTGATTAATAGTGA
AGCCACAGATGTATTAATCAGAGACTTCAGGCGGTTGCCTACTGCC
TCGGA Map2k1.1200:
(SEQ ID NO: 203)
TGCTGTTGACAGTGAGCGAGCCTCTCAGCTCATATGGAATTAGTGA
AGCCACAGATGTAATTCCATATGAGCTGAGAGGCCTGCCTACTGCC
TCGGA Map2k1.2337:
(SEQ ID NO: 204)
TGCTGTTGACAGTGAGCGCCAAGATGTTTATCAAATCTAATAGTGA
AGCCACAGATGTATTAGATTTGATAAACATCTTGATGCCTACTGCC
TCGGA Mn1.1403:
(SEQ ID NO: 205)
TGCTGTTGACAGTGAGCGCAACGGTACCCTAGACAACCAATAGTGA
AGCCACAGATGTATTGGTTGTCTAGGGTACCGTTATGCCTACTGCC
TCGGA Mn1.2545:
(SEQ ID NO: 206)
TGCTGTTGACAGTGAGCGCCAGCGCGGTTGCAGCCGGTAATAGTGA
AGCCACAGATGTATTACCGGCTGCAACCGCGCTGTTGCCTACTGCC
TCGGA Mn1.5760:
(SEQ ID NO: 207)
TGCTGTTGACAGTGAGCGCTTGGTTTAGCAGGAAGAATAATAGTGA
AGCCACAGATGTATTATTCTTCCTGCTAAACCAAATGCCTACTGCC
TCGGA Mn1.5864:
(SEQ ID NO: 208)
TGCTGTTGACAGTGAGCGCATCGCTATTGCACATGTATAATAGTGA
AGCCACAGATGTATTATACATGTGCAATAGCGATTTGCCTACTGCC
TCGGA Ptgs2.1082:
(SEQ ID NO: 209)
TGCTGTTGACAGTGAGCGCCAAGATAGTGATCGAAGACTATAGTGA
AGCCACAGATGTATAGTCTTCGATCACTATCTTGATGCCTACTGCC
TCGGA Ptgs2.2058:
(SEQ ID NO: 210)
TGCTGTTGACAGTGAGCGCCCGGTGTTTGTCCTTTAAATATAGTGA
AGCCACAGATGTATATTTAAAGGACAAACACCGGATGCCTACTGCC
TCGGA Ptgs2.284:
(SEQ ID NO: 211)
TGCTGTTGACAGTGAGCGAAAGAATCAAATTACTGCTGAATAGTGA
AGCCACAGATGTATTCAGCAGTAATTTGATTCTTGTGCCTACTGCC
TCGGA Ptgs2.3711:
(SEQ ID NO: 212)
TGCTGTTGACAGTGAGCGCAACGTTCATGGATAAATTCTATAGTGA
AGCCACAGATGTATAGAATTTATCCATGAACGTTATGCCTACTGCC
TCGGA Renilla.713:
(SEQ ID NO: 213)
TGCTGTTGACAGTGAGCGCAGGAATTATAATGCTTATCTATAGTGA
AGCCACAGATGTATAGATAAGCATTATAATTCCTATGCCTACTGCC
TCGGA Trp53.1224:
(SEQ ID NO: 214)
TGCTGTTGACAGTGAGCGCCCACTACAAGTACATGTGTAATAGTGA
AGCCACAGATGTATTACACATGTACTTGTAGTGGATGCCTACTGCC
TCGGA

---

We claim:

1. A method for treating chemotherapeutic-resistant acute myeloid leukemia in a subject in need thereof, wherein the subject exhibits a known genotype associated with a chemotherapy-resistant leukemia, the method comprising:
administering to the subject an RNAi molecule directed against a gene whose expression is necessary for survival of the chemotherapy-resistant acute myeloid leukemia cell with said known genotype and is dispensable for the growth of non-transformed hematopoietic cells, wherein the gene is AOF2, EED, HDAC3, SMARCA4, SMARCD1, SUZ12 or WHSC111 so as to inhibit survival of acute myeloid leukemia cells in the subject, and thereby treat the chemotherapeutic-resistant acute myeloid leukemia in the subject.

2. The method of claim 1, wherein the known genotype comprises a chromosomal rearrangement resulting in a MLL fusion protein, or AML1/ETO fusion protein.

3. The method of claim 2, wherein the MLL or AML fusion protein is selected from the group consisting of MLL/ENL, MLL/AF9, AML1/ETO9a.

4. The method of claim 1, wherein the RNAi molecule is directed against the gene EED or SUZ12.

5. The method of claim 4, wherein the RNAi molecule comprises a nucleotide sequence shown in SEQ ID NOs: 223-228 or 75-80.

6. A method for treating chemotherapeutically resistant acute myeloid leukemia in a subject in need thereof, the method comprising: administering to the subject an RNAi molecule directed against a gene whose expression is necessary for survival of the chemotherapeutically resistant acute myeloid leukemia cell and is dispensable for the growth of non-transformed hematopoietic cells, wherein the RNAi molecule is directed against the gene EED or SUZ12 so as to inhibit survival of chemotherapeutically resistant acute myeloid leukemia cells in the subject, and thereby treat the chemotherapeutically resistant acute myeloid leukemia in the subject.

7. The method of claim 6, wherein the RNAi molecule comprises a nucleotide sequence shown in SEQ ID NOs: 223-228 or 75-80.

* * * * *

SEQUENCE LISTING

<160> NUMBER OF SEQ ID NOS: 239

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1
caucuuaugu ccaguuuaa                                           19

<210> SEQ ID NO 2
<211> LENGTH: 19
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 2
caccaucuug uguacaucu                                                  19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cagaucuuug aaacuauuu                                                  19

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cagucaaugu cgucaaugua u                                               21

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gccuugagaa gaagaagua                                                  19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guuggacucc gagaguugu                                                  19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cggaacaaag cccggaaga                                                  19

<210> SEQ ID NO 8
<211> LENGTH: 97
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 8
tgctgttgac agtgagcgca catcttatgt ccagtttaaa tagtgaagcc acagatgtat    60
ttaaactgga cataagatgt atgcctactg cctcgga                            97

<210> SEQ ID NO 9
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgctgttgac agtgagcgac caccatcttg tgtacatctt tagtgaagcc acagatgtaa    60
agatgtacac aagatggtgg ctgcctactg cctcgga                            97

<210> SEQ ID NO 10
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgctgttgac agtgagcgcg cagatctttg aaactattta tagtgaagcc acagatgtat    60
aaatagtttc aaagatctgc ttgcctactg cctcgga                            97

<210> SEQ ID NO 11
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgctgttgac agtgagcgac cagtcaatgt cgtcaatgta tagtgaagcc acagatgtat    60
acattgacga cattgactgg ctgcctactg cctcgga                            97

<210> SEQ ID NO 12
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgctgttgac agtgagcgcg gccttgagaa gaagaagtat tagtgaagcc acagatgtaa    60
tacttcttct tctcaaggcc ttgcctactg cctcgga                            97

<210> SEQ ID NO 13
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
tgctgttgac agtgagcgac gttggactcc gagagttgta tagtgaagcc acagatgtat      60
acaactctcg gagtccaacg ctgcctactg cctcgga                              97
```

<210> SEQ ID NO 14
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

```
tgctgttgac agtgagcgac cggaacaaag cccggaagaa tagtgaagcc acagatgtat      60
tcttccgggc tttgttccgg gtgcctactg cctcgga                              97
```

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
aattcgtaaa acgcgtacga cggcct                                          26
```

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

```
aattaggccg tcgtacgcgt tttacg                                          26
```

<210> SEQ ID NO 17
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
tgctgttgac agtgagcgcg gaaatattct ggtatgatta tagtgaagcc acagatgtat      60
aatcatacca gaatatttcc ttgcctactg cctcgga                              97
```

<210> SEQ ID NO 18
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
tgctgttgac agtgagcgag gaactgatgg agtagagtat tagtgaagcc acagatgtaa      60
tactctactc catcagttcc ctgcctactg cctcgga                              97
```

<210> SEQ ID NO 19
<211> LENGTH: 97
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 19
tgctgttgac agtgagcgag aggcttgaag ctttcctttca tagtgaagcc acagatgtat    60
aaaggaaagc ttcaagcctc ctgcctactg cctcgga                             97

<210> SEQ ID NO 20
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgctgttgac agtgagcgcg tccattgtct gttatttcat tagtgaagcc acagatgtaa    60
tgaaataaca gacaatggac ttgcctactg cctcgga                             97

<210> SEQ ID NO 21
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgctgttgac agtgagcgcc gatatgggct gaatacaaat tagtgaagcc acagatgtaa    60
tttgtattca gcccatatcg ttgcctactg cctcgga                             97

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cagaaggctc gagaaggtat attgctgttg acagtgagcg                          40

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctaaagtagc cccttgaatt ccgaggcagt aggca                               35

<210> SEQ ID NO 24
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
ctcgagaagg tatattgctg ttgacagtga gcgcggaaat attctggtat gattatagtg    60
```
aagccacaga tgtataatca taccagaata tttccttgcc tactgcctcg gaattc        116

<210> SEQ ID NO 25
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ctcgagaagg tatattgctg ttgacagtga gcgaggaact gatggagtag agtattagtg     60
aagccacaga tgtaatactc tactccatca gttccctgcc tactgcctcg gaattc        116

<210> SEQ ID NO 26
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ctcgagaagg tatattgctg ttgacagtga gcgagaggct tgaagctttc ctttatagtg     60
aagccacaga tgtataaagg aaagcttcaa gcctcctgcc tactgcctcg gaattc        116

<210> SEQ ID NO 27
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
ctcgagaagg tatattgctg ttgacagtga gcgcgtccat tgtctgttat ttcattagtg     60
aagccacaga tgtaatgaaa taacagacaa tggacttgcc tactgcctcg gaattc        116

<210> SEQ ID NO 28
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
ctcgagaagg tatattgctg ttgacagtga gcgccgatat gggctgaata caaattagtg     60
aagccacaga tgtaatttgt attcagccca tatcgttgcc tactgcctcg gaattc        116

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tcccgcctca gccacctact acag        24

<210> SEQ ID NO 30
<211> LENGTH: 23

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgtggtgggc ttcttgcgca gtt                                           23

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctaccgagcc atgaagaacc                                               20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agaggaaggc ccattgctga a                                             21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gttccgcaca ggagcaaagt                                               20

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acggcgcaac tgctcac                                                  17

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ctcacagatt ccagcttcgg a                                             21

<210> SEQ ID NO 36
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 36
tgcgctccaa cggactttta                                                   19

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctctgtgtgg atcggtggct                                                   20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gctgatccac atctgctgga aa                                                22

<210> SEQ ID NO 39
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgctgttgac agtgagcgcc tggaaatgac tatgatttaa tagtgaagcc acagatgtat       60
taaatcatag tcatttccag atgcctactg cctcgga                                97

<210> SEQ ID NO 40
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tgctgttgac agtgagcgcg actgatatta caaagctta tagtgaagcc acagatgtat        60
aagctttgtt aatatcagtc ttgcctactg cctcgga                                97

<210> SEQ ID NO 41
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgctgttgac agtgagcgac cgggagaaca gggtatgata tagtgaagcc acagatgtat       60
atcataccct gttctcccgg ctgcctactg cctcgga                                97
```

```
<210> SEQ ID NO 42
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tgctgttgac agtgagcgac agtagaaatt atatgcatta tagtgaagcc acagatgtat      60
aatgcatata atttctactg ctgcctactg cctcgga                              97

<210> SEQ ID NO 43
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tgctgttgac agtgagcgaa agagtcactg tctgaatgaa tagtgaagcc acagatgtat      60
tcattcagac agtgactctt ctgcctactg cctcgga                              97

<210> SEQ ID NO 44
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgctgttgac agtgagcgaa acagcctcga tttttaagaa tagtgaagcc acagatgtat      60
tcttaaaaat cgaggctgtt ctgcctactg cctcgga                              97

<210> SEQ ID NO 45
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tgctgttgac agtgagcgcg gactggttat agatttataa tagtgaagcc acagatgtat      60
tataaatcta taaccagtcc atgcctactg cctcgga                              97

<210> SEQ ID NO 46
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tgctgttgac agtgagcgaa agatgtaaca agatcagcaa tagtgaagcc acagatgtat      60
tgctgatctt gttacatctt ctgcctactg cctcgga                              97

<210> SEQ ID NO 47
<211> LENGTH: 97
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tgctgttgac agtgagcgct acgttgtttc ttatagattt tagtgaagcc acagatgtaa     60
aatctataag aaacaacgta atgcctactg cctcgga                             97

<210> SEQ ID NO 48
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tgctgttgac agtgagcgct atgtagacat tgtaaataaa tagtgaagcc acagatgtat     60
ttatttacaa tgtctacata atgcctactg cctcgga                             97

<210> SEQ ID NO 49
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tgctgttgac agtgagcgac ggaattgtaa ggaactagaa tagtgaagcc acagatgtat     60
tctagttcct tacaattccg gtgcctactg cctcgga                             97

<210> SEQ ID NO 50
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tgctgttgac agtgagcgcc accctcatcc tctaattcaa tagtgaagcc acagatgtat     60
tgaattagag gatgagggtg atgcctactg cctcgga                             97

<210> SEQ ID NO 51
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tgctgttgac agtgagcgac tgcccgaatt tggaaatctt tagtgaagcc acagatgtaa     60
agatttccaa attcgggcag ctgcctactg cctcgga                             97

<210> SEQ ID NO 52
<211> LENGTH: 97
<212> TYPE: DNA
<213> ORGANISM: Artificial Sequence
<220> FEATURE:
<223> OTHER INFORMATION: Description of Artificial Sequence: Synthetic
```

```
    oligonucleotide

<400> SEQUENCE: 52
tgctgttgac agtgagcgct ccatgtatct cagtcactaa tagtgaagcc acagatgtat    60
tagtgactga gatacatgga atgcctactg cctcgga                            97

<210> SEQ ID NO 53
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tgctgttgac agtgagcgcc ccaagtaata cttaatgcaa tagtgaagcc acagatgtat    60
tgcattaagt attacttggg atgcctactg cctcgga                            97

<210> SEQ ID NO 54
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tgctgttgac agtgagcgac acaaccattt gaatccagaa tagtgaagcc acagatgtat    60
tctggattca aatggttgtg ctgcctactg cctcgga                            97

<210> SEQ ID NO 55
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tgctgttgac agtgagcgca agaaatattg ttcaatttaa tagtgaagcc acagatgtat    60
taaattgaac aatatttctt atgcctactg cctcgga                            97

<210> SEQ ID NO 56
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tgctgttgac agtgagcgcg gagtacagct gtgtaataaa tagtgaagcc acagatgtat    60
ttattacaca gctgtactcc ttgcctactg cctcgga                            97

<210> SEQ ID NO 57
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
```
tgctgttgac agtgagcgcc cgcatgatct tatcggcaaa tagtgaagcc acagatgtat    60
ttgccgataa gatcatgcgg ttgcctactg cctcgga    97

<210> SEQ ID NO 58
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 58
tgctgttgac agtgagcgca aggaagatac taatcgcttt tagtgaagcc acagatgtaa    60
aagcgattag tatcttcctt atgcctactg cctcgga    97

<210> SEQ ID NO 59
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 59
tgctgttgac agtgagcgca aggaagactc ctgcagttta tagtgaagcc acagatgtat    60
aaactgcagg agtcttcctt atgcctactg cctcgga    97

<210> SEQ ID NO 60
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 60
tgctgttgac agtgagcgcg cgactcctat aatttctaat tagtgaagcc acagatgtaa    60
ttagaaatta taggagtcgc ttgcctactg cctcgga    97

<210> SEQ ID NO 61
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 61
tgctgttgac agtgagcgca aaagtgatac ttcaatatat tagtgaagcc acagatgtaa    60
tatattgaag tatcactttt atgcctactg cctcgga    97

<210> SEQ ID NO 62
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 62
tgctgttgac agtgagcgac cggaattgta aggaactaga tagtgaagcc acagatgtat    60
ctagttcctt acaattccgg gtgcctactg cctcgga    97

<210> SEQ ID NO 63
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tgctgttgac agtgagcgaa aggtagagta tgtcatcaaa tagtgaagcc acagatgtat      60
ttgatgacat actctacctt ctgcctactg cctcgga                              97

<210> SEQ ID NO 64
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tgctgttgac agtgagcgcc tggagtcaga cagtaataaa tagtgaagcc acagatgtat      60
ttattactgt ctgactccag ttgcctactg cctcgga                              97

<210> SEQ ID NO 65
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tgctgttgac agtgagcgac tccgtcaagg tgaagatcaa tagtgaagcc acagatgtat      60
tgatcttcac cttgacggag ctgcctactg cctcgga                              97

<210> SEQ ID NO 66
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgctgttgac agtgagcgcc tgatgaacac tattatgcaa tagtgaagcc acagatgtat      60
tgcataatag tgttcatcag ttgcctactg cctcgga                              97

<210> SEQ ID NO 67
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tgctgttgac agtgagcgcc aggcttgatg gaaccacaaa tagtgaagcc acagatgtat      60
ttgtggttcc atcaagcctg atgcctactg cctcgga                              97

<210> SEQ ID NO 68
<211> LENGTH: 97
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 68
tgctgttgac agtgagcgcc agcgactcac tgacagagaa tagtgaagcc acagatgtat    60
tctctgtcag tgagtcgctg ttgcctactg cctcgga                            97

<210> SEQ ID NO 69
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tgctgttgac agtgagcgaa agcactgtgg cagtatatta tagtgaagcc acagatgtat    60
aatatactgc cacagtgctt gtgcctactg cctcgga                            97

<210> SEQ ID NO 70
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tgctgttgac agtgagcgct aggacctcta gatagtgtta tagtgaagcc acagatgtat    60
aacactatct agaggtccta ttgcctactg cctcgga                            97

<210> SEQ ID NO 71
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tgctgttgac agtgagcgcc gcggccttgt ccaaatatga tagtgaagcc acagatgtat    60
catatttgga caaggccgcg ttgcctactg cctcgga                            97

<210> SEQ ID NO 72
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tgctgttgac agtgagcgcc acctgttatc ccgtcctgta tagtgaagcc acagatgtat    60
acaggacggg ataacaggtg atgcctactg cctcgga                            97

<210> SEQ ID NO 73
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 73
tgctgttgac agtgagcgac aggtttgtca cccggagtta tagtgaagcc acagatgtat    60
aactccgggt gacaaacctg gtgcctactg cctcgga                              97

<210> SEQ ID NO 74
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tgctgttgac agtgagcgcc acaatgaaga gggtgtcaca tagtgaagcc acagatgtat    60
gtgacaccct cttcattgtg atgcctactg cctcgga                              97

<210> SEQ ID NO 75
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tgctgttgac agtgagcgat aggatagatg tttcaatcaa tagtgaagcc acagatgtat    60
tgattgaaac atctatccta gtgcctactg cctcgga                              97

<210> SEQ ID NO 76
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tgctgttgac agtgagcgac tggcagtttc cagtaatgaa tagtgaagcc acagatgtat    60
tcattactgg aaactgccag gtgcctactg cctcgga                              97

<210> SEQ ID NO 77
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tgctgttgac agtgagcgat cggagtttct tgaatctgaa tagtgaagcc acagatgtat    60
tcagattcaa gaaactccga ctgcctactg cctcgga                              97

<210> SEQ ID NO 78
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tgctgttgac agtgagcgat aggtgtagaa ttattgctta tagtgaagcc acagatgtat    60

```
aagcaataat tctacaccta ctgcctactg cctcgga                               97
```

<210> SEQ ID NO 79
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79

```
tgctgttgac agtgagcgct aaatgtttat tgaaatcaa tagtgaagcc acagatgtat       60
tgatttcaaa taaacattta atgcctactg cctcgga                              97
```

<210> SEQ ID NO 80
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80

```
tgctgttgac agtgagcgac gcggtgttgc cggtgaagaa tagtgaagcc acagatgtat     60
tcttcaccgg caacaccgcg gtgcctactg cctcgga                              97
```

<210> SEQ ID NO 81
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81

```
tgctgttgac agtgagcgca cgaagggtat tggtaacaaa tagtgaagcc acagatgtat     60
ttgttaccaa taccttcgt ttgcctactg cctcgga                               97
```

<210> SEQ ID NO 82
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82

```
tgctgttgac agtgagcgac tcacccgaga ttaaactaaa tagtgaagcc acagatgtat     60
ttagtttaat ctcgggtgag ctgcctactg cctcgga                              97
```

<210> SEQ ID NO 83
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

```
tgctgttgac agtgagcgca tcagcttgta tgaaactcaa tagtgaagcc acagatgtat     60
tgagtttcat acaagctgat ttgcctactg cctcgga                              97
```

```
<210> SEQ ID NO 84
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tgctgttgac agtgagcgcc tgactattac cattcagaaa tagtgaagcc acagatgtat      60
ttctgaatgg taatagtcag ttgcctactg cctcgga                              97

<210> SEQ ID NO 85
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tgctgttgac agtgagcgct acctctaaga cggaagtcaa tagtgaagcc acagatgtat      60
tgacttccgt cttagaggta atgcctactg cctcgga                              97

<210> SEQ ID NO 86
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tgctgttgac agtgagcgcc gggaatacaa aggtcatgaa tagtgaagcc acagatgtat      60
tcatgacctt tgtattcccg ttgcctactg cctcgga                              97

<210> SEQ ID NO 87
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tgctgttgac agtgagcgaa aagagaaatc tcgactccaa tagtgaagcc acagatgtat      60
tggagtcgag atttctcttt ctgcctactg cctcgga                              97

<210> SEQ ID NO 88
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tgctgttgac agtgagcgcc agcatttcac tttactgcaa tagtgaagcc acagatgtat      60
tgcagtaaag tgaaatgctg ttgcctactg cctcgga                              97

<210> SEQ ID NO 89
<211> LENGTH: 97
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 89
tgctgttgac agtgagcgct acgaccacgt cagttacaaa tagtgaagcc acagatgtat    60
ttgtaactga cgtggtcgta ttgcctactg cctcgga                             97

<210> SEQ ID NO 90
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tgctgttgac agtgagcgac aggagcaaga tgagttacta tagtgaagcc acagatgtat    60
agtaactcat cttgctcctg ctgcctactg cctcgga                             97

<210> SEQ ID NO 91
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tgctgttgac agtgagcgac ccttctgtgt tggtgagata tagtgaagcc acagatgtat    60
atctcaccaa cacagaaggg ctgcctactg cctcgga                             97

<210> SEQ ID NO 92
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tgctgttgac agtgagcgca tgaagctgca tattatgaaa tagtgaagcc acagatgtat    60
ttcataatat gcagcttcat ttgcctactg cctcgga                             97

<210> SEQ ID NO 93
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgctgttgac agtgagcgac accagcgttc aatagctgaa tagtgaagcc acagatgtat    60
tcagctattg aacgctggtg ctgcctactg cctcgga                             97

<210> SEQ ID NO 94
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 94
tgctgttgac agtgagcgcc tgaagattgc ctgtacctaa tagtgaagcc acagatgtat    60
taggtacagg caatcttcag atgcctactg cctcgga    97

<210> SEQ ID NO 95
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tgctgttgac agtgagcgac cgggagaaca gggtatgata tagtgaagcc acagatgtat    60
atcataccct gttctcccgg ctgcctactg cctcgga    97

<210> SEQ ID NO 96
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tgctgttgac agtgagcgac agtagaaatt atatgcatta tagtgaagcc acagatgtat    60
aatgcatata atttctactg ctgcctactg cctcgga    97

<210> SEQ ID NO 97
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tgctgttgac agtgagcgcc ccgattcatt gcaagttgta tagtgaagcc acagatgtat    60
acaacttgca atgaatcggg atgcctactg cctcgga    97

<210> SEQ ID NO 98
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tgctgttgac agtgagcgcg cacaggaatt tgtttaata tagtgaagcc acagatgtat    60
attaaacaaa attcctgtgc atgcctactg cctcgga    97

<210> SEQ ID NO 99
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tgctgttgac agtgagcgac tggcctgcgc tactatacaa tagtgaagcc acagatgtat    60
tgtatagtag cgcaggccag ctgcctactg cctcgga                                     97

<210> SEQ ID NO 100
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tgctgttgac agtgagcgcc agtgagtata gggacaataa tagtgaagcc acagatgtat           60
tattgtccct atactcactg atgcctactg cctcgga                                     97

<210> SEQ ID NO 101
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgctgttgac agtgagcgcc tggattgact acaagttgaa tagtgaagcc acagatgtat           60
tcaacttgta gtcaatccag atgcctactg cctcgga                                     97

<210> SEQ ID NO 102
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tgctgttgac agtgagcgag agccacttct gggaacacaa tagtgaagcc acagatgtat           60
tgtgttccca gaagtggctc ctgcctactg cctcgga                                     97

<210> SEQ ID NO 103
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tgctgttgac agtgagcgcc tagcagttgt aagcaatcaa tagtgaagcc acagatgtat           60
tgattgctta caactgctag ttgcctactg cctcgga                                     97

<210> SEQ ID NO 104
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tgctgttgac agtgagcgca acaagcaagg tattactgta tagtgaagcc acagatgtat           60
acagtaatac cttgcttgtt ttgcctactg cctcgga                                     97

<210> SEQ ID NO 105

```
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tgctgttgac agtgagcgcc agaacctcat taaagttgaa tagtgaagcc acagatgtat      60
tcaactttaa tgaggttctg atgcctactg cctcgga                              97

<210> SEQ ID NO 106
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tgctgttgac agtgagcgcc cgaaggctca tgtacttcaa tagtgaagcc acagatgtat      60
tgaagtacat gagccttcgg ttgcctactg cctcgga                              97

<210> SEQ ID NO 107
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tgctgttgac agtgagcgcc tggaccacaa gcatccttaa tagtgaagcc acagatgtat      60
taaggatgct tgtggtccag ttgcctactg cctcgga                              97

<210> SEQ ID NO 108
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tgctgttgac agtgagcgcc tggtatattt gagaagacaa tagtgaagcc acagatgtat      60
tgtcttctca aatataccag atgcctactg cctcgga                              97

<210> SEQ ID NO 109
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tgctgttgac agtgagcgca ccaggtgaac cagaatttaa tagtgaagcc acagatgtat      60
taaattctgg ttcacctggt ttgcctactg cctcgga                              97

<210> SEQ ID NO 110
<211> LENGTH: 97
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 110
tgctgttgac agtgagcgcc ccacagagca tctcactaaa tagtgaagcc acagatgtat      60
ttagtgagat gctctgtggg ttgcctactg cctcgga                              97

<210> SEQ ID NO 111
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tgctgttgac agtgagcgac tgcatcttat gtgcaagaaa tagtgaagcc acagatgtat      60
ttcttgcaca taagatgcag gtgcctactg cctcgga                              97

<210> SEQ ID NO 112
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tgctgttgac agtgagcgcc aggaatttgg ttaaatggaa tagtgaagcc acagatgtat      60
tccatttaac caaattcctg ttgcctactg cctcgga                              97

<210> SEQ ID NO 113
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tgctgttgac agtgagcgct ccaacgacag tggtattcaa tagtgaagcc acagatgtat      60
tgaataccac tgtcgttgga ttgcctactg cctcgga                              97

<210> SEQ ID NO 114
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tgctgttgac agtgagcgcc aggaagttct tcgatcaata tagtgaagcc acagatgtat      60
attgatcgaa gaacttcctg ttgcctactg cctcgga                              97

<210> SEQ ID NO 115
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
```

```
tgctgttgac agtgagcgcc tcaatctcat tggtggctta tagtgaagcc acagatgtat    60
aagccaccaa tgagattgag atgcctactg cctcgga                             97
```

<210> SEQ ID NO 116
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116

```
tgctgttgac agtgagcgca gcgagaacca gtgagaaata tagtgaagcc acagatgtat    60
atttctcact ggttctcgct ttgcctactg cctcgga                             97
```

<210> SEQ ID NO 117
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117

```
tgctgttgac agtgagcgac accatcttga atgagttcta tagtgaagcc acagatgtat    60
agaactcatt caagatggtg ctgcctactg cctcgga                             97
```

<210> SEQ ID NO 118
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118

```
tgctgttgac agtgagcgcg aggagaatta taaactgaaa tagtgaagcc acagatgtat    60
ttcagtttat aattctcctc atgcctactg cctcgga                             97
```

<210> SEQ ID NO 119
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119

```
tgctgttgac agtgagcgaa aggagactaa tgaacagaaa tagtgaagcc acagatgtat    60
ttctgttcat tagtctcctt ctgcctactg cctcgga                             97
```

<210> SEQ ID NO 120
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120

```
tgctgttgac agtgagcgac aaggtgacat cagaagtaaa tagtgaagcc acagatgtat    60
ttacttctga tgtcaccttg ctgcctactg cctcgga                             97
```

```
<210> SEQ ID NO 121
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tgctgttgac agtgagcgcc agtaggatac tacacagtta tagtgaagcc acagatgtat    60
aactgtgtag tatcctactg atgcctactg cctcgga                            97

<210> SEQ ID NO 122
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
tgctgttgac agtgagcgaa agagccttag cagtcaggca tagtgaagcc acagatgtat    60
gcctgactgc taaggctctt ctgcctactg cctcgga                            97

<210> SEQ ID NO 123
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tgctgttgac agtgagcgcc aggcggaaac tgatcagctt tagtgaagcc acagatgtaa    60
agctgatcag tttccgcctg atgcctactg cctcgga                            97

<210> SEQ ID NO 124
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tgctgttgac agtgagcgat tggttcatgt gcaaattcat tagtgaagcc acagatgtaa    60
tgaatttgca catgaaccaa ctgcctactg cctcgga                            97

<210> SEQ ID NO 125
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tgctgttgac agtgagcgcg acggaaacac taatagtgta tagtgaagcc acagatgtat    60
acactattag tgtttccgtc atgcctactg cctcgga                            97

<210> SEQ ID NO 126
<211> LENGTH: 97
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tgctgttgac agtgagcgca agaatctgat tgaaaccata tagtgaagcc acagatgtat     60
atggtttcaa tcagattctt atgcctactg cctcgga                             97

<210> SEQ ID NO 127
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tgctgttgac agtgagcgaa ccagggtaat taatcacaaa tagtgaagcc acagatgtat     60
ttgtgattaa ttaccctggt gtgcctactg cctcgga                             97

<210> SEQ ID NO 128
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tgctgttgac agtgagcgac ccgaaattac aactgcatta tagtgaagcc acagatgtat     60
aatgcagttg taatttcggg gtgcctactg cctcgga                             97

<210> SEQ ID NO 129
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tgctgttgac agtgagcgcc aacaggaagt cagacatcta tagtgaagcc acagatgtat     60
agatgtctga cttcctgttg atgcctactg cctcgga                             97

<210> SEQ ID NO 130
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tgctgttgac agtgagcgac tctagtatat ttcacagaaa tagtgaagcc acagatgtat     60
ttctgtgaaa tatactagag ctgcctactg cctcgga                             97

<210> SEQ ID NO 131
<211> LENGTH: 97
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 131
tgctgttgac agtgagcgag agcagtaacc tgacaactaa tagtgaagcc acagatgtat    60
tagttgtcag gttactgctc ctgcctactg cctcgga                             97

<210> SEQ ID NO 132
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tgctgttgac agtgagcgca aactaggtta taacctataa tagtgaagcc acagatgtat    60
tataggttat aacctagttt ttgcctactg cctcgga                             97

<210> SEQ ID NO 133
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tgctgttgac agtgagcgac agcagtttct tatacctaca tagtgaagcc acagatgtat    60
gtaggtataa gaaactgctg gtgcctactg cctcgga                             97

<210> SEQ ID NO 134
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tgctgttgac agtgagcgca tggttcatct ttatgccaaa tagtgaagcc acagatgtat    60
ttggcataaa gatgaaccat ttgcctactg cctcgga                             97

<210> SEQ ID NO 135
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tgctgttgac agtgagcgct ccgataattt cagagcataa tagtgaagcc acagatgtat    60
tatgctctga aattatcgga atgcctactg cctcgga                             97

<210> SEQ ID NO 136
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136

```
tgctgttgac agtgagcgcc agattcttca ttgtataaat tagtgaagcc acagatgtaa      60
tttatacaat gaagaatctg ttgcctactg cctcgga                              97
```

<210> SEQ ID NO 137
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137

```
tgctgttgac agtgagcgcc agaattataa caggcaaata tagtgaagcc acagatgtat      60
atttgcctgt tataattctg atgcctactg cctcgga                              97
```

<210> SEQ ID NO 138
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138

```
tgctgttgac agtgagcgaa cggacattgt acccagataa tagtgaagcc acagatgtat      60
tatctgggta caatgtccgt ctgcctactg cctcgga                              97
```

<210> SEQ ID NO 139
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139

```
tgctgttgac agtgagcgaa agagtcactg tctgaatgaa tagtgaagcc acagatgtat      60
tcattcagac agtgactctt ctgcctactg cctcgga                              97
```

<210> SEQ ID NO 140
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140

```
tgctgttgac agtgagcgcg gactggttat agatttataa tagtgaagcc acagatgtat      60
tataaatcta taccagtcc atgcctactg cctcgga                               97
```

<210> SEQ ID NO 141
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141

```
tgctgttgac agtgagcgct gcctcagtga tacagtataa tagtgaagcc acagatgtat      60
tatactgtat cactgaggca atgcctactg cctcgga                              97
```

<210> SEQ ID NO 142
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tgctgttgac agtgagcgca aggagcagac tgtacttgta tagtgaagcc acagatgtat      60
acaagtacag tctgctcctt atgcctactg cctcgga                              97

<210> SEQ ID NO 143
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tgctgttgac agtgagcgct ccatgtatct cagtcactaa tagtgaagcc acagatgtat      60
tagtgactga gatacatgga atgcctactg cctcgga                              97

<210> SEQ ID NO 144
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tgctgttgac agtgagcgcc ccaagtaata cttaatgcaa tagtgaagcc acagatgtat      60
tgcattaagt attacttggg atgcctactg cctcgga                              97

<210> SEQ ID NO 145
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tgctgttgac agtgagcgac acaaccattt gaatccagaa tagtgaagcc acagatgtat      60
tctggattca aatggttgtg ctgcctactg cctcgga                              97

<210> SEQ ID NO 146
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
tgctgttgac agtgagcgag aaacgacgag aacagttgaa tagtgaagcc acagatgtat      60
tcaactgttc tcgtcgtttc ctgcctactg cctcgga                              97

<210> SEQ ID NO 147
<211> LENGTH: 97
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 147
tgctgttgac agtgagcgca cgacgagaac agttgaaaca tagtgaagcc acagatgtat    60
gtttcaactg ttctcgtcgt ttgcctactg cctcgga                            97

<210> SEQ ID NO 148
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
tgctgttgac agtgagcgcc tgcctcaaac ttaaatagta tagtgaagcc acagatgtat    60
actatttaag tttgaggcag ttgcctactg cctcgga                            97

<210> SEQ ID NO 149
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
tgctgttgac agtgagcgcc cgccagtaca ccaacaagaa tagtgaagcc acagatgtat    60
tcttgttggt gtactggcgg atgcctactg cctcgga                            97

<210> SEQ ID NO 150
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tgctgttgac agtgagcgcc agaagatcaa tgcacataaa tagtgaagcc acagatgtat    60
ttatgtgcat tgatcttctg ttgcctactg cctcgga                            97

<210> SEQ ID NO 151
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tgctgttgac agtgagcgaa aggataaagc tactggagaa tagtgaagcc acagatgtat    60
tctccagtag ctttatcctt ctgcctactg cctcgga                            97

<210> SEQ ID NO 152
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 152
tgctgttgac agtgagcgcc tgcaatatca gtgagttcaa tagtgaagcc acagatgtat     60
tgaactcact gatattgcag atgcctactg cctcgga     97

<210> SEQ ID NO 153
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tgctgttgac agtgagcgcc agacatgttg aagtgaataa tagtgaagcc acagatgtat     60
tattcacttc aacatgtctg ttgcctactg cctcgga     97

<210> SEQ ID NO 154
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tgctgttgac agtgagcgac acaaggttca tcaggatcta tagtgaagcc acagatgtat     60
agatcctgat gaaccttgtg gtgcctactg cctcgga     97

<210> SEQ ID NO 155
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tgctgttgac agtgagcgca ccctcattct taccatccaa tagtgaagcc acagatgtat     60
tggatggtaa gaatgagggt atgcctactg cctcgga     97

<210> SEQ ID NO 156
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tgctgttgac agtgagcgcc tgcagcaaga ctgagatcaa tagtgaagcc acagatgtat     60
tgatctcagt cttgctgcag atgcctactg cctcgga     97

<210> SEQ ID NO 157
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tgctgttgac agtgagcgac agatcaagta tggacactga tagtgaagcc acagatgtat     60

```
cagtgtccat acttgatctg ctgcctactg cctcgga                               97
```

<210> SEQ ID NO 158
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158

```
tgctgttgac agtgagcgca acagagaaag tgcctataaa tagtgaagcc acagatgtat     60
ttataggcac tttctctgtt atgcctactg cctcgga                              97
```

<210> SEQ ID NO 159
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159

```
tgctgttgac agtgagcgaa tcaatgatct tgacgctaaa tagtgaagcc acagatgtat     60
ttagcgtcaa gatcattgat gtgcctactg cctcgga                              97
```

<210> SEQ ID NO 160
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160

```
tgctgttgac agtgagcgat cgggtgaatt tgcacgtata tagtgaagcc acagatgtat     60
atacgtgcaa attcacccga ctgcctactg cctcgga                              97
```

<210> SEQ ID NO 161
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161

```
tgctgttgac agtgagcgcc cgggaagtat ccctgcttaa tagtgaagcc acagatgtat     60
taagcaggga tacttcccgg atgcctactg cctcgga                              97
```

<210> SEQ ID NO 162
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162

```
tgctgttgac agtgagcgct gcctccaagt ttctaagcaa tagtgaagcc acagatgtat     60
tgcttagaaa cttggaggca atgcctactg cctcgga                              97
```

```
<210> SEQ ID NO 163
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tgctgttgac agtgagcgaa acgaccatgg cgatgagaaa tagtgaagcc acagatgtat      60
ttctcatcgc catggtcgtt ctgcctactg cctcgga                              97

<210> SEQ ID NO 164
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
tgctgttgac agtgagcgca aggagtgatg tgcaatactt tagtgaagcc acagatgtaa      60
agtattgcac atcactcctt ttgcctactg cctcgga                              97

<210> SEQ ID NO 165
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tgctgttgac agtgagcgcc aggatgctta tcaaggagta tagtgaagcc acagatgtat      60
actccttgat aagcatcctg atgcctactg cctcgga                              97

<210> SEQ ID NO 166
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tgctgttgac agtgagcgcg cccacctgaa tgtcaataaa tagtgaagcc acagatgtat      60
ttattgacat tcaggtgggc atgcctactg cctcgga                              97

<210> SEQ ID NO 167
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tgctgttgac agtgagcgca gggaccttaa tactcagata tagtgaagcc acagatgtat      60
atctgagtat taaggtccct ttgcctactg cctcgga                              97

<210> SEQ ID NO 168
<211> LENGTH: 97
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 168
tgctgttgac agtgagcgaa ccgttgatat ccacatgaaa tagtgaagcc acagatgtat      60
ttcatgtgga tatcaacggt gtgcctactg cctcgga                              97

<210> SEQ ID NO 169
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tgctgttgac agtgagcgac tcagcctcac tttcaataaa tagtgaagcc acagatgtat      60
ttattgaaag tgaggctgag gtgcctactg cctcgga                              97

<210> SEQ ID NO 170
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tgctgttgac agtgagcgcc acgaacaaga accgctacaa tagtgaagcc acagatgtat      60
tgtagcggtt cttgttcgtg ttgcctactg cctcgga                              97

<210> SEQ ID NO 171
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tgctgttgac agtgagcgca ccagacaagt tccagaataa tagtgaagcc acagatgtat      60
tattctggaa cttgtctggt ttgcctactg cctcgga                              97

<210> SEQ ID NO 172
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tgctgttgac agtgagcgaa gcctccataa ttgtcaataa tagtgaagcc acagatgtat      60
tattgacaat tatggaggct gtgcctactg cctcgga                              97

<210> SEQ ID NO 173
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 173
tgctgttgac agtgagcgcc aagtgaagat tgaccggaaa tagtgaagcc acagatgtat    60
ttccggtcaa tcttcacttg ttgcctactg cctcgga                              97

<210> SEQ ID NO 174
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
tgctgttgac agtgagcgcc agattctata tgccaatgaa tagtgaagcc acagatgtat    60
tcattggcat atagaatctg atgcctactg cctcgga                              97

<210> SEQ ID NO 175
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
tgctgttgac agtgagcgcc cgcatgatct tatcggcaaa tagtgaagcc acagatgtat    60
ttgccgataa gatcatgcgg ttgcctactg cctcgga                              97

<210> SEQ ID NO 176
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tgctgttgac agtgagcgca aaagtgatac ttcaatatat tagtgaagcc acagatgtaa    60
tatattgaag tatcactttt atgcctactg cctcgga                              97

<210> SEQ ID NO 177
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tgctgttgac agtgagcgcc agacaaatgg tggaagcaca tagtgaagcc acagatgtat    60
gtgcttccac catttgtctg atgcctactg cctcgga                              97

<210> SEQ ID NO 178
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tgctgttgac agtgagcgca acattgagtc cgaccttcaa tagtgaagcc acagatgtat    60

```
tgaaggtcgg actcaatgtt ttgcctactg cctcgga                              97
```

<210> SEQ ID NO 179
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179

```
tgctgttgac agtgagcgaa acgaggtcat cgtgaataaa tagtgaagcc acagatgtat    60
ttattcacga tgacctcgtt ctgcctactg cctcgga                              97
```

<210> SEQ ID NO 180
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180

```
tgctgttgac agtgagcgcc tggttctatt ggagcatcaa tagtgaagcc acagatgtat    60
tgatgctcca atagaaccag ttgcctactg cctcgga                              97
```

<210> SEQ ID NO 181
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181

```
tgctgttgac agtgagcgca aacgtataaa tgctatccaa tagtgaagcc acagatgtat    60
tggatagcat ttatacgttt atgcctactg cctcgga                              97
```

<210> SEQ ID NO 182
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182

```
tgctgttgac agtgagcgac tgggactaga tagccagttt tagtgaagcc acagatgtaa    60
aactggctat ctagtcccag gtgcctactg cctcgga                              97
```

<210> SEQ ID NO 183
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183

```
tgctgttgac agtgagcgac agcatgtcta cagtctgaat tagtgaagcc acagatgtaa    60
ttcagactgt agacatgctg gtgcctactg cctcgga                              97
```

<210> SEQ ID NO 184

```
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tgctgttgac agtgagcgcc gaggagatca tgtccaagta tagtgaagcc acagatgtat      60
acttggacat gatctcctcg ttgcctactg cctcgga                              97

<210> SEQ ID NO 185
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tgctgttgac agtgagcgcc aggagctact tgatgaaatt tagtgaagcc acagatgtaa      60
atttcatcaa gtagctcctg atgcctactg cctcgga                              97

<210> SEQ ID NO 186
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tgctgttgac agtgagcgca agcaactact ggctgatgaa tagtgaagcc acagatgtat      60
tcatcagcca gtagttgctt atgcctactg cctcgga                              97

<210> SEQ ID NO 187
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tgctgttgac agtgagcgca atggatatta aagagaataa tagtgaagcc acagatgtat      60
tattctcttt aatatccatt ttgcctactg cctcgga                              97

<210> SEQ ID NO 188
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tgctgttgac agtgagcgac aagattgtca tagtgagcaa tagtgaagcc acagatgtat      60
tgctcactat gacaatcttg gtgcctactg cctcgga                              97

<210> SEQ ID NO 189
<211> LENGTH: 97
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 189
tgctgttgac agtgagcgaa cgccagaaga tggaatctat tagtgaagcc acagatgtaa      60
tagattccat cttctggcgt ctgcctactg cctcgga                              97

<210> SEQ ID NO 190
<211> LENGTH: 97
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 190
tgctgttgac agtgagcgcc tcgaatagac taagatgaaa tagtgaagcc acagatgtat      60
ttcatcttag tctattcgag ttgcctactg cctcgga                              97

<210> SEQ ID NO 191
<211> LENGTH: 97
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 191
tgctgttgac agtgagcgct agcataatga caattattta tagtgaagcc acagatgtat      60
aaataattgt cattatgcta atgcctactg cctcgga                              97

<210> SEQ ID NO 192
<211> LENGTH: 97
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 192
tgctgttgac agtgagcgcc ccattgtttc ttccaactta tagtgaagcc acagatgtat      60
aagttggaag aaacaatggg atgcctactg cctcgga                              97

<210> SEQ ID NO 193
<211> LENGTH: 97
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 193
tgctgttgac agtgagcgct agggtgatgt ctcacttgaa tagtgaagcc acagatgtat      60
tcaagtgaga catcacccta ttgcctactg cctcgga                              97

<210> SEQ ID NO 194
<211> LENGTH: 97
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 194
tgctgttgac agtgagcgat tccgtgacat tcaacgttta tagtgaagcc acagatgtat    60
aaacgttgaa tgtcacggaa gtgcctactg cctcgga                             97

<210> SEQ ID NO 195
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tgctgttgac agtgagcgac accctggtca ttacagaata tagtgaagcc acagatgtat    60
attctgtaat gaccagggtg gtgcctactg cctcgga                             97

<210> SEQ ID NO 196
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tgctgttgac agtgagcgcc agatggactt tcaagaccta tagtgaagcc acagatgtat    60
aggtcttgaa agtccatctg atgcctactg cctcgga                             97

<210> SEQ ID NO 197
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tgctgttgac agtgagcgat tggatattct tgaaagttta tagtgaagcc acagatgtat    60
aaactttcaa gaatatccaa gtgcctactg cctcgga                             97

<210> SEQ ID NO 198
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
tgctgttgac agtgagcgca gcgtgatggt tgatagctaa tagtgaagcc acagatgtat    60
tagctatcaa ccatcacgct atgcctactg cctcgga                             97

<210> SEQ ID NO 199
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tgctgttgac agtgagcgaa tggttgatag ctaaaggaaa tagtgaagcc acagatgtat    60
ttcctttagc tatcaaccat ctgcctactg cctcgga                             97

<210> SEQ ID NO 200
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tgctgttgac agtgagcgca acgggacaaa tgcaatagaa tagtgaagcc acagatgtat      60
tctattgcat ttgtcccgtt ttgcctactg cctcgga                              97

<210> SEQ ID NO 201
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tgctgttgac agtgagcgat ggcctagttg tgtaaatata tagtgaagcc acagatgtat      60
atatttacac aactaggcca ctgcctactg cctcgga                              97

<210> SEQ ID NO 202
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tgctgttgac agtgagcgcc cgcctgaagt ctctgattaa tagtgaagcc acagatgtat      60
taatcagaga cttcaggcgg ttgcctactg cctcgga                              97

<210> SEQ ID NO 203
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tgctgttgac agtgagcgag cctctcagct catatggaat tagtgaagcc acagatgtaa      60
ttccatatga gctgagaggc ctgcctactg cctcgga                              97

<210> SEQ ID NO 204
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tgctgttgac agtgagcgcc aagatgttta tcaaatctaa tagtgaagcc acagatgtat      60
tagatttgat aaacatcttg atgcctactg cctcgga                              97

<210> SEQ ID NO 205
<211> LENGTH: 97

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tgctgttgac agtgagcgca acggtaccct agacaaccaa tagtgaagcc acagatgtat    60
tggttgtcta gggtaccgtt atgcctactg cctcgga                            97

<210> SEQ ID NO 206
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
tgctgttgac agtgagcgcc agcgcggttg cagccggtaa tagtgaagcc acagatgtat    60
taccggctgc aaccgcgctg ttgcctactg cctcgga                            97

<210> SEQ ID NO 207
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tgctgttgac agtgagcgct tggtttagca ggaagaataa tagtgaagcc acagatgtat    60
tattcttcct gctaaaccaa atgcctactg cctcgga                            97

<210> SEQ ID NO 208
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tgctgttgac agtgagcgca tcgctattgc acatgtataa tagtgaagcc acagatgtat    60
tatacatgtg caatagcgat ttgcctactg cctcgga                            97

<210> SEQ ID NO 209
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
tgctgttgac agtgagcgcc aagatagtga tcgaagacta tagtgaagcc acagatgtat    60
agtcttcgat cactatcttg atgcctactg cctcgga                            97

<210> SEQ ID NO 210
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 210
tgctgttgac agtgagcgcc cggtgtttgt cctttaaata tagtgaagcc acagatgtat    60
atttaaagga caaacaccgg atgcctactg cctcgga    97

<210> SEQ ID NO 211
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tgctgttgac agtgagcgaa agaatcaaat tactgctgaa tagtgaagcc acagatgtat    60
tcagcagtaa tttgattctt gtgcctactg cctcgga    97

<210> SEQ ID NO 212
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tgctgttgac agtgagcgca acgttcatgg ataaattcta tagtgaagcc acagatgtat    60
agaatttatc catgaacgtt atgcctactg cctcgga    97

<210> SEQ ID NO 213
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
tgctgttgac agtgagcgca ggaattataa tgcttatcta tagtgaagcc acagatgtat    60
agataagcat tataattcct atgcctactg cctcgga    97

<210> SEQ ID NO 214
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tgctgttgac agtgagcgcc cactacaagt acatgtgtaa tagtgaagcc acagatgtat    60
tacacatgta cttgtagtgg atgcctactg cctcgga    97

<210> SEQ ID NO 215
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
aatgatacgg cgaccaccga ctaaagtagc cccttgaatt c                    41

<210> SEQ ID NO 216
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
caagcagaag acggcatacg atagtgaagc cacagatgta                      40

<210> SEQ ID NO 217
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tagccccttg aattccgagg cagtaggca                                  29

<210> SEQ ID NO 218
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tgctgttgac agtgagcgaa tggctgtcgt cagcaaacaa tagtgaagcc acagatgtat   60
tgtttgctga cgacagccat gtgcctactg cctcgga                          97

<210> SEQ ID NO 219
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tgctgttgac agtgagcgca ggcttggaca ttaaactgaa tagtgaagcc acagatgtat   60 tcagttttaat gtccaagcct ttgcctactg cctcgga                         97

<210> SEQ ID NO 220
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tgctgttgac agtgagcgct tggaagtaca gctccataaa tagtgaagcc acagatgtat   60
ttatggagct gtacttccaa atgcctactg cctcgga                          97

<210> SEQ ID NO 221
<211> LENGTH: 97
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 221
tgctgttgac agtgagcgac acaagtcaaa cctttattta tagtgaagcc acagatgtat      60
aaataaaggt tgacttgtg gtgcctactg cctcgga                                97

<210> SEQ ID NO 222
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tgctgttgac agtgagcgac aagctcttct agcaatacta tagtgaagcc acagatgtat      60
agtattgcta gaagagcttg ctgcctactg cctcgga                               97

<210> SEQ ID NO 223
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tgctgttgac agtgagcgac tggatctaga ggcattataa tagtgaagcc acagatgtat      60
tataatgcct ctagatccag ctgcctactg cctcgga                               97

<210> SEQ ID NO 224
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tgctgttgac agtgagcgcc agcctcaagg aagatcataa tagtgaagcc acagatgtat      60
tatgatcttc cttgaggctg ttgcctactg cctcgga                               97

<210> SEQ ID NO 225
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tgctgttgac agtgagcgca ggcgatttga tactttccaa tagtgaagcc acagatgtat      60
tggaaagtat caaatcgcct atgcctactg cctcgga                               97

<210> SEQ ID NO 226
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
```

```
tgctgttgac agtgagcgca aagatcatgc tttacggtta tagtgaagcc acagatgtat      60
aaccgtaaag catgatcttt atgcctactg cctcgga                              97

<210> SEQ ID NO 227
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tgctgttgac agtgagcgct agaagtaatg tatcttgcta tagtgaagcc acagatgtat      60
agcaagatac attacttcta ttgcctactg cctcgga                              97

<210> SEQ ID NO 228
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
tgctgttgac agtgagcgaa tcgacttcga taaactattt tagtgaagcc acagatgtaa      60
aatagtttat cgaagtcgat ctgcctactg cctcgga                              97

<210> SEQ ID NO 229
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tgctgttgac agtgagcgac ccggtgttgg acatatgaaa tagtgaagcc acagatgtat      60
ttcatatgtc caacaccggg ctgcctactg cctcgga                              97

<210> SEQ ID NO 230
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tgctgttgac agtgagcgac tggcattgac tcatagccta tagtgaagcc acagatgtat      60
aggctatgag tcaatgccag gtgcctactg cctcgga                              97

<210> SEQ ID NO 231
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tgctgttgac agtgagcgat ccctgggctg tgatcgatta tagtgaagcc acagatgtat      60
aatcgatcac agcccaggga gtgcctactg cctcgga                              97
```

<210> SEQ ID NO 232
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 232
tgctgttgac agtgagcgcg aggaacttcc ctatagtgaa tagtgaagcc acagatgtat      60
tcactatagg gaagttcctc atgcctactg cctcgga                              97

<210> SEQ ID NO 233
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 233
tgctgttgac agtgagcgcc catatgtggt tctagaatta tagtgaagcc acagatgtat      60
aattctagaa ccacatatgg ttgcctactg cctcgga                              97

<210> SEQ ID NO 234
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 234
tgctgttgac agtgagcgat tctgctatgt caatgacata tagtgaagcc acagatgtat      60
atgtcattga catagcagaa gtgcctactg cctcgga                              97

<210> SEQ ID NO 235
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 235
tgctgttgac agtgagcgcc accctcatcc tctaattcaa tagtgaagcc acagatgtat      60
tgaattagag gatgagggtg atgcctactg cctcgga                              97

<210> SEQ ID NO 236
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 236
tgctgttgac agtgagcgac ggaattgtaa ggaactagaa tagtgaagcc acagatgtat      60
tctagttcct tacaattccg gtgcctactg cctcgga                              97

<210> SEQ ID NO 237
<211> LENGTH: 97

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tgctgttgac agtgagcgac actgttatcc aagactacaa tagtgaagcc acagatgtat      60
tgtagtcttg gataacagtg gtgcctactg cctcgga                              97

<210> SEQ ID NO 238
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tgctgttgac agtgagcgac tgcccgaatt tggaaatctt tagtgaagcc acagatgtaa      60
agatttccaa attcgggcag ctgcctactg cctcgga                              97

<210> SEQ ID NO 239
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
tgctgttgac agtgagcgca aggaactaga aggccctata tagtgaagcc acagatgtat      60
atagggcctt ctagttcctt atgcctactg cctcgga                              97
```